(12) United States Patent
Sandanayaka et al.

(10) Patent No.: US 9,303,000 B2
(45) Date of Patent: Apr. 5, 2016

(54) OLEFIN CONTAINING NUCLEAR TRANSPORT MODULATORS AND USES THEREOF

(75) Inventors: Vincent P. Sandanayaka, Northboro, MA (US); Sharon Shacham, Newton, MA (US); Sharon Shechter, Andover, MA (US); Dilara McCauley, Natick, MA (US)

(73) Assignee: KARYOPHARM THERAPEUTICS INC., Newton, MA (US)

( * ) Notice: Subject to any disclaimer, the term of this patent is extended or adjusted under 35 U.S.C. 154(b) by 406 days.

(21) Appl. No.: 13/350,864

(22) Filed: Jan. 16, 2012

(65) Prior Publication Data

US 2012/0258986 A1 Oct. 11, 2012

Related U.S. Application Data

(60) Provisional application No. 61/433,501, filed on Jan. 17, 2011.

(51) Int. Cl.

| | |
|---|---|
| *C07D 413/06* | (2006.01) |
| *C07D 413/14* | (2006.01) |
| *A61K 31/4439* | (2006.01) |
| *C07D 401/06* | (2006.01) |
| *C07D 249/08* | (2006.01) |
| *C07D 403/06* | (2006.01) |
| *C07D 417/06* | (2006.01) |
| *A61P 9/10* | (2006.01) |
| *A61P 35/00* | (2006.01) |
| *A61P 31/12* | (2006.01) |
| *A61P 29/00* | (2006.01) |
| *A61P 19/02* | (2006.01) |
| *A61P 17/00* | (2006.01) |
| *A61P 17/06* | (2006.01) |
| *A61K 31/4245* | (2006.01) |
| *A61K 31/4196* | (2006.01) |

(52) U.S. Cl.
CPC ............ *C07D 249/08* (2013.01); *C07D 401/06* (2013.01); *C07D 403/06* (2013.01); *C07D 413/06* (2013.01); *C07D 413/14* (2013.01); *C07D 417/06* (2013.01)

(58) Field of Classification Search
CPC .. C07D 413/06; C07D 413/14; C07D 401/06; C07D 249/08; A61K 31/4245; A61K 31/4196; A61K 31/4439; A61P 9/10; A61P 35/00; A61P 31/12; A61P 29/00; A61P 19/02; A61P 17/00; A61P 17/06
USPC ............ 514/340, 364, 383; 548/143, 269.4; 546/269.1
See application file for complete search history.

(56) References Cited

U.S. PATENT DOCUMENTS

| | | | |
|---|---|---|---|
| 5,153,201 A | 10/1992 | Aono et al. | |
| 6,462,049 B1 * | 10/2002 | Ogura et al. ............. | 514/254.02 |
| 8,513,230 B2 | 8/2013 | Shacham et al. | |
| 8,999,996 B2 | 4/2015 | Sandanayaka et al. | |
| 9,079,865 B2 | 7/2015 | Sandanayaka et al. | |
| 9,096,543 B2 | 8/2015 | Sandanayaka et al. | |
| 2003/0018025 A1 | 1/2003 | Thurkauf et al. | |
| 2009/0221586 A1 | 9/2009 | Okada et al. | |
| 2009/0298896 A1 | 12/2009 | Sakuma et al. | |
| 2010/0056569 A1 | 3/2010 | Nan et al. | |
| 2011/0275607 A1 | 11/2011 | Shacham et al. | |
| 2012/0258986 A1 | 10/2012 | Sandanayaka et al. | |
| 2013/0317031 A1 | 11/2013 | Sandanayaka et al. | |
| 2014/0155370 A1 | 6/2014 | Shacham et al. | |
| 2014/0235653 A1 | 8/2014 | Sandanayaka et al. | |
| 2014/0364408 A1 | 12/2014 | Sandanayaka et al. | |
| 2015/0018332 A1 | 1/2015 | Sandanayaka et al. | |
| 2015/0111893 A1 | 4/2015 | Sandanayaka et al. | |

FOREIGN PATENT DOCUMENTS

| | | |
|---|---|---|
| CN | 101309912 | 11/2008 |
| CN | 101466687 | 6/2009 |
| EP | 1 939 180 A1 | 7/2008 |
| EP | 1992618 A1 * | 11/2008 |
| EP | 2 090 570 A1 | 8/2009 |
| WO | WO 2007/147336 A1 | 12/2007 |
| WO | WO2011/109799 A1 | 9/2011 |
| WO | WO2012/099807 | 7/2012 |

(Continued)

OTHER PUBLICATIONS

E. Yu. Shasheva, N. I. Vikrishchuk, L. D. Popov, A. D. Vikrishchuk, I. E. Mikhailov, K. A. Lysenko, and M. E. Kletskii, Reactions of Hydroxyphenyl-Substituted 1,2,4-Triazoles with Electrophylic Reagents, Russian Journal of General Chemistry, 2009, vol. 79, No. 10, pp. 2234-2243.*

(Continued)

*Primary Examiner* — Sarah Pihonak
*Assistant Examiner* — Jason A Deck
(74) *Attorney, Agent, or Firm* — Foley Hoag LLP

(57) ABSTRACT

The invention generally relates to the field of nuclear transport modulators, e.g., CRM1 inhibitors, and more particularly to new substituted-heterocyclic azole compounds, the synthesis and use of these compounds and their pharmaceutical compositions, e.g., in the treatment, modulation and/or prevention of physiological conditions associated with CRM1 activity such as in treating cancer and other neoplastic disorders, inflammatory diseases, disorders of abnormal tissue growth and fibrosis including cardiomyopathy, pulmonary fibrosis, hepatic fibrosis, glomerulonephritis, and other renal disorders, and for the treatment of viral infections (both acute and chronic).

10 Claims, 4 Drawing Sheets

(56) References Cited

FOREIGN PATENT DOCUMENTS

| WO | WO2013/019548 | | 2/2013 |
| --- | --- | --- | --- |
| WO | WO2013/019561 | A1 | 2/2013 |
| WO | WO 2013/170068 | | 11/2013 |
| WO | WO 2014/144772 | A1 | 9/2014 |
| WO | WO 2014/152263 | A1 | 9/2014 |
| WO | WO 2014/205389 | A1 | 12/2014 |
| WO | WO 2014/205393 | A1 | 12/2014 |

OTHER PUBLICATIONS

Notification Concerning Transmittal of International Preliminary Report on Patentability for International Application No. PCT/US2011/027328, "Nuclear Transport Modulators and Uses Thereof" dated Sep. 20, 2012.
Notification Concerning Transmittal of International Preliminary Report on Patentability for International Application No. PCT/US2012/021406, "Olefin Containing Nuclear Transport Modulators and Uses Thereof" dated Jul. 25, 2013.
Hoffman, Thomas J., et al., "Synthesis of Vinyl-Functionalized Oxazoles by Olefin Cross-Metathesis", *J. Org. Chem.* 73: 2400-2403 (2008).
Notification Concerning Transmittal of International Preliminary Report on Patentability for International Application No. PCT/US2011/027328, "Nuclear Transport Modulators and Uses Thereof" dated Sep. 11, 2012.
Notification Concerning Transmittal of International Preliminary Report on Patentability for International Application No. PCT/US2012/021406, "Olefin Containing Nuclear Transport Modulators and Uses Thereof" dated Jul. 17, 2013.
Notification of Transmittal of the International Search Report and the Written Opinion of the International Searching Authority for International Application No. PCT/US2013/040404, "Nuclear Transport Modulators and Uses Thereof"; Date of Mailing: Nov. 18, 2013.
Written Opinion of the International Searching Authority for International Application No. PCT/US2012/048368, "Nuclear Transport Modulators and Uses Thereof" dated Sep. 21, 2012.
Written Opinion of the International Searching Authority for International Application No. PCT/US2012/048319, "Hydrazide Containing Nuclear Transport Modulators and Uses Thereof" dated Nov. 9, 2012.
International Search Report for International Application No. PCT/US2011/027328 dated Apr. 29, 2011.
Written Opinion of the International Searching Authority for International Application No. PCT/US2011/027328.
Van Neck, T., et al., "Inhibition of the CRM1-mediated nucleocytoplasmic transport by N-azolylacrylates: Structure-activity relationship and mechanism of action", Biorganic & Medicinal Chemistry 16:9487-9497 (2008).
Kau, T.R., et al., "A chemical genetic screen identifies inhibitors of regulated nuclear export of a Forkhead transcription factor in PTEN-deficient tumor cells", *Cancer Cell*, pp. 463-476 (2003).
Monecke, T., et al., "Crystal Structure of the Nuclear Export Receptor CRM1 in Complex with Snurportin1 and RanGTP", *Science*, 324:1087-1091 (May 22, 2009).
Balsamini, "(E)-3-(2-(N-Phenylcarbamoyl)vinyl)pyrrole-2-carboxylic Acid Derivatives. A Novel Class of Glycine Site Antagonists", *Journal of Medicinal Chemistry*, 41(6):808-820 (Jan. 1, 1998).
Cai, X., et al., "Inhibition of Thr-55 phosphorylation restores p53 nuclear localization and sensitizes cancer cells to DNA damage", *PNAS*, 105(44):16958-16963 (Nov. 4, 2008).
Cronshaw, J.M., et al., "The nuclear pore complex: disease associations and functional correlations", *TRENDS Endocrin Metab*. 15:34-39 (2004).
Daelemans, D., et al., "A synthetic HIV-1 Rev inhibitor interfering with the CRM1-mediated nuclear export", *PNAS*, 99(22):14440-14445 (Oct. 29, 2002).
Davis, J.R., et al., "Controlling protein compartmentalization to overcome disease" *Pharmaceut Res.*, 24:17-27 (2007).

Falini, B., et al., "Both carboxy-terminus NES motif and mutated tryptophan(2) are crucial for aberrant nuclear export of nucleophosmin leukemic mutants in NPMc+ AML", *Blood Journal*, 107(11):45144523.
Freundt, E.C., et al., "Molecular Determinants for Subcellular Localization of the Severe Acute Respiratory Syndrome Coronavirus Open Reading Frame 3b Protein", *Journal of Virology*, 83(13):6631-6640 (Jul. 2009).
Ghildyal, R., et al., "The Respiratory Syncytial Virus Matrix Protein Possesses a Crm1-Mediated Nuclear Export Mechanism", *Journal of Virology*, 83(11):5353-5362 (Jun. 2009).
Ghosh, C.C., et al., "Analysis of nucleocytoplasmic shuttling of NF kappa B proteins in human leukocytes", *Methods Mol. Biol.* 457:279-92. (2008).
Gupta, N., et. al., "Retinal tau pathology in human glaucomas" *Can J Ophthalmol.* 43(1):53-60 (Feb. 2008).
Hoshino, L., et al., "Combined effects of p53 gene therapy and leptomycin B in human esophageal squamous cell carcinoma", *Oncology*, 75:113-119 ((2008).
International Search Report for International Application No. PCT/US2012/048368 dated Sep. 21, 2012.
International Search Report for International Application No. PCT/US2012/048319 dated Jul. 29, 2011.
Lain, S. et al., "An inhibitor of nuclear export activates the p53 response and induces the localization of HDM2 and p53 to U1A-positive nuclear bodies associated with the PODs", *Exp Cell Res.* 248:457-472 (1999).
Lain, S. et al., "Accumulating active p53 in the nucleus by inhibition of nuclear export: a novel strategy to promote the p53 tumor suppressor function", *Exp Cell Res.* 253:315 (1999).
Modzelewska-Banachiewicz, B., et al., "Synthesis and biological activity of (Z) and (E) isomers of 3-(3,4-diaryl-1-1,2,4-triazole-5-yl)prop-2-enoic acid" *Monatsh Chem.* 140:439-444 (2009).
Modzelewska-Banachiewicz, B., et al., "Synthesis and biological activity of new derivatives of 3-(3,4-diaryl-1-1,2,4-triazole-5-yl)propenoic acid" *European Journal of Medicinal Chemistry*, 39:873-877 (2004).
Muller, P.A.J., et al., "Nuclear-Cytosolic Transport of COMMD1 Regulates NF-κb and HIF-1 Activity", *Traffic*, 10:514-527 (2009).
Mutka, S., et al., "Nuclear export inhibitors (NEIs) as novel cancer therapeutics", *98th AACr Ann. Mtg.*, 2 pgs (Apr. 14-18, 2007).
Nakahara, J., et al., "Abnormal expression of TIP30 and arrested nucleocytoplasmic transport within oligodendrocyte precursor cells in multiple sclerosis", *Journal of Clinical Investigation*, 119(1):169-181 (Jan. 2009).
Noske, A., et al., "Expression of the Nuclear Export Protein Chromosomal Region Maintenance/Exportin 1/Xpo1 is a Prognostic Factor in Human Ovarian Cancer", *Cancer*, 112(8):1733-1743 (Apr. 15, 2008).
Notification of Transmittal of the International Search Report and the Written Opinion of the International Searching Authority, or the Declaration for International Application No. PCT/US2012/021406 dated Apr. 30, 2012.
Patani, G.A., et al., "Bioisosterism: A Rational Approach in Drug Design", *Amer. Chem. Soc.*, 96:3147-3176 (1996).
Rawlinson, S.M., et al., "CRM1-mediated Nuclear Export of Dengue Virus RNA Polymerase NS5 Modulates Interleukin-8 Induction and Virus Production", *Journal of Biological Chemistry*, 284(23):15589-15597 (Jun. 5, 2009).
Sanchez, V., et al., "Nuclear Export of the Human Cytomegalovirus Tegument Protein pp65 Requires Cyclin-Dependent Kinase Activity and the Crm1 Exporter", *Journal of Virology*, 81(21):11730-11736 (Nov. 2007).
Sorokin, A.V., et al., "Nuclcocytoplasmic Transport of Proteins", *Biochemistry*, 72(13):1439-1457 (2007).
Terry, L.J., et al., "Crossing the Nuclear Envelope: Hierarchical Regulation of Nucleocytoplasmic Transport", *Science*, 318:1412-1416(Nov. 30, 2007).
van der Watt, P.J., et al., "The Karyopherin proteins, Crm1 and Karyopherin β1, are overexpressed in cervical cancer and are critical for cancer cell survival and proliferation", *Int. J. Cancer*, 124:1829-1840 (2009).

(56) References Cited

OTHER PUBLICATIONS

Walsh, Jr., M.D., et al., Exportin 1 Inhibition Attenuates Nuclear Factor—κB-Dependent Gene Expression, *Shock*, 29(2):160-166 (2008).

Williams, P., et al., "Characterization of a CRM1-Dependent Nuclear Export Signal in the C Terminus of Herpes Simplex Virus Type 1 Tegument Protein UL47", *Journal of Virology*, 82(21):10946-10952 (Nov. 2008).

Yao, Y., et al., "The expression of CRM1 is associated with prognosis in human osteosarcoma", *Oncology Reports*, 21:229-235 (2009).

Zimmerman, T.L., et al., "Nuclear Export of Retinoid X Receptor α in Response to Interleukin-1β-mediated Cell Signaling", *The Journal of Biological Chemistry*, 281(22):15434-15440 (Jun. 2, 2006.).

*Non-Final Office Action dated Sep. 21, 2012 for U.S. Appl. No. 13/041,377 "Nuclear Transport Modulators and Uses Thereof".

Li, A., et al., "Upregulation of CRM1 Relates to Neuronal Apoptosis after Traumatic Brain Injury in Adult Rats", *J Mol Neurosci*, DOI 10.1007/s12031-013-9994-7, Published online Mar. 15, 2013.

*Non-Final Office Action dated Jul. 3, 2014 for U.S. Appl. No. 14/219,638 "Hydrazide Containing Nuclear Transport Modulators and Uses Thereof".

*Non-Final Office Action for U.S. Appl. No. 13/891,044 "Nuclear Transport Modulators and Uses Thereof" dated Oct. 21, 2014.

*Notice of Allowability for U.S. Appl. No. 13/041,377 "Nuclear Transport Modulators and Uses Thereof", mailed May 2, 2013.

*Notice of Allowability for U.S. Appl. No. 14/219,638 "Hydrazide Containing Nuclear Transport Modulators and Uses Thereof", mailed Oct. 10, 2014.

Brekhov, Y., et al., "Cyanomethyltetrazoles II reactions of the methylene Moiety", *Zhurnal organicheskoi Khimii*, 28(9): 1921-1925 (1992).

Buckler, R.T., et al., "Synthesis and Antiinflammatory Activity of Some 1,2,3- and 1,2,4- Triazolerpropionic Acids", *Journal of Medicinal Chemistry*, 21(12): 1254-1260 (1978).

Extended Search Report for EP Application No. 11751491.9, "Nuclear Transport Modulators and Uses Thereof", Date of Completion of the Search: Dec. 17, 2013.

Extended Search Report for EP Application No. 12736172.3, "Olefin Containing Nuclear Transport Modulators and Uses Thereof", Date of Completion of the Search: May 8, 2014.

Lapalombella, R., et al., "Selective Inhibitors of nuclear exports show that CRM1/XPO1 is a target in chronic lymphocytic leukemia", *Blood*, 120(23): 4621-4634 (Nov. 29, 2012).

Notification Concerning Transmittal of International Preliminary Report on Patentability for International Application No. PCT/US2012/048368, "Nuclear Transport Modulators and Uses Thereof"; Date of Issuance of the Report: Feb. 4, 2014.

Notification Concerning Transmittal of International Preliminary Report on Patentability for International Application No. PCT/US2012/048319, "Hydrazide Containing Nuclear Transport Modulators and Uses Thereof"; Date of Issuance of the Report: Feb. 4, 2014.

Notification of Transmittal of the International Search Report and the Written Opinion of the International Searching Authority, or the Declaration for International Application No. PCT/US2014/027136 "Exo Olefin-Containing Nuclear Transport Modulators and Uses Thereof"; Date of Mailing: Jul. 11, 2014.

Notification of Transmittal of the International Search Report and the Written Opinion of the International Searching Authority, or the Declaration for International Application No. PCT/US2014/043484 "Nuclear Transport Modulators and Uses Thereof"; Date of Mailing: Sep. 2, 2014.

Notification of Transmittal of the International Search Report and the Written Opinion of the International Searching Authority, or the Declaration for International Application No. PCT/US2014/029322 "Methods of Promoting Wound Healing Using CRM1 Inhibitors"; Date of Mailing: May 28, 2014.

Notification of Transmittal of the International Search Report and the Written Opinion of the International Searching Authority, or the Declaration for International Application No. PCT/US2014/043479 "Nuclear Transport Modulators and Uses Thereof"; Date of Mailing: Sep. 17, 2014.

Quan, M.L., et al., "Design and Synthesis of Isoxazoline Derivatives as Factor Xa Ihibitors", *J. Med. Chem.* 42: 2760-2773 (1999).

Sun Q., et al., "Nuclear export inhibition through covalent conjugation and hydrolysis of Leptomycin B by CRM1", *PNAS*, 110(4): 1303-1308 (Jan. 22, 2013).

Golub, T.R., et al., "Molecular Classification of Cancer: Class Discovery and Class Prediction by Gene Expression Monitoring", *Science*, 286: 531-536 (1999).

Ghosh, C.C., et al., "Analysis of nucleocytoplasmic shuttling of NF kappa B proteins in human leukocytes", Methods Mol. Biol. 457:279-92 (2008).

Huff, J., "HIV Protease: A Novel Chemotherapeutic Target for AIDS", *Journal of Medicinal Chemistry*, 34(8): 2305-2314 (1991).

Lala, P.K., et al., "Role of nitric oxide in tumor progression: Lessons from experimental tumors", *Cancer and Metastasis Reviews*, 17: 91-106 (1998).

Yu, E., "Reactions of Hydroxyphenyl-Substituted 1,2,4-Triazoles with Electrophylic Reagents", Russian Journal of General Chemistry, 79(10): 2234-2243 (2009).

*Non-Final Office Action dated Oct. 21, 2014 for U.S. Appl. No. 13/891,044 "Nuclear Transport Modulators and Uses Thereof".

*Non-Final Office Action for U.S. Appl. No. 13/931,372 "Nuclear Transport Modulators and Uses Thereof" dated Feb. 9, 2015.

*Non-Final Office Action for U.S. Appl. No. 14/399,868 "Nuclear Transport Modulators and Uses Thereof" dated Feb. 13, 2015.

*Notice of Allowability for U.S. Appl. No. 14/235,306 "Hydrazide Containing Nuclear Transport Modulators and Uses Thereof", mailed Apr. 6, 2015.

*Notice of Allowance for U.S. Appl. No. 13/891,044 "Nuclear Transport Modulators and Uses Thereof", mailed Apr. 7, 2015.

Notification Concerning Transmittal of International Preliminary Report on Patentability for International Application No. PCT/US2013/040404, "Nuclear Transport Modulators and Uses Thereof"; Date of Issuance of the Report: Nov. 11, 2014.

Shaoyong, Ke., et al., "Research Advance of Acylhydrazine Derivatives with Biological Activities", *Chinese Journal of Organic Chemistry* 30(12): 1820-1830 (2010).

* cited by examiner

OLEFIN CONTAINING NUCLEAR TRANSPORT MODULATORS AND USES THEREOF

CROSS REFERENCE TO RELATED APPLICATIONS

The present application claims priority to U.S. provisional application Ser. No. 61/433,501, filed Jan. 17, 2011, which is hereby incorporated by reference in its entirety.

TECHNICAL FIELD OF THE INVENTION

The present invention relates to compounds useful as nuclear transport modulators. The invention also provides pharmaceutically acceptable compositions comprising compounds of the present invention and methods of using said compositions in the treatment of various disorders.

BACKGROUND OF THE INVENTION

Cells from most major human solid and hematologic malignancies exhibit abnormal cellular localization of a variety of oncogenic proteins, tumor suppressor proteins, and cell cycle regulators (Cronshaw et al, 2004, Falini et al 2006). For example, certain p53 mutations lead to localization in the cytoplasm rather than in the nucleus. This results in the loss of normal growth regulation, despite intact tumor suppressor function. In other tumors, wild-type p53 is sequestered in the cytoplasm or rapidly degraded, again leading to loss of its suppressor function. Restoration of appropriate nuclear localization of functional p53 protein can normalize some properties of neoplastic cells (Cai et al, 2008; Hoshino et al 2008; Lain et al 1999a; Lain et al 1999b; Smart et al 1999) and can restore sensitivity of cancer cells to DNA damaging agents (Cai et al, 2008). Similar data have been obtained for other tumor suppressor proteins such as forkhead (Turner and Sullivan 2008) and c-Abl (Vignari and Wang 2001). In addition, abnormal localization of several tumor suppressor and growth regulatory proteins may be involved in the pathogenesis of autoimmune diseases (Davis 2007, Nakahara 2009).

Specific proteins and RNAs are carried into and out of the nucleus by specific transporters, which are classified as importins if they transport molecules into the nucleus, and exportins if they transport molecules out of the nucleus (Terry et al, 2007; Sorokin et al 2007). Proteins that are transported into or out of the nucleus contain nuclear import/localization (NLS) or export (NES) sequences that allow them to interact with specific transporters. Crm1, which is also called exportin-1 or Xpo1, is a major exportin.

Overexpression of Crm1 has been reported in several tumors, including human ovarian cancer (Noske et al, 2008), cervical cancer (van der Watt et al, 2009) and osteosarcoma (Yao et al, 2009) and is independently correlated with poor clinical outcomes in these tumor types.

Inhibition of Crm1 blocks the exodus of tumor suppressor proteins and/or growth regulators such as p53, c-Abl, p21, p27, pRB, BRCA1, IkB or forkhead proteins (e.g. FOXO3a) from the nucleus. Crm1 inhibitors have been shown to induce apoptosis in cancer cells even in the presence of activating oncogenic or growth stimulating signals, while sparing normal (untransformed) cells. Crm1 inhibitors are effective and well-tolerated in animal tumor models (Yang et al, 2007, Yang et al, 2008, Mutka et al, 2009). Therefore, nuclear export inhibitors could have beneficial effects in neoplastic and other proliferative disorders.

In addition to tumor suppressor proteins, Crm1 also exports several key proteins that are involved in many inflammatory processes. These include IkB, NF-kB, Cox-2, RXRα-Commd1, HIF1, HMGB1 and others. The nuclear factor kappa B (NF-kB/rel) family of transcriptional activators, named for the discovery that it drives immunoglobulin kappa gene expression, regulate the mRNA expression of variety of genes involved in inflammation, proliferation, immunity and cell survival. Under basal conditions, a protein inhibitor of NF-kB, called IkB, binds to NF-kB in the nucleus and the complex IkB-NF-kB renders the NF-kB transcriptional function inactive. In response to inflammatory stimuli, IkB dissociates from the IkB-NF-kB complex, which releases NF-kB and unmasks its potent transcriptional activity. Many signals that activate NF-kB do so by targeting IkB for proteolysis (Phosphorylation of IkB renders it "marked" for ubiquitination and then proteolysis). The nuclear IkBa-NF-kB complex can be exported to the cytoplasm by Crm1 where it dissociates and NF-kB can be reactivated. Ubiquitinated IkB may also dissociate from the NF-kB complex, restoring NF-kB transcriptional activity. Inhibition of Crm1 induced export in human neutrophils and macrophage like cells (U937) by LepB not only results in accumulation of transcriptionally inactive, nuclear IkBa-NF-kB complex but also prevents the initial activation of NF-kB even upon cell stimulation (Ghosh 2008). In a different study, treatment with Lep B inhibited IL-1β induced NF-kB DNA binding (the first step in NF-kB transcriptional activation), IL-8 expression and intercellular adhesion molecule expression in pulmonary microvascular endothelial cells (Walsh 2008). COMMD1 is another nuclear inhibitor of both NF-kB and hypoxia-inducible factor 1 (HIF1) transcriptional activity. Blocking the nuclear export of COMMD1 by inhibiting Crm1 results in increased inhibition of NF-kB and HIF1 transcriptional activity (Muller 2009).

Crm1 also mediates Retinoid X receptor α (RXRα) transport. RXRα is highly expressed in the liver and plays a central role in regulating bile acid, cholesterol, fatty acid, steroid and xenobiotic metabolism and homeostasis. During liver inflammation, nuclear RXRα levels are significantly reduced, mainly due to inflammation-mediated nuclear export of RXRα by Crm1. Lep B is able to prevent IL-1β induced cytoplasmic increase in RXRα levels in human liver derived cells (Zimmerman 2006). NOTE: This result strongly suggests that inflammation itself stimulates Crm1 mediated nuclear export, and therefore, blocking nuclear export can be potentially beneficial in many inflammatory processes.

Intact nuclear export, primarily mediated through Crm1, is also required for the intact maturation of many viruses. Viruses where nuclear export, and/or Crm1 itself, has been implicated in their lifecycle include human immunodeficiency virus (HIV), influenza (usual strains as well as H1N1 and avian H5N1 strains), hepatitis B (HBV) and C(HCV) viruses, human papilomavirus (HPV), respiratory syncytial virus (RSV), Dungee, the Severe Acute Respiratory Syndrome coronavirus, tallow fever virus, West Nile Virus, herpes simplex virus (HSV), cytomegalovirus (CMV), and Merkel cell polyomavirus (MCV). It is anticipated that additional viral infections reliant on intact nuclear export will be uncovered in the near future.

The HIV-1 Rev protein, which traffics through nucleolus and shuttles between the nucleus and cytoplasm, facilitates export of unspliced and singly spliced HIV transcripts containing Rev Response Elements (RRE) RNA by the Crm1 export pathway. Inhibition of Rev-mediated RNA transport using Crm1 inhibitors such as LepB or PKF050-638 can arrest the HIV-1 transcriptional process, inhibit the production of new HIV-1 virions, and thereby reduce HIV-1 levels (Pollard 1998, Daelemans 2002).

Dengue virus (DENV) is the causative agent of the common arthropod-borne viral disease, dengue fever (DF), and its more severe and potentially deadly dengue hemorrhagic fever (DHF). DHF appears to be the result of an over exuberant inflammatory response to DENV. NS5 is the largest and most conserved protein of DENV. Crm1 regulates the transport of NS5 from the nucleus to the cytoplasm, where most of the NS5 functions are mediated. Inhibition of Crm1 mediated export of NS5 results in altered kinetics of virus production and reduces induction of the inflammatory chemokine interleukin-8 (IL-8), presenting a new avenue for the treatment of diseases caused by DENV and other medically important flaviviruses including Hepatitis C virus (Rawlinson 2009).

Other virus-encoded RNA-binding proteins that use Crm1 to exit the nucleus include the HSV type 1 tegument protein (VP13/14, or hUL47), human CMV protein pp65, the SARS Coronavirus ORF 3b Protein, and the RSV matrix (M) protein (Williams 2008, Sanchez 2007, Freundt 2009, Ghildyal 2009).

Interestingly, many of these viruses are associated with specific types of human cancer including hepatocellular carcinoma (HCC) due to chronic HBV or HCV infection, cervical cancer due to HPV, and Merkel cell carcinoma associated with MCV. Crm1 inhibitors could therefore have salutary effects on both the viral infectious process as well as on the process of neoplastic transformation due to these viruses.

CRM1 has also been linked to other disorders. Leber's disorder, a hereditary disorder characterized by degeneration of retinal ganglion cells and visual loss, is associated with inaction of the CRM1 switch (Gupta N 2008). There is also evidence linking neurodegenerative disorders to abnormalities in nuclear transport.

SUMMARY OF THE INVENTION

It has now been found that compounds of this invention, and pharmaceutically acceptable compositions thereof, are effective as nuclear transport modulators. Such compounds have the general formula I:

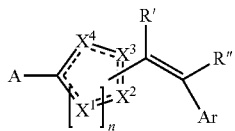

or a pharmaceutically acceptable salt thereof, wherein each of $X^1$, $X^2$, $X^3$, $X^4$, A, Ar, R' and R" is as defined and described herein.

Compounds of the present invention, and pharmaceutically acceptable compositions thereof, are useful for treating a variety of diseases, disorders or conditions, associated with abnormal cellular responses triggered by improper nuclear transport. Such diseases, disorders, or conditions include those described herein.

Compounds provided by this invention are also useful for the study of nuclear transport modulation in biological and pathological phenomena; the study of intracellular signal transduction pathways mediated by such kinases; and the comparative evaluation of new nuclear transport modulators.

DETAILED DESCRIPTION OF CERTAIN EMBODIMENTS

Figure 1:
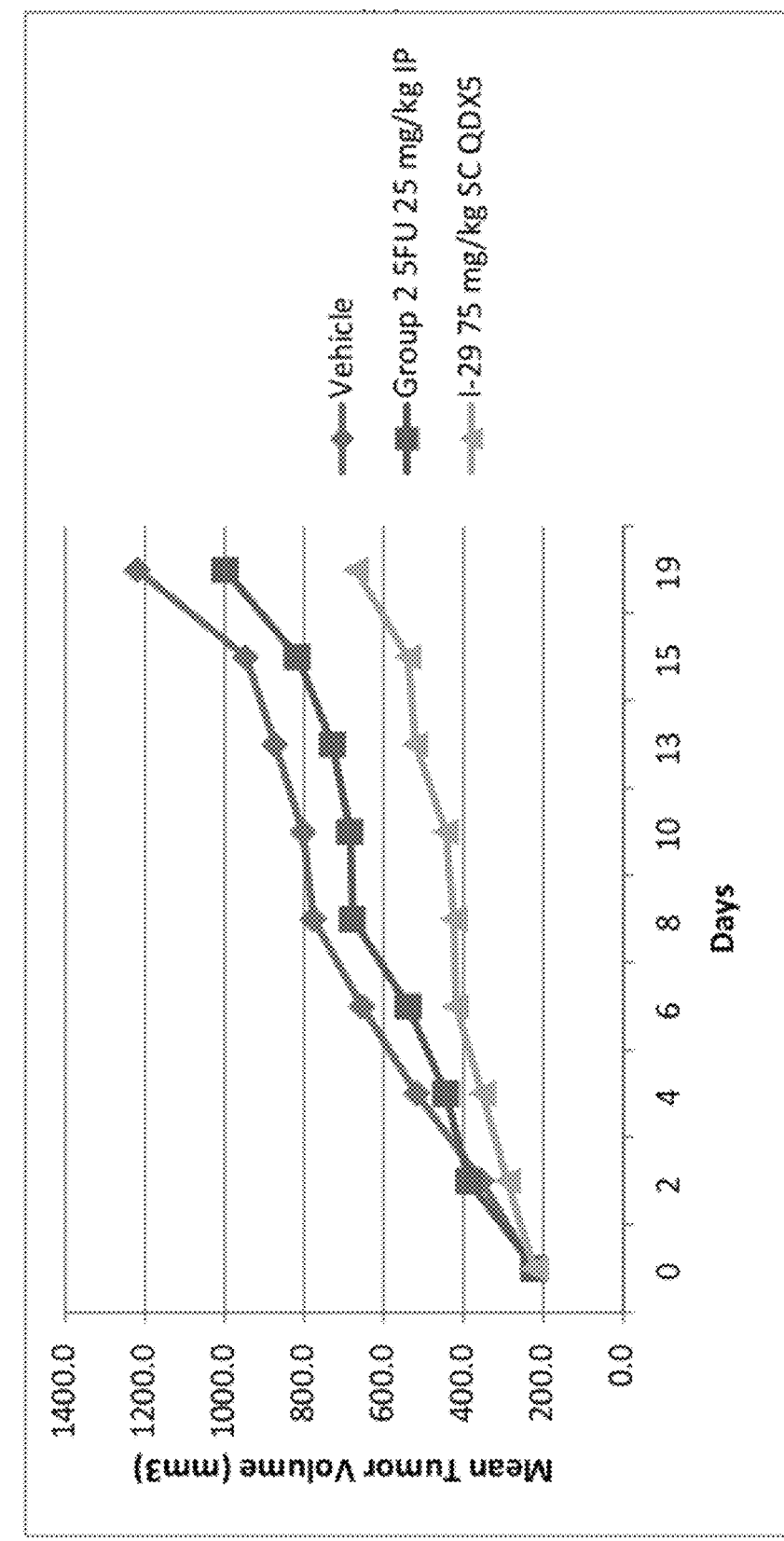
FIG. 1 is a graph depicting the results of an HCT-116 colorectal carcinoma xenograft model. HCT-116 cells were inoculated into female athymic Balb c. nu$^+$/nu$^+$ mice. Once tumors reached an average volume of 200 mm$^3$, the animals were dosed with vehicle, 25 mg/kg 5-fluorouracil intraperitoneally and 75 mg/kg I-29 subcutaneously. Following 3 weeks of dosing (5 times/week) I-29 displayed 50% reduction in tumor growth in a statistically significant manner where 5-FU (standard of care) did not display efficacy.

1. General Description of Compounds of the Invention

In certain embodiments, the present invention provides a compound of formula I:

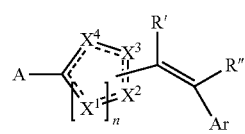

or a pharmaceutically acceptable salt thereof, wherein:
  each ------ is independently a double or single bond provided that two adjacent double bonds do not exist;
  n is 1 or 2;
  each of $X^1$, $X^2$, $X^3$ and $X^4$ is independently selected from N, N($R^a$), and C($R^2$), as valency permits, wherein at least one of $X^1$, $X^2$, $X^3$ and $X^4$ is either N or NR$^a$;

A and Ar are independently phenyl, a 5-6 membered monocyclic heteroaryl ring having 1-3 heteroatoms independently selected from nitrogen, oxygen, or sulfur, an 8-10 membered bicyclic aryl ring, or an 8-10 membered bicyclic heteroaryl ring having 1-4 heteroatoms independently selected from nitrogen, oxygen, or sulfur, wherein A and Ar are optionally and independently substituted with one or more R' substituents;

each $R^1$ is independently selected from the group of halogen (F, Cl, Br, I), —$NO_2$, —CN, —$N_3$, or -$L^1$-R;

each R is independently optionally substituted $C_{1-8}$ alkyl, $C_{2-8}$ alkenyl, $C_{2-8}$ alkynyl, haloalkyl, phenyl, a 3-7 membered saturated or partially unsaturated cycloalkyl ring, an 8-10 membered bicyclic saturated, partially unsaturated or aryl carbocyclic ring, a 4-7-membered saturated or partially unsaturated heterocycloalkyl ring having 1-4 heteroatoms independently selected from nitrogen, oxygen, or sulfur; a 5-6 membered monocyclic heteroaryl ring having 1-3 heteroatoms independently selected from nitrogen, oxygen, or sulfur; or an 8-10 membered bicyclic heteroaryl ring having 1-4 heteroatoms independently selected from nitrogen, oxygen, or sulfur;

$L^1$ is a covalent bond or an optionally substituted bivalent $C_{1-6}$ hydrocarbon chain, wherein one or more methylene units of $L^1$ is optionally and independently replaced by -Cy-, —O—, —S—, —N($R^a$)—, —C(O)—, —C(S)—, —C(O)N($R^a$)—, —N($R^a$)C(O)N($R^a$)—, —N($R^a$)C(O)—, —N($R^a$)C(O)O—, —OC(O)N($R^a$)—, —S(O)—, —S(O)$_2$—, —S(O)$_2$N($R^a$)—, —N($R^a$)S(O)$_2$—, —OC(O)—, or —C(O)O—;

-Cy- is an optionally substituted bivalent ring selected from a 3-7 membered saturated or partially unsaturated cycloalkylene ring, a 4-7-membered saturated or partially unsaturated heterocycloalkylene ring having 1-4 heteroatoms independently selected from nitrogen, oxygen, or sulfur, phenylene, a 5-6 membered monocyclic heteroarylene having 1-3 heteroatoms independently selected from nitrogen, oxygen, or sulfur, an 8-10 membered bicyclic arylene, or an 8-10 membered bicyclic heteroarylene having 1-4 heteroatoms independently selected from nitrogen, oxygen, or sulfur;

each $R^a$ is independently —H, —R or —C(O)R; and each $R^2$, R' and R" is independently —H, halogen (F, Cl, Br, I), —$NO_2$, —CN, —$N_3$, or -$L^1$-R.

In some embodiments, the present invention provides a compound of formula I wherein said compound is not one disclosed in Van Neck et al. Bioorgan. Med. Chem. 16 (2008) 9487-9497.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, deuterium substitutions, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention.

Generally, reference to a certain element such as hydrogen or H is meant to, if appropriate, include all isotopes of that element.

The term "alkyl" as used herein means a straight- or branched-chain hydrocarbon radical; in one aspect, having from one to eight carbon atoms, and includes, for example, and without being limited thereto, methyl, ethyl, propyl, isopropyl, t-butyl and the like. As noted above, "alkyl" encompasses substituted alkyl. Substituted alkyl includes, for example, and without being limited thereto, haloalkyl, hydroxyalkyl, cyanoalkyl, and the like. This is applied to any of the groups mentioned herein. Groups such as "alkenyl", "alkynyl", "aryl", etc. encompass substituted "alkenyl", "alkynyl", "aryl", etc.

The term "alkenyl" as used herein means a straight- or branched-chain alkenyl radical; in one aspect, having from two to eight carbon atoms, and includes, for example, and without being limited thereto, ethenyl, 1-propenyl, 1-butenyl and the like. The term "alkenyl" encompass radicals having "cis" and "trans" orientations, or alternatively, "E" and "Z" orientations.

The term "alkynyl" as used herein means a straight- or branched-chain alkynyl radical; in one aspect, having from two to eight carbon atoms, and includes, for example, and without being limited thereto, 1-propynyl (propargyl), 1-butynyl and the like.

The term "cycloalkyl" as used herein means a carbocyclic system (which may be unsaturated) containing one or more rings wherein such rings may be attached together in a pendent manner or may be fused. In one aspect, the ring(s) may have from three to seven carbon atoms, and includes, for example, and without being limited thereto, cyclopropyl, cyclohexyl, cyclohexenyl and the like.

The term "heterocycloalkyl" as used herein means a heterocyclic system (which may be unsaturated) having at least one heteroatom selected from N, S and/or O and containing one or more rings wherein such rings may be attached together in a pendent manner or may be fused. In one aspect, the ring(s) may have a three- to seven-membered cyclic group and includes, for example, and without being limited thereto, piperidinyl, piperazinyl, pyrrolidinyl, tetrahydrofuranyl and the like.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy" as used herein means a straight- or branched-chain alkoxy radical; in one aspect, having from one to eight carbon atoms and includes, for example, and without being limited thereto, methoxy, ethoxy, propyloxy, isopropyloxy, t-butoxy and the like.

The term "halo" as used herein means halogen and includes, for example, and without being limited thereto, fluoro, chloro, bromo, iodo and the like, in both radioactive and non-radioactive forms.

The term "alkylene" as used herein means a difunctional branched or unbranched saturated hydrocarbon radical; in one aspect, having one to eight carbon atoms, and includes, for example, and without being limited thereto, methylene, ethylene, n-propylene, n-butylene and the like.

The term "alkenylene" as used herein means a difunctional branched or unbranched hydrocarbon radical; in one aspect, having two to eight carbon atoms, and having at least one double bond, and includes, for example, and without being limited thereto, ethenylene, n-propenylene, n-butenylene and the like.

The term "alkynylene" as used herein means a difunctional branched or unbranched hydrocarbon radical; in one aspect, having two to eight carbon atoms, and having at least one triple bond, and includes, for example, and without being limited thereto, ethynylene, n-propynylene, n-butynylene and the like.

The term "aryl", alone or in combination, as used herein means a carbocyclic aromatic system containing one or more rings wherein such rings may be attached together in a pendent manner or may be fused. In particular embodiments, aryl is one, two or three rings. In one aspect, the aryl has five to twelve ring atoms. The term "aryl" encompasses aromatic radicals such as phenyl, naphthyl, tetrahydronaphthyl, indanyl, biphenyl, phenanthryl, anthryl or acenaphthyl. The "aryl" group may have 1 to 4 substituents such as lower alkyl, hydroxyl, halo, haloalkyl, nitro, cyano, alkoxy, lower alkylamino and the like.

The term "heteroaryl", alone or in combination, as used herein means an aromatic system having at least one heteroatom selected from N, S and/or O and containing one or more rings wherein such rings may be attached together in a pendent manner or may be fused. In particular embodiments, heteroaryl is one, two or three rings. In one aspect, the heteroaryl has five to twelve ring atoms. The term "heteroaryl" encompasses heteroaromatic groups such as triazolyl, imidazolyl, pyrrolyl, tetrazolyl, pyridyl, indolyl, furyl, benzofuryl, thienyl, benzothienyl, quinolyl, oxazolyl and the like. The "heteroaryl" group may have 1 to 4 substituents such as lower alkyl, hydroxyl, halo, haloalkyl, nitro, cyano, alkoxy, lower alkylamino and the like.

It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon or on different carbons, as long as a stable structure results.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$—CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^{\bullet}$, -(haloR$^{\bullet}$), (CH$_2$)$_{0-2}$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_1$ straight or branched alkylene)C(O)OR$^{\bullet}$, or —SSR$^{\bullet}$ wherein each R$^{\bullet}$ is unsubstituted or where preceded by "halo" is substituted only with one or more halogens, and is independently selected from C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "pharmaceutically acceptable salt" means either an acid addition salt or a basic addition salt which is compatible with the treatment of patients.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating or lessening the severity of one or more symptoms of a disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is pharmaceutically acceptable oil typically used for parenteral administration.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

3. Description of Exemplary Compounds

In certain embodiments, the present invention provides a compound of formula I:

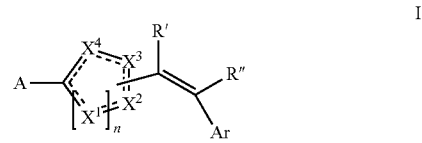

or a pharmaceutically acceptable salt thereof, wherein $X^1$, $X^2$, $X^3$, $X^4$, A, Ar, R' and R" is as defined above and described herein.

In some embodiments, n is 1. In other embodiments, n is 2.

In some embodiments, the exocyclic double bond in Formula I may be either trans or cis. Alternatively, a trans double bond may be referred to as being in the (E) configuration, whereas the cis double bond may be referred to as being in the (Z) configuration. In some embodiments, the exocyclic double bond in Formula I is in the (E) configuration. In other embodiments, the exocyclic double bond of formula I is in the (Z) configuration.

As defined above, each of $X^1$, $X^2$, $X^3$ and $X^4$ is independently selected from N, N($R^a$), and C($R^2$), as valency permits, wherein at least one of $X^1$, $X^2$, $X^3$ and $X^4$ is either N or $NR^a$. In some embodiments, one of $X^1$, $X^2$, $X^3$ and $X^4$ is either N or $NR^a$. In some such embodiments, one of $X^1$, $X^2$, $X^3$ and $X^4$ is N. In other such embodiments, one of $X^1$, $X^2$, $X^3$ and $X^4$ is $NR^a$.

In some embodiments, n is 1 and one of $X^1$, $X^2$, $X^3$ and $X^4$ is N. In some such embodiments, n is 1 and $X^1$ is N. In some such embodiments, n is 1 and $X^2$ is N. In some such embodiments, n is 1 and $X^3$ is N. In some such embodiments, n is 1 and $X^4$ is N. In some embodiments, n is 1 and one of $X^1$, $X^2$, $X^3$ and $X^4$ is $NR^a$.

In some embodiments, two of $X^1$, $X^2$, $X^3$ and $X^4$ is either N or $NR^a$. In some such embodiments, two of $X^1$, $X^2$, $X^3$ and $X^4$ is N. In other such embodiments, two of $X^1$, $X^2$, $X^3$ and $X^4$ is $NR^a$.

In some embodiments, n is 1 and two of $X^1$, $X^2$, $X^3$ and $X^4$ is N. In some such embodiments, n is 1, and $X^1$ and $X^4$ are N. In other such embodiments, n is 1, and $X^1$ and $X^3$ are N. In some embodiments, n is 1, $X^1$ and $X^2$ are N. In some such embodiments, n is 1, and $X^3$ and $X^4$ are N. In some such embodiments, n is 1, and $X^2$ and $X^3$ are N. In some such embodiments, n is 1, and $X^2$ and $X^4$ are N. In other embodiments, n is 1 and two of $X^1$, $X^2$, $X^3$ and $X^4$ is $NR^a$.

As defined above, $R^a$ is —H, —$R^a$ or —C(O)R, wherein R is as defined above and described herein. In some embodiments, $R^a$ is —H. In some embodiments, $R^a$ is —R. In some embodiments, $R^a$ is —C(O)R.

As defined above, A and Ar are independently phenyl, a 5-6 membered monocyclic heteroaryl ring having 1-3 heteroatoms independently selected from nitrogen, oxygen, or sulfur, an 8-10 membered bicyclic aryl ring, or an 8-10 membered bicyclic heteroaryl ring having 1-4 heteroatoms independently selected from nitrogen, oxygen, or sulfur, wherein A and Ar are optionally and independently substituted with one or more $R^1$ substituents.

In some embodiments, A is optionally substituted phenyl. In some embodiments, A is an optionally substituted 5-6 membered monocyclic heteroaryl ring having 1-3 heteroatoms independently selected from nitrogen, oxygen, or sulfur. In some embodiments, A is an optionally substituted 5-membered monocyclic heteroaryl ring having 1-3 heteroatoms independently selected from nitrogen, oxygen, or sulfur. In some embodiments, A is an optionally substituted 5-membered monocyclic heteroaryl ring having 1 heteroatom independently selected from nitrogen, oxygen, or sulfur. In some embodiments, A is an optionally substituted 5-membered monocyclic heteroaryl ring having 1-2 heteroatoms independently selected from nitrogen, oxygen, or sulfur. In some embodiments, A is an optionally substituted 5-membered monocyclic heteroaryl ring having 2 heteroatoms independently selected from nitrogen, oxygen, or sulfur. In some embodiments, A is an optionally substituted 5-membered monocyclic heteroaryl ring having 3 heteroatoms independently selected from nitrogen, oxygen, or sulfur. Exemplary A groups include optionally substituted pyrrolyl, furanyl, thiophenyl, pyrazolyl, imidazolyl, thiazolyl, isothiazolyl, oxazolyl, isoxazolyl, triazolyl, thiadiazolyl or oxadiazolyl.

In some embodiments, A is an optionally substituted 6-membered monocyclic heteroaryl ring having 1-3 nitrogens. In some embodiments, A is an optionally substituted 6-membered monocyclic heteroaryl ring having 1 nitrogen. In some embodiments, A is an optionally substituted 6-membered monocyclic heteroaryl ring having 1-2 nitrogens. In some embodiments, A is an optionally substituted 6-membered monocyclic heteroaryl ring having 2 nitrogens. In some embodiments, A is an optionally substituted 6-membered monocyclic heteroaryl ring having 3 nitrogens. Exemplary A groups include optionally substituted pyridinyl, pyrimidinyl, pyrazinyl, pyridazinyl and triazinyl.

In some embodiments, A is an optionally substituted 8-10 membered bicyclic aryl ring. In some embodiments, A is an optionally substituted 8-membered bicyclic aryl ring. In some embodiments, A is an optionally substituted 9-membered bicyclic aryl ring. In some embodiments, A is an optionally substituted 10-membered bicyclic aryl ring.

In some embodiments, A is an optionally substituted 8-10 membered bicyclic heteroaryl ring having 1-4 heteroatoms independently selected from nitrogen, oxygen, or sulfur. In some embodiments, A is an optionally substituted 8-membered bicyclic heteroaryl ring having 1-4 heteroatoms independently selected from nitrogen, oxygen, or sulfur. In some embodiments, A is an optionally substituted 8-membered bicyclic heteroaryl ring having 1 heteroatom independently selected from nitrogen, oxygen, or sulfur. In some embodiments, A is an optionally substituted 8-membered bicyclic heteroaryl ring having 1-2 heteroatoms independently selected from nitrogen, oxygen, or sulfur. In some embodiments, A is an optionally substituted 8-membered bicyclic heteroaryl ring having 2 heteroatoms independently selected from nitrogen, oxygen, or sulfur. In some embodiments, A is an optionally substituted 8-membered bicyclic heteroaryl ring having 3 heteroatoms independently selected from nitrogen, oxygen, or sulfur. In some embodiments, A is an optionally substituted 8-membered bicyclic heteroaryl ring having 4 heteroatoms independently selected from nitrogen, oxygen, or sulfur.

In some embodiments, A is an optionally substituted 9-membered bicyclic heteroaryl ring having 1-4 heteroatoms independently selected from nitrogen, oxygen, or sulfur. In some embodiments, A is an optionally substituted 9-membered bicyclic heteroaryl ring having 1 heteroatom independently selected from nitrogen, oxygen, or sulfur. In some embodiments, A is an optionally substituted 9-membered bicyclic heteroaryl ring having 1-2 heteroatoms independently selected from nitrogen, oxygen, or sulfur. In some embodiments, A is an optionally substituted 9-membered bicyclic heteroaryl ring having 2 heteroatoms independently selected from nitrogen, oxygen, or sulfur. In some embodiments, A is an optionally substituted 9-membered bicyclic heteroaryl ring having 3 heteroatoms independently selected from nitrogen, oxygen, or sulfur. In some embodiments, A is an optionally substituted 9-membered bicyclic heteroaryl ring having 4 heteroatoms independently selected from nitrogen, oxygen, or sulfur.

In some embodiments, A is an optionally substituted 10-membered bicyclic heteroaryl ring having 1-4 heteroatoms independently selected from nitrogen, oxygen, or sulfur. In some embodiments, A is an optionally substituted 10-membered bicyclic heteroaryl ring having 1 heteroatom independently selected from nitrogen, oxygen, or sulfur. In some embodiments, A is an optionally substituted 10-membered bicyclic heteroaryl ring having 1-2 heteroatoms independently selected from nitrogen, oxygen, or sulfur. In some embodiments, A is an optionally substituted 10-membered bicyclic heteroaryl ring having 2 heteroatoms independently selected from nitrogen, oxygen, or sulfur. In some embodiments, A is an optionally substituted 10-membered bicyclic heteroaryl ring having 3 heteroatoms independently selected from nitrogen, oxygen, or sulfur. In some embodiments, A is an optionally substituted 10-membered bicyclic heteroaryl ring having 4 heteroatoms independently selected from nitrogen, oxygen, or sulfur.

In some embodiments, Ar is optionally substituted phenyl. In some embodiments, Ar is an optionally substituted 5-6 membered monocyclic heteroaryl ring having 1-3 heteroatoms independently selected from nitrogen, oxygen, or sulfur. In some embodiments, Ar is an optionally substituted 5-membered monocyclic heteroaryl ring having 1-3 heteroatoms independently selected from nitrogen, oxygen, or sulfur. In some embodiments, Ar is an optionally substituted 5-membered monocyclic heteroaryl ring having 1 heteroatom independently selected from nitrogen, oxygen, or sulfur. In some embodiments, Ar is an optionally substituted 5-membered monocyclic heteroaryl ring having 1-2 heteroatoms independently selected from nitrogen, oxygen, or sulfur. In some embodiments, Ar is an optionally substituted 5-membered monocyclic heteroaryl ring having 2 heteroatoms independently selected from nitrogen, oxygen, or sulfur. In some embodiments, Ar is an optionally substituted 5-membered monocyclic heteroaryl ring having 3 heteroatoms independently selected from nitrogen, oxygen, or sulfur. Exemplary Ar groups include optionally substituted pyrrolyl, furanyl, thiophenyl, pyrazolyl, imidazolyl, thiazolyl, isothiazolyl, oxazolyl, isoxazolyl, triazolyl, thiadiazolyl or oxadiazolyl.

In some embodiments, Ar is an optionally substituted 6-membered monocyclic heteroaryl ring having 1-3 nitrogens. In some embodiments, Ar is an optionally substituted 6-membered monocyclic heteroaryl ring having 1 nitrogen. In some embodiments, Ar is an optionally substituted 6-membered monocyclic heteroaryl ring having 1-2 nitrogens. In some embodiments, Ar is an optionally substituted 6-membered monocyclic heteroaryl ring having 2 nitrogens. In some embodiments, Ar is an optionally substituted 6-membered monocyclic heteroaryl ring having 3 nitrogens. Exemplary Ar groups include optionally substituted pyridinyl, pyrimidinyl, pyrazinyl, pyridazinyl and triazinyl.

In some embodiments, Ar is an optionally substituted 8-10 membered bicyclic aryl ring. In some embodiments, Ar is an optionally substituted 8-membered bicyclic aryl ring. In some embodiments, Ar is an optionally substituted 9-membered bicyclic aryl ring. In some embodiments, Ar is an optionally substituted 10-membered bicyclic aryl ring.

In some embodiments, Ar is an optionally substituted 8-10 membered bicyclic heteroaryl ring having 1-4 heteroatoms independently selected from nitrogen, oxygen, or sulfur. In some embodiments, Ar is an optionally substituted 8-membered bicyclic heteroaryl ring having 1-4 heteroatoms independently selected from nitrogen, oxygen, or sulfur. In some embodiments, Ar is an optionally substituted 8-membered bicyclic heteroaryl ring having 1 heteroatom independently selected from nitrogen, oxygen, or sulfur. In some embodiments, Ar is an optionally substituted 8-membered bicyclic heteroaryl ring having 1-2 heteroatoms independently selected from nitrogen, oxygen, or sulfur. In some embodiments, Ar is an optionally substituted 8-membered bicyclic heteroaryl ring having 2 heteroatoms independently selected from nitrogen, oxygen, or sulfur. In some embodiments, Ar is an optionally substituted 8-membered bicyclic heteroaryl ring having 3 heteroatoms independently selected from nitrogen, oxygen, or sulfur. In some embodiments, Ar is an optionally substituted 8-membered bicyclic heteroaryl ring having 4 heteroatoms independently selected from nitrogen, oxygen, or sulfur.

In some embodiments, Ar is an optionally substituted 9-membered bicyclic heteroaryl ring having 1-4 heteroatoms independently selected from nitrogen, oxygen, or sulfur. In some embodiments, Ar is an optionally substituted 9-membered bicyclic heteroaryl ring having 1 heteroatom independently selected from nitrogen, oxygen, or sulfur. In some embodiments, Ar is an optionally substituted 9-membered bicyclic heteroaryl ring having 1-2 heteroatoms independently selected from nitrogen, oxygen, or sulfur. In some embodiments, Ar is an optionally substituted 9-membered bicyclic heteroaryl ring having 2 heteroatoms independently selected from nitrogen, oxygen, or sulfur. In some embodiments, Ar is an optionally substituted 9-membered bicyclic heteroaryl ring having 3 heteroatoms independently selected from nitrogen, oxygen, or sulfur. In some embodiments, Ar is an optionally substituted 9-membered bicyclic heteroaryl ring having 4 heteroatoms independently selected from nitrogen, oxygen, or sulfur. Exemplary Ar groups include benzoxazolyl, benzothiazolyl, benzimidazolyl, indazolyl and indolyl.

In some embodiments, Ar is an optionally substituted 10-membered bicyclic heteroaryl ring having 1-4 heteroatoms independently selected from nitrogen, oxygen, or sulfur. In some embodiments, Ar is an optionally substituted 10-membered bicyclic heteroaryl ring having 1 heteroatom independently selected from nitrogen, oxygen, or sulfur. In some embodiments, Ar is an optionally substituted 10-membered bicyclic heteroaryl ring having 1-2 heteroatoms independently selected from nitrogen, oxygen, or sulfur. In some embodiments, Ar is an optionally substituted 10-membered bicyclic heteroaryl ring having 2 heteroatoms independently selected from nitrogen, oxygen, or sulfur. In some embodiments, Ar is an optionally substituted 10-membered bicyclic heteroaryl ring having 3 heteroatoms independently selected from nitrogen, oxygen, or sulfur. In some embodiments, Ar is an optionally substituted 10-membered bicyclic heteroaryl ring having 4 heteroatoms independently selected from nitrogen, oxygen, or sulfur.

In some embodiments, Ar is selected from the group consisting of:

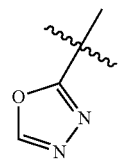

v

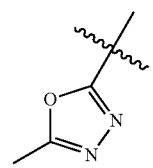

vi

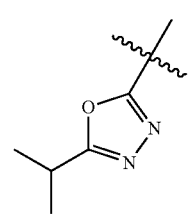

vii

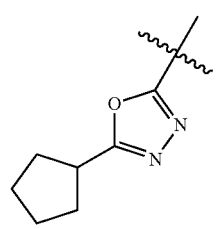

viii

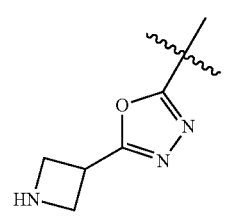

ix

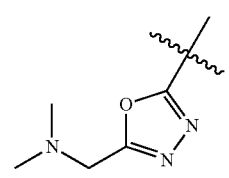

x

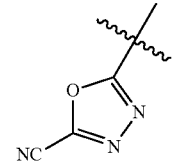

xi

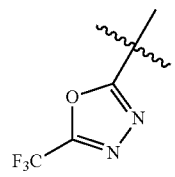

xii xiii 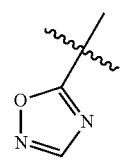
xiv 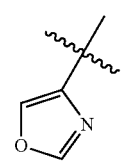
xv 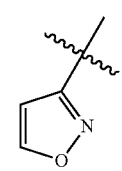
xvi 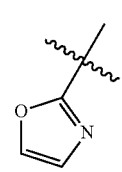
xvii 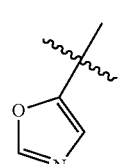
xviii 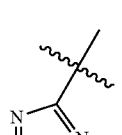
xix 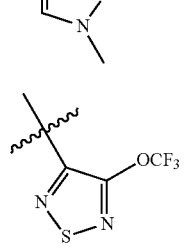
xx 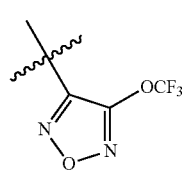
xxi 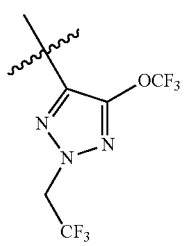
xxii 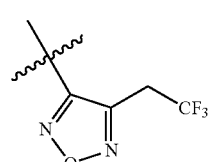
xxiii 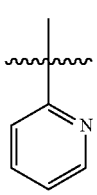
xxiv 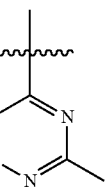
xxv 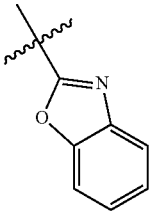
In some embodiments, A is selected from the group consisting of:
xxvi 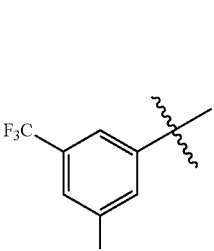
xxvii 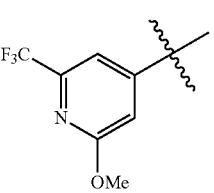
xxviii 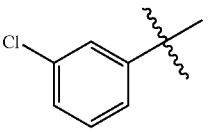

-continued

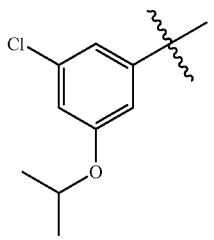

xxix

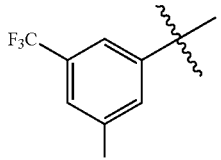

xxxvi

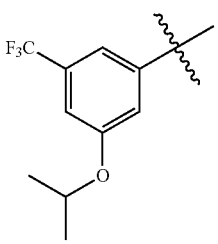

xxx

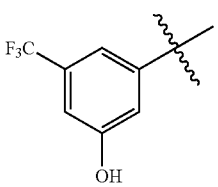

xxxvii

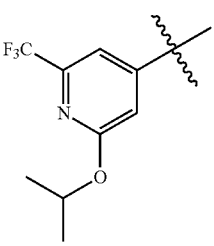

xxxi

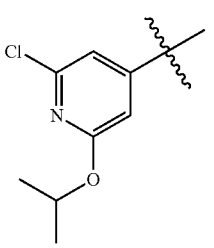

xxxii

As defined above, $R^1$ is independently selected from the group of halogen (F, Cl, Br, I), —$NO_2$, —CN, —$N_3$, or -$L^1$-R. In some embodiments, $R^1$ is halogen. In some embodiments, $R^1$ is F. In some embodiments, $R^1$ is Cl. In some embodiments, $R^1$ is Br. In some embodiments, $R^1$ is I. In some embodiments, $R^1$ is $NO_2$. In some embodiments, $R^1$ is CN. In some embodiments, $R^1$ is $N_3$. In some embodiments, $R^1$ is -$L^1$-R.

As defined above, $R^2$ is independently selected from the group of halogen (F, Cl, Br, I), —$NO_2$, —CN, —$N_3$, or -$L^1$-R. In some embodiments, $R^2$ is halogen. In some embodiments, $R^2$ is F. In some embodiments, $R^2$ is Cl. In some embodiments, $R^2$ is Br. In some embodiments, $R^2$ is I. In some embodiments, $R^2$ is $NO_2$. In some embodiments, $R^2$ is CN. In some embodiments, $R^2$ is $N_3$. In some embodiments, $R^2$ is -$L^1$-R.

As defined above, R' is independently selected from the group of halogen (F, Cl, Br, I), —$NO_2$, —CN, —$N_3$, or -$L^1$-R. In some embodiments, R' is hydrogen. In some embodiments, R' is halogen. In some embodiments, R' is F. In some embodiments, R' is Cl. In some embodiments, R' is Br. In some embodiments, R' is I. In some embodiments, R' is $NO_2$. In some embodiments, R' is CN. In some embodiments, R' is $N_3$. In some embodiments, R' is -$L^1$-R.

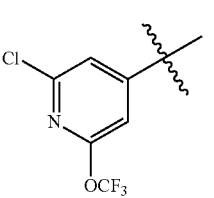

xxxiii

As defined above, R" is independently selected from the group of halogen (F, Cl, Br, I), —$NO_2$, —CN, —$N_3$, or -$L^1$-R. In some embodiments, R" is hydrogen. In some embodiments, R" is halogen. In some embodiments, R" is F. In some embodiments, R" is Cl. In some embodiments, R" is Br. In some embodiments, R" is I. In some embodiments, R" is $NO_2$. In some embodiments, R" is CN. In some embodiments, R" is $N_3$. In some embodiments, R" is -$L^1$-R.

In some embodiments, both R' and R" are hydrogen.

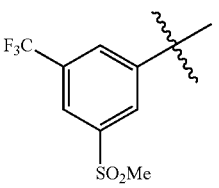

xxxiv

As defined above, $L^1$ is a covalent bond or an optionally substituted bivalent $C_{1-6}$ hydrocarbon chain, wherein one or more methylene units of $L^1$ is optionally and independently replaced by -Cy-, —O—, —S—, —N($R^a$)—, —C(O)—, —C(S)—, —C(O)N($R^a$)—, —N($R^a$)C(O)N($R^a$)—, —N($R^a$)C(O)—, —N($R^a$)C(O)O—, —OC(O)N($R^a$)—, —S(O)—, —S(O)$_2$—, —S(O)$_2$N($R^a$)—, —N($R^a$)S(O)$_2$—, —OC(O)—, or —C(O)O—, wherein $R^a$ and -Cy- are as defined above and described herein.

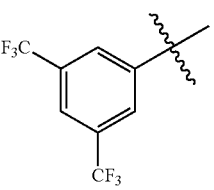

xxxv

In some embodiments, $L^1$ is a covalent bond. In some embodiments, $L^1$ is an optionally substituted bivalent $C_{1-6}$ hydrocarbon. In some such embodiments, $L^1$ is an optionally substituted bivalent $C_{1-4}$ hydrocarbon. In some embodiments, $L^1$ is an optionally substituted bivalent $C_{1-2}$ hydrocarbon. In some embodiments, $L^1$ is —$CH_2$—. In some embodiments, $L^1$ is —$CH_2CH_2$—. In certain embodiments, $L^1$ is —CH (CH$_3$)—. In some embodiments, L$^1$ is —CH(CH$_2$CH$_3$)—. In some embodiments, L$^1$ is —CH$_2$C(O)—. In some embodiments, L$^1$ is —C(O)CH$_2$—. In some embodiments, L$^1$ is —OC(O)—. In some embodiments, L$^1$ is —C(O)O—. In some embodiments, L$^1$ is —N(R$^a$)C(O)—. In some embodiments, L$^1$ is —C(O)N(R$^a$)—. In some embodiments, L$^1$ is —C(O)N(H)—. In some embodiments, L$^1$ is —N(H)C(O)—. In some embodiments, L$^1$ is —C(O)N(CH$_3$)—. In some embodiments, L$^1$ is —N(CH$_3$)C(O)—. In some embodiments, L$^1$ is —S(O)$_2$N(R$^a$)—. In some embodiments, L$^1$ is —N(R$^a$)S(O)$_2$—. In some embodiments, L$^1$ is —N(R$^a$)CH$_2$—.

In some embodiments, L$^1$ is optionally substituted C$_{2-6}$ hydrocarbon, wherein at least one carbon-carbon bond is unsaturated. In some embodiments, L$^1$ is optionally substituted C$_2$ hydrocarbon, wherein the carbon-carbon bond is unsaturated. In some such embodiments, L$^1$ is optionally substituted ethenylene or ethynylene. In some embodiments, L$^1$ is optionally substituted C$_3$ hydrocarbon, wherein at least one carbon-carbon bond is unsaturated. In some such embodiments, L$^1$ is optionally substituted propenylene, also known as allylene, or propynylene. In some embodiments, L$^1$ is optionally substituted C$_4$ hydrocarbon, wherein at least one carbon-carbon bond is unsaturated. In some such embodiments, L$^1$ is optionally substituted butenylene, 2-methyl-propenylene, 1,3-butadienylene or butynylene. In some embodiments, L$^1$ is optionally substituted C$_5$ hydrocarbon, wherein at least one carbon-carbon bond is unsaturated. In some such embodiments, L$^1$ is optionally substituted pentenylene, isoamylenyl or pentynylene. In some embodiments, L$^1$ is optionally substituted C$_6$ hydrocarbon, wherein at least one carbon-carbon bond is unsaturated. In some such embodiments, L$^1$ is optionally substituted hexenylene or hexynylene.

In some embodiments, L$^1$ is -Cy-. In some embodiments, -Cy- is a 3-7 membered saturated or partially unsaturated cycloalkylene. In some embodiments, -Cy- is optionally substituted 3-7 membered saturated cycloalkylene. In some embodiments, -Cy- is optionally substituted 3-7 membered partially unsaturated cycloalkylene. Exemplary -Cy- groups include cyclopropylene, cyclobutylene, cyclopentylene, cyclohexylene, cycloheptylene, cyclobutenylene, cyclopentenylene, cyclohexenylene and cycloheptenylene.

In some embodiments, -Cy- is a 4-7-membered saturated or partially unsaturated heterocycloalkylene having 1-4 heteroatoms independently selected from nitrogen, oxygen, or sulfur. In some embodiments, -Cy- is an optionally substituted 4-7 membered saturated heterocycloalkylene having 1-2 heteroatoms independently selected from nitrogen, oxygen, or sulfur. In some embodiments, -Cy- is an optionally substituted 4-7 membered saturated heterocycloalkylene having 2 heteroatoms independently selected from nitrogen, oxygen, or sulfur. In some embodiments, -Cy- is an optionally substituted 4-7 membered saturated heterocycloalkylene having 1 heteroatom selected from nitrogen, oxygen, or sulfur.

In some embodiments, -Cy- is an optionally substituted 4-7 membered partially unsaturated heterocycloalkylene having 1-2 heteroatoms independently selected from nitrogen, oxygen or sulfur. In some embodiments, -Cy- is an optionally substituted 4-7 membered partially unsaturated heterocycloalkylene having 2 heteroatoms independently selected from nitrogen, oxygen or sulfur. In some embodiments, -Cy- is an optionally substituted 4-7 membered partially unsaturated heterocycloalkylene having 1 heteroatom selected from nitrogen, oxygen or sulfur. Exemplary -Cy- groups include aziridinyl, oxiranyl, thiiranyl, azetidinyl, oxetanyl, thietanyl, pyrrolidinyl, furanyl, imidazolidinyl, pyrazolidinyl, oxazolidinyl, isoxazolidinyl, thiazolidinyl, isothiazolidinyl, dioxolanyl, oxathiolanyl, dithiolanyl, piperidinyl, tetrahydropyranyl, thianyl, pyranyl, thiopyranyl, piperazinyl, morpholinyl, dithianyl, and dioxanyl.

In some embodiments, -Cy- is phenylene.

In some embodiments, -Cy- is a 5-6 membered monocyclic heteroarylene having 1-3 heteroatoms independently selected from nitrogen, oxygen, or sulfur. In some embodiments, -Cy- is an optionally substituted 5-6 membered monocyclic heteroarylene having 1-3 heteroatoms independently selected from nitrogen, oxygen, or sulfur. In some embodiments, -Cy- is an optionally substituted 5-membered monocyclic heteroarylene having 1-3 heteroatoms independently selected from nitrogen, oxygen, or sulfur. In some embodiments, -Cy- is an optionally substituted 5-membered monocyclic heteroarylene having 1 heteroatom selected from nitrogen, oxygen, or sulfur. In some embodiments, -Cy- is selected from pyrrolyl, furanyl, thiophenyl or pyridinyl.

In some embodiments, -Cy- is an optionally substituted 5-membered heteroarylene having 2 heteroatoms selected from nitrogen, oxygen, or sulfur. In certain embodiments, -Cy- is an optionally substituted 5-membered heteroarylene having 1 nitrogen atom, and an additional heteroatom selected from sulfur or oxygen. Exemplary -Cy- groups include optionally substituted pyrazolyl, imidazolyl, tetrazolyl, thiazolyl, isothiazolyl, oxazolyl or isoxazolyl.

In some embodiments, -Cy- is an optionally substituted 5-membered heteroarylene having 3 heteroatoms selected from nitrogen, oxygen or sulfur. In certain embodiments, -Cy- is an optionally substituted 5-membered heteroarylene having 1 nitrogen atom, and two additional heteroatoms selected from sulfur or oxygen. In other embodiments, -Cy- is an optionally substituted 5-membered heteroarylene having 2 nitrogen atoms, and an additional heteroatom selected from sulfur or oxygen. Exemplary -Cy- groups include optionally substituted triazolyl, thiadiazolyl, oxadiazolyl.

In some embodiments, -Cy- is a 6-membered heteroarylene having 1-3 nitrogens. In other embodiments, -Cy- is an optionally substituted 6-membered heteroarylene having 1-2 nitrogens. In some embodiments, -Cy- is an optionally substituted 6-membered heteroarylene having 2 nitrogens. In certain embodiments, -Cy- is an optionally substituted 6-membered heteroarylene having 1 nitrogen. Exemplary -Cy- groups include optionally substituted pyridinyl, pyrimidinyl, pyrazinyl, pyridazinyl, triazinyl, or tetrazinyl.

In some embodiments, -Cy- is an 8-10 membered bicyclic arylene. In some embodiments, -Cy- is an 8-membered bicyclic arylene. In some embodiments, -Cy- is an 9-membered bicyclic arylene. In some embodiments, -Cy- is an 10-membered bicyclic arylene.

In some embodiments, -Cy- is an 8-10 membered bicyclic heteroarylene having 1-4 heteroatoms independently selected from nitrogen, oxygen, or sulfur. In certain embodiments, -Cy- is an optionally substituted 8-10 membered bicyclic heteroarylene having 1-4 heteroatoms independently selected from nitrogen, oxygen, or sulfur. In some embodiments, -Cy- is an optionally substituted 5,6-fused heteroarylene having 1-4 heteroatoms independently selected from nitrogen, oxygen, or sulfur. In other embodiments, -Cy- is an optionally substituted 5,6-fused heteroarylene having 1-2 heteroatoms independently selected from nitrogen, oxygen, or sulfur. In certain embodiments, -Cy- is an optionally substituted 5,6-fused heteroarylene having 1 heteroatom independently selected from nitrogen, oxygen, or sulfur. In some embodiments, -Cy- is an optionally substituted indolylene. In certain embodiments, -Cy- is an optionally substituted 5,6-fused heteroarylene having 2 heteroatoms independently selected from nitrogen, oxygen, or sulfur. In certain embodiments, -Cy- is an optionally substituted azaindolylene. In some embodiments, -Cy- is an optionally substituted benzimidazolylene. In some embodiments, -Cy- is an optionally substituted benzothiazolylene. In some embodiments, -Cy- is an optionally substituted benzoxazolylene. In some embodiments, -Cy- is an optionally substituted indazole. In certain embodiments, -Cy- is an optionally substituted 5,6-fused heteroarylene having 3 heteroatoms independently selected from nitrogen, oxygen, or sulfur.

In certain embodiments, -Cy- is an optionally substituted 6,6-fused heteroarylene having 1-4 heteroatoms independently selected from nitrogen, oxygen, or sulfur. In some embodiments, -Cy- is an optionally substituted 6,6-fused heteroarylene having 1-2 heteroatoms independently selected from nitrogen, oxygen, or sulfur. In other embodiments, -Cy- is an optionally substituted 6,6-fused heteroarylene having 1 heteroatom independently selected from nitrogen, oxygen, or sulfur. In some embodiments, -Cy- is an optionally substituted quinolinylene. In some embodiments, -Cy- is an optionally substituted isoquinolinylene. According to one aspect, -Cy- is an optionally substituted 6,6-fused heteroarylene having 2 heteroatoms independently selected from nitrogen, oxygen, or sulfur. In some embodiments, -Cy- is a quinazolinylene or a quinoxalinylene.

As defined above, R is optionally substituted $C_{1-8}$ alkyl, $C_{2-8}$ alkenyl, $C_{2-8}$ alkynyl, haloalkyl, phenyl, a 3-7 membered saturated or partially unsaturated cycloalkyl ring, an 8-10 membered bicyclic saturated, partially unsaturated or aryl carbocyclic ring, a 4-7-membered saturated or partially unsaturated heterocycloalkyl ring having 1-4 heteroatoms independently selected from nitrogen, oxygen, or sulfur; a 5-6 membered monocyclic heteroaryl ring having 1-3 heteroatoms independently selected from nitrogen, oxygen, or sulfur; or an 8-10 membered bicyclic heteroaryl ring having 1-4 heteroatoms independently selected from nitrogen, oxygen, or sulfur In some embodiments, R is optionally substituted $C_{1-8}$ alkyl, $C_{2-8}$ alkenyl or $C_{2-8}$ alkynyl. In some embodiments, R is optionally substituted $C_{1-8}$ alkyl. In some embodiments, R is optionally substituted $C_{1-7}$ alkyl. In some embodiments, R is optionally substituted $C_{1-6}$ alkyl. In some embodiments, R is optionally substituted $C_{1-5}$ alkyl. In some embodiments, R is optionally substituted $C_{1-4}$ alkyl. In some embodiments, R is optionally substituted $C_{1-3}$ alkyl. In some embodiments, R is optionally substituted $C_{1-2}$ alkyl. In some embodiments, R is —$CH_3$.

In some embodiments, R is optionally substituted $C_{2-8}$ alkenyl. In some embodiments, R is optionally substituted $C_{2-7}$ alkenyl. In some embodiments, R is optionally substituted $C_{2-6}$ alkenyl. In some embodiments, R is optionally substituted $C_{2-5}$ alkenyl. In some embodiments, R is optionally substituted $C_{2-4}$ alkenyl. In some embodiments, R is optionally substituted $C_{2-3}$ alkenyl. In some embodiments, R is optionally substituted ethenyl.

In some embodiments, R is optionally substituted $C_{2-8}$ alkynyl. In some embodiments, R is optionally substituted $C_{2-7}$ alkynyl. In some embodiments, R is optionally substituted $C_{2-6}$ alkynyl. In some embodiments, R is optionally substituted $C_{2-5}$ alkynyl. In some embodiments, R is optionally substituted $C_{2-4}$ alkynyl. In some embodiments, R is optionally substituted $C_{2-3}$ alkynyl. In some embodiments, R is optionally substituted ethynyl. Exemplary R groups include methyl, ethyl, propyl, isopropyl, n-butyl, sec-butyl, iso-butyl, tert-butyl, n-pentyl, iso-pentyl, neo-pentyl, n-hexyl, propenyl, butenyl, pentenyl, hexenyl, propynyl, butynyl, pentynyl and hexynyl.

In some embodiments, R is haloalkyl. In some embodiments, R is halomethyl. In some embodiments, R is dihalomethyl. In some embodiments, R is trihalomethyl. In some embodiments, R is fluoromethyl. In some embodiments, R is difluoromethyl. In some embodiments, R is trifluoromethyl.

In some embodiments, R is a 3-7-membered saturated or partially unsaturated heterocycloalkyl ring having 1-4 heteroatoms independently selected from nitrogen, oxygen, or sulfur. In some embodiments, R is an optionally substituted 3-7 membered saturated heterocycloalkyl ring having 1-2 heteroatoms independently selected from nitrogen, oxygen, or sulfur. In some embodiments, R is an optionally substituted 3-7 membered saturated heterocycloalkyl ring having 2 heteroatoms independently selected from nitrogen, oxygen, or sulfur. In some embodiments, R is an optionally substituted 3-7 membered saturated heterocycloalkyl ring having 1 heteroatom selected from nitrogen, oxygen, or sulfur.

In some embodiments, R is an optionally substituted 3-7 membered partially unsaturated heterocycloalkyl ring having 1-2 heteroatoms independently selected from nitrogen, oxygen or sulfur. In some embodiments, R is an optionally substituted 3-7 membered partially unsaturated heterocycloalkyl ring having 2 heteroatoms independently selected from nitrogen, oxygen or sulfur. In some embodiments, R is an optionally substituted 3-7 membered partially unsaturated heterocycloalkyl ring having 1 heteroatom selected from nitrogen, oxygen or sulfur. Exemplary R groups include aziridinyl, oxiranyl, thiiranyl, azetidinyl, oxetanyl, thietanyl, pyrrolidinyl, furanyl, imidazolidinyl, pyrazolidinyl, oxazolidinyl, isoxazolidinyl, thiazolidinyl, isothiazolidinyl, dioxolanyl, oxathiolanyl, dithiolanyl, piperidinyl, tetrahydropyranyl, thianyl, pyranyl, thiopyranyl, piperazinyl, morpholinyl, dithianyl, and dioxanyl.

In some embodiments, R is phenyl.

In some embodiments, R is a 5-6 membered monocyclic heteroaryl ring having 1-3 heteroatoms independently selected from nitrogen, oxygen, or sulfur. In some embodiments, R is an optionally substituted 5-6 membered monocyclic heteroaryl ring having 1-3 heteroatoms independently selected from nitrogen, oxygen, or sulfur. In some embodiments, R is an optionally substituted 5-membered monocyclic heteroaryl ring having 1-3 heteroatoms independently selected from nitrogen, oxygen, or sulfur. In some embodiments, R is an optionally substituted 5-membered monocyclic heteroaryl ring having 1 heteroatom selected from nitrogen, oxygen, or sulfur. In some embodiments, R is selected from pyrrolyl, furanyl, thiophenyl or pyridinyl.

In some embodiments, R is an optionally substituted 5-membered heteroaryl ring having 2 heteroatoms selected from nitrogen, oxygen, or sulfur. In certain embodiments, R is an optionally substituted 5-membered heteroaryl ring having 1 nitrogen atom, and an additional heteroatom selected from sulfur or oxygen. Exemplary R groups include optionally substituted pyrazolyl, imidazolyl, tetrazolyl, thiazolyl, isothiazolyl, oxazolyl or isoxazolyl.

In some embodiments, R is an optionally substituted 5-membered heteroaryl ring having 3 heteroatoms selected from nitrogen, oxygen or sulfur. In certain embodiments, R is an optionally substituted 5-membered heteroaryl ring having 1 nitrogen atom, and two additional heteroatoms selected from sulfur or oxygen. In other embodiments, R is an optionally substituted 5-membered heteroaryl ring having 2 nitrogen atoms, and an additional heteroatom selected from sulfur or oxygen. Exemplary R groups include optionally substituted triazolyl, thiadiazolyl, oxadiazolyl.

In some embodiments, R is a 6-membered heteroaryl ring having 1-3 nitrogens. In other embodiments, R is an optionally substituted 6-membered heteroaryl ring having 1-2 nitrogens. In some embodiments, R is an optionally substituted 6-membered heteroaryl ring having 2 nitrogens. In certain embodiments, R is an optionally substituted 6-membered heteroaryl ring having 1 nitrogen. Exemplary R groups include optionally substituted pyridinyl, pyrimidinyl, pyrazinyl, pyridazinyl, triazinyl, or tetrazinyl.

In some embodiments, R is an 8-10 membered bicyclic aryl ring. In some embodiments, R is an 8-membered bicyclic aryl ring. In some embodiments, R is an 9-membered bicyclic aryl ring. In some embodiments, R is an 10-membered bicyclic aryl ring.

In some embodiments, R is an 8-10 membered bicyclic heteroaryl ring having 1-4 heteroatoms independently selected from nitrogen, oxygen, or sulfur. In certain embodiments, R is an optionally substituted 8-10 membered bicyclic heteroaryl ring having 1-4 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having 1 heteroatom independently selected from nitrogen, oxygen, or sulfur. In some embodiments, R is an optionally substituted indolyl. In certain embodiments, R is an optionally substituted 5,6-fused heteroaryl ring having 2 heteroatoms independently selected from nitrogen, oxygen, or sulfur. In certain embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazole. In certain embodiments, R is an optionally substituted 5,6-fused heteroaryl ring having 3 heteroatoms independently selected from nitrogen, oxygen, or sulfur.

In certain embodiments, R is an optionally substituted 6,6-fused heteroaryl ring having 1-4 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having 1 heteroatom independently selected from nitrogen, oxygen, or sulfur. In some embodiments, R is an optionally substituted quinolinyl. In some embodiments, R is an optionally substituted isoquinolinyl. According to one aspect, R is an optionally substituted 6,6-fused heteroaryl ring having 2 heteroatoms independently selected from nitrogen, oxygen, or sulfur. In some embodiments, R is a quinazolinyl or a quinoxalinyl.

In some embodiments of $R^1$, $L^1$ is a covalent bond and R is haloalkyl. In some such embodiments, $R^1$ is —$CF_3$.

In some embodiments of $R^1$, $L^1$ is a covalent bond and R is $C_{1-8}$ alkyl. In some such embodiments, $R^1$ is methyl, ethyl or isopropyl.

In some embodiments of $R^1$, $L^1$ is —O— and R is haloalkyl. In some such embodiments, $R^1$ is —$OCF_3$.

In some embodiments of $R^1$, $L^1$ is —O— and R is $C_{1-8}$ alkyl. In some such embodiments, $R^1$ is —OMe. In some embodiments of $R^1$, $L^1$ is a covalent bond and R is selected from the group consisting of:

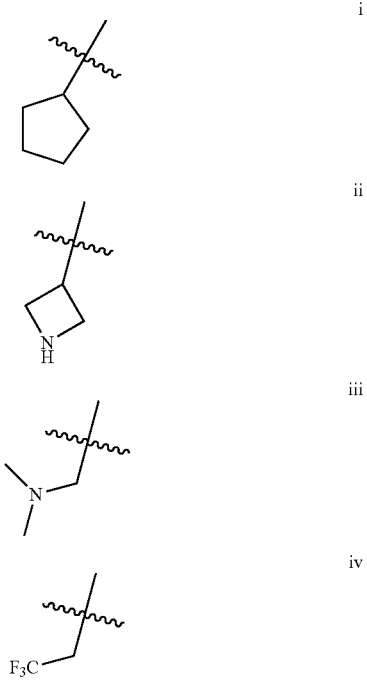

In some embodiments, formula I does not encompass a compound disclosed in Van Neck et al. Bioorgan. Med. Chem. 16 (2008) 9487-9497. Accordingly, in some embodiments, a compound of the present invention is not disclosed in Van Neck et al. Bioorgan. Med. Chem. 16 (2008) 9487-9497.

In a further embodiment, the acid addition salt is formed from hydrochloric acid, hydrobromic acid, sulfuric acid, phosphoric acid, acid metal salt, monocarboxylic acids, dicarboxylic acids, or tricarboxylic acids.

In some embodiments, the present invention provides a compound of formula II:

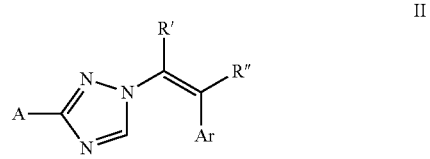

or a pharmaceutically acceptable salt thereof, wherein each of A, Ar, R' and R" is as defined above and described herein.

In some embodiments, A and Ar, each is a mono-substituted aryl (e.g., a mono-substituted phenyl and oxazole). In other embodiments, A and Ar, each is phenyl substituted with one or two $R_1$ groups. In some embodiments, each $R_1$ is independently halogen, —O-4-chlorophenyl, —OR°, $CF_3$, $OCF_3$, CN, or —N(R°)$_2$. In certain embodiments, A and Ar, each is phenyl or pyridine substituted with one or two groups selected from chloro, —O-isopropyl, —$OCH_3$, $CF_3$, $OCF_3$, CN, or —NH($CH_3$).

In some embodiments, the present invention provides a compound of formula III or III-a:

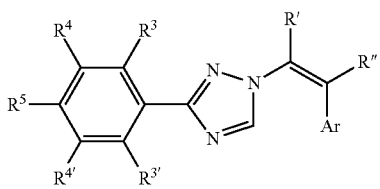

III

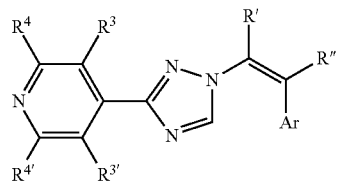

III-a

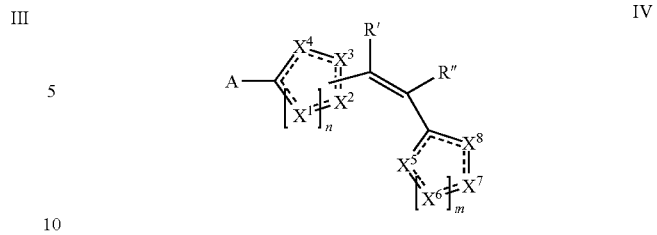

IV or a pharmaceutically acceptable salt thereof, wherein each of $X^1$, $X^2$, $X^3$, $X^4$, A, R', R" and n is as defined above and described herein, and wherein:

each of $X^5$, $X^6$, $X^7$ and $X^8$ is independently selected from O, S, N, $N(R^a)$, and $C(R^2)$, as valency permits, wherein at least one of $X^5$, $X^6$, $X^7$ and $X^8$ is either N or $NR^a$, wherein $R^a$ and $R^2$ is a defined above and described herein; and m is 1 or 2.

In some embodiments of formula IV, m is 1. In other embodiments of formula IV, m is 2.

In some embodiments, at least one of $X^5$, $X^6$, $X^7$ and $X^8$ is either N or $NR^a$. In some embodiments, at least one of $X^5$, $X^6$, $X^7$ and $X^8$ is N. In some embodiments, at least two of $X^5$, $X^6$, $X^7$ and $X^8$ is either N or $NR^a$. In some embodiments, at least two of $X^5$, $X^6$, $X^7$ and $X^8$ is N. In some embodiments, at least two of $X^5$, $X^6$, $X^7$ and $X^8$ is either N or O. In some embodiments, at least two of $X^5$, $X^6$, $X^7$ and $X^8$ is either N or S. In some embodiments, at least three of $X^5$, $X^6$, $X^7$ and $X^8$ is N. In some embodiments, at least three of $X^5$, $X^6$, $X^7$ and $X^8$ is either N or O. In some embodiments, at least three of $X^5$, $X^6$, $X^7$ and $X^8$ is either N or S.

In some embodiments, m is 1 and $X^5$ is O. In some embodiments, m is 1, $X^5$ is O and $X^8$ is N. In some embodiments, m is 1, $X^5$ is O, and $X^7$ and $X^8$ are N. In some embodiments, m is 1, $X^5$ is O, $X^6$ is $C(R^2)$ and $X^7$ and $X^8$ are N. In some embodiments, m is 1, $X^5$ is O, $X^6$ is $C(R^2)$ and $X^7$ and $X^8$ are N, wherein $R^2$ is selected from hydrogen, —CN, —$CF_3$, —$CH_3$, —$CH(CH_3)_2$, cyclopentyl, azetidinyl, and —$CH_2N(CH_3)_2$.

In some embodiments, m is 1, $X^5$ is O, and $X^6$ and $X^8$ are N. In some embodiments, m is 1, $X^5$ is O, $X^6$ is N, $X^7$ is $C(R^2)$ and $X^8$ is N. In some embodiments, m is 1, $X^5$ is O, $X^6$ is N, $X^7$ is $C(R^2)$ and $X^8$ is N, wherein $R^2$ is hydrogen.

In some embodiments, m is 1, $X^6$ is O and $X^8$ is N. In some embodiments, m is 1, $X^6$ is O, $X^6$ and $X^7$ are $C(R^2)$ and $X^8$ is N. In some embodiments, m is 1, $X^6$ is O, $X^6$ and $X^7$ are $C(R^2)$ and $X^8$ is N, wherein $R^2$ is hydrogen.

In some embodiments, m is 1, $X^7$ is O and $X^8$ is N. In some embodiments, m is 1, $X^5$ and $X^6$ are $C(R^2)$, $X^7$ is O and $X^8$ is N. In some embodiments, m is 1, $X^5$ and $X^6$ are $C(R^2)$, $X^7$ is O and $X^8$ is N, wherein $R^2$ is hydrogen.

In some embodiments, m is 1, $X^5$ is O and $X^8$ is N. In some embodiments, m is 1, $X^5$ is O, $X^6$ and $X^7$ are $C(R^2)$ and $X^8$ is N. In some embodiments, m is 1, $X^5$ is O, $X^6$ and $X^7$ are $C(R^2)$ and $X^8$ is N, wherein $R^2$ is hydrogen.

In some embodiments, m is 1, $X^5$ is O and $X^7$ is N. In some embodiments, m is 1, $X^5$ is O, $X^6$ is $C(R^2)$, $X^7$ is N and $X^8$ is $C(R^2)$. In some embodiments, m is 1, $X^5$ is O, $X^6$ is $C(R^2)$, $X^7$ is N and $X^8$ is $C(R^2)$, wherein $R^2$ is hydrogen.

In some embodiments, m is 1, $X^5$ is N, $X^7$ is $NR^a$ and $X^8$ is N. In some embodiments, m is 1, $X^5$ is N, $X^6$ is $C(R^2)$, $X^7$ is $NR^a$ and $X^8$ is N. In some embodiments, m is 1, $X^5$ is N, $X^6$ is $C(R^2)$, $X^7$ is $NR^a$ and $X^8$ is N, wherein $R^a$ is —$CH_3$. In some embodiments, m is 1, $X^5$ is N, $X^6$ is $C(R^2)$, $X^7$ is $NR^a$ and $X^8$ is N, wherein $R^a$ is —$CH_3$ and $R^2$ is hydrogen.

or a pharmaceutically acceptable salt thereof, wherein each of Ar, R' and R" is as defined above and described herein and wherein:

each $R^3$, $R^{3'}$, $R^4$, $R^{4'}$ and $R^5$ is independently for each occurrence —H, halogen (F, Cl, Br, I), —$NO_2$, —CN, —$N_3$, or -$L^1$-R, wherein $L^1$ and R are as defined above and described herein.

In some embodiments, at least one of $R^3$, $R^{3'}$, $R^4$, $R^{4'}$ and $R^5$ is halogen. In certain embodiments, at least one of $R^3$, $R^{3'}$, $R^4$, $R^{4'}$ and $R^5$ is fluoro. In certain embodiments, at least one of $R^3$, $R^{3'}$, $R^4$, $R^{4'}$ and $R^5$ is chloro. In certain embodiments, at least one of $R^3$, $R^{3'}$, $R^4$, $R^{4'}$ and $R^5$ is bromo. In some embodiments, $R^4$ is chloro.

In some embodiments, at least one of $R^3$, $R^{3'}$, $R^4$, $R^{4'}$ and $R^5$ is alkyl. In some embodiments, at least one of $R^3$, $R^{3'}$, $R^4$, $R^{4'}$ and $R^5$ is haloalkyl. In certain embodiments, at least one of $R^3$, $R^{3'}$, $R^4$, $R^{4'}$ and $R^5$ is $CF_3$. In some embodiments, $R^3$ is $CF_3$. In some embodiments, $R^4$ is $CF_3$. In some embodiments, $R^5$ is $CF_3$.

In some embodiments, at least one of $R^3$, $R^{3'}$, $R^4$, $R^{4'}$ and $R^5$ is -$L^1$-R. In some embodiments, at least one of $R^3$, $R^{3'}$, $R^4$, $R^{4'}$ and $R^5$ is —OR, wherein R is $C_{1-8}$ alkyl. In some embodiments, at least one of $R^3$, $R^{3'}$, $R^4$, $R^{4'}$ and $R^5$ is —$OCH_3$. In some embodiments, $R^3$ or $R^{3'}$ is —$OCH_3$. In some embodiments, $R^4$ or $R^{4'}$ is —$OCH_3$. In some embodiments, $R^5$ is —$OCH_3$. In some embodiments, at least one of $R^3$, $R^{3'}$, $R^4$, $R^{4'}$ and $R^5$ is —OR, wherein R is haloalkyl. In some embodiments, at least one of $R^3$, $R^{3'}$, $R^4$, $R^{4'}$ and $R^5$ is —$OCF_3$. In some embodiments, $R^3$ or $R^{3'}$ is —$OCF_3$. In some embodiments, $R^4$ or $R^{4'}$ is —$OCF_3$. In some embodiments, $R^5$ is —$OCF_3$. In certain embodiments, $R^4$ is —$CF_3$ and $R^{4'}$ is —OMe. In certain other embodiments, $R^4$ is —Cl and $R^{4'}$ is —OMe.

In some embodiments of formula III or III-a, Ar is a monosubstituted aryl (e.g., a mono-substituted oxadiazole). In some embodiments, Ar is oxadiazole substituted with one or two $R^1$ groups. In some embodiments, each $R^1$ is independently halogen, —O-4-chlorophenyl, CN, —OR°, or —$N(R°)_2$. In certain embodiments, Ar is oxadiazole substituted with one or two groups selected from chloro, —O-isopropyl, —$OCH_3$, or —$NH(CH_3)$.

In some embodiments, the present invention provides a compound of formula IV:

In some embodiments, m is 1, $X^5$ is N, $X^6$ is S and $X^7$ is N. In some embodiments, m is 1, $X^5$ is N, $X^6$ is S, $X^7$ is N and $X^8$ is $C(R^2)$. In some embodiments, m is 1, $X^5$ is N, $X^6$ is S, $X^7$ is N and $X^8$ is $C(R^2)$, wherein $R^2$ is —OR. In some embodiments, m is 1, $X^5$ is N, $X^6$ is S, $X^7$ is N and $X^8$ is $C(R^2)$, wherein $R^2$ is —OCH$_3$. In some embodiments, m is 1, $X^5$ is N, $X^6$ is S, $X^7$ is N and $X^8$ is $C(R^2)$, wherein $R^2$ is —OCF$_3$.

In some embodiments, m is 1, $X^5$ is N, $X^6$ is O and $X^7$ is N. In some embodiments, m is 1, $X^5$ is N, $X^6$ is O, $X^7$ is N and $X^8$ is $C(R^2)$. In some embodiments, m is 1, $X^5$ is N, $X^6$ is O, $X^7$ is N and $X^8$ is $C(R^2)$, wherein $R^2$ is —CH$_2$CF$_3$. In some embodiments, m is 1, $X^5$ is N, $X^6$ is O, $X^7$ is N and $X^8$ is $C(R^2)$, wherein $R^2$ is —OR. In some embodiments, m is 1, $X^5$ is N, $X^6$ is O, $X^7$ is N and $X^8$ is $C(R^2)$, wherein $R^2$ is —OCH$_3$. In some embodiments, m is 1, $X^5$ is N, $X^6$ is O, $X^7$ is N and $X^8$ is $C(R^2)$, wherein $R^2$ is —OCF$_3$.

In some embodiments, m is 1, $X^5$ is N, $X^6$ is NR$^a$ and $X^7$ is N. In some embodiments, m is 1, $X^5$ is N, $X^6$ is NR$^a$, $X^7$ is N and $X^8$ is $C(R^2)$. In some embodiments, m is 1, $X^5$ is N, $X^6$ is NR$^a$, $X^7$ is N and $X^8$ is $C(R^2)$, wherein $R^2$ is —OR. In some embodiments, m is 1, $X^5$ is N, $X^6$ is NR$^a$, $X^7$ is N and $X^8$ is $C(R^2)$, wherein $R^2$ is —OCH$_3$. In some embodiments, m is 1, $X^5$ is N, $X^6$ is NR$^a$, $X^7$ is N and $X^8$ is $C(R^2)$, wherein $R^2$ is —OCF$_3$. In some embodiments, m is 1, $X^5$ is N, $X^6$ is NR$^a$, $X^7$ is N and $X^8$ is $C(R^2)$, wherein $R^2$ is —OR and $R^a$ is —CH$_2$CF$_3$. In some embodiments, m is 1, $X^5$ is N, $X^6$ is NR$^a$, $X^7$ is N and $X^8$ is $C(R^2)$, wherein $R^2$ is —OCH$_3$ and $R^a$ is —CH$_2$CF$_3$. In some embodiments, m is 1, $X^5$ is N, $X^6$ is NR$^a$, $X^7$ is N and $X^8$ is $C(R^2)$, wherein $R^2$ is —OCF$_3$ and $R^a$ is —CH$_2$CF$_3$.

In some embodiments, the present invention provides a compound of formula V:

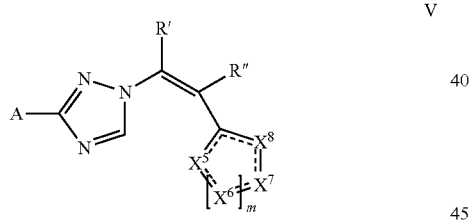

V or a pharmaceutically acceptable salt thereof, wherein each of m, A, R', R", $X^5$, $X^6$, $X^7$ and $X^8$ are as defined above and described herein.

In some embodiments of formula V, m is 1. In other embodiments of formula V, m is 2.

In some embodiments, the present invention provides a compound of formulae VI, VII, VIII, IX, X, XI, XII, XIII, XIV and XV:

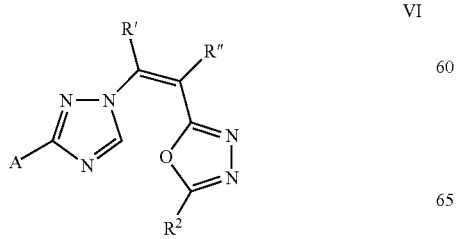

VI

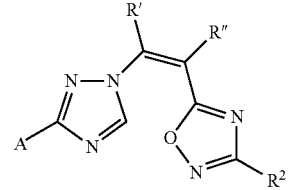

VII

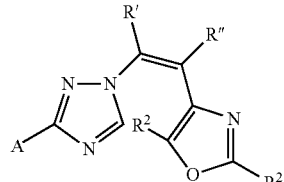

VIII

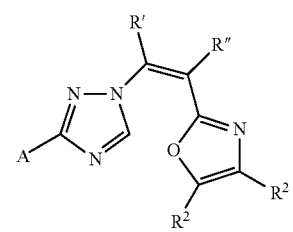

IX

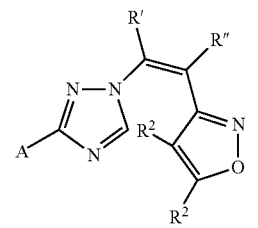

X

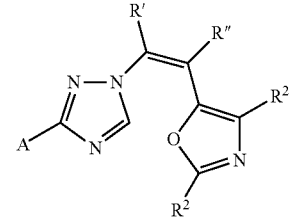

XI

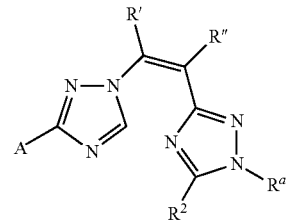

XII

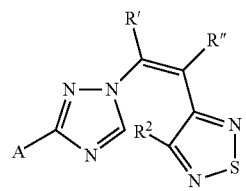

XIII

XIX

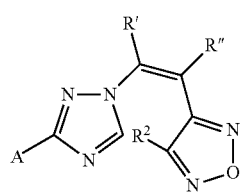

XV

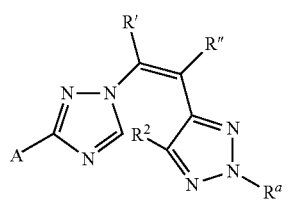

or a pharmaceutically acceptable salt thereof, wherein each of A, R', R", $R^a$ and $R^2$ is as defined above and described herein.

In other embodiments, the present invention provides a compound of formula XVI:

XVI

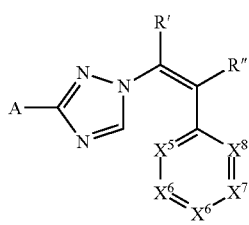

or a pharmaceutically acceptable salt thereof, wherein each of A, R', R", $X^5$, $X^6$, $X^7$ and $X^8$ is as defined above and described herein.

In some embodiments of formula XVI, at least one of $X^5$, $X^6$, $X^7$ and $X^8$ is N.

In some embodiments, the present invention provides a compound of formulae XVII, XVIII, XIX, XX, XXI, XXII, XXIII, XXIV, XXV, XXVI and XXVII:

XVII

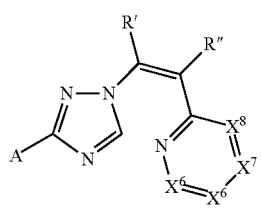

XVIII

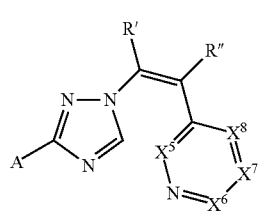

XIX

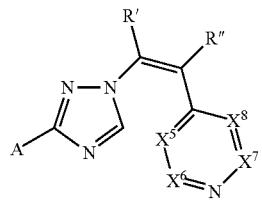

XX

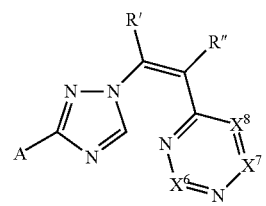

XXI

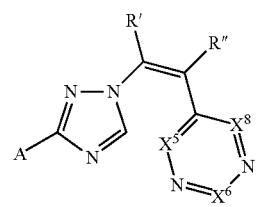

XXII

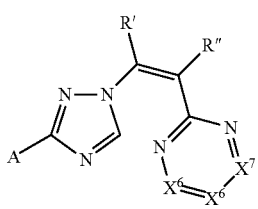

XXIII

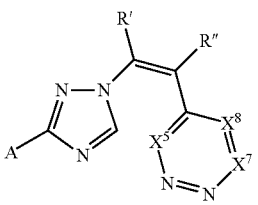

XXIV

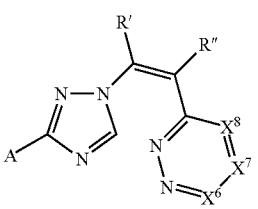

XXV

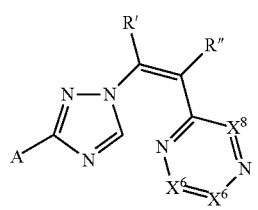

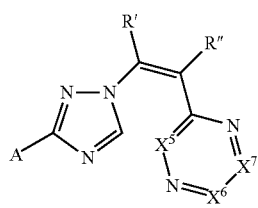
XXVI
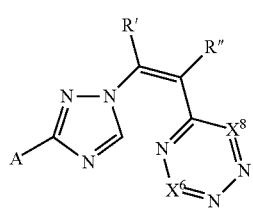
XXVII
or a pharmaceutically acceptable salt thereof, wherein each of A, R', R'', $X^5$, $X^6$, $X^7$ and $X^8$ is as defined above and described herein.
In some embodiments, the present invention provides a compound selected from:
I-1
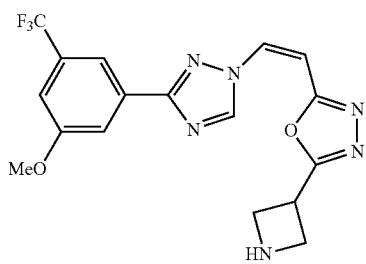
I-5
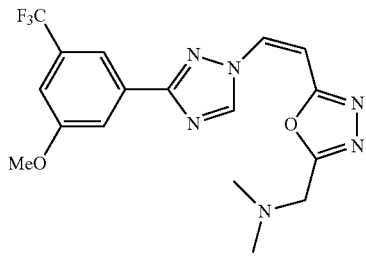
I-6
I-2
I-7
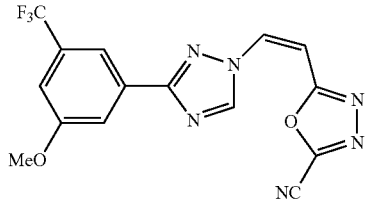
I-3
I-8
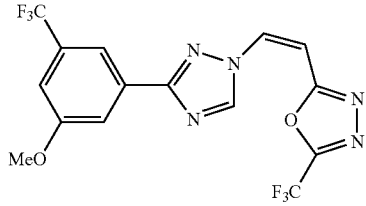
I-9
I-4
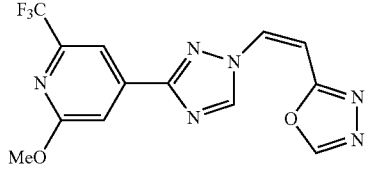
I-10
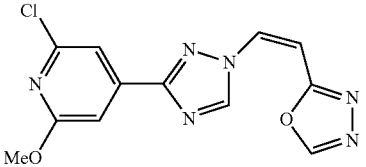
I-11
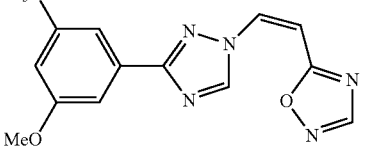

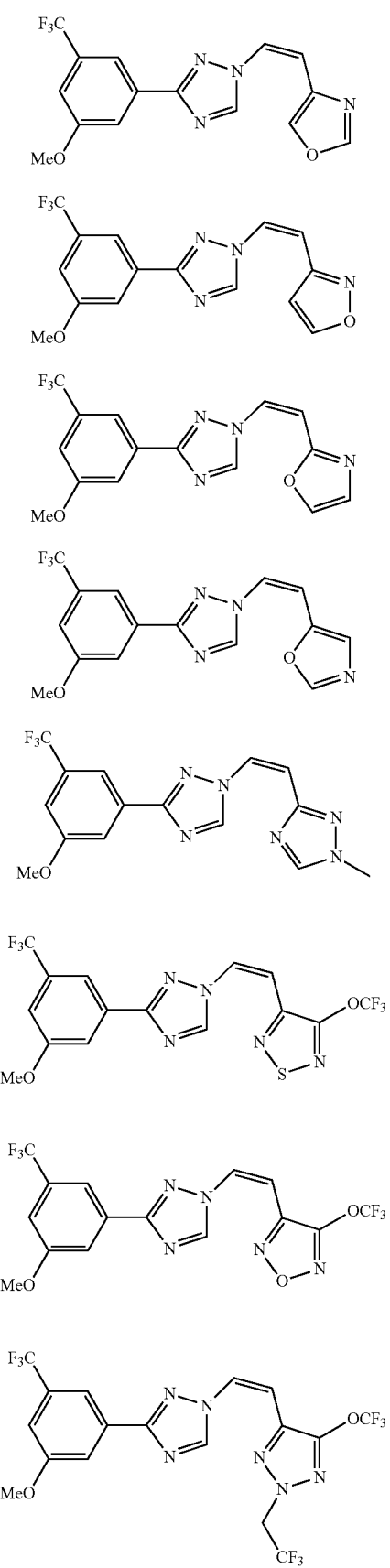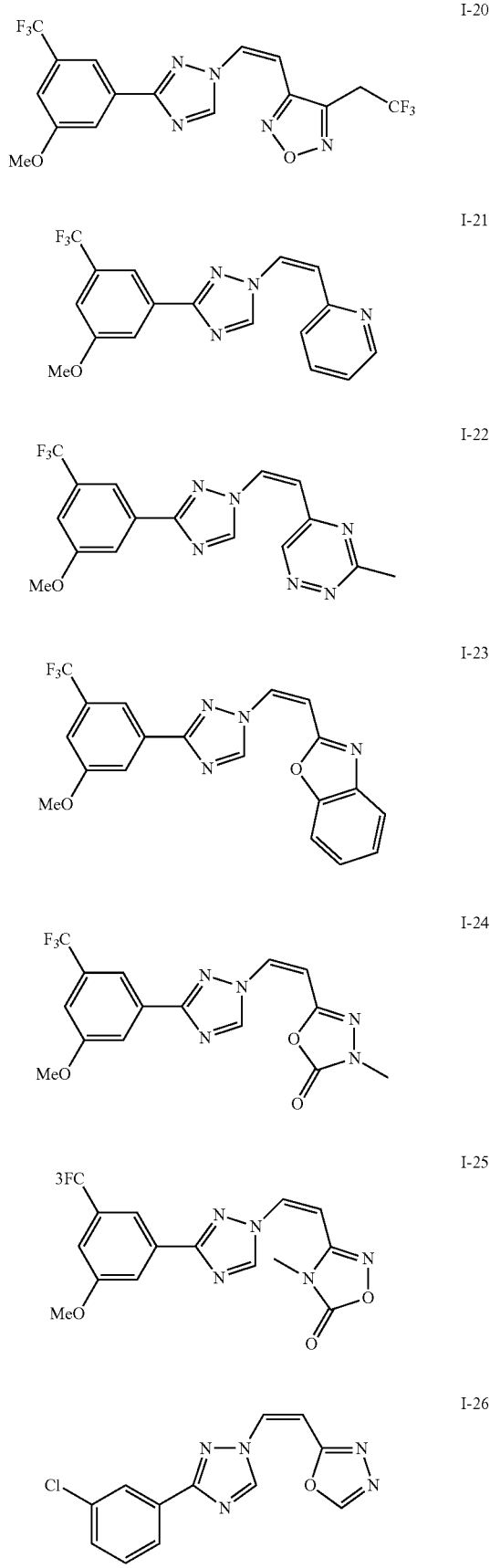

-continued
I-27
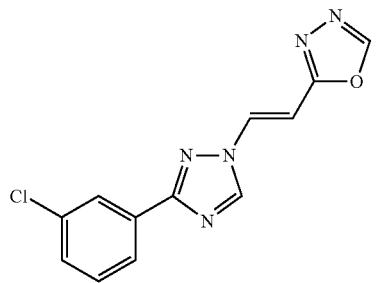
I-28
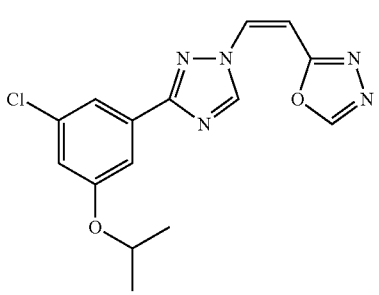
I-29
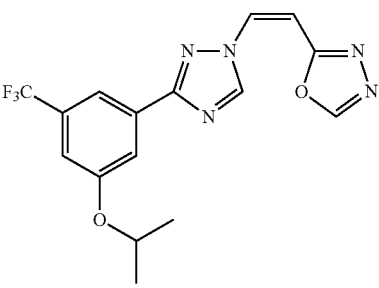
I-30
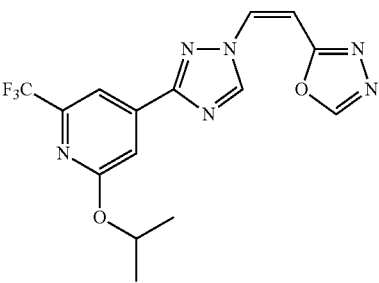
I-31
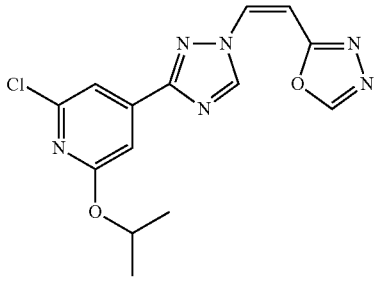
-continued
I-32
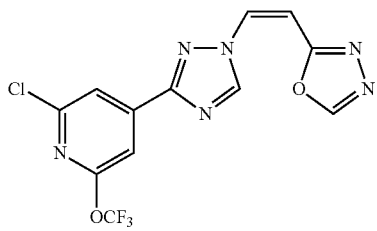
I-33
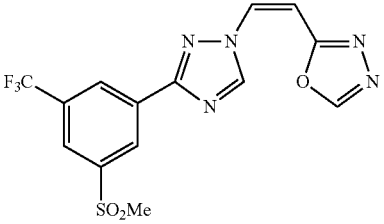
I-34
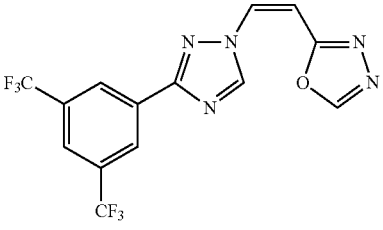
I-35
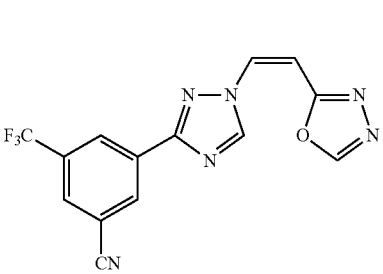
I-36
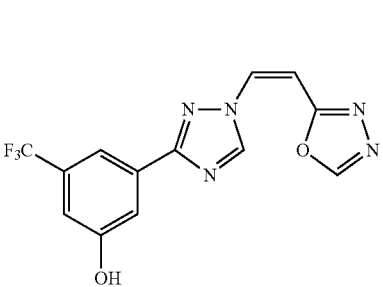
I-37
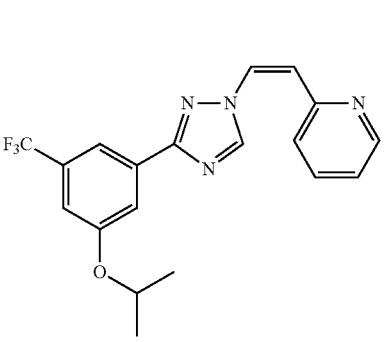

-continued

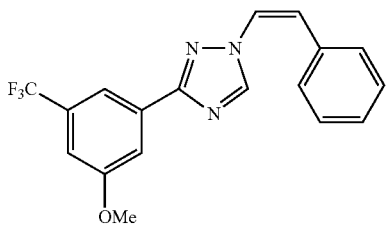
I-38

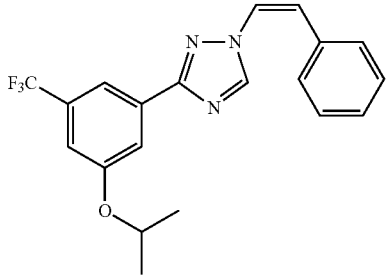
I-39 or a pharmaceutically acceptable salt thereof.

In some embodiments, the present invention provides a compound of formula I-a:

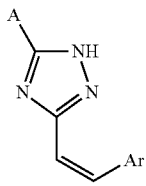
I-a or a pharmaceutically acceptable salt thereof, wherein each of A and Ar is as defined above and described herein.

In some embodiments of formula I-a, each A and Ar is a mono-substituted aryl (e.g., a mono-substituted phenyl or oxadiazole).

In some embodiments, the present invention provides a compound of formula I-b:

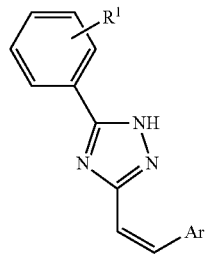
I-b or a pharmaceutically acceptable salt thereof; wherein each of $R^1$ and Ar is as defined above and described herein.

In some embodiments of formula I-b, $R^1$ is halo. In certain embodiments, $R^1$ is chloro.

In some embodiments of formula I-b, $R^1$ is alkyl. In certain embodiments, $R^1$ is $CF_3$.

In some embodiments of formula I-b, $R^1$ is O-alkyl. In certain embodiments, $R^1$ is $OCH_3$. In certain embodiments, $R^1$ is $OCF_3$.

In some embodiments of formula I-b, Ar is a mono-substituted aryl (e.g., a mono-substituted oxadiazole).

In other embodiments of formula I-b, Ar is oxadiazole substituted with one or two $R^1$ groups. In some embodiments, each $R^1$ is independently halogen, —O-4-chlorophenyl, CN, —OR°, or —N(R°)$_2$. In certain embodiments, Ar is oxadiazole substituted with one or two groups selected from chloro, —O-isopropyl, $CF_3$, $OCF_3$, CN, —$OCH_3$, or —$NH(CH_3)$.

In some embodiments, the present invention provides a compound of formula I-c:

I-c or a pharmaceutically acceptable salt thereof, wherein each of $R^1$ and Ar is as defined above and described herein.

In some embodiments of Formula I-c, $R^1$ is halo (e.g., chloro). In some embodiments, Ar is phenyl substituted with one or two $R^1$ groups. In some embodiments, each $R^1$ is independently halogen, —O-4-chlorophenyl, —OR°, $CF_3$, $OCF_3$, CN, or —N(R°)$_2$. In certain embodiments, Ar is phenyl substituted with, one or two groups selected from chloro, —O-isopropyl, —$OCH_3$, or —$NH(CH_3)$.

In some embodiments, the present invention provides a compound of formula I-d:

I-d or a pharmaceutically acceptable salt thereof, wherein Z is =CH— or =N—; and each of $R^2$, $R^4$ and $R^{4'}$ is as defined above and described herein.

In some embodiments of formula I-d, each of $R^4$ and $R^{4'}$ is independently selected from hydrogen, halo, —CN, —OH, —$C_1$-$C_4$ alkyl, —$C_1$-$C_4$ haloalkyl, —O—$C_1$-$C_4$ alkyl, —O—$C_1$-$C_4$ haloalkyl, and —S(O)$_2$—$C_1$-$C_4$ alkyl, wherein at least one of $R^4$ and $R^{4'}$ is other than hydrogen; and $R^2$ is hydrogen or $C_1$-$C_4$ alkyl.

In some embodiments of formula I-d, each of $R^4$ and $R^{4'}$ is independently selected from hydrogen, chloro, —CN, —OH, —$CH_3$, —$CH_2CH_3$, —$CH(CH_3)_2$, $CF_3$, —O—$CH_3$, —O—$CH(CH_3)_2$, —O—$CH_2CH_3$, —$OCF_3$, and S(O)$_2$—$CH_3$, wherein at least one of $R^4$ and $R^{4'}$ is other than hydrogen. In more specific embodiments, at least one of $R^4$ or $R^{4'}$ is chloro or —$CF_3$.

In some embodiments of formula I-d, $R^2$ is hydrogen, —$CH_3$, —$CH_2CH_3$, or —$CH(CH_3)_2$.

In some embodiments, the present invention provides a compound having the structure:

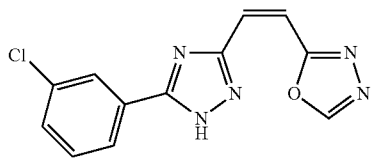 [SMILES: Clc1cccc(-c2nc(/C=C\c3nnco3)n[nH]2)c1]

or a pharmaceutically acceptable salt thereof.

In one aspect, the invention features a pharmaceutical composition comprising a compound described herein, or a pharmaceutically acceptable salt or N-oxide thereof, and a pharmaceutically acceptable carrier.

In another aspect, the invention features a method of treating a neoplastic or inflammatory or viral disorder in a subject, comprising administering a pharmaceutically effective amount of a compound or composition described herein.

Also provided herein are methods of treating a disease associated with expression or activity of p53, p73, p21, pRB, p27, IκB, NFκB, c-Abl, FOXO proteins, Cox-2 in a subject comprising administering to the patient a therapeutically effective amount of a compound described herein. For example, provided herein are methods of treating various cancers in mammals specifically including humans, dogs, cats, and farm animals, including hematologic malignancies (leukemias, lymphomas, myelomas, myelodysplastic and myeloproliferative syndromes) and solid tumors (carcinomas such as prostate, breast, lung, colon, pancreatic, renal, ovarian as well as soft tissue and osteo- sarcomas, and stromal tumors), inflammatory disorders such as rheumatoid arthritis, systemic lupus, systemic sclerosis, vasculitis syndromes (small, medium and large vessel), atherosclerosis, psoriasis and other dermatological inflammatory disorders (such as pemphigous, pemphigoid, allergic dermatitis), and urticarial syndromes comprising administering a compound represented by formula I.

Also provided are compounds represented by formula I for use in therapy and/or for the manufacture of a medicament for the treatment of a disease associated with expression or activity of p53, p73, p21, pRB, p27, IκB, NFκB, c-Abl, FOXO proteins or Cox-2 in a subject.

In yet another aspect, the compound or composition is administrable intravenously and/or intraperitoneally.

In certain embodiments, the present invention provides a method for treating a CRM1-mediated disorder or condition in a patient, comprising administering to the patient a pharmaceutically acceptable composition comprising a compound set forth in Table A, or a pharmaceutically acceptable salt thereof, and a pharmaceutically acceptable carrier, adjuvant, or vehicle:

In some embodiments, the present invention provides a method for inhibiting CRM1 in a biological sample or in a patient, comprising contacting the biological sample with, or administering to the patient, a pharmaceutically acceptable salt of a compound set forth in Table A or pharmaceutically acceptable composition thereof.

4. General Synthetic Methods

Several general methods for preparing compounds of Formula I are illustrated in the following Schemes and Examples. Starting materials and the requisite intermediates are in some cases commercially available or can be prepared according to literature procedures (Bioorg. Med. Chem. 16, 2008, 9487-9497; Bioorg. Med. Chem. 16, 2008, 10031-10310; Synthetic Comm. 35, 2005, 761-764) or as illustrated herein.

Certain azole compounds of Formula I, wherein the group A is selected from aryl and heteroaryl optionally substituted with one or more substituents and the Het is a triazole group with the double bond substituted at one N, and one WG is hydrogen while the other is either carboxylic acid, carboxylic ester, carboxylic amides, cyano, etc., can be prepared in accordance with general Scheme 1. In, the steps where product was obtained as a mixture of cis- and trans-isomers of the double bond, pure isomers can be easily separated using chromatographic methods in the literature.

It is understood that the functional groups present in compounds described in the Schemes below can be further manipulated, when appropriate, using the standard functional group transformation techniques available to those skilled in the art, to provide desired compounds described in this invention. Other variations or modifications, which will be obvious to those skilled in the art, are within the scope and teachings of this invention.

Scheme 1

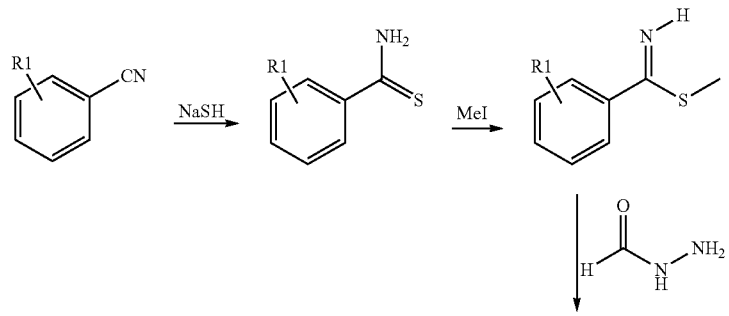

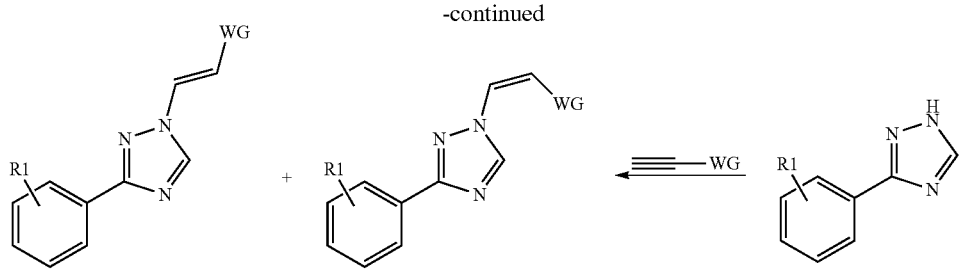

In Scheme 1, a general method is described for the preparation of certain azoles compounds of Formula I, wherein the group A is selected from aryl and heteroaryl optionally substituted with one or more substituents and the Het is a triazole group with the double bond substituted at one C, one WG is hydrogen and the other is either carboxylic acid, carboxylic ester, carboxylic amides, cyano, etc., and the group —CH=C(WG)$_2$ is attached to X$_1$, can be prepared in accordance with general Scheme 2 and Scheme 3.

In accordance with Scheme 2, carboxylic acid derivatives are coupled with t-butyl carbazate by activation with HOBt (Hydroxybenzotriazole) in the presence of a suitable carbodiimiide such as EDC [1-(3-dimethylaminopropyl-3(ethyl-carbodiimide)] in presence of diisopropylethylamine (DIEA) as base in dichloromethane to provide hydrazide intermediate (Advance Org. Chem. 5$^{th}$ ed., John Wiley & Sons, New York, pp. 506-512, 2001).

As shown in Scheme 3, hydrazide intermediate was used to construct the 1,2,4-Triazole cores, wherein the substitution of the double-bond is made via a carbon atom and can be ester, acid, amide etc. In the steps where product was obtained as a mixture of cis- and trans-isomers of the double bond, pure isomers can be easily separated using chromatographic methods known for those skilled in the art in the literature.

Scheme 3

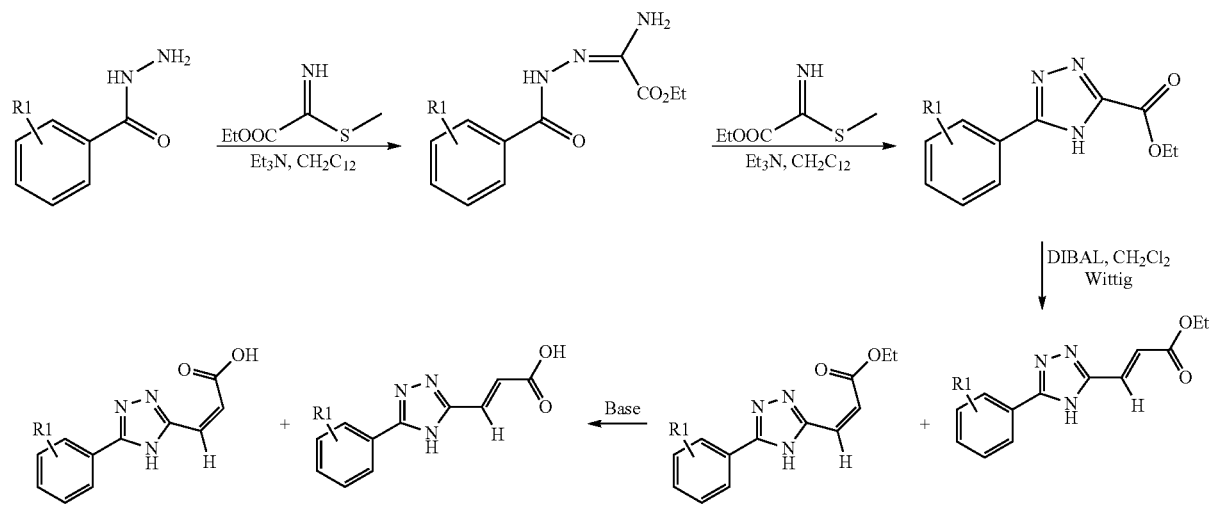

In Scheme 4, pure cis-isomer was converted to the corresponding oxadiazole derivative in a series of steps.

Scheme 2

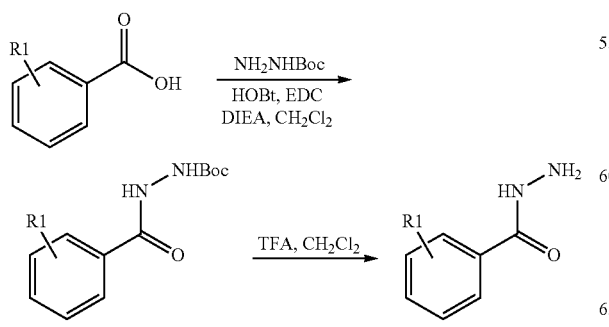

Scheme 4

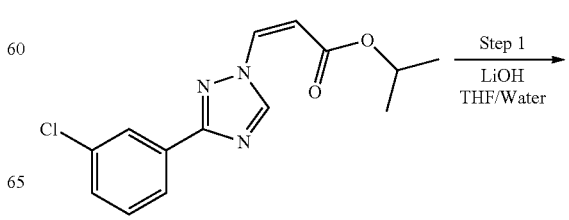

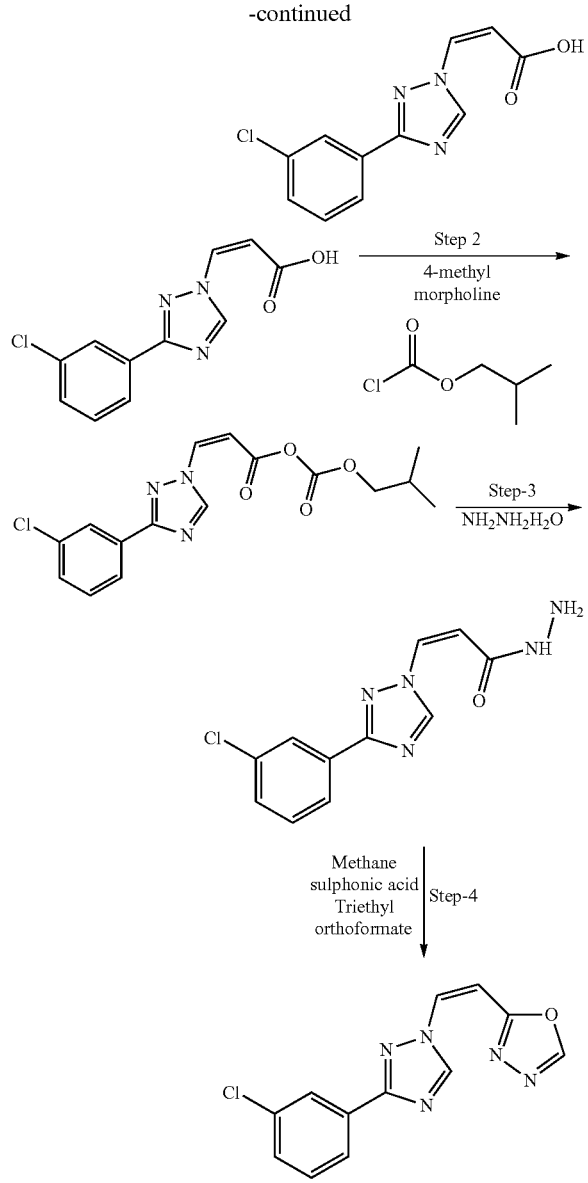

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CRM1, in a biological sample or in a patient. In certain embodiments, the amount of compound in compositions of this invention is such that is effective to measurably inhibit CRM1 in a biological sample or in a patient. In certain embodiments, a composition of this invention is formulated for administration to a patient in need of such composition. In some embodiments, a composition of this invention is formulated for oral administration to a patient.

The terms "patient" and "subject" are interchangeable and are used herein to mean an animal. In some embodiments, the animal is a mammal. In certain embodiments, the patient is a veterinary patient (i.e., a non-human mammal patient). In some such embodiments, a veterinary patient includes dogs, cats, mice, horses, non-human primates, rats, guinea pigs, sheep, cow, pig, etc. In some embodiments, the patient is a dog. In other embodiments, the patient is a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch.

When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intra-peritoneal administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-$\alpha$-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-$\beta$-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Uses of Compounds and Pharmaceutically Acceptable Compositions

Compounds and compositions described herein are generally useful for the inhibition of CRM1.

The activity of a compound utilized in this invention as an inhibitor of CRM1 may be assayed in vitro, in vivo or in a cell line. Detailed conditions for assaying a compound utilized in this invention as an inhibitor of CRM1 are set forth in the Examples below.

The compounds and compositions described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

In some embodiments, the invention provides a method of treating spontaneous tumors in a dog comprising the step of administering to the dog in need thereof a compound of this invention or a pharmaceutical composition thereof. In some such embodiments, the spontaneous tumor is selected from mast cell tumor, metastatic hemangiosarcoma and diffuse large B cell lymphoma.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

Provided compounds are inhibitors of CRM1 and are therefore useful for treating one or more disorders associated with activity of CRM1. Thus, in certain embodiments, the present invention provides a method for treating a CRM1-mediated disorder comprising the step of administering to a patient in need thereof a compound of the present invention, or pharmaceutically acceptable composition thereof.

As used herein, the term "CRM1-mediated" disorder or condition, as used herein, means any disease or other deleterious condition in which CRM1 is known to play a role. Accordingly, another embodiment of the present invention relates to treating or lessening the severity of one or more diseases in which CRM1 is known to play a role. Specifically, the present invention relates to a method of treating or lessening the severity of a disease or condition selected from a proliferative disorder, wherein said method comprises administering to a patient in need thereof a compound or composition according to the present invention. Such disorders are set forth in detail below.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, lymphomas, myeloma and other malignant plasma cell disorders, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated or prevented in accordance with the methods described herein.

Cancer Combination Therapies

In some embodiments, a compound described herein is administered together with an additional cancer treatment. Exemplary cancer treatments include, for example: chemotherapy, targeted therapies such as antibody therapies, immunotherapy, and hormonal therapy. Examples of each of these treatments are provided below.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g. Gleevec (Vignari and Wang 2001).

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Inflammation and Autoimmune Disease

The compounds and methods described herein may be used to treat or prevent a disease or disorder associated with inflammation in humans as well as other mammals. A compound described herein may be administered prior to the onset of, at, or after the initiation of inflammation. When used prophylactically, the compounds are preferably provided in advance of any inflammatory response or symptom. Administration of the particles may prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g. giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a particle or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The particles may be used to treat chronic hepatitis infection, including hepatitis B and hepatitis C.

Additionally, a particle or method described herein may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacyl-morphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papavereturn, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a particle described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib). It was surprisingly found that a provided compound in combination with Dox or bortezomib resulted in a synergystic effect (i.e., more than additive).

Viral Infections

Compounds and methods described herein may be used to treat or prevent a disease or disorder associated with a viral infection humans as well as other mammals. A compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT)), and inhibition of the release of virus (e.g., zanamivir and oseltamivir).

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g. VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

As previously mentioned, DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off. This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including $O^6$-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Figure 3:
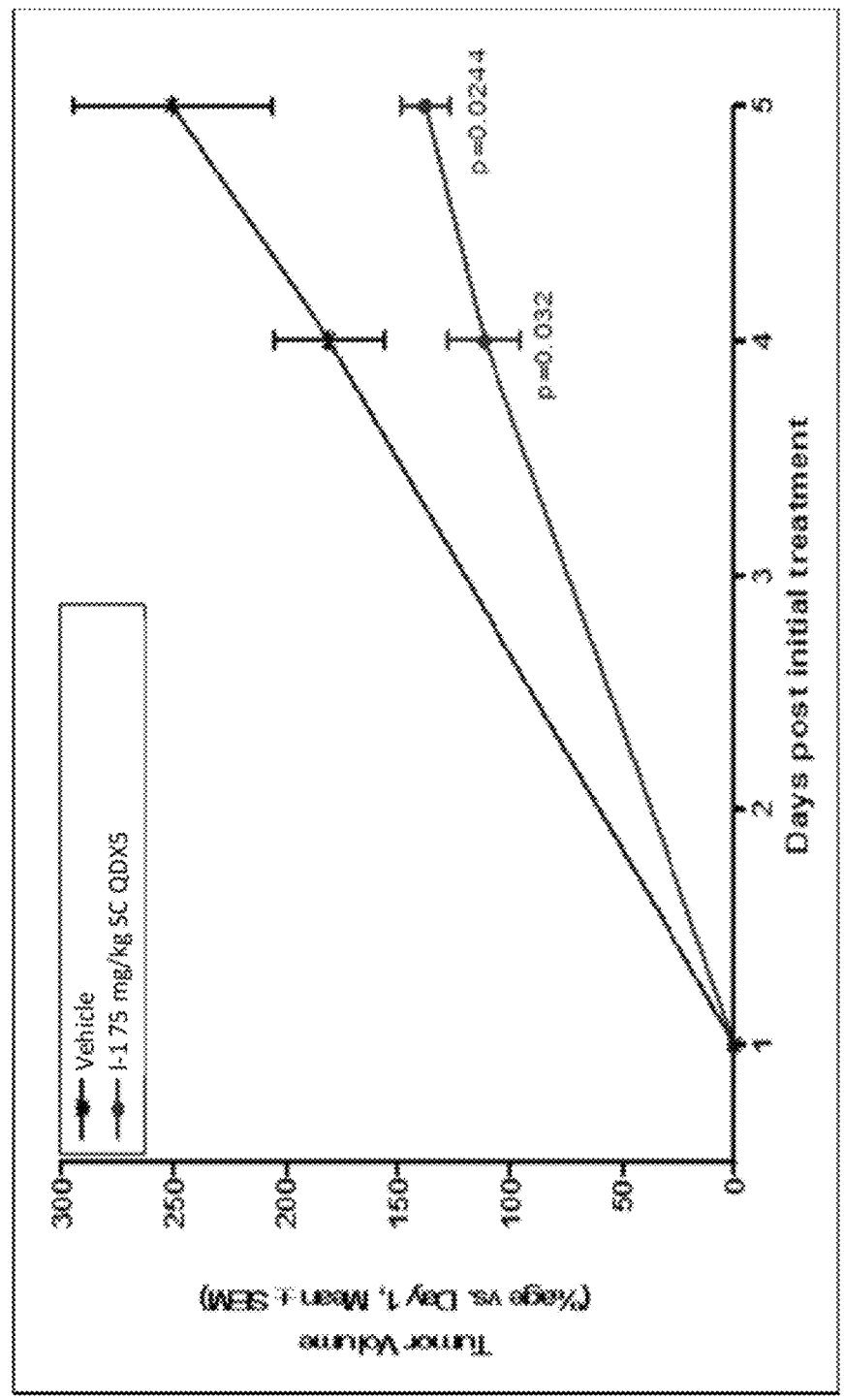
FIG. 3 is a graph depicting the results of a MM1.S multiple myeloma model. MM1.S cells were inoculated into female athymic Balb c. nu$^+$/nu$^+$mice. Once tumors reached an average volume of 780 mm$^3$ the animals were dosed with vehicle and 75 mg/kg I-1 subcutaneously. Following 3 doses I-1 caused 50% reduction in tumor growth in a statistically significant manner.

Fragile X syndrome gets its name from the way the part of the X chromosome that contains the gene abnormality looks under a microscope; it usually appears as if it is hanging by a thread and easily breakable (FIG. 3). The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucleotides and siRNA.

Ophthamology

Compounds and methods described herein may be used to treat or prevent an ophthamology disorder. Exemplary ophthamology disorders include macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative Disease

Neurodegeneration is umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Other Disorders

Compounds and compositions described herein may also be used to treat disorders of abnormal tissue growth and fibrosis including cardiomyopathy, pulmonary fibrosis, hepatic fibrosis, glomerulonephritis, and other renal disorders.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations atm Atmosphere
aq. Aqueous
BINAP 2,2'-bis(diphenylphosphino)-1,1'-binaphthyl
Boc tert-butoxycarbonyl
CDI N,N'-Carbonyldiimidazole
DCC N,N-Dicyclohexylcarbodiimide
DCM Dichloromethane
DBU Diaza(1,3)bicyclo[5.4.0]undecane
DEA N,N-Diisopropyl ethylamine
DIBAL-H Diisobutylaluminium hydride
DIC N,N'-Diisopropylcarbodiimide
DMAP N,N-Dimethyl-4-aminopyridine
DMF Dimethylformamide
DMSO Dimethylsulfoxide
DPPF Diphenylphosphinoferrocene
EA Ethyl acetate
EDCI N-[3-(dimethylamino)propyl]-N'-ethylcarbodiimide hydrochloride
EDC 1-Ethyl-3-(3-dimethylaminopropyl)carbodiimide
$Et_2O$ Diethylether
EtOAc Ethyl acetate
EtOH Ethanol
EtI Iodoethane
Et Ethyl
Fmoc 9-fluorenylmethyloxycarbonyl
h hour(s)
HetAr Heteroaryl
HOBt N-Hydroxybenzotriazole
HBTU O-(Benzotriazol-1-yl)-N,N,N',N'-tetramethyluronium hexafluorophosphate
HPLC High performance liquid chromatography
LAH Lithium aluminium hydride
LCMS HPLC mass spec
MCPBA m-Chlorbenzoic acid
MeCN Acetonitrile
MeOH Methanol
min Minutes
MeI Iodomethane
MeMgCl Methyl magnesium chloride
Me Methyl
n-BuLi 1-Butyllithium
NaOAc Sodium acetate
NMR Nuclear magnetic resonance
NMP N-Methyl pyrrolidinone
nBuLi 1-Butyl lithium
o.n. Over night
RT, rt, r.t. Room temperature
TEA Triethylamine
THF Tetrahydrofurane
nBu normal Butyl
OMs Mesylate or methane sulfonate ester
OTs Tosylate, toluene sulfonate or 4-methylbenzene sulfonate ester
PCC Pyridinium chlorochromate
PPTS Pyridinium p-toluenesulfonate
TBAF Tetrabutylammonium fluoride
pTsOHp-Toluenesulfonic acid
SPE Solid phase extraction (usually containing silica gel for mini-chromatography)
sat. Saturated
GP Protecting group
mins minutes Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

Synthetic procedures for several carboxylic acid intermediates in the following Examples may be found in International Patent Application Number PCT/US2011/027328, filed Mar. 5, 2011 and published as WO 2011/109799, which is hereby incorporated by reference in its entirety. Synthetic process for some compounds are given in the schemes below. In a similar manner the other compounds can be synthesized:

EXPERIMENTAL

Example 1

Synthesis of (Z)-2-(2-(3-(3-chlorophenyl)-1H-1,2,4-triazol-1-yl)vinyl)-1,3,4-oxadiazole (I-26)

Synthesis of (Z)-3-(3-(3-chlorophenyl)-1H-1,2,4-triazol-1-yl)acrylic acid

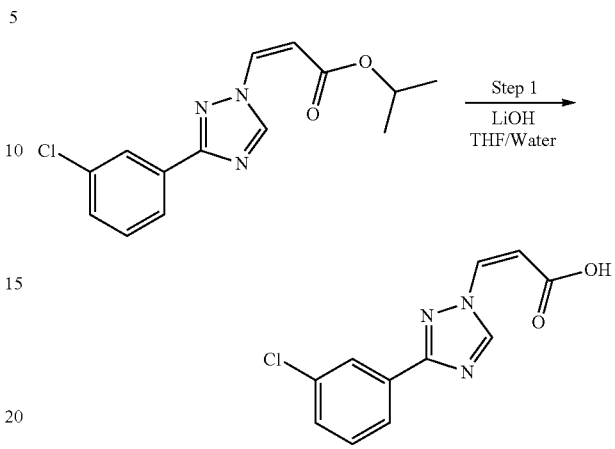

In 3-neck 100 mL RBF, (Z)-isopropyl 3-(3-(3-chlorophenyl)-1H-1,2,4-triazol-1-yl)acrylate (1.0 g, 1 eq.) was mixed with THF-Water (1:1) (20 mL, 20 Vol.) and LiOH (0.288 g, 2.0 eq.) was added. The reaction mixture was stirred at RT for 2-3 h. Reaction completion was monitored on TLC using neat ethyl acetate as mobile phase. Reaction mixture was quenched into the ice-water slurry (50 mL) and acidified with approximately 5 N HCl to 4 PH. Compound was extracted in the ethylacetate (50 mL×3) and organic layer was washed with brine solution (50 mL×3) followed by drying using anhydrous sodium sulphate. Organic layer was concentrated under reduced pressure to afford 0.7 g of pure (Z)-3-(3-(3-chlorophenyl)-1H-1,2,4-triazol-1-yl)acrylic acid. Yield (81.8%). LC/MS: 250.0

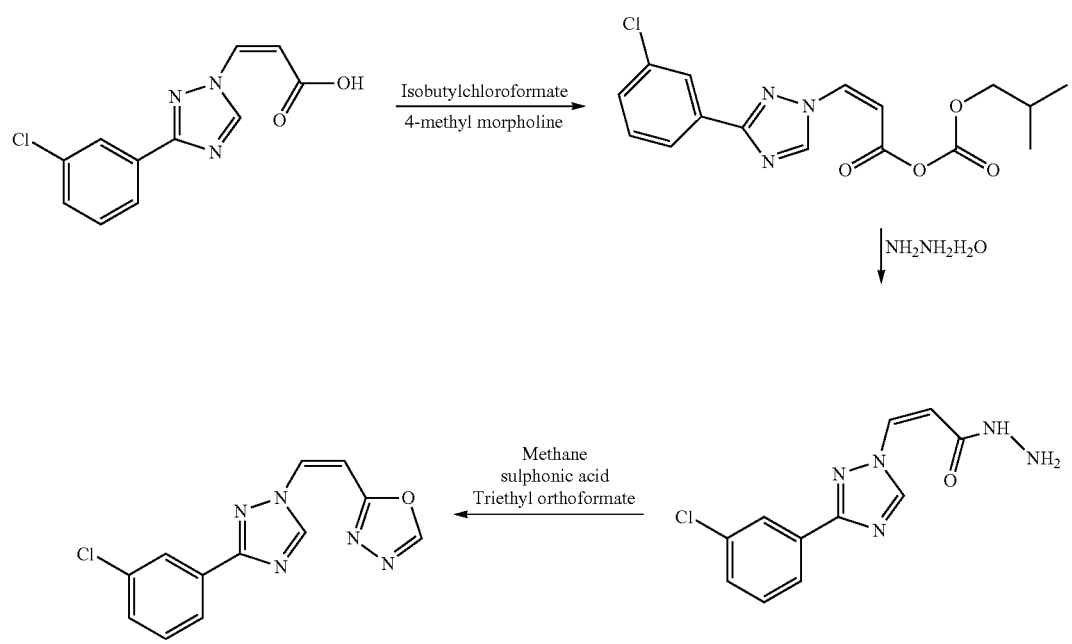

Synthesis of (Z)-3-(3-(3-chlorophenyl)-1H-1,2,4-triazol-1-yl)acrylic (isobutyl carbonic) anhydride

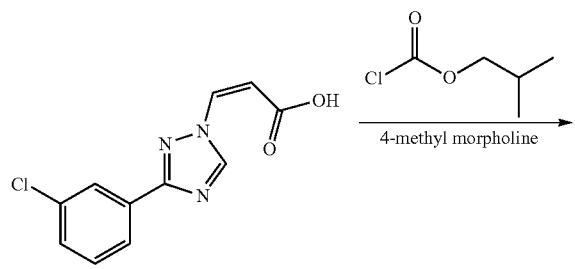

In a 3-neck 25 mL round-bottomed flask, (Z)-3-(3-(3-chlorophenyl)-1H-1,2,4-triazol-1-yl)acrylic acid (0.10 g, 1.0 eq.) was dissolved in of THF (16 mL) at 0° C. under $N_2$ atmosphere and 4-methyl morpholine (0.056 g, 1.4 eq.) was added followed by Isobutylchloroformate (0.085 g, 1.5 eq.). Reaction mixture was stirred at 0 C for 1 h. The progress of the reaction was monitored by TLC using MeOH: dichloromethane (1.5:8.5) as mobile phase. The reaction mass was filtered and filtrate was used without any further purification. LC/MS: 349.8.

Synthesis of (Z)-3-(3-(3-chlorophenyl)-1H-1,2,4-triazol-1-yl)acrylohydrazide

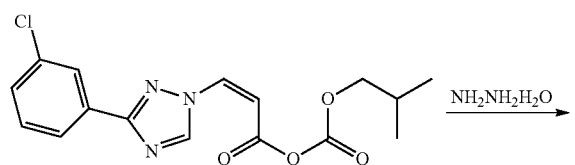

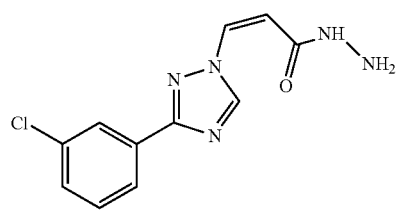

In a 3-neck 25 mL round-bottomed flask, (Z)-3-(3-(3-chlorophenyl)-1H-1,2,4-triazol-1-yl)acrylic (isobutyl carbonic) anhydride (0.140 g, 1.0 eq.) (mother liquor of previous step) and hydrazine hydrate (0.114 g, 5.6 eq.) was slowly mixed at 0° C. under $N_2$ atmosphere added. Reaction mixture was further stirred at 0° C. for 1 h. The progress of reaction was monitored by TLC using ethylacetate: n-hexane (1:1) as mobile phase. The resulting yellow reaction mass was poured into ice-water slurry (50 mL) and compound was extracted with ethylacetate (3×20 mL). Organic layer was washed with brine solution followed by drying using anhydrous sodium sulphate. Organic layer was concentrated under reduced pressure to afford 0.180 g of crude (Z)-3-(3-(3-chlorophenyl)-1H-1,2,4-triazol-1-yl)acrylohydrazide, which was used without further purification. LC/MS: 263.8.

Synthesis of (Z)-2-(2-(3-(3-chlorophenyl)-1H-1,2,4-triazol-1-yl)vinyl)-1,3,4-oxadiazole (I-26)

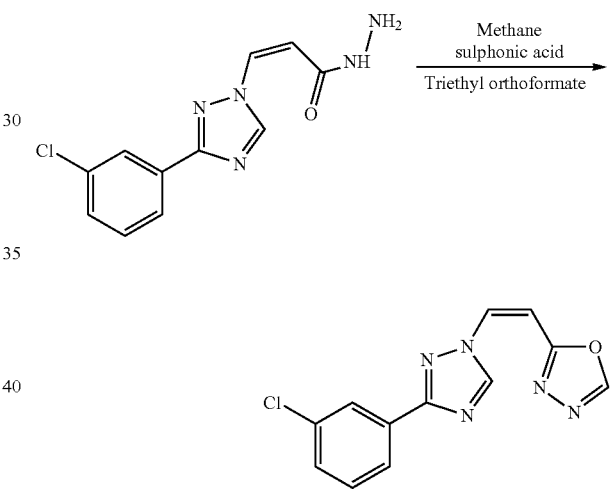

In a 3-neck 25 mL round-bottomed flask, (Z)-3-(3-(3-chlorophenyl)-1H-1,2,4-triazol-1-yl)acrylohydrazide (0.180 g, 1.0 eq.), triethyl orthoformate (0.2006 g, 1.9 eq.) and Methane sulphonic acid (0.009 g, 0.1 eq.) was mixed. Reaction was carried out under $N_2$ atmosphere. Reaction mixture was refluxed at 80° C. for 1 h. Completion of the reaction was monitored on TLC using ethyl acetate:n-hexane (1:1) as mobile phase. The resulting reaction mass was poured in ice-water slurry (50 mL) and extracted with ethylacetate (3×20 mL). Organic layer was washed with brine solution followed by drying using anhydrous sodium sulphate. Organic layer was concentrated under reduced pressure to afford 0.150 g of crude compound which was further purified using column chromatography to afford 0.045 g pure compound (Yield 24.2%): $^1$H NMR (400 MHz, CDCl$_3$) δ 10.21 (S, 1H), 8.5 (S, 1H), 8.18 (S, 1H), 8.05-8.06 (t, 1H), 7.50-7.53 (d, J=10.8 Hz, 1H), 7.40-7.43 (t, 1H), 6.25-6.27 (d, J=11.2 Hz, 1H): LCMS for $C_{12}H_8ClN_5O$ [M+1]$^+$ 273.68 found 273.80 at 3.336 min.

Example 2

Synthesis of (E)-2-(2-(3-(3-chlorophenyl)-1H-1,2,4-triazol-1-yl)vinyl)-1,3,4-oxadiazole (I-27)

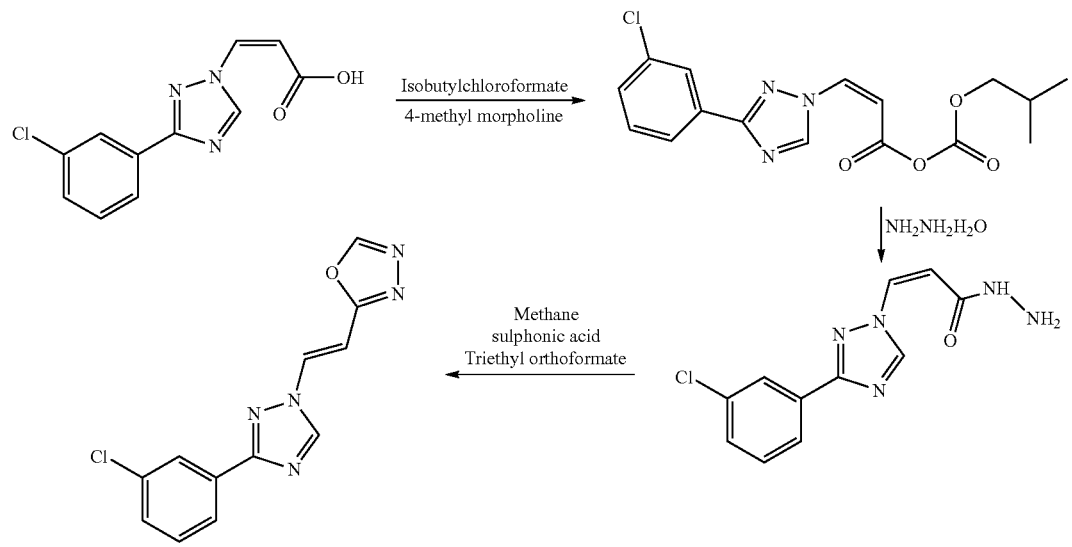

Synthesis of (Z)-3-(3-(3-chlorophenyl)-1H-1,2,4-triazol-1-yl)acrylic (isobutyl carbonic) anhydride

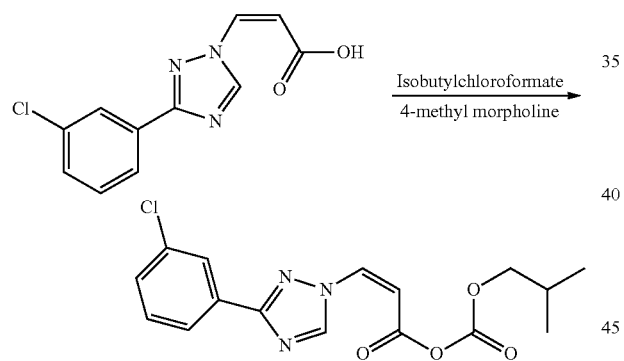

In a 3-neck 25 mL round-bottomed flask, (Z)-3-(3-(3-chlorophenyl)-1H-1,2,4-triazol-1-yl)acrylic acid (0.10 g, 1.0 eq.) was dissolved in of THF (16 mL) at 0° C. under $N_2$ atmosphere and 4-methyl morpholine (0.056 g, 1.4 eq.) was added followed by Isobutylchloroformate (0.085 g, 1.5 eq.). Reaction mixture was stirred at 0° C. for 1 h. The progress of the reaction was monitored by TLC using MeOH: dichloromethane (1.5:8.5) as mobile phase. The reaction mass was filtered and filtrate was used without any further purification.

Synthesis of (Z)-3-(3-(3-chlorophenyl)-1H-1,2,4-triazol-1-yl)acrylohydrazide

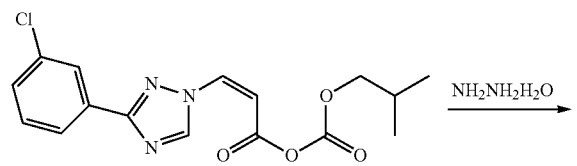

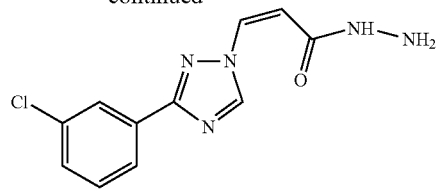

In a 3-neck 25 mL round-bottomed flask, (Z)-3-(3-(3-chlorophenyl)-1H-1,2,4-triazol-1-yl)acrylic (isobutyl carbonic) anhydride (0.140 g, 1.0 eq.) (mother liquor of previous step) and hydrazine hydrate (0.114 g, 5.6 eq.) was slowly mixed at 0° C. under $N_2$ atmosphere added. Reaction mixture was further stirred at 0° C. for 1 h. The progress of reaction was monitored by TLC using ethylacetate: n-hexane (1:1) as mobile phase. The resulting yellow reaction mass was poured into ice-water slurry (50 mL) and compound was extracted with ethylacetate (3×20 mL). Organic layer was washed with brine solution followed by drying using anhydrous sodium sulphate. Organic layer was concentrated under reduced pressure to afford 0.180 g of crude (Z)-3-(3-(3-chlorophenyl)-1H-1,2,4-triazol-1-yl)acrylohydrazide and it was used without further purification.

Synthesis of (E)-2-(2-(3-(3-chlorophenyl)-1H-1,2,4-triazol-1-yl)vinyl)-1,3,4-oxadiazole (I-27)

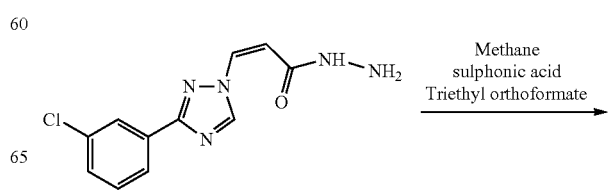

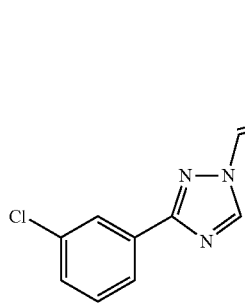

In a 3-neck 25 mL round-bottomed flask, (Z)-3-(3-(3-chlorophenyl)-1H-1,2,4-triazol-1-yl)acrylohydrazide (0.180 g, 1.0 eq) under N₂ atmosphere was added Triethyl orthoformate (0.20 g, 1.9 eq) and Methane sulphonic acid (0.009 g, 0.1 eq). Reaction mixture was refluxed at 80° C. for 4 h. Completion of the reaction was monitored on TLC using ethyl acetate:hexane (1:1) as mobile phase. The resulting reaction mass was poured in 50 mL water and extracted with 3×20 mL ethylacetate. Organic layer was washed with brine solution followed by drying using anhydrous sodium sulphate. Organic layer was concentrated under reduced pressure to afford 0.150 g of crude compound which was further purified using column chromatography to afford 0.05 g pure compound (Yield 25%); (E)-2-(2-(3-(3-chlorophenyl)-1H-1,2,4-triazol-1-yl)vinyl)-1,3,4-oxadiazole: ¹H NMR (400 MHz, DMSO) δ, 8.46 (s, 1H), 8.40 (s, 1H), 8.22 (s, 1H), 8.09-8.11 (d, 1H), 8.01-8.05 (d, J=14.0 Hz, 1H), 7.45-7.46 (d, 2H), 7.38-7.46 (d, J=14.0 Hz, 1H); LCMS for Chemical Formula: $C_{12}H_8ClN_5O$ [M+H]⁺ 273.7 found 273.92 at RT 3.412 min, purity (99.92%).

Example 3

Synthesis of (Z)-2-(2-(3-(3-chloro-5-isopropoxyphenyl)-1H-1,2,4-triazol-1-yl)vinyl)-1,3,4-oxadiazole (I-28)

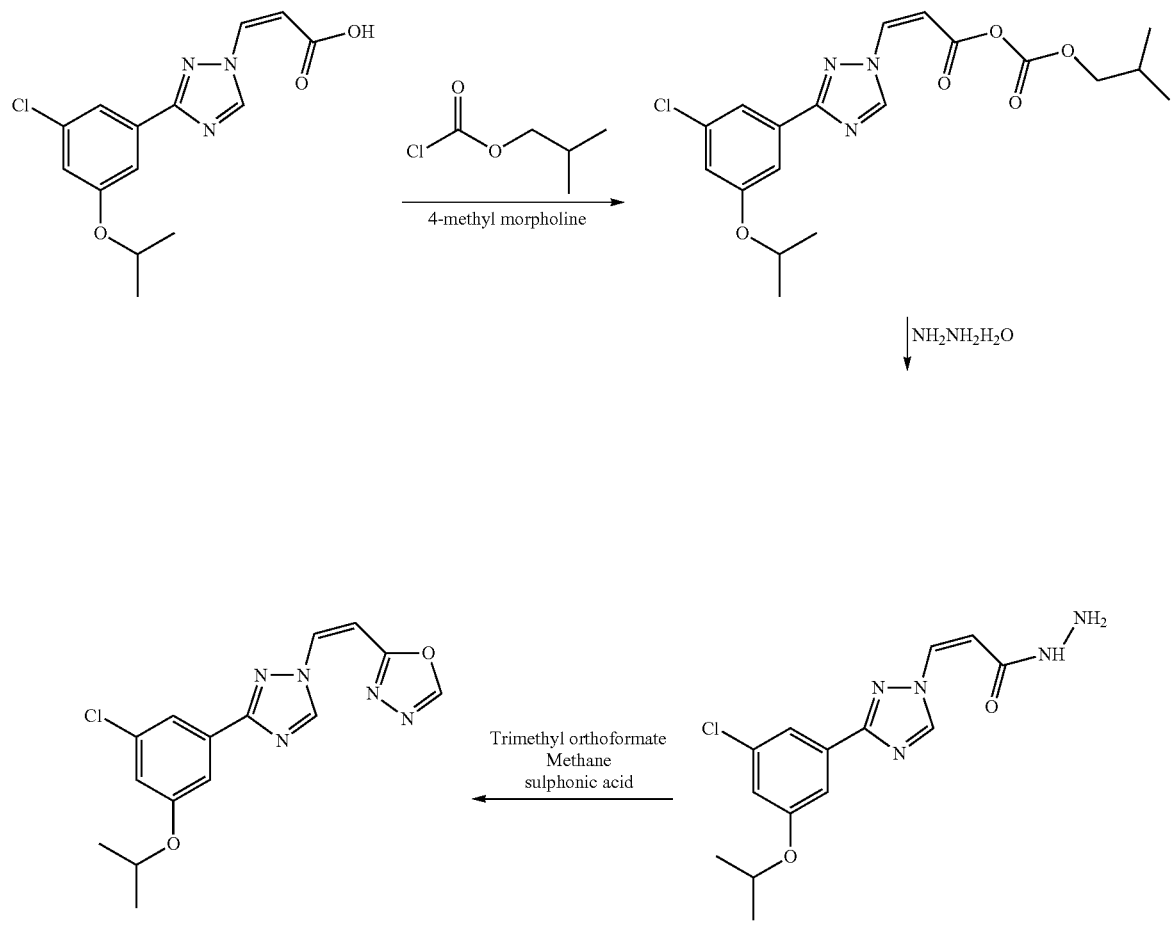

Synthesis of (Z)-3-(3-(3-chloro-5-isopropoxyphenyl)-1H-1,2,4-triazol-1-yl)acrylic (isobutyl carbonic) anhydride

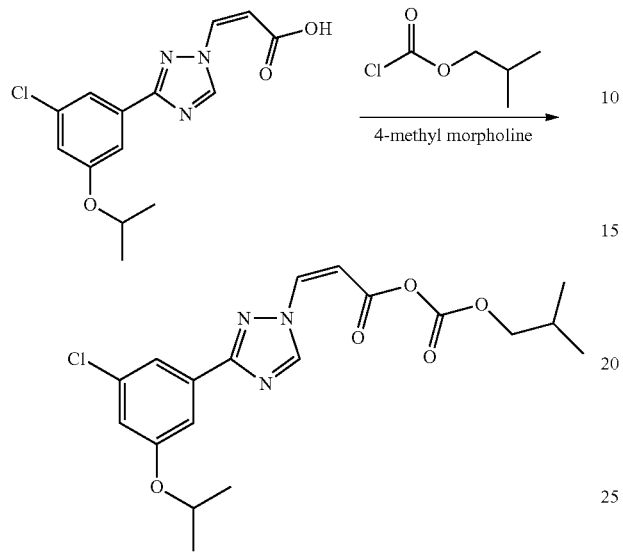

In a 25-mL, 3N RBF equipped with nitrogen inlet, and a rubber septum, (Z)-3-(3-(3-chloro-5-isopropoxyphenyl)-1H-1,2,4-triazol-1-yl)acrylic acid (0.4 g, 1.0 eq.) was dissolved in THF (10 mL). The reaction mixture was cooled at 0° C. To this reaction mixture Isobutyl chloroformate (0.284 g, 1.6 eq) and 4-methylmorpholine (0.185 g, 1.4 eq) was added. The reaction mixture was maintained at 0° C. for 1 h. The progress of the reaction was followed by TLC analysis on silica gel with 10% MeOH-DCM as mobile phase. SM $R_f$=0.20 and Product $R_f$=0.6. Reaction mixture was filtered through celite bed. The filtrate was used for next step without any work up and purification.

Synthesis of (Z)-3-(3-(3-chloro-5-isopropoxyphenyl)-1H-1,2,4-triazol-1-yl)acrylohydrazide

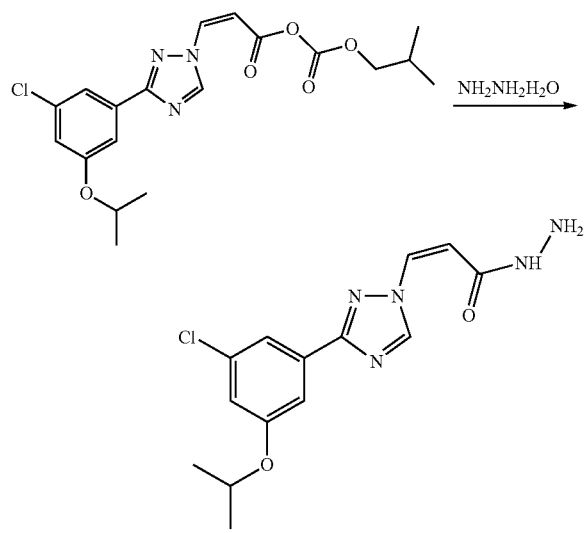

In a 25-mL, 3N round-bottomed flask equipped with nitrogen inlet, and a rubber septum, (Z)-3-(3-(3-chloro-5-isopropoxyphenyl)-1H-1,2,4-triazol-1-yl)acrylic (isobutyl carbonic) anhydride was cooled to 0° C. and added hydrazine hydrate (0.372 g, 5.7 eq.) dropwise. Reaction mixture was stirred at 0° C. for 1 h. The progress of the reaction was followed by TLC analysis on silica gel with 50% EtOAc-hexane as mobile phase. SM $R_f$=0.6 and Product $R_f$=0.4. Reaction mixture was poured into ice water (5 mL) slurry and extracted with EtOAc (3×5 mL). The combined organic layers were washed with Brine solution. (3×5 mL), dried over $MgSO_4$, filtered, and concentrated by rotary evaporation (25° C., 20 mmHg) to afford 0.3 g of Crude compound which was used for next step without any purification.

Synthesis of (Z)-2-(2-(3-(3-chloro-5-isopropoxyphenyl)-1H-1,2,4-triazol-1-yl)vinyl)-1,3,4-oxadiazole (I-28)

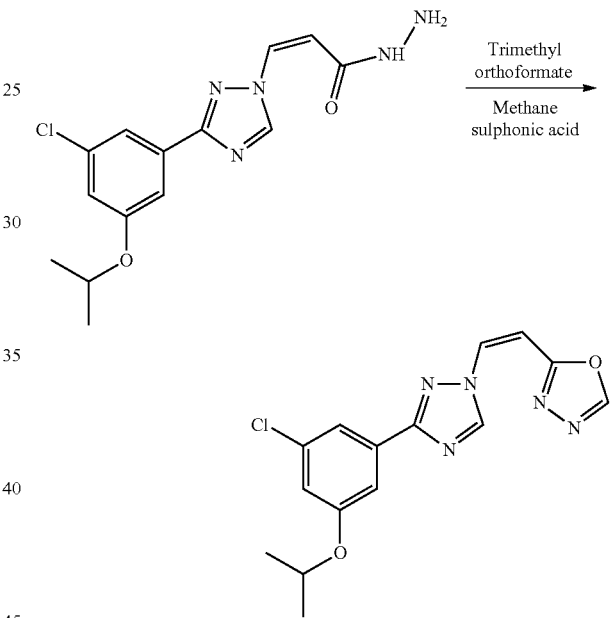

In a 25-mL, 3N round-bottomed flask equipped with nitrogen inlet, and a rubber septum, (Z)-3-(3-(3-chloro-5-isopropoxyphenyl)-1H-1,2,4-triazol-1-yl)acrylohydrazide (0.3 g, 1.0 eq.) was dissolved in THF (7.5 mL, 25V) and trimethylorthoformate (0.109 g, 1.1 eq) and added Methanesulphonic acid (0.053 g, 0.5 eq) was added into it. The Reaction mixture was refluxed at 70° C. for 2-3 h. The progress of the reaction was followed by TLC analysis on silica gel with 50% EtOAc-hexane as mobile phase. SM $R_f$=0.40 and Product $R_f$=0.5. Reaction mixture was poured into ice water (10 mL) slurry and compound was extracted with EtOAc (3×15 mL). The combined organic layers was washed with brine solution (3×15 mL), dried over $MgSO_4$, filtered, and concentrated by rotary evaporation (25° C., 20 mmHg) to afford 0.28 g of Crude compound. evaporation (25° C., 20 mmHg) to afford 3.25 g of a yellow oil. The resulting crude compound was subjected to column purification. The crude reaction mixture was purified by column chromatography using silica 60/120 using ethyl acetate:hexane as mobile phase. The column (5×10 cm) was packed in hexane and started eluting in ethyl acetate in gradient manner starting with fraction collection (25-mL fractions) from 35% to 40% ethyl acetate in hexane. Compound started eluting with 35% ethylacetate in hexane. Fraction containing such TLC profile was collected together to obtain pure compound (50 mg), Yield (16.18%). $^1$H NMR (400 MHz, CDCl$_3$) δ 10.3 (s, 1H), 8.50 (s, 1H), 8.46 (s, 1H), 7.74 (s, 1H), 7.63 (s, 1H) 7.50-7.53 (d, J=12 Hz, 1H) 7.01 (s, 1H) 6.27-6.30 (d, J=12 Hz, 1H) 4.65-4.71 (m, 1H) 1.39-1.40 (d, J=4 Hz, 6H) LCMS C$_{11}$H$_7$ClF$_3$N$_3$ (331.76)[M+1] found 331.85 at 3.910. (LCMS 99.67%).

Example 4

Synthesis of (Z)-2-(2-(3-(3-isopropoxy-5-(trifluoromethyl)phenyl)-1H-1,2,4-triazol-1-yl)vinyl)-1,3,4-oxadiazole (I-29)

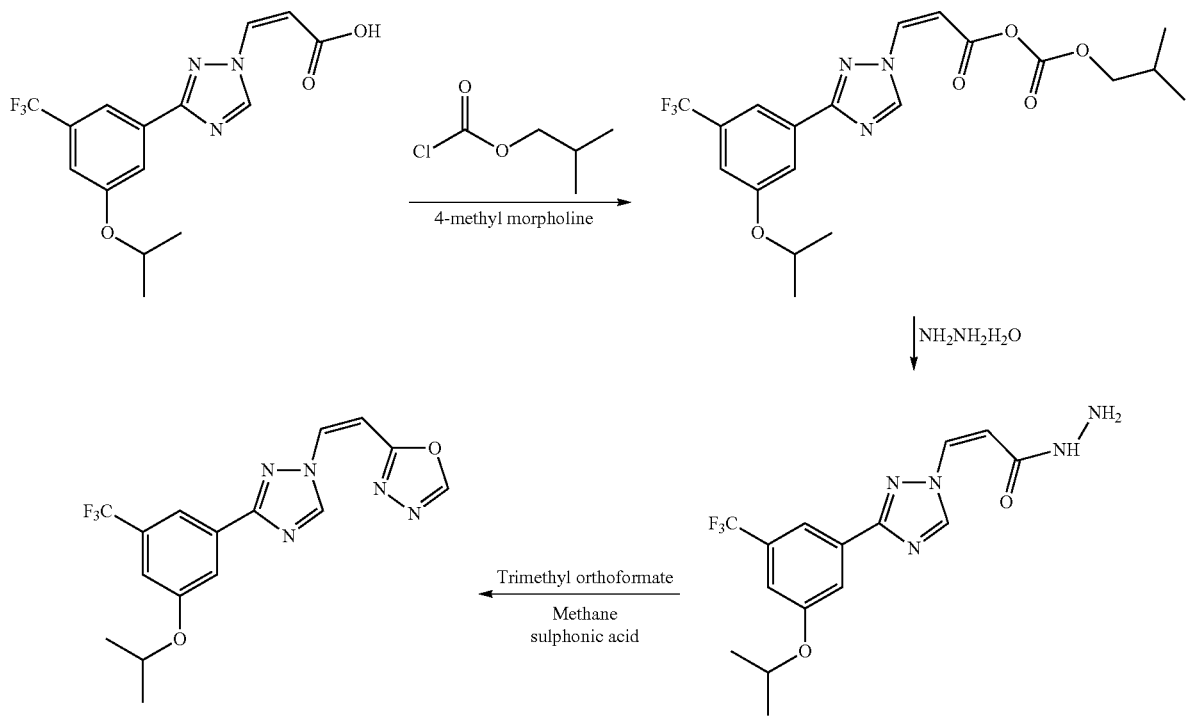

Synthesis of (isobutyl carbonic) (Z)-3-(3-(3-isopropoxy-5-(trifluoromethyl)phenyl)-1H-1,2,4-triazol-1-yl)acrylic anhydride

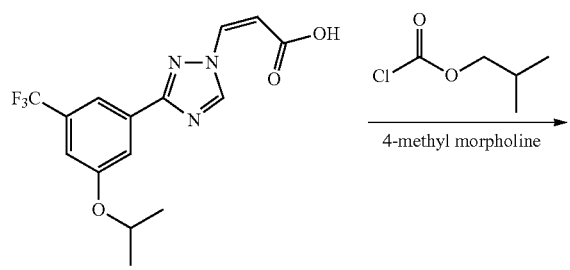

In a 25 mL, 3N round-bottomed flask equipped with nitrogen inlet, and a rubber septum, (Z)-3-(3-(3-isopropoxy-5-(trifluoromethyl)phenyl)-1H-1,2,4-triazol-1-yl)acrylic acid (0.3 g, 1.0 eq.) was dissolved in THF (7.5 mL). The reaction mixture was cooled to 0° C. To this reaction mixture was added Isobutyl chloroformate (0.192 g, 1.6 eq.) and 4-methylmorpholine (0.124 g, 1.4 eq.). The reaction mixture was maintained at 0° C. for 1 h. The progress of the reaction was followed by TLC analysis on silica gel with 10% MeOH-dichloromethane as mobile phase. SM R$_f$=0.20 and Product R$_f$=0.6. Reaction mixture was filtered through celite bed. The filtrate was used for next step without any work up and purification.

77

Synthesis of (Z)-3-(3-(3-isopropoxy-5-(trifluoromethyl)phenyl)-1H-1,2,4-triazol-1-yl)acrylohydrazide

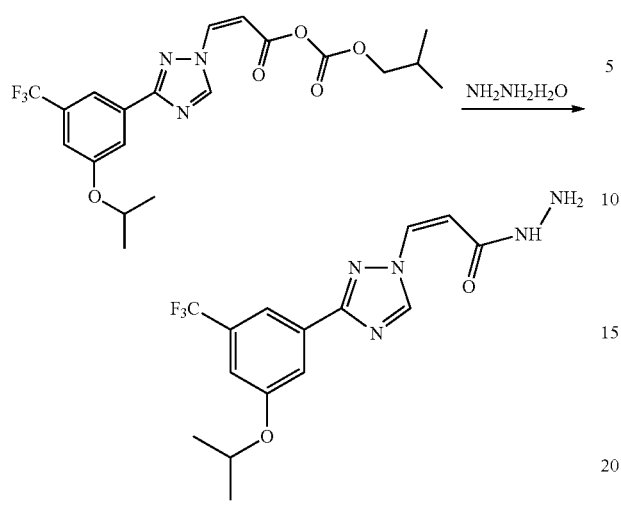

In a 25-mL, 3N round-bottomed flask equipped with nitrogen inlet, and a rubber septum, (isobutyl carbonic) (Z)-3-(3-(3-isopropoxy-5-(trifluoromethyl)phenyl)-1H-1,2,4-triazol-1-yl)acrylic anhydride was cooled at 0° C. and added Hydrazine hydrate (0.372 g, 5.7 eq.). Reaction mixture was stirred at 0° C. for 1 h. The progress of the reaction was followed by TLC analysis on silica gel with 50% EtOAc-hexane as mobile phase. SM $R_f$=0.6 and Product $R_f$=0.4. Reaction mixture was poured into ice water (5 mL) and extracted with EtOAc (3×5 mL). The combined organic layers were washed with Brine solution (3×5 mL), dried over $MgSO_4$, filtered, and concentrated by rotary evaporation (25° C., 20 mmHg) to afford 0.29 g of crude compound which was used for next step without any purification.

Synthesis of (Z)-2-(2-(3-(3-isopropoxy-5-(trifluoromethyl)phenyl)-1H-1,2,4-triazol-1-yl)vinyl)-1,3,4-oxadiazole (I-29)

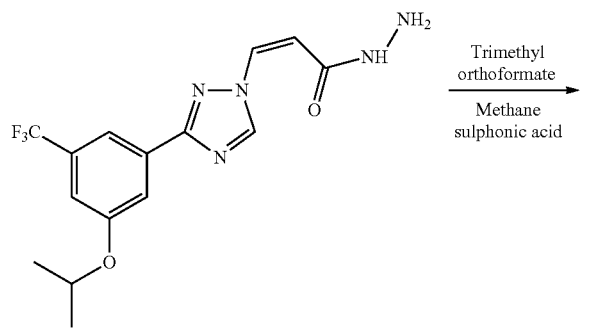

78

-continued

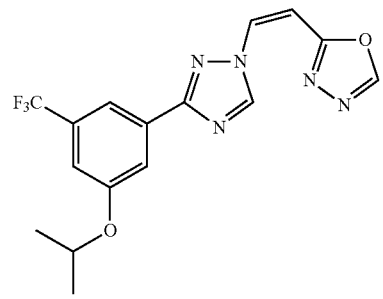

In a 25-mL, 3N round-bottomed flask equipped with nitrogen inlet, and a rubber septum, (Z)-3-(3-(3-isopropoxy-5-(trifluoromethyl)phenyl)-1H-1,2,4-triazol-1-yl)acrylohydrazide (0.29 g, 1.0 eq.) was dissolved in THF (7.5 mL, 26V), added trimethylorthoformate (0.095 g, 1.1 eq) and added methanesulphonic acid (0.048 g, 0.5 eq). The Reaction mixture was refluxed at 70° for 2-3 h. The progress of the reaction was followed by TLC analysis on silica gel with 50% EtOAc-hexane as mobile phase. SM $R_f$=0.40 and Product $R_f$=0.5. Reaction mixture was poured in to ice water (10 mL) and extracted with EtOAc (3×15 mL). The combined organic layers were washed with Brine solution. (3×15 mL), dried over $MgSO_4$, filtered, and concentrated by rotary evaporation (25° C., 20 mmHg) to afford 0.28 g of crude compound. The crude reaction mixture was purified by column chromatography using silica 60/120 using ethyl acetate:hexane as mobile phase. The column (5×10 cm) was packed in hexane and started eluting in ethyl acetate in gradient manner starting with fraction collection (25-mL fractions) from 35% to 40% ethyl acetate in hexane. Compound started eluting with 35% ethylacetate in hexane. Fraction containing such TLC profile was collected together to obtain pure compound (40 mg), Yield (13.42%). $^1$H NMR (400 MHz, $CDCl_3$) δ8.46-8.54 (d, 1H), 8 (t, 2H), 7.89 (s, 1H), 7.38-7.42 (d, 1H), 7.28 (d, 1H), 7.01-7.23 (d, 1H), 4.72-4.75 (d, J=11.6 Hz, 1H), 1.59 (d, 6H): LCMS for $C_{16}H_{14}F_3N_5O_2$ [M+1]$^+$ 365.31 found 365.89 at 3.986 min(LCMS 95.75%).

Example 5

Synthesis of (Z)-2-(2-(3-(3-methoxy-5-(trifluoromethyl)phenyl)-1H-1,2,4-triazol-1-yl)vinyl)-1,3,4-oxadiazole (I-1)

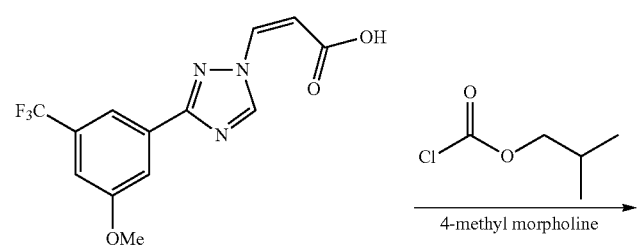

$\downarrow NH_2NH_2H_2O$

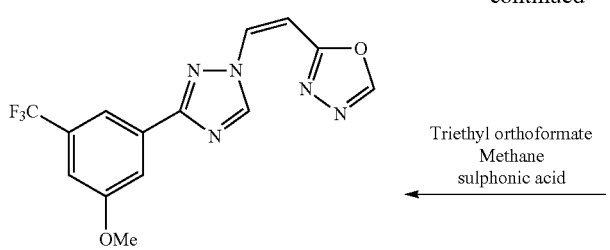

Synthesis of (isobutyl carbonic) (Z)-3-(3-(3-methoxy-5-(trifluoromethyl)phenyl)-1H-1,2,4-triazol-1-yl)acrylic anhydride

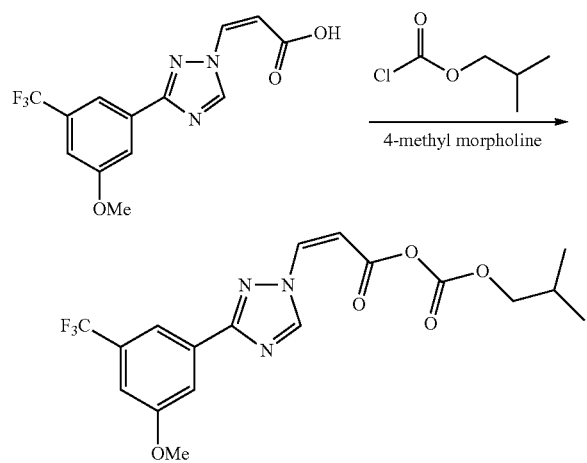

In a 50 mL, 3N round-bottomed flask equipped with nitrogen inlet, and a rubber septum, (Z)-3-(3-(3-methoxy-5-(trifluoromethyl)phenyl)-1H-1,2,4-triazol-1-yl)acrylic acid (1.0 g, 1.0 eq.) was dissolved in THF (25 mL). The reaction mixture was cooled to 0° C. To this reaction mixture was added Isobutyl chloroformate (0.697 g, 1.6 eq.) and 4-methylmorpholine (0.453 g, 1.4 eq.). The reaction mixture was maintained at 0° C. for 1 h. The progress of the reaction was followed by TLC analysis on silica gel with 10% MeOH-dichloromethane as mobile phase. SM $R_f$=0.20 and Product $R_f$=0.6. Reaction mixture was filtered through celite bed. The filtrate was used for next step without any work up and purification.

Synthesis of (Z)-3-(3-(3-methoxy-5-(trifluoromethyl)phenyl)-1H-1,2,4-triazol-1-yl)acrylohydrazide

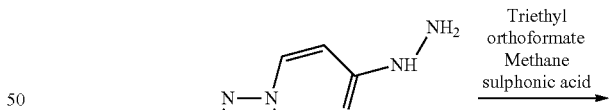

In a 50-mL, 3N round-bottomed flask equipped with nitrogen inlet, and a rubber septum, (isobutyl carbonic) (Z)-3-(3-(3-methoxy-5-(trifluoromethyl)phenyl)-1H-1,2,4-triazol-1-yl)acrylic anhydride was cooled at 0° C. and added Hydrazine hydrate (0.911 g, 5.7 eq.). Reaction mixture was stirred at 0° C. for 1 h. The progress of the reaction was followed by TLC analysis on silica gel with 50% EtOAc-hexane as mobile phase. SM $R_f$=0.6 and Product $R_f$=0.4. Reaction mixture was poured into ice water (50 mL) and extracted with EtOAc (3×50 mL). The combined organic layers were washed with brine solution (3×50 mL), dried over $MgSO_4$, filtered, and concentrated by rotary evaporation (25° C., 20 mmHg) to afford 0.920 g of Crude compound which was used for next step without further purification.

Synthesis of (Z)-2-(2-(3-(3-methoxy-5-(trifluoromethyl)phenyl)-1H-1,2,4-triazol-1-yl)vinyl)-1,3,4-oxadiazole (I-1)

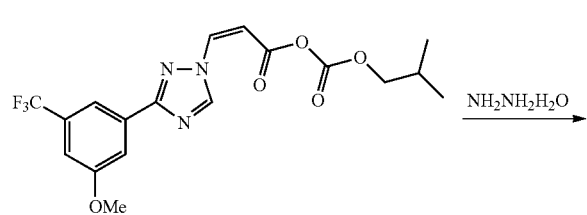

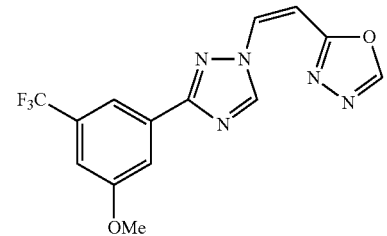

81

In a 50-mL, 3N round-bottomed flask equipped with nitrogen inlet, and a rubber septum, (Z)-3-(3-(3-methoxy-5-(trifluoromethyl)phenyl)-1H-1,2,4-triazol-1-yl)acrylohydrazide (0.920 g, 1.0 eq.) was dissolved in THF (23 mL, 25V), added trimethylorthoformate (0.328 g, 1.1 eq.) and added methanesulphonic acid (0.161 g, 0.5 eq.). The Reaction mixture was refluxed at 70° C. for 2-3 h. The progress of the reaction was followed by TLC analysis on silica gel with 50% EtOAc-hexane as mobile phase. SM $R_f$=0.40 and Product $R_f$=0.5. Reaction mixture was poured into ice water (50 mL) and extracted with EtOAc (3×50 mL). The combined organic layers were washed with brine solution (3×50 mL), dried over $MgSO_4$, filtered, and concentrated by rotary evaporation (25° C., 20 mmHg) to afford 0.60 g of crude compound. The crude reaction mixture was purified by column chromatography using silica 60/120 using ethyl acetate:hexane as mobile phase. The column (5×10 cm) was packed in hexane and started eluting in ethyl acetate in gradient manner starting with fraction collection (25-mL fractions) from 35% to 40% ethyl acetate in hexane. Compound started eluting with 35% ethylacetate in hexane. Fraction containing such TLC profile was collected together to obtain pure compound (100 mg), Yield (10.54). $^1$H NMR (400 MHz, $CDCl_3$) δ 10.25 (S, 1H), 8.5 (S, 1H), 8.04 (S, 1H), 7.89 (S, 1H), 7.51-7.54 (d, J=11.2 Hz, 1H), 7.28 (S, 1H), 7.23 (S, 1H), 6.27-6.30 (d, J=10.8 Hz, 1H), 3.35 (S, 3H): LCMS for $C_{14}H_{10}F_3N_5O_2$ [M+1]$^+$ 337.3 at 3.60 min (LCMS 93.43%).

Example 6

Synthesis of (Z)-2-(2-(3-(3-methoxy-5-(trifluoromethyl)phenyl)-1H-1,2,4-triazol-1-yl)vinyl)-5-methyl-1,3,4-oxadiazole

82

Synthesis of (isobutyl carbonic) (Z)-3-(3-(3-methoxy-5-(trifluoromethyl)phenyl)-1H-1,2,4-triazol-1-yl)acrylic anhydride

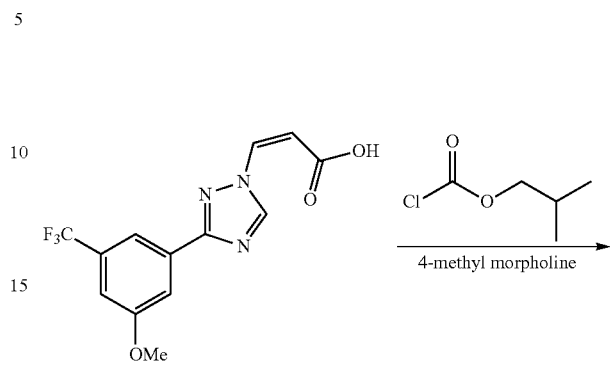

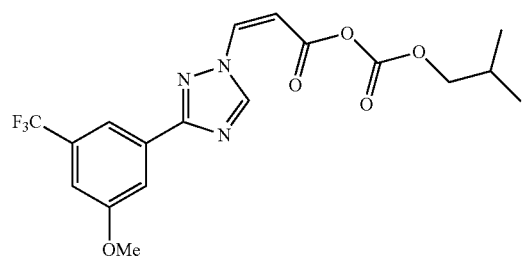

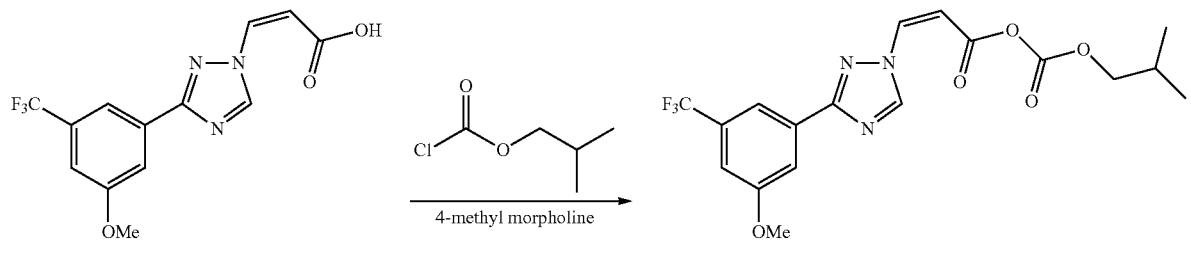

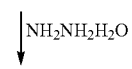

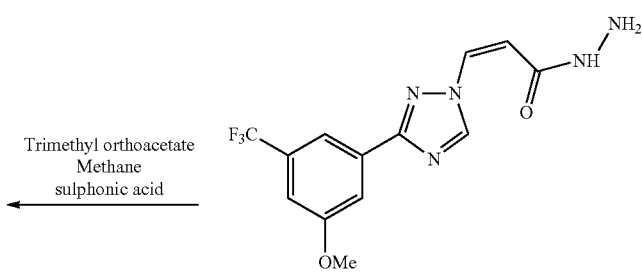

In a 500 mL, 3N round-bottomed flask equipped with nitrogen inlet, and a rubber septum, (Z)-3-(3-(3-methoxy-5-(trifluoromethyl)phenyl)-1H-1,2,4-triazol-1-yl)acrylic acid (25 g, 1.0 eq.) was dissolved in THF (200 mL). The reaction mixture was cooled to 0° C. To this reaction mixture was added Isobutyl chloroformate (24.9 mL, 2.4 eq.) and 4-methylmorpholine (18.5 mL, 2.1 eq.). The reaction mixture was maintained at 0° C. for 1 h. The progress of the reaction was followed by TLC analysis on silica gel with 10% MeOH-dichloromethane as mobile phase. SM $R_f$=0.20 and Product $R_f$=0.6. Reaction mixture was filtered through celite bed. The filtrate was used for next step without any work up and purification.

Synthesis of (Z)-3-(3-(3-methoxy-5-(trifluoromethyl)phenyl)-1H-1,2,4-triazol-1-yl)acrylohydrazide

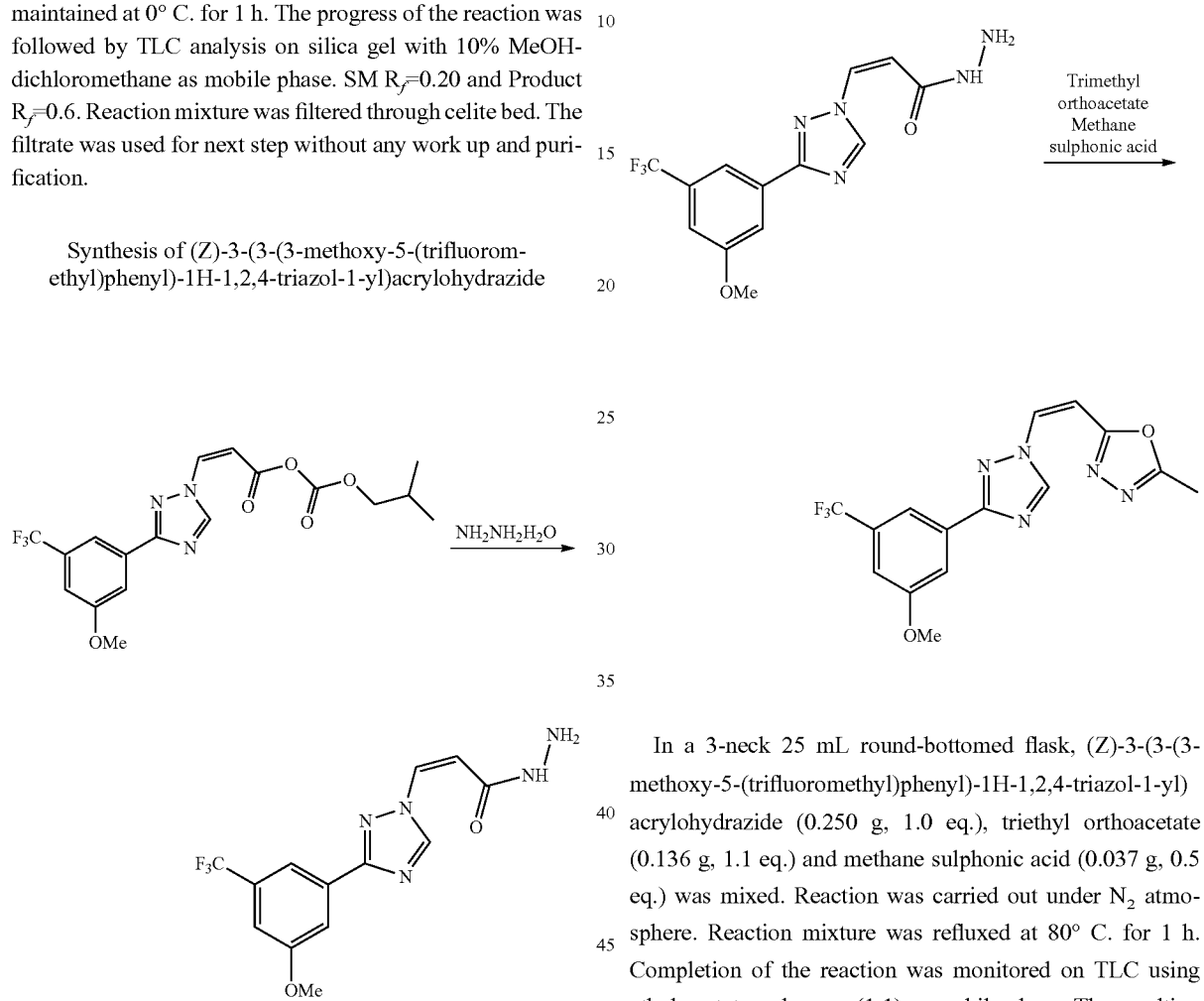

Synthesis of (Z)-2-(2-(3-(3-methoxy-5-(trifluoromethyl)phenyl)-1H-1,2,4-triazol-1-yl)vinyl)-5-methyl-1,3,4-oxadiazole (I-2)

In a 500-mL, 3N round-bottomed flask equipped with nitrogen inlet, and a rubber septum, (isobutyl carbonic) (Z)-3-(3-(3-methoxy-5-(trifluoromethyl)phenyl)-1H-1,2,4-triazol-1-yl)acrylic anhydride was cooled at 0° C. and added hydrazine hydrate (22.32 mL, 5.7 eq.). Reaction mixture was stirred at 0° C. for 1 h. The progress of the reaction was followed by TLC analysis on silica gel with 10% MeOH-dichloromethane as mobile phase. SM $R_f$=0.6 and Product $R_f$=0.4. Reaction mixture was filtered through celite bed. Filtrate was poured into ice water (5000 mL) and extracted with EtOAc (3×500 mL). The combined organic layers were washed with brine solution (3×50 mL), dried over MgSO$_4$, filtered, and concentrated by rotary evaporation (25° C., 20 mmHg) to afford 0.920 g of crude compound which was used for next step without further purification.

In a 3-neck 25 mL round-bottomed flask, (Z)-3-(3-(3-methoxy-5-(trifluoromethyl)phenyl)-1H-1,2,4-triazol-1-yl) acrylohydrazide (0.250 g, 1.0 eq.), triethyl orthoacetate (0.136 g, 1.1 eq.) and methane sulphonic acid (0.037 g, 0.5 eq.) was mixed. Reaction was carried out under N$_2$ atmosphere. Reaction mixture was refluxed at 80° C. for 1 h. Completion of the reaction was monitored on TLC using ethyl acetate: n-hexane (1:1) as mobile phase. The resulting reaction mass was poured in ice-water slurry (50 mL) and extracted with ethylacetate (3×20 mL). Organic layer was washed with brine solution followed by drying using anhydrous sodium sulphate. Organic layer was concentrated under reduced pressure to afford 0.155 g of crude compound which was further purified using column chromatography to afford 0.044 g pure compound (Yield 24.2%); (Z)-2-(2-(3-(3-methoxy-5-(trifluoromethyl)phenyl)-1H-1,2,4-triazol-1-yl)vinyl)-5-methyl-1,3,4-oxadiazole: $^1$H NMR (400 MHz, DMSO) δ, 9.47 (s, 1H), 7.81 (s, 1H), 7.76 (s, 1H), 7.70-7.67 (d, J=10.4 Hz, 1H), 7.39 (s, 1H), 6.60-6.57 (d, J=10 Hz, 1H), 4.21 (s, 3H), 3.38 (s, 3H); LCMS for Chemical Formula: $C_{15}H_{12}F_3N_5O_2$ [M+H]$^+$ 351.28. found 351.82 at RT 3.66 min, purity (97.78%).

Example 7
Synthesis of (Z)-2-(2-(3-(2-chloro-6-methoxypyridin-4-yl)-1H-1,2,4-triazol-1-yl)vinyl)-1,3,4-oxadiazole (I-10)
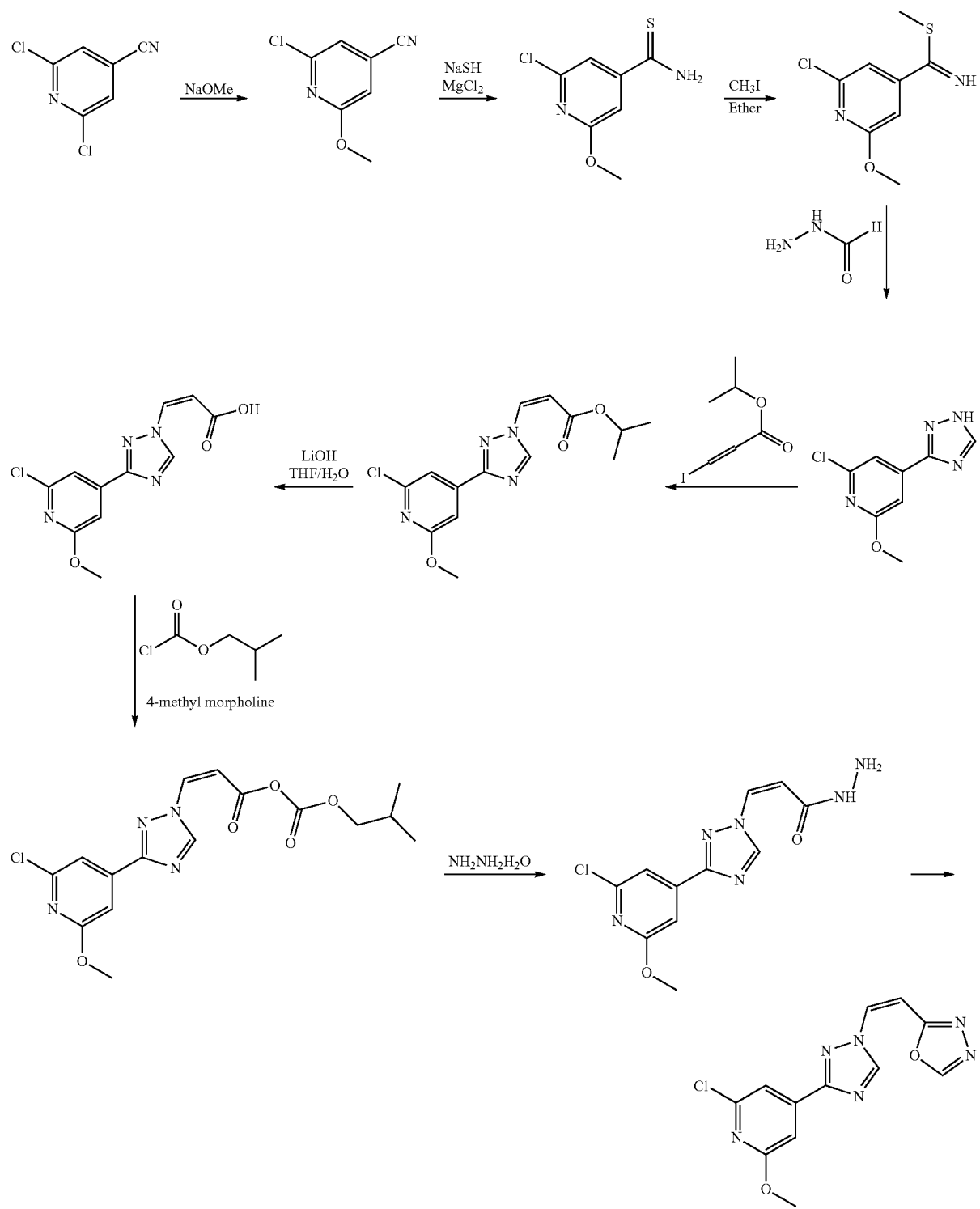

Synthesis of 2-chloro-6-methoxyisonicotinonitrile

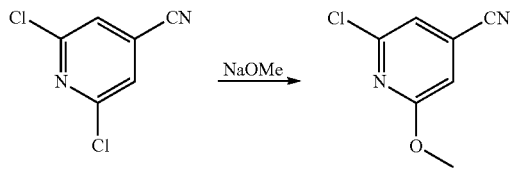

In a 25-mL, 3N round-bottomed flask equipped with thermometer pocket fitted with an nitrogen inlet and a rubber septum, NaH (0.112 g, 1.0 eq.), methanol (0.11 mL, 1.0 eq.), suspended in N-methylpyrrolidine (5 mL). The reaction mixture was stir at 25-30 C for 30 minutes. To this reaction mixture 2,6-dichloroisonicotinonitrile was added at 0-5 C. The progress of the reaction was followed by TLC analysis on silica gel with 10% EtOAc-hexane as mobile phase which shows that starting material was consumed after 2 hours staring at 0-5 C. Reaction was quenched by water, precipitate was observed that was filter by filter paper and wash with hexane to give required compound (0.51 g, crude). Reaction was stirred for 20 min with water solid was separated and compound was collected by filtration on a Buchner funnel and washed with of hexane (30 mL); Yield: 0.51 g crude 2-chloro-6-methoxyisonicotinonitrile.

Synthesis of 2-chloro-6-methoxypyridine-4-carbothioamide

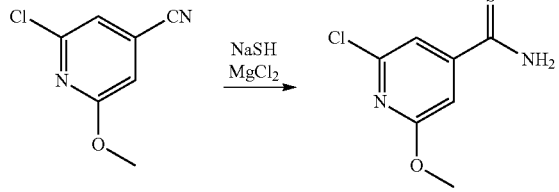

In a 25-mL, 3N round-bottomed flask equipped with Thermometer pocket fitted with nitrogen inlet and a rubber septum, 2-chloro-6-methoxyisonicotinonitrile (0.25 g, 1.0 eq.), MgCl$_2$ 6H$_2$O (0.3616 g, 1.2 eq.), NaSH (0.099 g) was dissolved in DMF (3 mL). The reaction mixture was stir at 25-30 C. The progress of the reaction was followed by TLC analysis on silica gel with 30% EtOAc-hexane as mobile phase which shows that starting material was consumed after 30 minutes staring at 25-30 C. Reaction was quenched by water, precipitate was observed that was filter by filter paper and wash with hexane to give required compound; Reaction was stirred for 10 min with water solid were separated and compound was collected by filtration on a Buchner funnel and washed with of hexane (30 mL); Yield: 0.180 g (60%); Mass: (ES+) 202.7 (M+1), 200.8 (M−1).

Synthesis of methyl 2-chloro-6-methoxypyridine-4-carbimidothioate

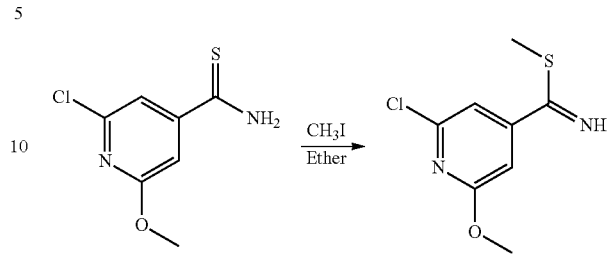

In a 100-mL, 3N round-bottomed flask equipped with Thermometer pocket fitted with water condenser, nitrogen inlet and a rubber septum, 2-chloro-6-methoxypyridine-4-carbothioamide (0.58 g, 1.0 eq.), methyl iodide (0.89 mL, 5.0 eq.) was dissolved in diethyl ether (60 mL) resulting reaction mixture was stir at RT. The progress of the reaction was followed by TLC analysis on silica gel with 20% acetone: hexane as mobile phase which shows that starting material was consumed after 15 h. Precipitate was observed that was collected by filtration on Buchner funnel. Solid was separated and compound was collected by filtration on a Buchner funnel and washed with hexane (100 mL); Yield: 0.257 g (41.44%); LCMS (%): 27.07% [M+H]$^+$ 217.92 RT: 4.216 min. (Crude).

Synthesis of 2-chloro-6-methoxy-4-(1H-1,2,4-triazol-3-yl)pyridine

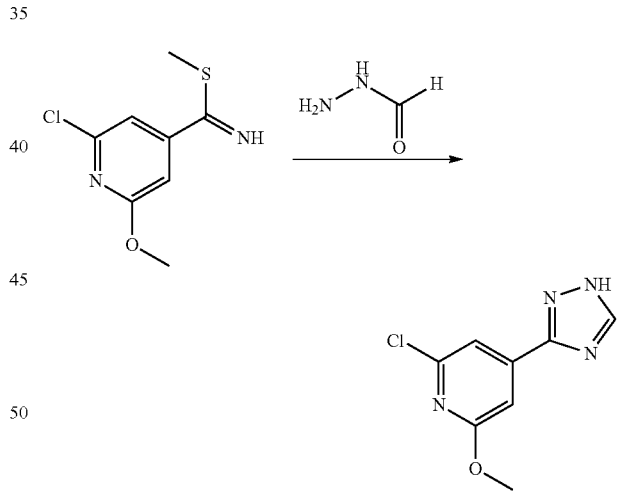

In a 50-mL, 3N round-bottomed flask equipped with thermometer pocket fitted with nitrogen inlet and a rubber septum, methyl 2-chloro-6-methoxypyridine-4-carbimidothioate (2.2 g, 1.0 eq.), formylhydrazide (1.22 g, 2.0 eq.) was dissolved in DMF (25 mL) resulting reaction mixture was stir at 25-30° C. for 15-20 min then heat it at 80-90 C. The progress of the reaction was followed by TLC analysis on silica gel with 50% EtOAc-hexane as mobile phase which shows that starting material was consumed after 5 h. Reaction was quenched by water, solid material was follow out that was collected by filtration on Buchner funnel to give crude material. The crude compound was purified by column chromatography using 60/120 silica gel and ethyl acetate in hexane as mobile phase. The column was packed in hexane and started eluting in ethyl acetate in gradient manner starting with fraction collection. The compound started eluting from 15% ethyl acetate in hexane. Fractions containing such TLC profile were collected together to obtain pure compound 0.320 g yield (14.96%); LCMS (%): 86.61% [M+H]$^+$ 210.9 RT: 2.821 min.

Synthesis of (Z)-isopropyl 3-(3-(2-chloro-6-methoxypyridin-4-yl)-1H-1,2,4-triazol-1-yl)acrylate

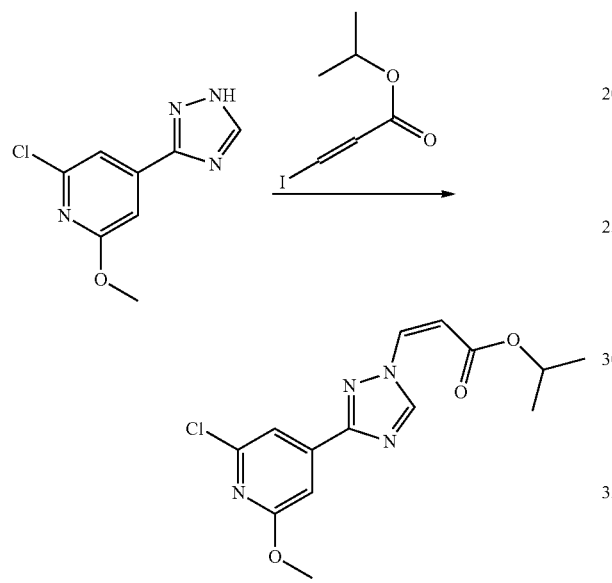

In a 25-mL, 3N round-bottomed flask equipped with Thermometer pocket fitted with nitrogen inlet and a rubber septum, 2-chloro-6-methoxy-4-(1H-1,2,4-triazol-3-yl)pyridine (0.4 g, 1.0 eq.), isopropyl 3-iodo acrylate (1.0285 g, 1.5 eq.) and NaOH (0.2285 g, 3 eq) was dissolved in DMF (4 mL) resulting reaction mixture was stir at 0-5° C. The progress of the reaction was followed by TLC analysis on silica gel with 20% EtOAc-hexane as mobile phase which shows that starting material was consumed after 3 h. Reaction was quenched by water, extract by ethyl acetate (20×3 mL), combined organic layer were dried over sodium sulfate and concentrate under reduce pressure to obtain crude material (0.600 g), crude material was subjected to column chromatography using ethyl acetate hexane as mobile phase. The crude compound was purified by column chromatography using 60/120 silica gel and ethyl acetate in hexane as mobile phase. The column was packed in hexane and started eluting in ethyl acetate in gradient manner starting with fraction collection. The compound started eluting from 4% ethyl acetate in hexane. Fractions containing such TLC profile were collected together to obtain pure compound 0.380 g yield (61.99%); LCMS (%): 99.82% [M+H]$^+$ 322.84 RT: 4.269 min; (Z)-isopropyl 3-(3-(2-chloro-6-methoxy pyridine-4-yl)-1H-1,2,4-triazole-1-yl)acrylate: 400 MHz, CDCl$_3$, δ=9.72 (s, 1H), 7.64 (s, 1H), 7.39 (s, 1H), 7.26-7.29 (d, 1H, J=10.8 Hz), 5.74-5.76 (s, 1H J=10.8 Hz), 5.11-5.17 (q, 1H), 4.00 (s, 1H), 1.32-1.34 (d, 6H); LCMS: Calculated for C$_{14}$H$_{15}$ClN$_4$O$_3$ (M+H)$^+$ 322 Found: 322 Retention time: 4.269 min (99.82%).

Synthesis of (Z)-3-(3-(2-chloro-6-methoxypyridin-4-yl)-1H-1,2,4-triazol-1-yl)acrylic acid

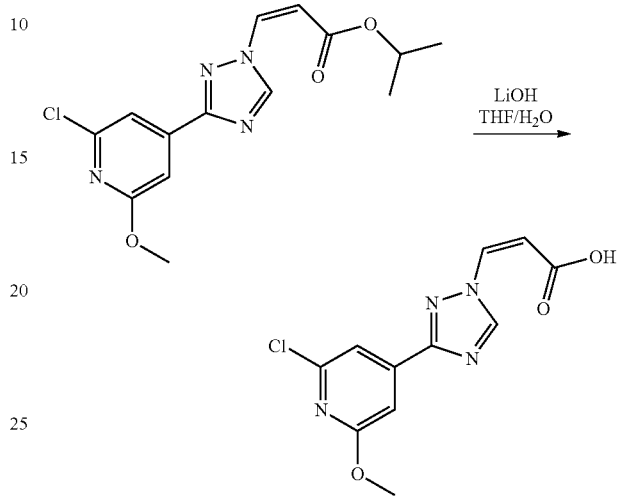

In a 25-mL, 3N round-bottomed flask equipped with Thermometer pocket and rubber septum, (Z)-isopropyl 3-(3-(2-chloro-6-methoxypyridin-4-yl)-1H-1,2,4-triazol-1-yl)acrylate (0.7 g, 1.0 eq.) dissolve in THF (4 ml) was added lithium hydroxide (0.182 g, 2.0 eq.) (dissolved in water), resulting reaction mixture was stir at RT. The progress of the reaction was followed by TLC analysis on silica gel with 20% EtOAc-hexane as mobile phase which shows that starting material was consumed after 5 h. THF was removed under reduce pressure, aqueous layer washed with ethyl acetate then acidified to 3-5 pH and extract by ethyl acetate (30 ml×3), combined organic layer were dried over sodium sulfate and concentrate under reduce pressure to obtain crude material (0.228 g), crude material was subjected to column purification. The crude compound was purified by column chromatography using 60/120 silica gel and ethyl acetate in hexane as mobile phase. The column was packed in hexane and started eluting in ethyl acetate in gradient manner starting with fraction collection. The compound started eluting from 10% ethyl acetate in hexane. Fractions containing such TLC profile were collected together to obtain pure compound 0.180 g yield (29.97%); LCMS (%): 93.46% [M+H]$^+$ 280.81 RT: 3.213 min.

Synthesis of (Z)-3-(3-(2-chloro-6-methoxypyridin-4-yl)-1H-1,2,4-triazol-1-yl)acrylic (isobutyl carbonic) anhydride

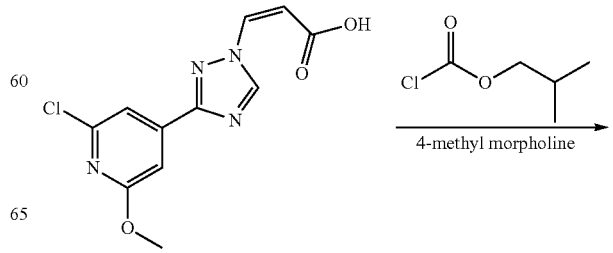

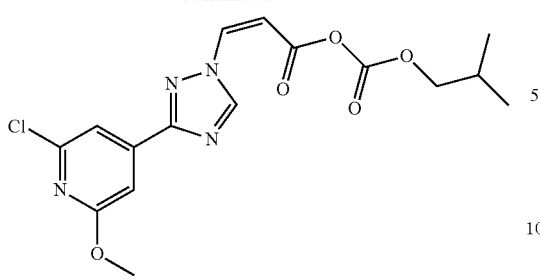

In a 25-mL, 3N round-bottomed flask equipped with Thermometer pocket fitted with nitrogen inlet and a rubber septum, (Z)-3-(3-(2-chloro-6-methoxypyridin-4-yl)-1H-1,2,4-triazol-1-yl)acrylic acid (0.18 g, 1.0 eq.), isobutyl chloroformate (0.13 mL, 1.6 eq.) and N-methyl morpholine (0.09 mL, 1.4 eq) was dissolved in THF (25 mL) resulting reaction mixture was stir at 0° C. The progress of the reaction was followed by TLC analysis on silica gel with 80% EtOAc-hexane as mobile phase which shows that starting material was consumed after 3 h. Reaction was filtered through celite bed on Buchner funnel, filtrate was directly use for next step; Yield: 0.244 g (Crude).

Synthesis of (Z)-3-(3-(2-chloro-6-methoxypyridin-4-yl)-1H-1,2,4-triazol-1-yl)acrylohydrazide

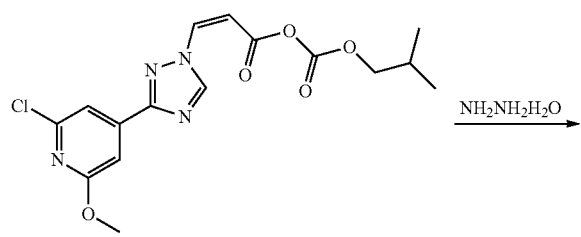

In a 25-mL, 3N round-bottomed flask equipped with Thermometer pocket fitted with condenser, nitrogen inlet and a rubber septum, (Z)-3-(3-(2-chloro-6-methoxypyridin-4-yl)-1H-1,2,4-triazol-1-yl)acrylic (isobutyl carbonic) anhydride (0.244 g, 1.0 eq.), hydrazine hydrate (0.2 mL, 5.7 eq.) was dissolved in THF (3 mL) resulting reaction mixture was stir at 0° C. The progress of the reaction was followed by TLC analysis on silica gel with 80% EtOAc-hexane as mobile phase which shows that starting material was consumed after 3 h. Reaction mass was diluted by ethyl acetate, organic layer were wash by water, dried over sodium sulfate to give crude (0.722 g) material. Crude material was directly use for next step; Yield: 0.722 g (Crude).

Synthesis of (Z)-2-(2-(3-(2-chloro-6-methoxypyridin-4-yl)-1H-1,2,4-triazol-1-yl)vinyl)-1,3,4-oxadiazole (I-10)

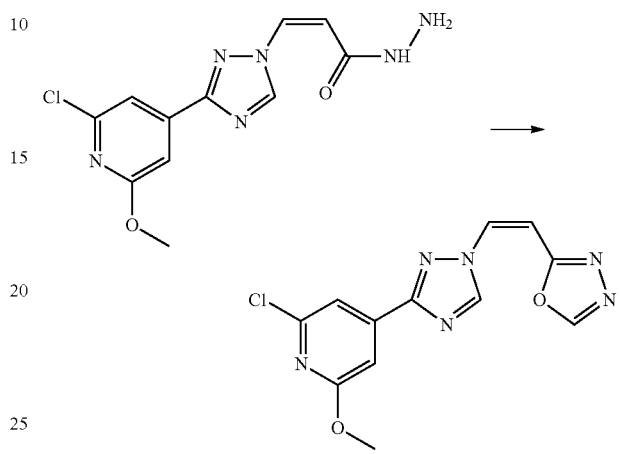

In a 100-mL, 3N round-bottomed flask equipped with Thermometer pocket fitted with nitrogen inlet, condenser and a rubber septum, (Z)-3-(3-(2-chloro-6-methoxypyridin-4-yl)-1H-1,2,4-triazol-1-yl)acrylohydrazide (0.7 g, 1.0 eq.), trimethyl orthoformate (0.3 mL, 1.1 eq.) and methane sulfonic acid (0.07 mL, 0.5 eq) was dissolved in THF (70 mL) resulting reaction mixture was stir at reflux temperature. The progress of the reaction was followed by TLC analysis on silica gel with 80% EtOAc-hexane as mobile phase which shows that starting material was consumed after 3 h. Reaction was quenched by water, solid material was observed that was filter on Buchner funnel to give crude material (0.490 g). The crude material was subjected to combiflash purification using ethyl acetate:hexane as mobile phase; Yield: 0.03 g (4.14%); (Z)-2-(2-(3-(2-chloro-6-methoxypyridine-4-yl)-1H-1,2,4-triazol-1-yl)vinyl)-1,3,4-oxadiazole: $^1$H NMR: (400 MHz, DMSO) δ=9.45 (s, 1H), 9.36 (s, 1H), 7.737-7.762 (d, J=10 Hz, 1H), 7.48 (s, 1H), 7.24 (s, 1H), 6.719-6.745 (d, J=10.4 Hz, 1H), 3.92 (s, 3H). LC-MS: Calculated for $C_{12}H_9ClN_6O_2$ (M+H)$^+$ 304.69 Found: 304.81 Retention time: 3.354 min (100%).

Example 8

Synthesis of (Z)-2-(2-(3-(3-methoxy-5-(trifluoromethyl)phenyl)-1H-1,2,4-triazol-1-yl)vinyl)pyridine (I-21)

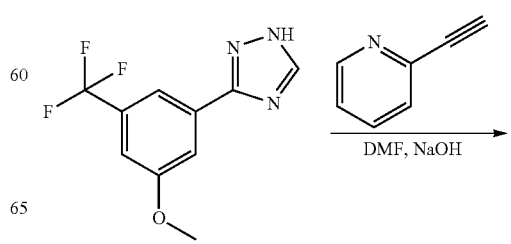

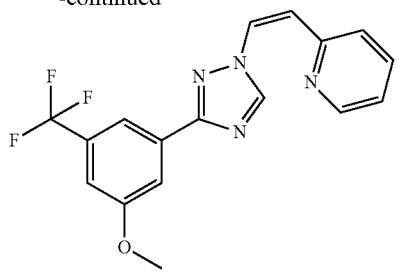

In a 25 mL, 3 Neck round-bottomed flask equipped with nitrogen inlet and a rubber septum, 3-(3-methoxy-5-(trifluoromethyl)phenyl)-1H-1,2,4-triazole (0.25 g, 1.0 eq.), 2-ethynylpyridine (0.1 ml, 1.0 eq.) and sodium hydroxide (0.1028 g, 2.5 eq.) were dissolved in DMF (5.0 mL). The reaction mixture was stirred at 75-80° C. The progress of the reaction was followed by TLC analysis on silica gel with 50% ethyl acetate-hexane as mobile phase which shows that starting material was consumed after 15 h. Reaction mixture was diluted by water and extracted with ethyl acetate, combined organic layer was dried over sodium sulphate and distilled under reduce pressure (25° C., 20 mmHg) to obtain crude material. The crude compound was purified by column chromatography using 60/120 silica gel and ethyl acetate in hexane as mobile phase. The column was packed in Hexane and started eluting in ethyl acetate in gradient manner starting with fraction collection. The compound started eluting from 18% ethyl acetate in hexane. Fractions containing such TLC profile were collected together to obtain pure compound 0.005 g; LCMS (%): Retention time 3.476 min (97.44%); (Z)-2-(2-(3-(3-methoxy-5-(trifluoromethyl)phenyl)-1H-1H-1,2,4-triazole-1-yl)vinyl)pyridine: $^1$H NMR (400 MHz, DMSO) δ: 9.61 (s, 1H), 8.67-8.68 (d, 1H, J=4.8 Hz), 8.03 (S 1H), 7.86 (s, 1H), 7.71-7.76 (doublet of triplet, 1H), 7.30-7.732 (d, 1H, J=8 Hz), 7.20 (s, 1H), 7.14-7.16 (d, 1H, J=10.4 Hz), 6.40-6.42 (d, 1H, J=10.8 Hz), 3.94 (s, 1H). LCMS for $C_{17}H_{13}F_3N_4O$ [M+H]$^+$ 1345.3 found at 346.8 at 3.476 min (LCMS: 97.44%).

Example 9

Synthesis of (Z)-2-(2-(3-(2-isopropoxy-6-(trifluoromethyl)pyridin-4-yl)-1H-1,2,4-triazol-1-yl)vinyl)-1,3,4-oxadiazole (I-30)

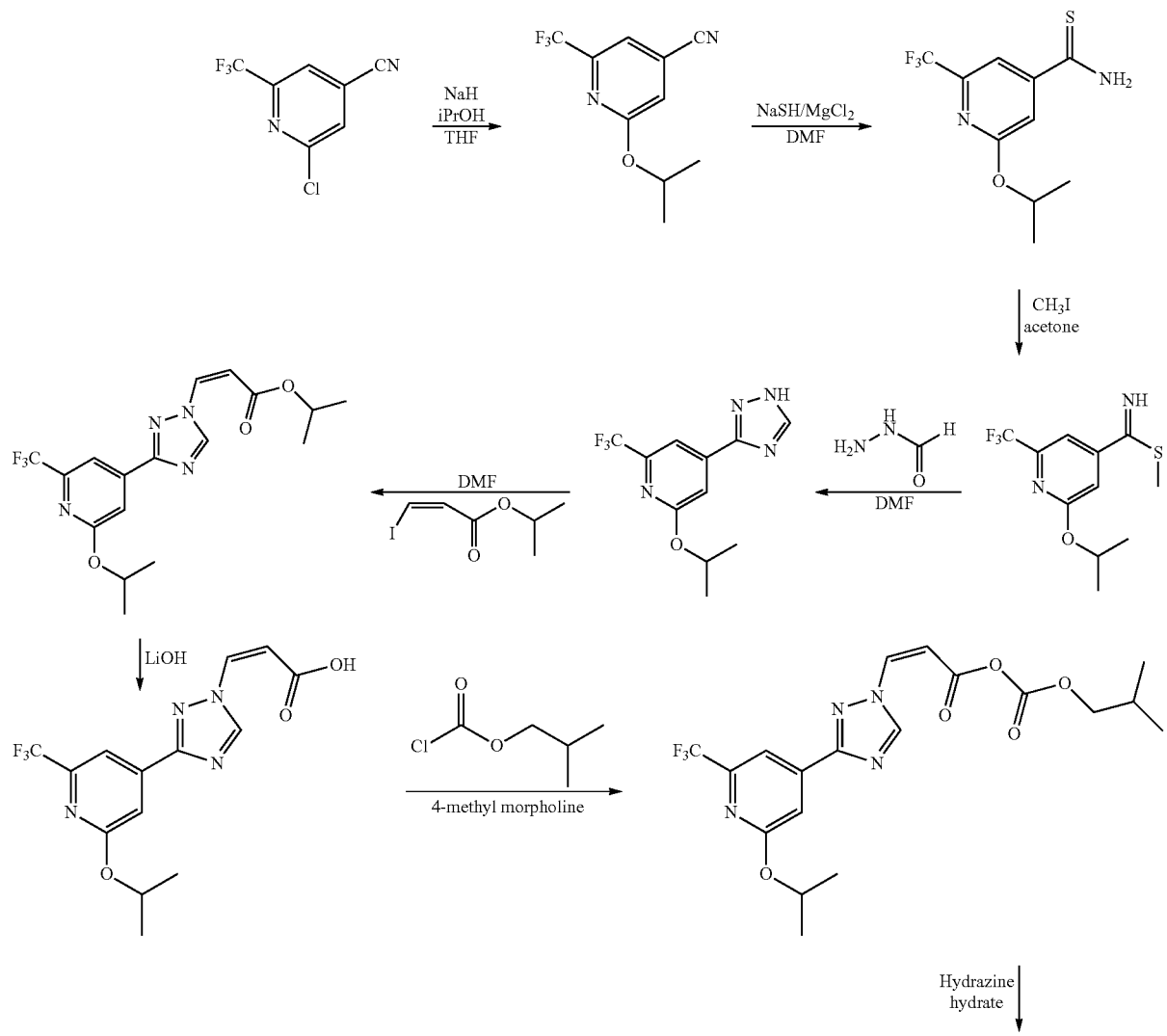

-continued

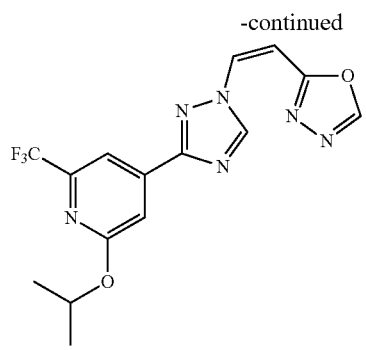
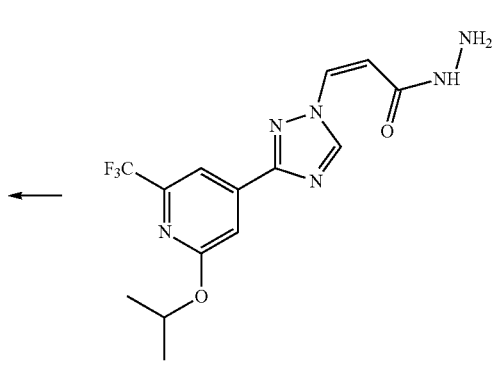

Synthesis of 2-isopropoxy-6-(trifluoromethyl)isonicotinonitrile

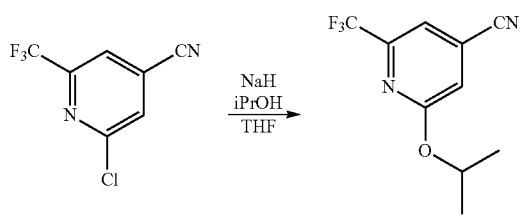 [SMILES: N#Cc1cc(Cl)nc(C(F)(F)F)c1 ; CC(C)Oc1cc(C#N)cc(C(F)(F)F)n1 ; "THF" ; "NaHiPrOH"]

In a 250-ml capacity 3 neck flask (1.39 g) NaH suspended in 100 ml THF. At 0° C. IPA (4.36 g) in 20 ml THF added in this reaction flask. Allow it to stir at RT for 3 h. At 0° C. 2-chloro-6-trifluoromethylisonicotinonitrile (10 g) in 80 mL THF added in the flask in dropwise manner. Maintained 0° C. temperature for 30 min. Completion of reaction conformed by TLC. Reaction mixture was dumped in ice water. Extract compound in ethyl acetate. Organic layer was washed by water two times & dried over $Na_2SO_4$, filtered, and concentrated by rotary evaporation (40° C., 20 mmHg) to afford 8 g of yellow oil. The resulting crude compound forwarded for next step.

Synthesis of 2-isopropoxy-6-(trifluoromethyl)pyridine-4-carbothioamide

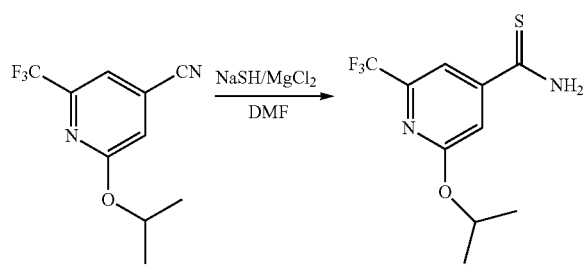

In a 500 ml capacity 3-neck round-bottomed flask attached with nitrogen bubbler & magnetic stirrer 2-isopropoxy-6-(trifluoromethyl)isonicotinonitrile (7.5 g), NaSH (2.73 g), $MgCl_2$ (9.92 g) was dissolved/suspended in 75 ml DMF at RT. Stirred it for 3 h. The completion of the reaction was confirmed by TLC with 20% EtOAc-hexane as mobile phase. Reaction mixture was poured in ice water and compound extracted with (50 mL×3) ethylacetate. Organic layer dried over $Na_2SO_4$, filtered, and concentrated by rotary evaporation to afford 7.5 g of yellow oil. The resulting crude 2-isopropoxy-6-(trifluoromethyl)pyridine-4-carbothioamide was forwarded to next step.

Synthesis of methyl 2-isopropoxy-6-(trifluoromethyl)pyridine-4-carbimidothioate

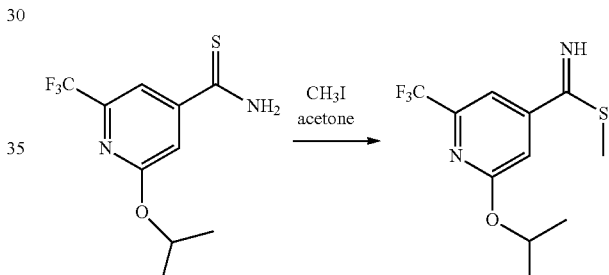

In a 100 mL capacity 3-neck round-bottomed flask attached with nitrogen bubbler & magnetic stirrer 2-isopropoxy-6-(trifluoromethyl)pyridine-4-carbothioamide (7.5 g), $CH_3I$ (10.18 g), dissolved in 75 ml acetone at RT. Reflux it for 2 h. The completion of the reaction was confirmed by TLC with 20% acetone-hexane as mobile phase. The reaction mixture was distilled & crude 2-isopropoxy-6-(trifluoromethyl) pyridine-4-carbimidothioate forwarded to next step.

Synthesis of 2-isopropoxy-4-(1H-1,2,4-triazol-3-yl)-6-(trifluoromethyl)pyridine

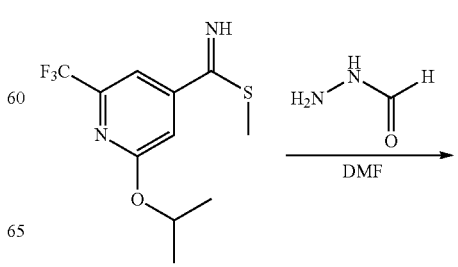

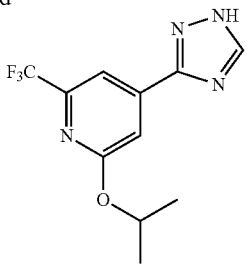

In a 50 ml capacity 3-neck round-bottomed flask attached with nitrogen bubbler, reflux condenser & magnetic stirrer methyl 2-isopropoxy-6-(trifluoromethyl)pyridine-4-carbimidothioate (5 g), formic hydrazide (0.431), dissolved in 50 ml DMF at RT for 20 min to form uncyclised form of 2-isopropoxy-4-(1H-1,2,4-triazol-3-yl)-6-(trifluoromethyl)pyridine which was confirmed by mass and on TLC as a polar spot as compared to starting material. Heated the reaction mixture at 80-90° C. for 6 h, which gave a non polar spot as compared to uncyclised form. The completion of the reaction was confirmed by TLC with 50% EtOAc-hexane as mobile phase. The reaction mixture was poured in ice water solution & extract with ethyl acetate (3×200 ml). Organic layer dried over Na$_2$SO$_4$ and concentrated to give crude product (5 g). The crude reaction mixture was purified by column chromatography using silica 60/120 using ethyl acetate:hexane as mobile phase. The column was packed in hexane and started eluting in ethyl acetate in gradient manner starting with fraction collection (25-mL fractions) from 5% to 25% ethyl acetate in hexane. Compound started eluting with 25% ethylacetate in hexane. Fraction containing such TLC profile was collected together to obtain pure 2-isopropoxy-4-(1H-1,2,4-triazol-3-yl)-6-(trifluoromethyl)pyridine (3.5 g).

Synthesis of (Z)-isopropyl 3-(3-(2-isopropoxy-6-(trifluoromethyl)pyridin-4-yl)-1H-1,2,4-triazol-1-yl) acrylate

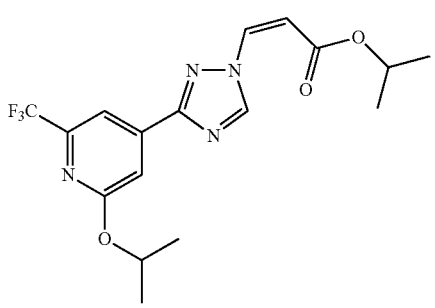

In a 50 ml capacity 3-neck round-bottomed flask attached with nitrogen bubbler, & magnetic stirrer 2-isopropoxy-4-(1H-1,2,4-triazol-3-yl)-6-(trifluoromethyl)pyridine (1 g), dissolved in 10 ml DMF at RT. Ethyl iodo acrylate (1.310 g) in DMF (1 ml) dropwise added in the reaction mixture. Then NaOH (0.291 g) added and stirred the reaction mixture for 12 h at 0° C. Completion of the reaction confirmed on TLC in 30% ethyl acetate/hexane mobile phase. Reaction gives two isomeric compounds (cis/trans). The reaction mixture was poured in ice water solution & extract with ethylacetate (3×50 mL). Organic layer dried over Na$_2$SO$_4$ & concentrate to give crude product (1.1 g). The crude reaction mixture was purified by column chromatography using silica 60/120 using ethyl acetate:hexane as mobile phase. The column was packed in hexane and started eluting in ethyl acetate in gradient manner starting with fraction collection (25-mL fractions) from 1% to 5% ethyl acetate in hexane. Compound started eluting with 5% ethyl acetate in hexane. Fractions containing such TLC profile was collected together to obtain pure (Z)-isopropyl 3-(3-(2-isopropoxy-6-(trifluoromethyl) pyridin-4-yl)-1H-1,2,4-triazol-1-yl)acrylate (500 mg).

Synthesis of (Z)-3-(3-(2-isopropoxy-6-(trifluoromethyl)pyridin-4-yl)-1H-1,2,4-triazol-1-yl)acrylic acid

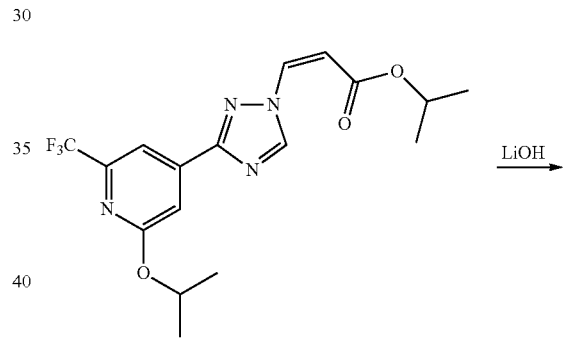

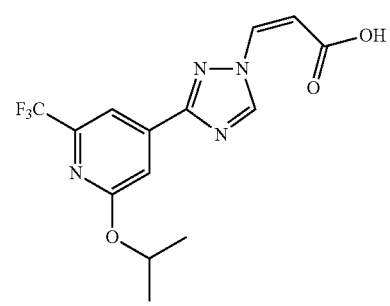

In a 50 mL 1-neck round-bottomed flask attached with magnetic stirrer (Z)-isopropyl 3-(3-(2-isopropoxy-6-(trifluoromethyl)pyridin-4-yl)-1H-1,2,4-triazol-1-yl)acrylate (250 mg), dissolved in 2.5 ml THF and 2.5 mL water at RT. Then LiOH (54.5 mg) added & stirred the reaction mixture for 2 h at RT. Completion of the reaction confirmed on TLC in 50% ethylacetate/Hexane mobile phase. The reaction mixture was poured in ice water solution, acidify with 1N HCl & extract with ethylacetate (3×50 mL). Organic layer dried over Na$_2$SO$_4$ & concentrate to give crude product (180 mg). Crude (Z)-3-(3-(2-isopropoxy-6-(trifluoromethyl)pyridin-4-yl)-1H-1,2,4-triazol-1-yl)acrylic acid was forwarded to next step.

Synthesis of (isobutyl carbonic) (Z)-3-(3-(2-isopropoxy-6-(trifluoromethyl)pyridin-4-yl)-1H-1,2,4-triazol-1-yl)acrylic anhydride

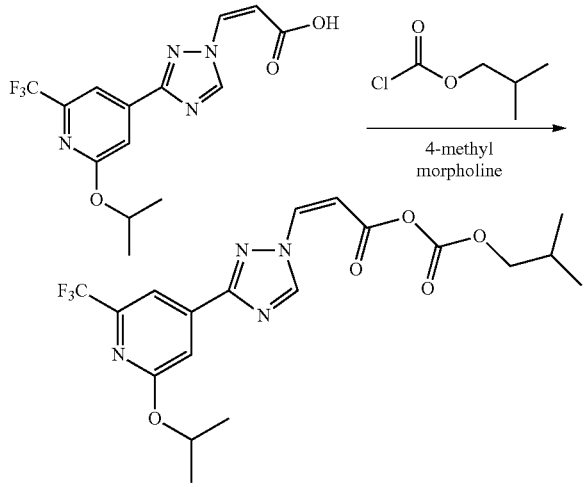

In a 50 ml capacity 1-neck round-bottomed flask attached with magnetic stirrer ((Z)-3-(3-(2-isopropoxy-6-(trifluoromethyl)pyridin-4-yl)-1H-1,2,4-triazol-1-yl)acrylic acid (170 mg), dissolved in 5 ml THF. Then N-methyl morpholine (70.55 mg) and isobutyl chloroformate (108.6 mg) added at 0° C. and stirred for 2 h. Completion of the reaction was confirmed on TLC in 10% MeOH/mobile phase. The reaction mixture was filtered under $N_2$ and carried forwarded to the next step.

Synthesis of (Z)-3-(3-(2-isopropoxy-6-(trifluoromethyl)pyridin-4-yl)-1H-1,2,4-triazol-1-yl)acrylohydrazide

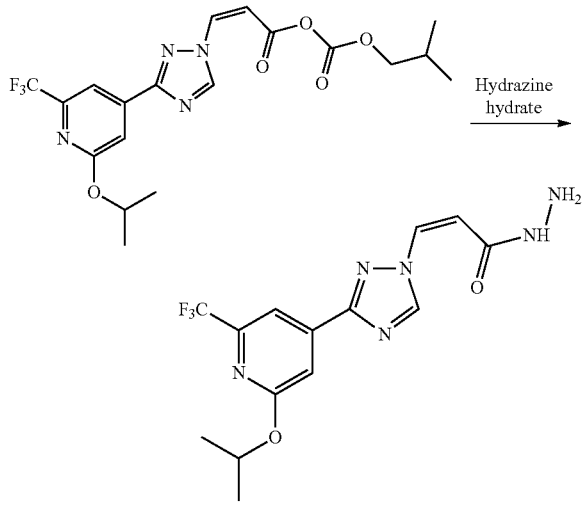

In a 50 ml capacity 1-neck round-bottomed flask attached with magnetic stirrer (isobutylcarbonic) (Z)-3-(3-(2-isopropoxy-6-(trifluoromethyl)pyridin-4-yl)-1H-1,2,4-triazol-1-yl)acrylic anhydride in THF prepared in previous step was charged at 0° C. under $N_2$. Hydrazine hydrate (99%) added dropwise. Stir it for 30 min at 0° C. Completion of the reaction confirmed on TLC in 50% ethylacetate/hexane mobile phase. The reaction mixture was poured in ice water solution, and extracted with ethylacetate (3×50 ml). Organic layer dried over $Na_2SO_4$ and concentrated to give crude product (180 mg). Crude product was forwarded to next step.

Synthesis of (Z)-2-(2-(3-(2-isopropoxy-6-(trifluoromethyl)pyridin-4-yl)-1H-1,2,4-triazol-1-yl)vinyl)-1,3,4-oxadiazole (I-30)

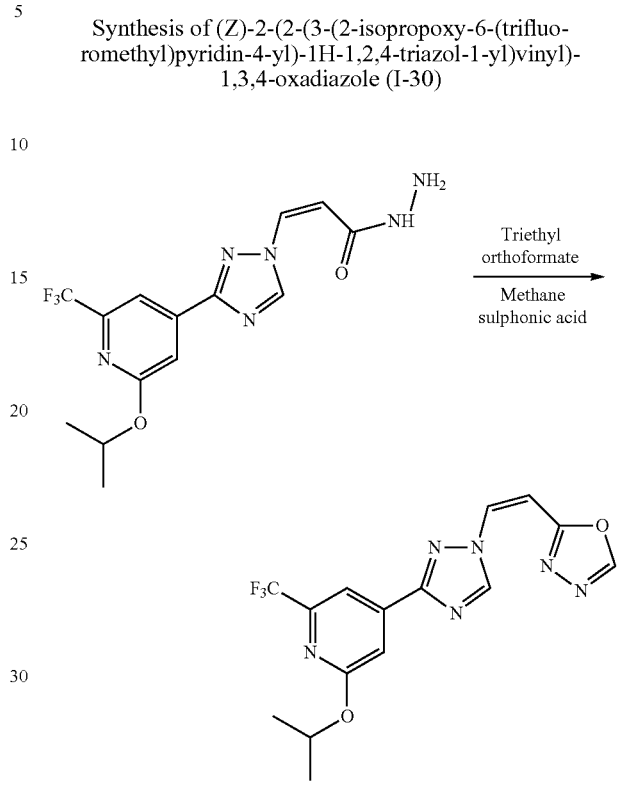

In a 50 ml capacity 1-neck round-bottomed flask attached with magnetic stirrer (Z)-3-(3-(2-isopropoxy-6-(trifluoromethyl)pyridin-4-yl)-1H-1,2,4-triazol-1-yl)acrylohydrazide (220 mg), dissolved in 3 ml THF. Then Trimethyl ortho formate and methane sulphonic acid added simultaneously at rt. Heated it for 1 h at 60-70° C. Completion of the reaction confirmed on TLC in 50% ethyl acetate/Hexane mobile phase. The reaction mixture was poured in ice water solution, and extracted with ethyl acetate (3×50 ml). Organic layer dried over $Na_2SO_4$ and concentrate to give crude product (180 mg). The crude reaction mixture was purified by column chromatography using silica 60/120 using ethyl acetate:hexane as mobile phase. The column was packed in hexane and started eluting in ethyl acetate in gradient manner starting with fraction collection (25-mL fractions) from 1% to 35% ethyl acetate in hexane. Compound started eluting with 35% ethyl acetate in hexane. Fraction containing such TLC profile was collected together to obtain pure compound (80 mg); (Z)-2-(2-(3-(2-isopropoxy-6-(trifluoromethyl)pyridine-4-yl)-1H-1,2,4-triazol-1-yl)vinyl)-1,3,4-oxadiazole; $^1$H NMR (400 MHz, CDCl$_3$) δ 10.31 (S, 1H), 8.49 (S, 2H), 7.56-7.59 (d, J=12.0 Hz, 1H), 7.34-7.36 (d, 1H), 6.24-6.27 (d, J=12.0, 1H), 5.50-5.53 (m, 1H), 1.45-1.47 (d, 6H): LCMS for $C_{15}H_{13}F_3N_6O_2$ [M+H]$^+$: 366.30 found 366.87 at RT 6.568 min, purity (99.90%).

Example 10

Synthesis of (Z)-2-(2-(3-(2-chloro-6-isopropoxypyridin-4-yl)-1H-1,2,4-triazol-1-yl)vinyl)-1,3,4-oxadiazole (I-31)

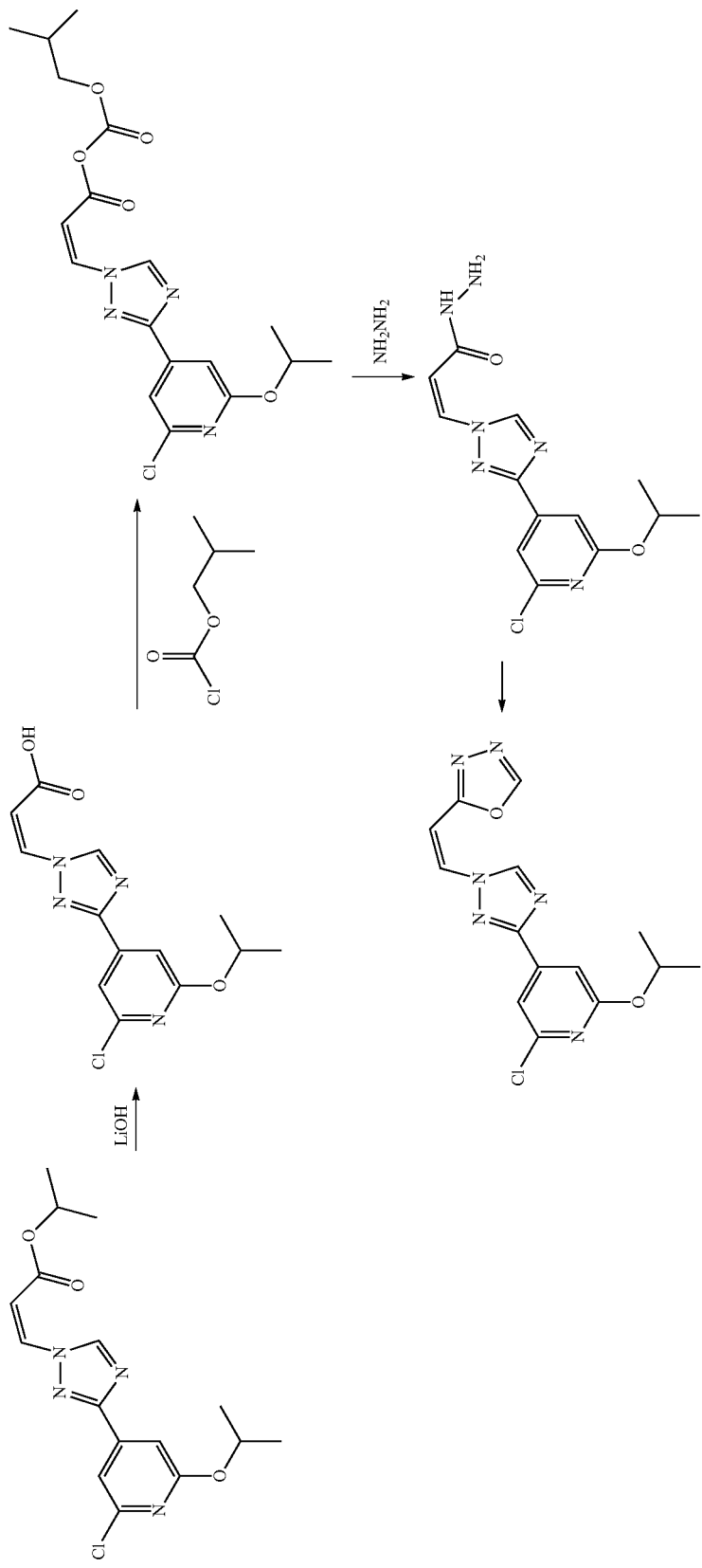

(Z)-isopropyl 3-(3-(2-chloro-6-isopropoxypyridin-4-yl)-1H-1,2,4-triazol-1-yl)acrylate, was synthesized by analogy to the synthesis of (Z)-isopropyl 3-(3-(2-chloro-6-methoxypyridin-4-yl)-1H-1,2,4-triazol-1-yl)acrylate in Example 7.

Synthesis of (Z)-3-(3-(2-chloro-6-isopropoxypyridin-4-yl)-1H-1,2,4-triazol-1-yl)acrylic acid

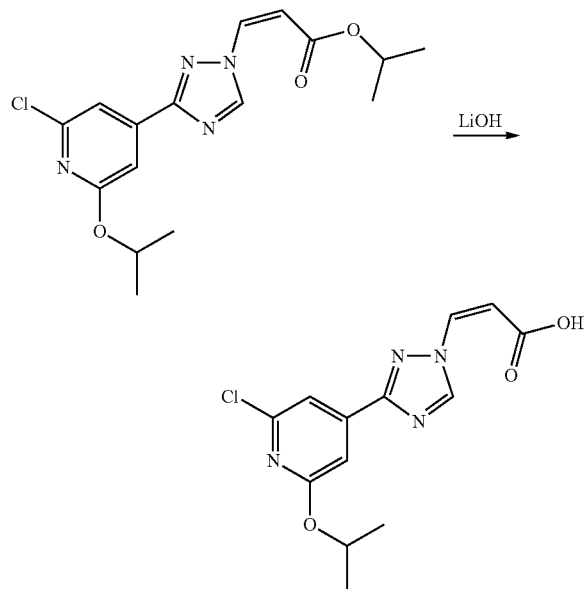

In a 250-mL, 2-neck round-bottomed flask equipped with rubber septum, (Z)-isopropyl 3-(3-(2-chloro-6-isopropoxypyridin-4-yl)-1H-1,2,4-triazol-1-yl)acrylate (2.0 g, 1.0 eq.) was dissolved in THF:Water (1:1) (20 mL: 20 mL). To this reaction mixture LiOH (0.478 g, 2 eq.) was added and reaction mixture was stirred at room temperature to 2-3 h. The progress of the reaction was followed by TLC analysis on silica gel with 20% ethyl acetate in hexane as mobile phase. Reaction mixture was quenched in water (500 mL) and acidified using dilute HCl. The aqueous layer was extracted multiple times with ethyl acetate (100 mL×3). The organic layer were washed with saturated brine solution and dried over anhydrous NaSO₄. The organic layer was concentrated under reduced pressure to obtain 1.61 g (91.7%) of desired compound.

Synthesis of (Z)-3-(3-(2-chloro-6-isopropoxypyridin-4-yl)-1H-1,2,4-triazol-1-yl)acrylic (isobutyl carbonic) anhydride

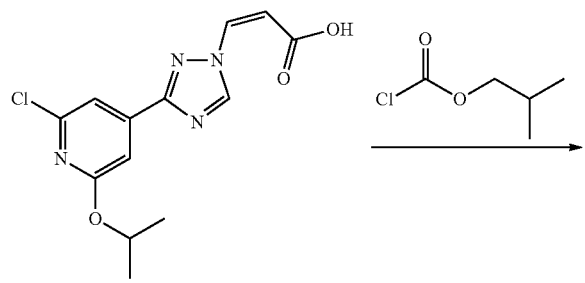

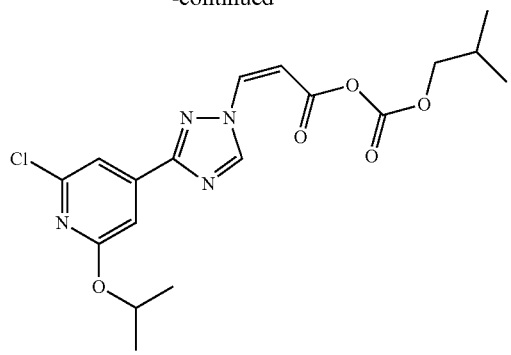

In a 100 mL, 2-neck round-bottomed flask equipped with nitrogen inlet, and a rubber septum, (Z)-3-(3-(2-chloro-6-isopropoxypyridin-4-yl)-1H-1,2,4-triazol-1-yl)acrylic acid (1.614 g, 1.0 eq.) was dissolved in THF (20 mL). The reaction mixture was cooled to 0° C. To this reaction mixture Isobutyl chloroformate (1.713 g, 2.4 eq.) and 4-methylmorpholine (1.107 g, 2.1 eq.) was added maintaining the temperature below 0° C. The reaction mixture was maintained at 0° C. for 1 h. The progress of the reaction was followed by TLC analysis on silica gel with 10% MeOH-dichloromethane as mobile phase. Reaction mixture was filtered through celite bed. The filtrate was used for next step without any work up and purification.

Synthesis of (Z)-3-(3-(2-chloro-6-isopropoxypyridin-4-yl)-1H-1,2,4-triazol-1-yl)acrylohydrazide

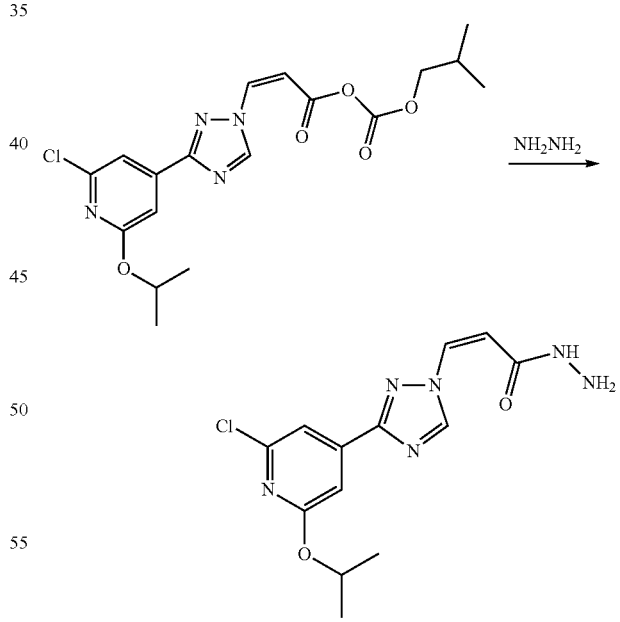

In a 100-mL, 3-neck round-bottomed flask equipped with nitrogen inlet, and a rubber septum, (Z)-3-(3-(2-chloro-6-isopropoxypyridin-4-yl)-1H-1,2,4-triazol-1-yl)acrylic (isobutyl carbonic) anhydride from previous step was cooled at 0° C. and hydrazine hydrate (1.48 g, 5.7 eq.) was added dropwise into the reaction mixture. Reaction mixture was stirred at 0° C. for 1 h. The progress of the reaction was followed by TLC analysis on silica gel with 10% MeOH-dichloromethane as mobile phase. Reaction mixture was poured into ice water (500 mL) and extracted with ethylacetate (3×100 mL). The combined organic layers were washed with saturated brine solution and dried over anhydrous NaSO$_4$. Organic layer was concentrated by rotary evaporation (25° C., 20 mmHg) to afford 1.48 g of crude (Z)-3-(3-(2-chloro-6-isopropoxypyridin-4-yl)-1H-1,2,4-triazol-1-yl) acrylohydrazide which was used for next step without any purification.

Synthesis of (Z)-2-(2-(3-(2-chloro-6-isopropoxypyridin-4-yl)-1H-1,2,4-triazol-1-yl)vinyl)-1,3,4-oxadiazole (I-31)

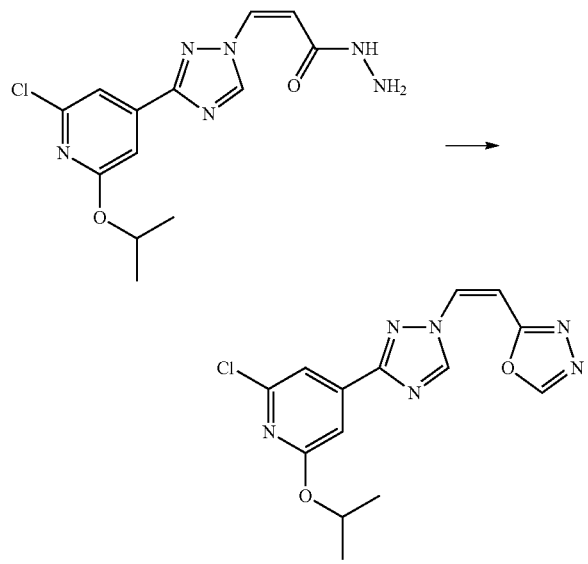

In a 100 mL, 3-neck round-bottomed flask equipped with nitrogen inlet, and a rubber septum, (Z)-3-(3-(2-chloro-6-isopropoxypyridin-4-yl)-1H-1,2,4-triazol-1-yl)acrylohydrazide (1.11 gm, 1.0 eq.) was dissolved in THF (17 mL, 15V). Trimethylorthoformate (0.364 g, 1.1 eq.) was added followed by methane sulphonic acid (0.178 g, 0.5 eq.). The Reaction mixture was refluxed at 70° C. for 2 h. The progress of the reaction was followed by TLC analysis on silica gel with 10% MeOH-dichloromethane as mobile phase. Reaction mixture was poured in to ice water (500 mL) and extracted with EtOAc (3×100 mL). The combined organic layers were washed with brine solution (3×15 mL), dried over NaSO$_4$, filtered, and concentrated by rotary evaporation (25° C., 20 mmHg) to afford 1 g of Crude compound. The crude reaction mixture was purified by column chromatography using silica 60/120 using ethyl acetate:hexane as mobile phase. The column (5×10 cm) was packed in hexane and started eluting in ethyl acetate in gradient manner starting with fraction collection (25 mL fraction each) from 35-40% ethyl acetate in hexane. Compound started eluting with 35% ethylacetate in hexane. Fraction containing such TLC profile was collected together to obtain pure compound (26 mg), Yield: 0.026 g (2.6%), $^1$H NMR: (400 MHz, DMSO) δ =10.25 (s, 1H), 8.50 (s, 1H), 7.608-7.610 (d, 1H), 7.524-7.496 (s, J=11.2, 1H), 6.359-6.360 (d, 1H), 6.316-7.288 (s, J=11.2, 1H), 5.385-5.323 (m, 1H), 1.42-1.38 (s, 6H). LC-MS: Calculated for C$_{15}$H$_{14}$ClN$_5$O$_2$(M+H)$^+$332.75 Found: 332.8 at 3.354 min (93.31%).

Example 11

Synthesis of (Z)-2-(2-(3-(3-chloro-5-(trifluoromethoxy)phenyl)-1H-1,2,4-triazol-1-yl)vinyl)-1,3,4-oxadiazole (I-32)

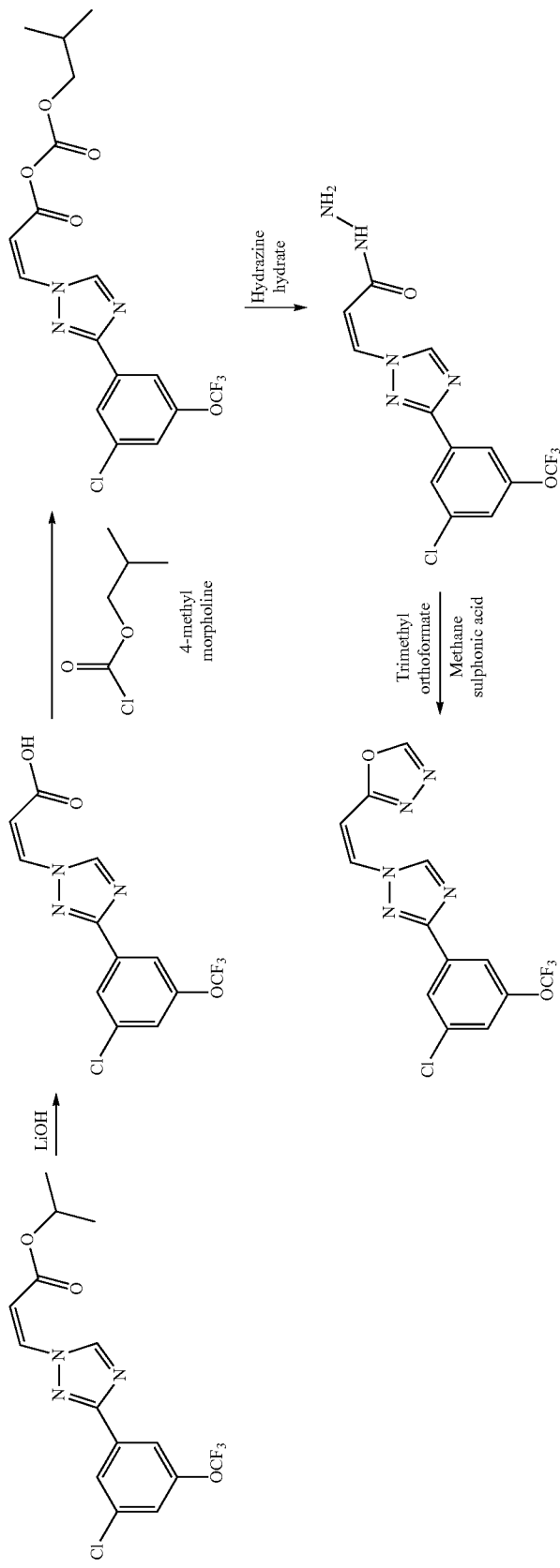

Synthesis of (Z)-3-(3-(3-chloro-5-(trifluoromethoxy) phenyl)-1H-1,2,4-triazol-1-yl)acrylic acid

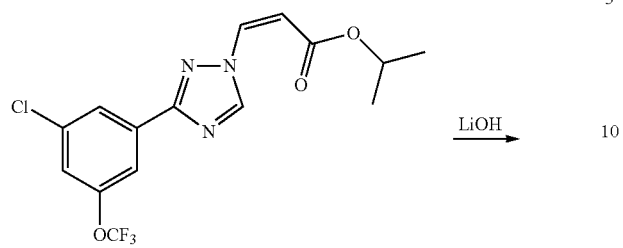

In a 100 mL, 3-neck round-bottomed flask equipped with nitrogen inlet, and a rubber septum, (Z)-isopropyl 3-(3-(3-chloro-5-(trifluoromethoxy)phenyl)-1H-1,2,4-triazol-1-yl) acrylate (0.750 g, 1.0 eq.) was dissolved in THF (30 mL, 40 V) and H$_2$O (30 mL, 40 V). The reaction mixture was added LiOH (0.419 g, 5 eq.). The reaction mixture was stirred at room temperature. The progress of the reaction was followed by TLC analysis on silica gel with 20% ethyl acetate in hexane as mobile phase. Reaction mixture was Quenched in 500 ml water and made acidic by dilute HCl. The aqueous layer was extracted with ethyl acetate. The organic layer were washed with Brine solution, dried over NaSO$_4$ and distilled under reduce pressure to obtain 0.620 g (93.23%) crude material.

Synthesis of (Z)-3-(3-(3-chloro-5-(trifluoromethoxy) phenyl)-1H-1,2,4-triazol-1-yl)acrylic (isobutyl carbonic) anhydride

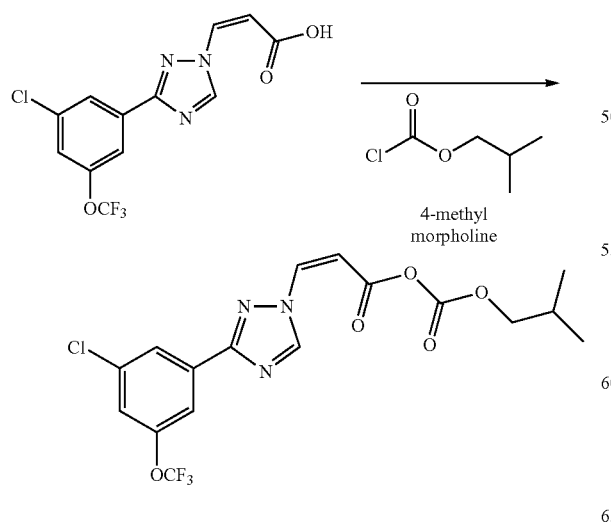

In a 100-mL, 3-Neck round-bottomed flask equipped with nitrogen inlet and a rubber septum, (Z)-3-(3-(3-chloro-5-(trifluoromethoxy)phenyl)-1H-1,2,4-triazol-1-yl)acrylic acid (0.620 g, 1.0 eq.) was dissolved in THF (25 mL). The reaction mixture was cooled at 0° C. Added isobutyl chloroformate (0.609 g, 2.4 eq.) and 4-methylmorpholine (0.393 g, 2.1 eq.). The reaction mixture was maintained at 0° C. for 1 h. The progress of the reaction was followed by TLC analysis on silica gel with 10% MeOH-dichloromethane as mobile phase. Reaction mixture was filtered through celite bed. The filtrate was used for next step without any work up and purification.

Synthesis of (Z)-3-(3-(3-chloro-5-(trifluoromethoxy) phenyl)-1H-1,2,4-triazol-1-yl)acrylohydrazide

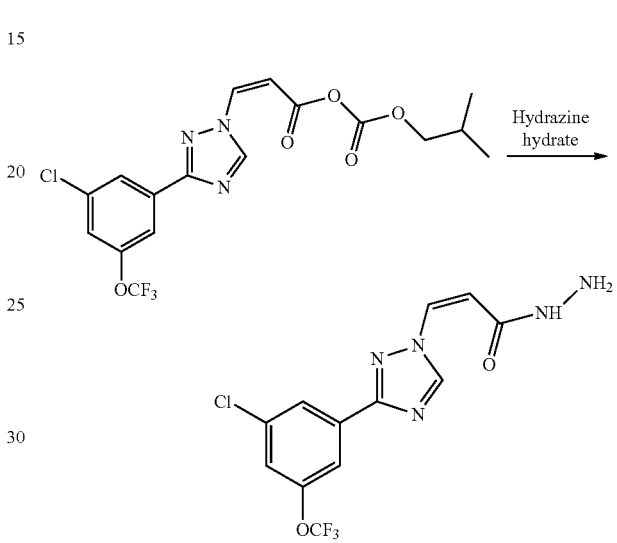

In a 100-mL, 3-neck round-bottomed flask equipped with nitrogen inlet and a rubber septum, (Z)-3-(3-(3-chloro-5-(trifluoromethoxy)phenyl)-1H-1,2,4-triazol-1-yl)acrylic (isobutyl carbonic) anhydride was cooled at 0° C. and added Hydrazine hydrate (0.527 g, 5.7 eq.). Reaction mixture was stirred at 0° C. for 1 h. The progress of the reaction was followed by TLC analysis on silica gel with 10% MeOH-dichloromethane as mobile phase. Reaction mixture was poured in to ice water (500 mL) and extracted with ethyl acetate (3×100 mL). The combined organic layers were washed with brine solution, dried over sodium sulfate, filtered and concentrated by rotary evaporation (25° C., 20 mmHg) to afford 0.597 g of crude compound which was used for next step without any purification.

Synthesis of (Z)-2-(2-(3-(3-chloro-5-(trifluoromethoxy)phenyl)-1H-1,2,4-triazol-1-yl)vinyl)-1,3,4-oxadiazole (I-32)

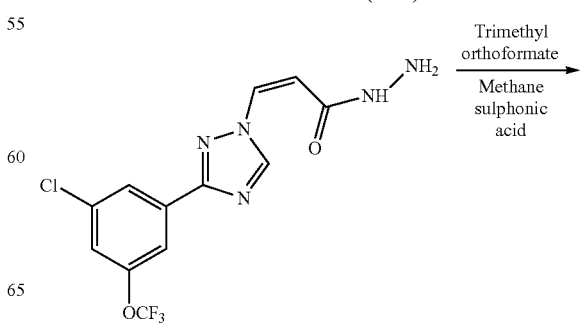

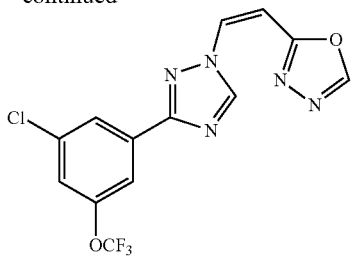

In a 100-mL, 3-neck round-bottomed flask equipped with nitrogen inlet, and a rubber septum, (Z)-3-(3-(3-chloro-5-(trifluoromethoxy)phenyl)-1H-1,2,4-triazol-1-yl)acrylohydrazide (0.537 gm, 1.0 eq.) was dissolved in THF (21 mL, 40 V), added trimethylorthoformate (0.179 g, 1.1 eq.) and added methane sulphonic acid (0.073 g, 0.5 eq.). The Reaction mixture was refluxed at 70° C. for 2 h. The progress of the reaction was followed by TLC analysis on silica gel with 10% MeOH-dichloromethane as mobile phase. Reaction mixture was poured in to ice water (500 mL) and extracted with EtOAc (3×100 mL). The combined organic layers were washed with brine solution. (3×15 mL), dried over sodium sulfate, filtered and concentrated by rotary evaporation (25° C., 20 mmHg) to afford 0.511 g of crude compound. The crude reaction mixture was purified by column chromatography using silica 60/120 using dichloromethane: Methanol as a mobile phase. The column (5×10 cm) was packed in dichloromethane and started eluting in dichloromethane in gradient manner starting with fraction collection (25-mL fractions) from 3% to 4% dichloromethane in methanol. Compound started eluting with 5% dichloromethane in methanol. Fractions containing such TLC profile were collected together to obtain pure compound (120 mg, 21.73%); (Z)-2-(2-(3-(3-chloro-5-(trifluoromethoxy)phenyl)-1H-1,2,4-triazol-1-yl)vinyl)-1,3,4-oxadiazole: 400 MHz, CDCl$_3$, δ=10.23 (s, 1H), 8.50 (s, 1H), 8.13 (s, 1H), 7.94 (s, 1H), 7.50-7.52 (d, 1H, J=11.2 Hz), 7.32 (s, 1H), 6.28-6.30 (d, 1H, J=11.2 Hz); LCMS: Calculated for C$_{13}$H$_7$ClF$_3$N$_5$O$_2$ (M+H)$^+$ 357.3 Found: 355.9 Retention time: 3.865 min (99.93%).

Example 12

Synthesis of (Z)-2-(2-(3-(3-(methylsulfonyl)-5-(trifluoromethyl)phenyl)-1H-1,2,4-triazol-1-yl)vinyl)-1,3,4-oxadiazole (I-33)

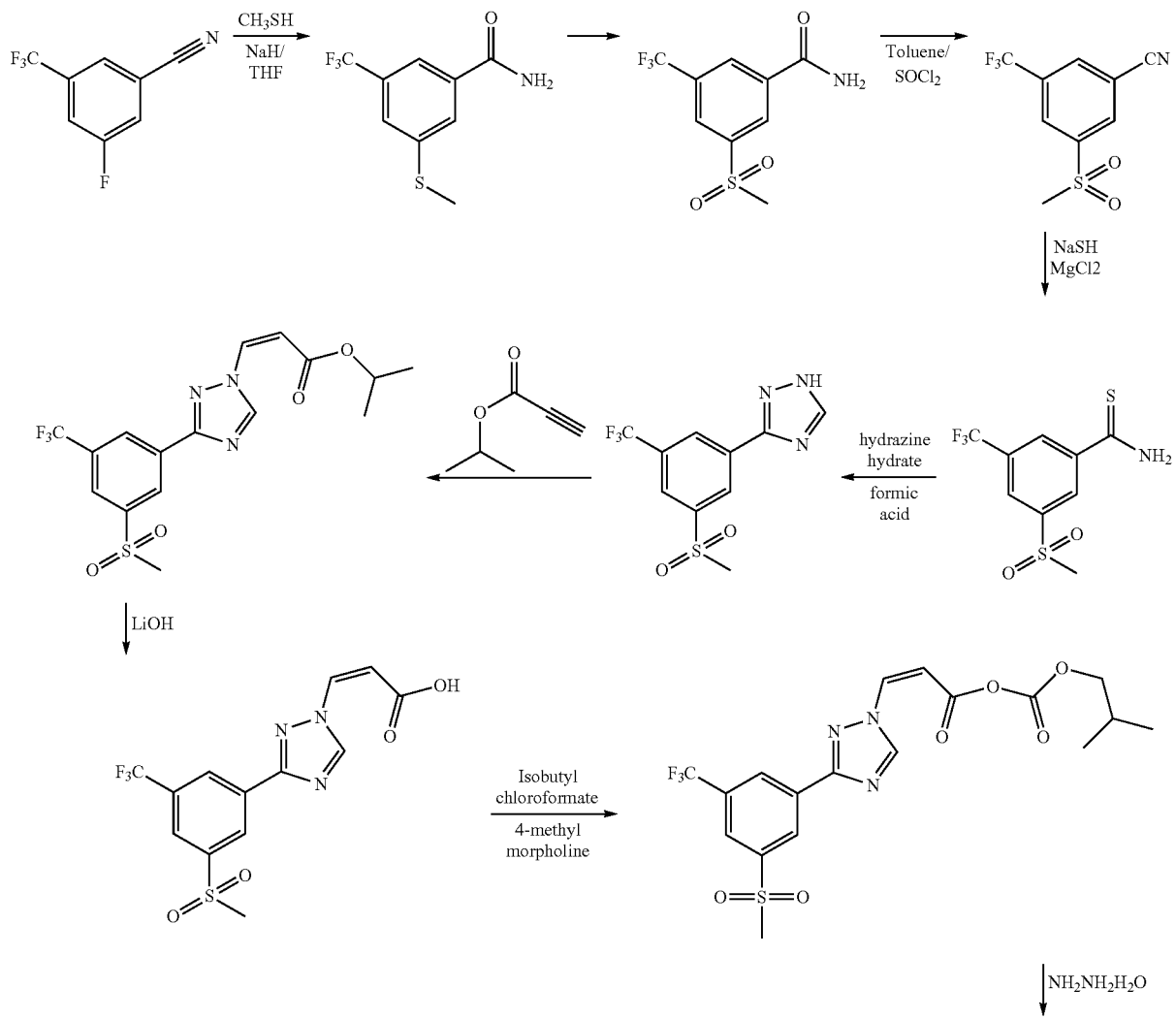

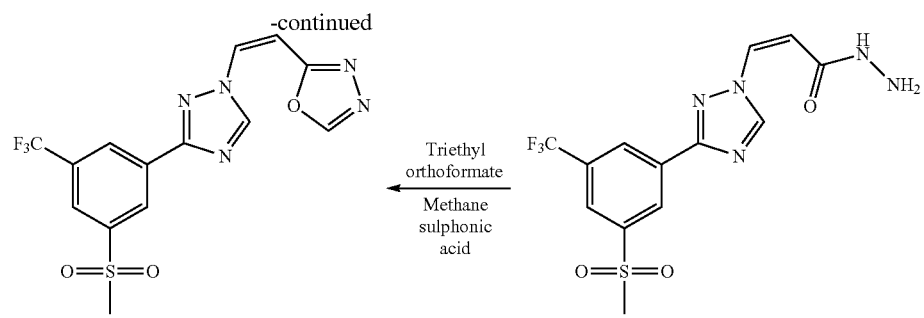

Synthesis of 3-(methylthio)-5-(trifluoromethyl)benzamide

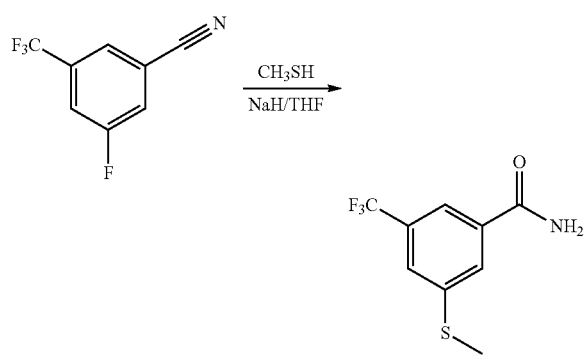

In a 500-mL, 3-neck round-bottomed flask equipped with an 100-mL pressure-equalizing addition funnel fitted with an nitrogen inlet, and a rubber septum, 3-fluoro-5-(trifluoromethyl)benzonitrile (8.0 g, 1.0 eq.), in acetone (40 mL). Sodiumthiomethoxide (3.42 g, 1.15 eq) was dissolved in water to make 21% aqueous solution and was added dropwise in 30 min at 5° C. temperature. The temperature of the reaction was slowly raised to RT and stirred for 3 h. Then temperature was raised to 50-60° C. and maintained for further 4-6 h. The progress of the reaction was followed by TLC analysis on silica gel with 10% MeOH-dichloromethane as mobile phase and visualization with UV, SM $R_f$=0.40 and Product $R_f$=0.25. Reaction was stirred for 3 hr at 25° C. and 4-6 hrs at 50-60° C. and reaction mixture was transparent. The reaction mass was quench by water and extracted by ethyl acetate (3×100 mL). The combined organic layer was washed with brine 50 mL and dried over sodium sulphate and evaporated on buchi rotaevaporator. The resulting crude compound (8 g) was subjected to further stage Yield (80.9%); Mass: (ES+) 235.94 (M+1).

Synthesis of 3-(methylsulfonyl)-5-(trifluoromethyl)benzamide

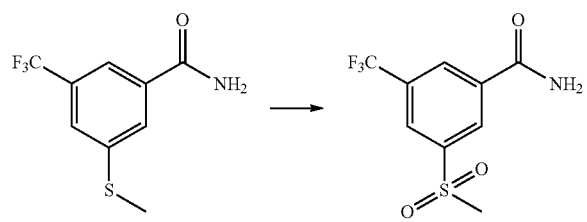 [SMILES: CSc1cc(C(N)=O)cc(C(F)(F)F)c1 ; CS(=O)(=O)c1cc(C(N)=O)cc(C(F)(F)F)c1]

In a 500-mL, 3-neck round-bottomed flask equipped with an 100-mL pressure-equalizing addition funnel fitted with an nitrogen inlet, and a rubber septum, 3-(methylthio)-5-(trifluoromethyl)benzamide (8.0 g, 1.0 eq.), in acetone (70 mL). Oxone (36.5 g, 2 eq.) was added at RT. The reaction was stirred for 12 h. The progress of the reaction was followed by TLC analysis on silica gel with 30% ethyl acetate-hexane as mobile phase and visualization with UV, SM $R_f$=0.30 and Product $R_f$=0.20. Reaction was stirred for 12 h and white solid (Oxone salts) was separated by filtration on a Büchner funnel and washed with acetone (100 mL). The combined acetone layer was concentrated by rotary evaporation (40° C., 20 mmHg) to afford 7.0 g of off white solid. The resulting crude compound off white (7 g) was subjected to further stage Yield (90.4%); Mass: (ES+) 267.89 (M+1).

Synthesis of 3-(methylsulfonyl)-5-(trifluoromethyl)benzonitrile

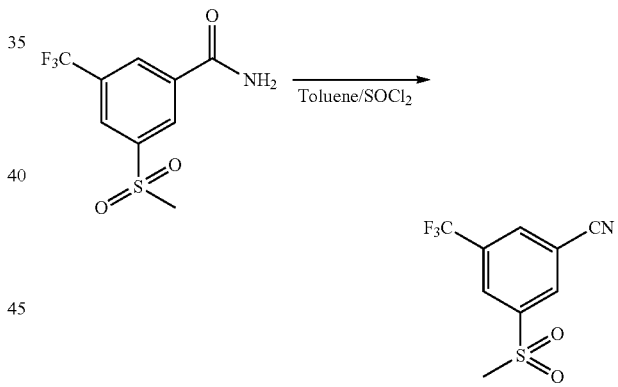

In a 3-neck 500 mL round-bottomed flask, 3-(methylsulfonyl)-5-(trifluoromethyl)benzamide (7 g, 1 eq.) was dissolved in DMF (70 mL, 10 Vol) and added thionylchloride (3.8 mL, 2.0 eq.) and reaction mixture was refluxed to 90° C. for 12 h. The progress of the reaction was followed by TLC analysis on silica gel with 30% ethyl acetate -Hexane as mobile phase and visualization with UV, SM $R_f$=0.20 and Product $R_f$=0.35. Reaction mixture was brought to room temperature and quenched into the ice-water slurry (300 mL) and neutralized with sodium bicarbonate solution. Compound was extracted in the ethyl acetate (100 mL×3). Organic layer was washed with brine solution (100 mL) followed by drying using anhydrous sodium sulphate. Organic layer was concentrated under reduced pressure to afford 5.0 g of crude compound, yield (95.0%). The crude reaction mixture was purified by column chromatography using silica 60/120 using ethyl acetate:hexane as mobile phase. The column (5×20 cm) was packed in hexane and started eluting in ethyl acetate in gradient manner starting with fraction collection (25-mL fractions) from 15% to 20% ethyl acetate in hexane. Compound started eluting with 15% ethylacetate in hexane. Fraction containing such TLC profile was collected together to obtain pure compound (4 g), Yield (62%); Mass: (ES−) 247.97 (M−1).

Synthesis of 3-(methylsulfonyl)-5-(trifluoromethyl) benzothioamide

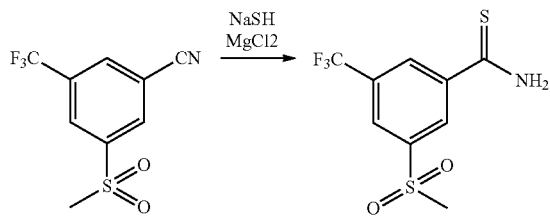 [SMILES: CS(=O)(=O)c1cc(C#N)cc(C(F)(F)F)c1 ; CS(=O)(=O)c1cc(C(N)=S)cc(C(F)(F)F)c1]

In a 1-neck 250 mL round-bottomed flask, 3-(methylsulfonyl)-5-(trifluoromethyl)benzonitrile (4.0 g, 1.0 eq.) was dissolved in DMF (40 mL, 10 V) and (1.80 g, 2.0 eq.) and MgCl$_2$ (3.58 g, 1.1 eq.) was added to the reaction mixture. The reaction mixture was stirred for 6-8 h at RT. The progress of the reaction was followed by TLC analysis on silica gel with 40% ethyl acetate:hexane as mobile phase and visualization with UV, SM R$_f$=0.30 and Product R$_f$=0.20. Reaction mixture was quenched into the ice-water slurry (300 mL) and extracted in the ethyl acetate (100 mL×3). Organic layer was washed with brine solution (100 mL) followed by drying using anhydrous sodium sulphate. Organic layer was concentrated under reduced pressure to afford 4.0 g of crude compound, yield (88%). This crude material was directly used for next step without purification; Mass: (ES−) 281.9 (M−1).

Synthesis of 3-(3-(methylsulfonyl)-5-(trifluoromethyl)phenyl)-1H-1,2,4-triazole

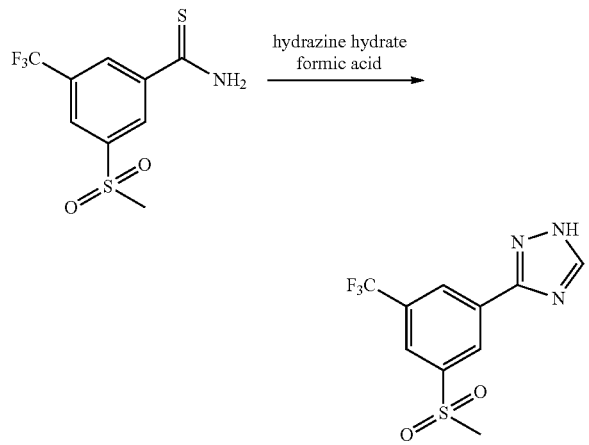

In a 1-neck 250 mL round-bottomed flask, 3-(methylsulfonyl)-5-(trifluoromethyl)benzothioamide (4.0 g, 1.0 eq.) was dissolved in DMF (40 mL, 10 V) added hydrazine hydrate (1.60 g, 2.0 eq.) and stirred reaction mixture for 3 h. Then formic acid (20 mL, vol) was added and stirred for 1 h at the same temperature. Then temperature increased to 90° C. and maintained for 10-12 hrs. The progress of the reaction was followed by TLC analysis on silica gel with 10% methanol: dichloromethane as mobile phase and visualization with UV, SM R$_f$=0.30 and Product R$_f$=0.20. Reaction mixture was quenched into the ice-water slurry (300 mL) and extracted in the ethyl acetate (100 mL×3). Organic layer was washed with sodium bicarbonate solution (100×3 mL) followed by drying using anhydrous sodium sulphate. Organic layer was concentrated under reduced pressure to afford 3.0 g of crude compound. The resulting crude compound (4.0 g) was subjected to column purification. The crude reaction mixture was purified by column chromatography using silica 60/120 using methanol: dichloromethane as mobile phase. The column (5×10 cm) was packed in dichloromethane and started eluting in Methanol in gradient manner starting with fraction collection (25 mL fractions) from 3-5% methanol in dichloromethane. Compound started eluting with 3% methanol in dichloromethane. Fraction containing such TLC profile was collected together to obtain pure compound (3.0 g), Yield (73.6%).

Synthesis of (Z)-isopropyl 3-(3-(3-(methylsulfonyl)-5-(trifluoromethyl)phenyl)-1H-1,2,4-triazol-1-yl) acrylate

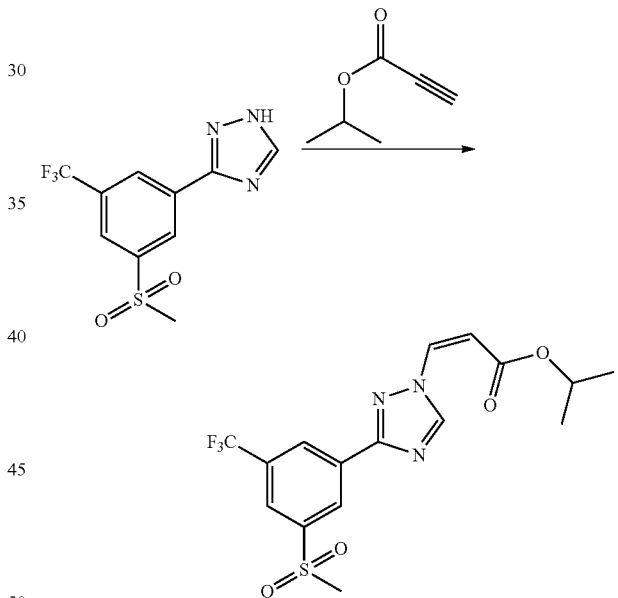

In a 1-neck 25 mL round-bottomed flask, 3-(3-(methylsulfonyl)-5-(trifluoromethyl)phenyl)-1H-1,2,4-triazole (0.10 g, 1.0 eq.), was dissolved in dichloromethane (5 mL, 50 vol.), added TEA (0.052 g, 1.2 eq.) and added Isopropyl propionate (0.056 g, 1.2 eq.). Reaction mixture was stirred at 0° C. for 2-3 h. The progress of the reaction was followed by TLC analysis on silica gel with 10% Methanol:dichloromethane as mobile phase and visualization with UV, SM R$_f$=0.20 and Product R$_f$=0.35. Reaction mixture was concentrated under reduced pressure to afford 0.250 g of crude compound. The resulting crude compound (0.250 g) was subjected to column purification. The crude reaction mixture was purified by column chromatography using silica 60/120 using methanol:dichloromethane as mobile phase. The column (2×10 cm) was packed in dichloromethane and started eluting in Methanol in gradient manner starting with fraction collection (25-mL fractions) from 1.5% to 2.5% methanol in dichloromethane. Compound started eluting with 1.5% methanol in dichloromethane. Fraction containing such TLC profile was collected together to obtain pure compound (0.025 g), Yield (18%); NMR (400 MHz, CDCl$_3$) δ 9.76 (S, 1H), 8.28-8.92 (m, 3H), 7.28-7.31 (d, J=10.8, 1H), 5.77-5.80 (d, J=10.8 Hz, 1H), 5.13-5.19 (m, 1H), 3.17 (S, 3H), 1.34-1.41 (d, 6H): LCMS for C$_{16}$H$_{16}$F$_3$N$_3$O$_4$S [M+Acetonitrile]$^+$ 403.4 found 444.71 at 6.653 min.

Synthesis of (Z)-3-(3-(3-(methylsulfonyl)-5-(trifluoromethyl)phenyl)-1H-1,2,4-triazol-1-yl)acrylic acid

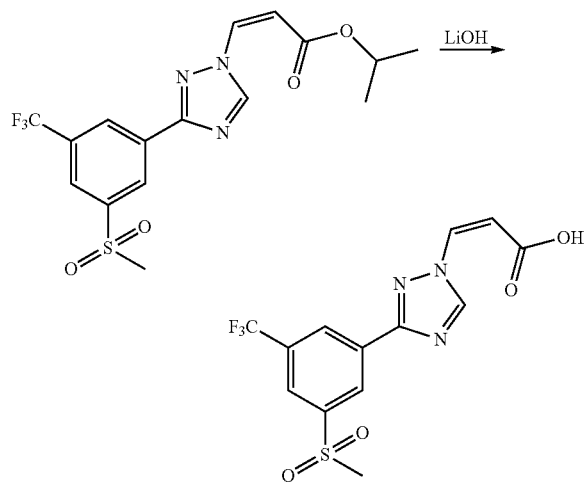

In a 1-neck 25 mL round-bottomed flask, (Z)-isopropyl 3-(3-(3-(methylsulfonyl)-5-(trifluoromethyl)phenyl)-1H-1,2,4-triazol-1-yl)acrylate (0.350 g, 1.0 eq.), was dissolved in THF (3.5 mL, 5 vol.), added water (3.5 mL, 3.5 Vol) and added LiOH (0.053 g, 1.5 eq.). Reaction mixture was stirred at RT for 2-3 hrs. The progress of the reaction was followed by TLC analysis on silica gel with 10% methanol: dichloromethane as mobile phase and visualization with UV, SM R$_f$=0.35 and Product R$_f$=0.15. Reaction mixture was quenched into the acidic ice-water slurry (30 mL) and extracted in the ethyl acetate (25 mL×3). Organic layer was washed with sodium bicarbonate solution (50 mL) followed by drying using anhydrous sodium sulphate. Organic layer was concentrated under reduced pressure to afford 270 mg of crude compound. The resulting crude compound off white was used for further stage, yield (83%); Mass: (ES+) 361.8 (M+1).

Synthesis of (isobutyl carbonic) (Z)-3-(3-(3-(methylsulfonyl)-5-(trifluoromethyl)phenyl)-1H-1,2,4-triazol-1-yl)acrylic anhydride

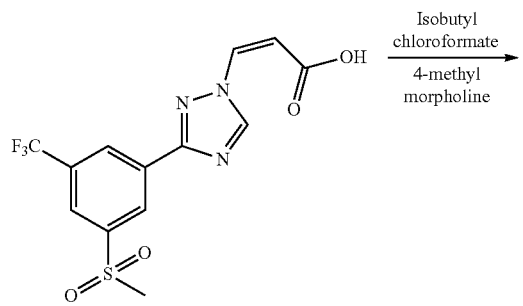

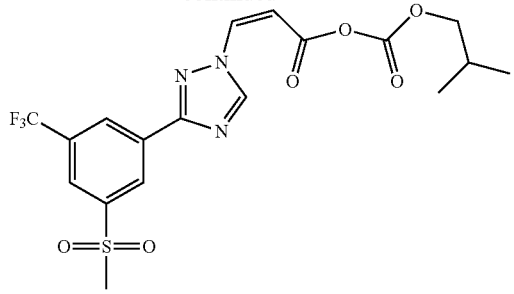

In a 3-neck 25 mL round-bottomed flask, (Z)-3-(3-(3-(methylsulfonyl)-5-(trifluoromethyl)phenyl)-1H-1,2,4-triazol-1-yl)acrylic acid (0.270 g, 1.0 eq.) was dissolved in 11 mL of THF at 0° C. under N$_2$ atmosphere, added 4-methyl morpholine (0.106 g, 1.4 eq.) and Iso butyl chloroformate (0.163 g, 1.5 eq.). Reaction mixture was stirred at 0° C. for 1 h. The progress of the reaction was followed by TLC analysis on silica gel with 10% methanol:dichloromethane as mobile phase and visualization with UV, SM R$_f$=0.15 and Product R$_f$=0.40. Reaction was stirred for 1 h and white solid was separated and compound was collected by filtration on a Büchner funnel and washed with THF (15 mL). The filtrate was followed as such for next stage; Mass: (ES+) 461.9 (M+1).

Synthesis of (Z)-3-(3-(3-(methylsulfonyl)-5-(trifluoromethyl)phenyl)-1H-1,2,4-triazol-1-yl)acrylohydrazide

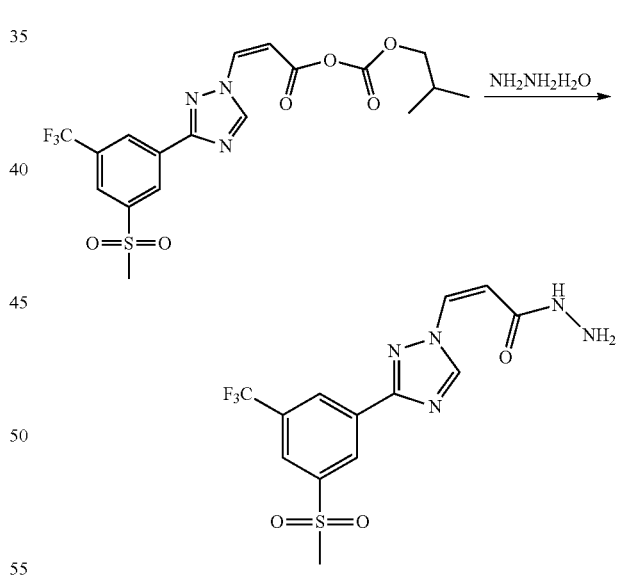

In a 3-neck 25 mL round-bottomed flask, (isobutyl carbonic) (Z)-3-(3-(3-(methylsulfonyl)-5-(trifluoromethyl)phenyl)-1H-1,2,4-triazol-1-yl)acrylic anhydride (mother liquor of step 1) at 0° C. under N$_2$ atmosphere added hydrazine hydrate (0.230 g, 5.7 eq). Reaction mixture was stirred at 0° C. for 1 h. The progress of the reaction was followed by TLC analysis on silica gel with 10% methanol: dichloromethane as mobile phase and visualization with UV, SM R$_f$=0.40 and Product R$_f$=0.25. The resulting yellow reaction mass was poured in 30 mL water and extracted with 3×20 mL ethylacetate. Organic layer was washed with brine solution followed by drying using anhydrous sodium sulphate. Organic layer was concentrated under reduced pressure to afford 0.300 g of crude compound and it was used as such without further purification; Mass: (ES−) 374.1 (M−1).

Synthesis of (Z)-2-(2-(3-(3-(methylsulfonyl)-5-(trifluoromethyl)phenyl)-1H-1,2,4-triazol-1-yl)vinyl)-1,3,4-oxadiazole (I-33)

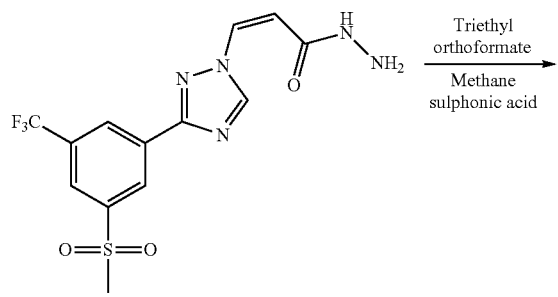

In a 3-neck 25 mL round-bottomed flask, (Z)-3-(3-(3-(methylsulfonyl)-5-(trifluoromethyl)phenyl)-1H-1,2,4-triazol-1-yl)acrylohydrazide (0.300 g, 1.0 eq.) under $N_2$ atmosphere was added trimethylorthoformate (0.26 g, 3.0 eq.) and Methane sulphonic acid (0.027 g, 0.1 eq.). Reaction mixture was refluxed at 80° C. for 1 h. The progress of the reaction was followed by TLC analysis on silica gel with 10% methanol: dichloromethane as mobile phase and visualization with UV, SM $R_f$=0.25 and Product $R_f$=0.41. The resulting yellow reaction mass was poured in 30 mL water and extracted with 3×20 mL ethylacetate. Organic layer was washed with brine solution followed by drying using anhydrous sodium sulphate. Organic layer was concentrated under reduced pressure to afford 0.250 g of crude compound. The crude reaction mixture was purified by column chromatography using silica 60/120 using methanol: dichloromethane as mobile phase. The column (2×10 cm) was packed in dichloromethane and started eluting in Methanol in gradient manner starting with fraction collection (25-mL fractions) from 1.5% to 2.5% methanol in dichloromethane. Compound started eluting with 1.5% methanol in dichloromethane. Fraction containing such TLC profile was collected together to obtain pure compound (0.060 g), Yield (20%) $^1$H NMR (400 MHz, $CDCl_3$) δ 9.76 (S, 1H), 7.2-8.6 (m, 7H), 7.39-7.41 (d, J=10.8, 1H), 5.58-5.88 (d, J=11.2 Hz, 1H), 5.39 (S, 2H), 4.70-4.73 (m, 1H), 1.39-1.41 (d, 6H): LCMS for $C_{21}H_{19}F_3N_4O_3$ [M+1]$^+$ 432.4 found 432.96 at RT 4.217 min.

Example 13

Synthesis of (Z)-2-(2-(3-(3,5-bis(trifluoromethyl)phenyl)-1H-1,2,4-triazol-1-yl)vinyl)-1,3,4-oxadiazole (I-34)

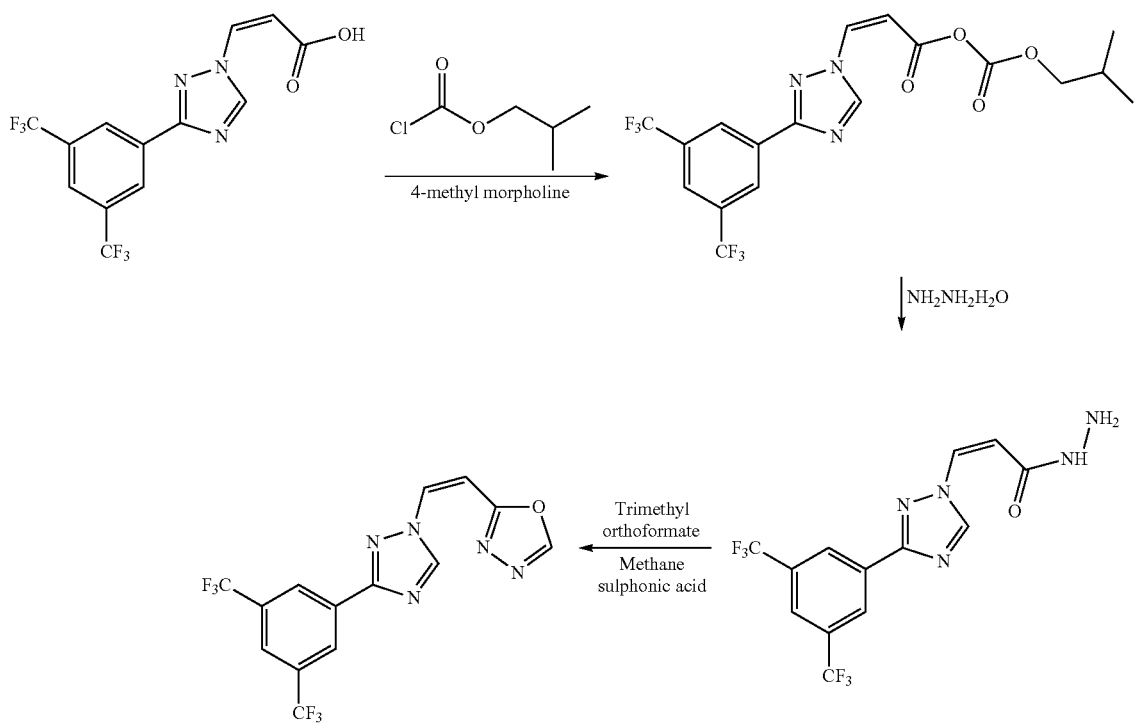

Synthesis of (Z)-3-(3-(3,5-bis(trifluoromethyl)phenyl)-1H-1,2,4-triazol-1-yl)acrylic (isobutyl carbonic) anhydride

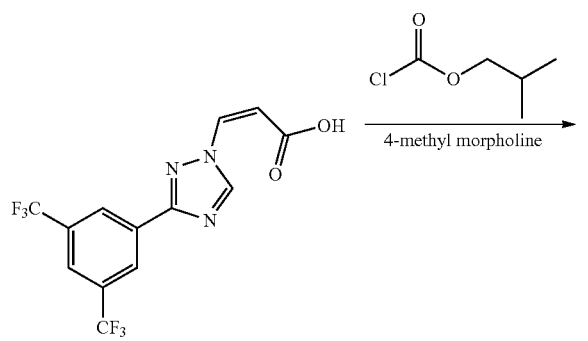

In a 250 mL, 3-neck round-bottomed flask equipped with nitrogen inlet, and a rubber septum, (Z)-3-(3-(3,5-bis(trifluoromethyl)phenyl)-1H-1,2,4-triazol-1-yl)acrylic acid (5 g, 1.0 eq.) was dissolved in THF (50 mL). The reaction mixture was cooled to 0° C. To this reaction mixture was added Isobutyl chloroformate (4.44 mL, 2.4 eq.) and 4-methylmorpholine (3.29 mL, 2.1 eq.). The reaction mixture was maintained at 0° C. for 30 min. The progress of the reaction was followed by TLC analysis on silica gel with 50% EtOAc in Hexane as mobile phase. Reaction mixture was filtered through celite bed. The filtrate was used for next step without any work up and purification.

Synthesis of (Z)-3-(3-(3,5-bis(trifluoromethyl)phenyl)-1H-1,2,4-triazol-1-yl)acrylohydrazide

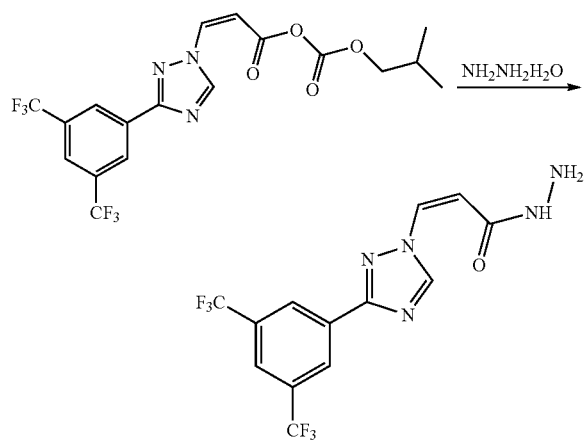

In a 250-mL, 3-neck round-bottomed flask equipped with nitrogen inlet, and a rubber septum, (Z)-3-(3-(3,5-bis(trifluoromethyl)phenyl)-1H-1,2,4-triazol-1-yl)acrylic (isobutyl carbonic) anhydride was cooled at 0° C. and added hydrazine hydrate (4.02 mL, 5.7 eq.) was added. Reaction mixture was stirred at 0° C. for 30 min. The progress of the reaction was followed by TLC analysis on silica gel with 50% EtOAc-hexane as mobile phase. Reaction mixture was poured into ice water (200 mL) and extracted with EtOAc (3×100 mL). The combined organic layers were washed with brine solution (3×50 mL), dried over MgSO$_4$, filtered, and concentrated by rotary evaporation to afford 5.2 g of crude compound which was used for next step without further purification.

Synthesis of (Z)-2-(2-(3-(3,5-bis(trifluoromethyl)phenyl)-1H-1,2,4-triazol-1-yl)vinyl)-1,3,4-oxadiazole (I-34)

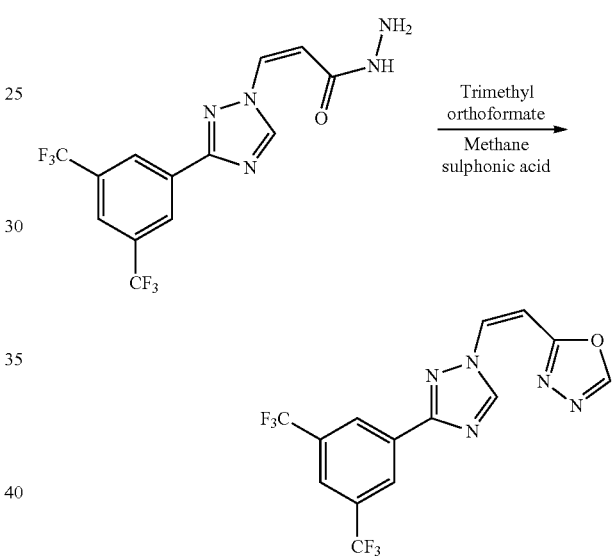

In a 100-mL, 3-neck round-bottomed flask equipped with nitrogen inlet, and a rubber septum, (Z)-3-(3-(3,5-bis(trifluoromethyl)phenyl)-1H-1,2,4-triazol-1-yl)acrylohydrazide (5.2 g, 1.0 eq.) was dissolved in THF (25 mL, 5V). Trimethylorthoformate (1.71 mL, 1.1 eq.) and methanesulphonic acid (0.46 mL, 0.5 eq.) were added and the reaction mixture was refluxed at 70° C. for 2 h. The progress of the reaction was followed by TLC analysis on silica gel with 5% MeOH in dichloromethane hexane as mobile phase. Reaction mixture was poured into ice water (50 mL) and extracted with EtOAc (3×50 mL). The combined organic layers were washed with brine solution (3×50 mL), dried over MgSO$_4$, filtered, and concentrated by rotary evaporation to afford 4 g of crude compound. The crude reaction mixture was purified by column chromatography using silica 60/120 using 0.5% MeOH in dichloromethane mobile phase to obtain pure compound (1.3 g), Yield (24%); (Z)-2-(2-(3-(3,5-bis(trifluoromethyl)phenyl)-1H-1,2,4-triazol-1-yl)vinyl)1,3,4-oxadiazole: $^1$H NMR (400 MHz, CDCl$_3$) δ 10.31 (S, 1H), 8.65 (S, 2H), 8.51 (S, 1H), 7.96 (S, 1H), 7.53-7.56 (d, J=12.0 Hz, 1H), 6.31-6.34 (d, J=12.0 Hz, 1H): LCMS for C$_{14}$H$_7$F$_6$N$_5$O [M+H]$^+$: 375.23 found 376.24 at RT 3.004 min, purity (99.87%).

123 124
Example 14
Synthesis of (Z)-3-(1-(2-(1,3,4-oxadiazol-2-yl)vinyl)-1H-1,2,4-triazol-3-yl)-5-(trifluoromethyl)benzonitrile (I-35)
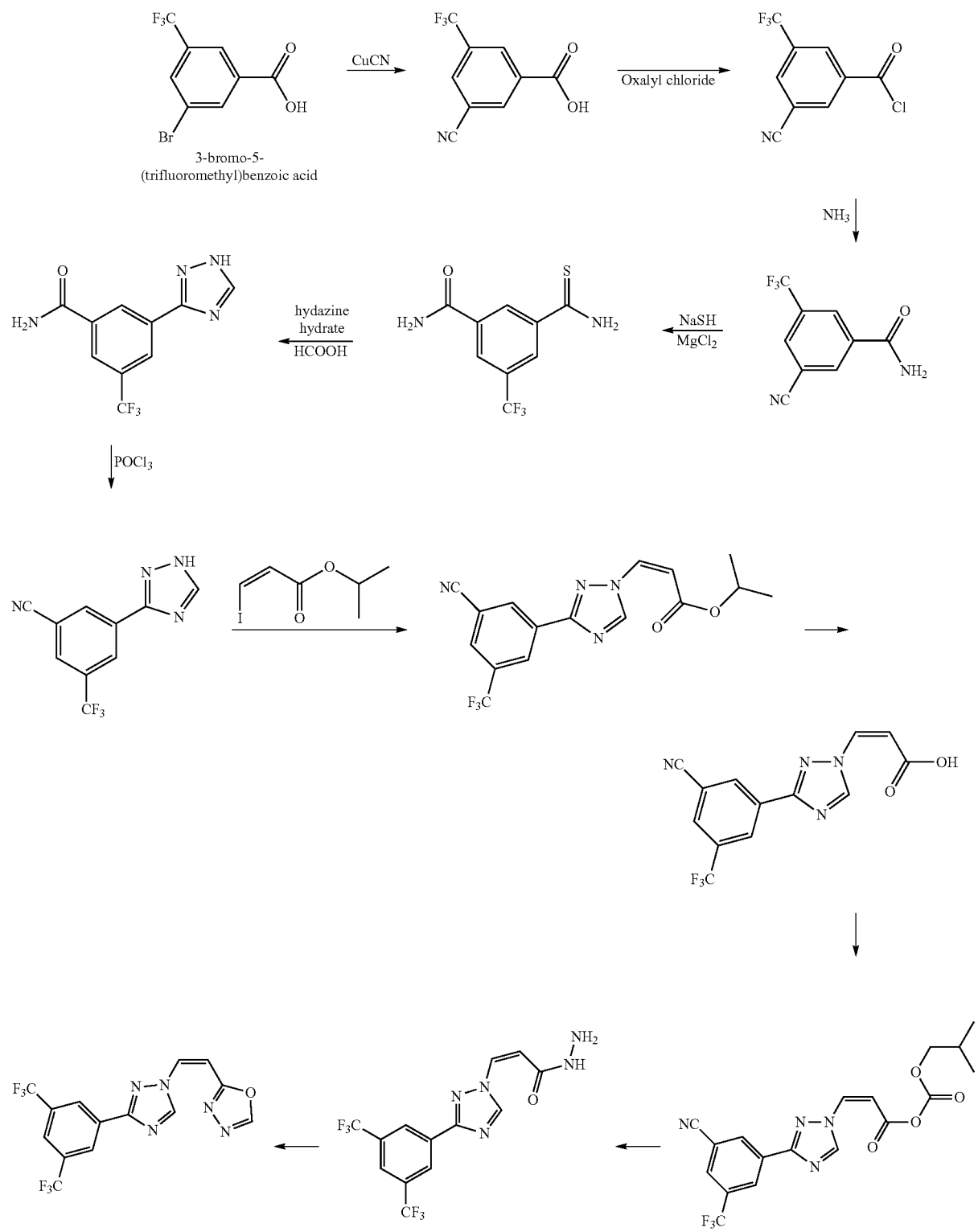

Synthesis of 3-cyano-5-(trifluoromethyl)benzoic acid

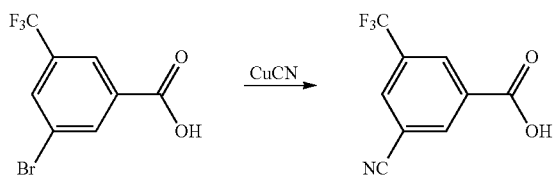

In a 3-neck 100 mL round-bottomed flask, 3-bromo-5-(trifluoromethyl)benzoic acid (10.0, 1.0 eq.) was dissolved in DMF (100 mL, 10 Vol). CuCN was added at RT and the reaction was stirred at 150° C. for 15-16 hr. Reaction completion was monitored on TLC using MeOH:dichloromethane (1:9) mobile phase. Reaction mixture was quenched into the ice-water slurry (1000 mL) and filtered over celite. Compound was extracted in the ethyl acetate (250 mL×3). Organic layer was washed with water (150 mL) followed by drying using anhydrous sodium sulphate. Organic layer was concentrated under reduced pressure. Then again the crude was dissolved in ethyl acetate and extracted with (250 mL×3). Combined aqueous layer was again acidified with dil HCl (350 mL) to get pH 3. Then aqueous layer was extracted with ethyl acetate (250 mL×3). This combined organic layer was washed with water (150 mL) followed by drying using anhydrous sodium sulphate. Organic layer was concentrated under reduced pressure to afford 6.0 g of crude compound, Yield (75.4%). This crude material was directly used for next step without purification; Mass: (ES−) 214.14 (M−1).

Synthesis of 3-cyano-5-(trifluoromethyl)benzoyl chloride

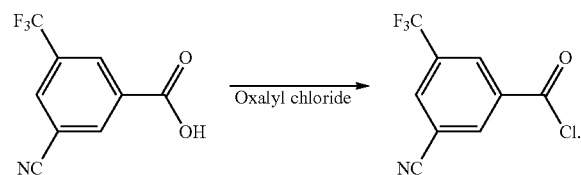 [SMILES: N#Cc1cc(C(=O)O)cc(C(F)(F)F)c1 ; "Oxalyl chloride" ; N#Cc1cc(C(=O)Cl)cc(C(F)(F)F)c1]

In a 3-neck 100 mL round-bottomed flask, 3-cyano-5-(trifluoromethyl)benzoic acid (2.5 g, 1 eq.) was dissolved in dichloromethane (25 mL, 10 Vol) and cool to 0° C. added DMF (0.2 mL, cat.). Then added oxalyl chloride drop wise in 0.5 hr. The reaction mixture was stirred at 0° C. for 1-2 hr. Reaction completion was monitored on TLC using MeOH:dichloromethane (1:9) mobile phase. Reaction mixture was concentrated under reduced pressure to afford 3.0 g of crude 3-cyano-5-(trifluoromethyl)benzoyl chloride, which was immediately used for next step.

Synthesis of 3-cyano-5-(trifluoromethyl)benzamide

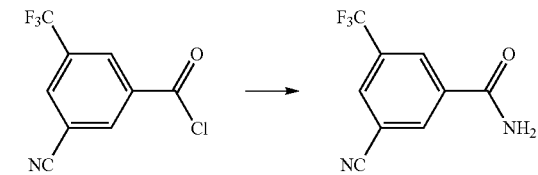 [SMILES: N#Cc1cc(C(=O)Cl)cc(C(F)(F)F)c1 ; N#Cc1cc(C(N)=O)cc(C(F)(F)F)c1]

In 1-neck 250 mL round-bottomed flask, 3-cyano-5-(trifluoromethyl)benzoyl chloride (3.0 g, 1.0 eq.) was dissolved in THF (30 mL, 10 V) at 0° C. Ammonia gas was added and the reaction mixture was stirred for 1-2 h at 0° C. The progress of the reaction was followed by TLC analysis on silica gel with ethyl acetate:hexane (5:5) as mobile phase and visualization with UV, SM $R_f$=0.10 and Product $R_f$=0.25. Reaction mixture was quenched into the ice-water slurry (100 mL) and extracted in the ethyl acetate (100 mL×3). Organic layer was washed with brine solution (100 mL) followed by drying using anhydrous sodium sulphate. Organic layer was concentrated under reduced pressure to afford 2.5 g of crude compound as white solid, yield (88%). This crude 3-cyano-5-(trifluoromethyl)benzamide was directly used for next step without purification; Mass: (ES−) 212.95 (M−1).

Synthesis of 3-carbamothioyl-5-(trifluoromethyl)benzamide

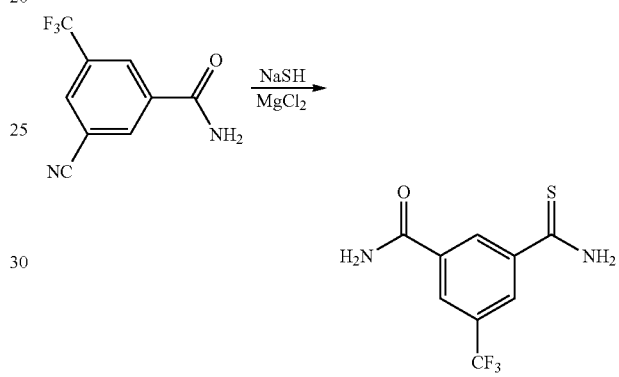

In 3-neck 100 mL round-bottomed flask, 3-cyano-5-(trifluoromethyl)benzamide (2.5 g, 1 eq.) was dissolved in DMF (25 mL, 10 Vol). NaSH (0.340 g, 1.3 eq.) and $MgCl_2$ (1.23 g, 1.3 eq) were added and the reaction mixture was stirred at room temperature for 1-2 h. The progress of the reaction was followed by TLC analysis on silica gel with ethyl acetate:hexane (4:6) mobile phase and visualization with UV, SM $R_f$=0.35 and Product $R_f$=0.25. Reaction mixture was quenched into the ice-water slurry (300 mL) and extracted in the ethyl acetate (100 mL×3). Organic layer was washed with sodium bicarbonate solution (100×3 mL) followed by drying using anhydrous sodium sulphate. Organic layer was concentrated under reduced pressure to afford 3.0 g of crude compound. The resulting crude 3-carbamothioyl-5-(trifluoromethyl)benzamide (3.0 g) was further used with purification; Mass: (ES+) 249.14 (M+1).

Synthesis of 3-(1H-1,2,4-triazol-3-yl)-5-(trifluoromethyl)benzamide

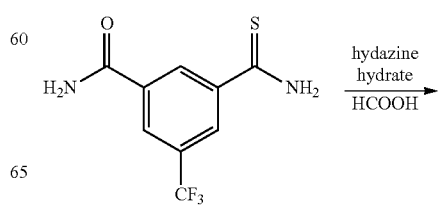

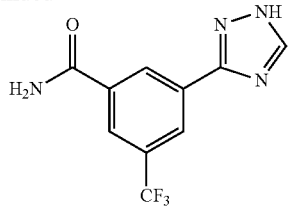

In 3-neck 100 mL round-bottomed flask, 3-carbamothioyl-5-(trifluoromethyl)benzamide (3.0 g, 1 eq.) was dissolved in DMF (30 mL, 10 Vol) and dropwise added hydrazine hydrate (1.27 mL, 2.0 eq.) and reaction mixture was stirred at room temperature for 1-2 h. The progress of the reaction was followed by TLC analysis on silica gel with ethyl acetate:hexane (2:8) mobile phase and visualization with UV, SM $R_f$=0.35 and Product $R_f$=0.15. Then formic acid (5 mL, 5 vol) was added and stirred for 1 h at the same temperature. Then temperature increased to 90° C. and maintained for 10-12 hrs. The progress of the reaction was followed by TLC analysis on silica gel with 10% methanol: dichloromethane as mobile phase and visualization with UV, SM $R_f$=0.30 and Product $R_f$=0.20. Reaction mixture was quenched into the ice-water slurry (300 mL) and extracted in the ethyl acetate (100 mL×3). Organic layer was washed with sodium bicarbonate solution (100×3 mL) followed by drying using anhydrous sodium sulphate. Organic layer was concentrated under reduced pressure to afford 3.0 g of crude compound. The crude reaction mixture was purified by column chromatography using silica 60/120 using methanol: dichloromethane as mobile phase. The column (5×10 cm) was packed in dichloromethane and started eluting in Methanol in gradient manner starting with fraction collection (25 mL fractions) from 3-5% methanol in dichloromethane. Compound started eluting with 3% methanol in dichloromethane. Fraction containing such TLC profile was collected together to obtain pure 3-(1H-1,2,4-triazol-3-yl)-5-(trifluoromethyl)benzamide (1.1 g), Yield (36.0%); Mass: (ES+) 257.14 (M+1).

Synthesis of 3-(1H-1,2,4-triazol-3-yl)-5-(trifluoromethyl)benzonitrile

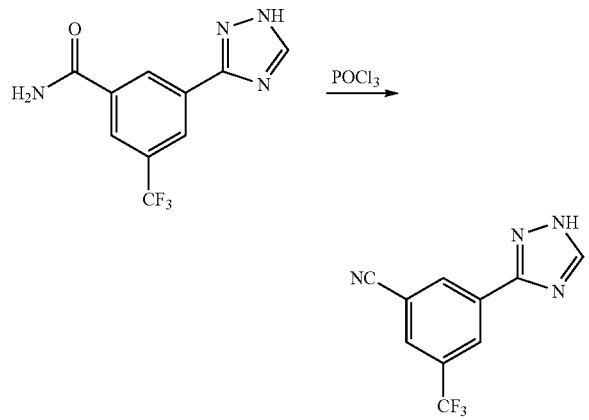

In 3-neck 50 mL round-bottomed flask, 3-(1H-1,2,4-triazol-3-yl)-5-(trifluoromethyl)benzamide (0.5 g, 1 eq.) and POCl$_3$ (2.0 mL, 4 eq.) was dissolved in DMF (15 mL, 15 Vol) and reaction mixture was stirred at 25° C. for 1-2 hr. The progress of the reaction was followed by TLC analysis on silica gel with 10% Methanol:dichloromethane as mobile phase and visualization with UV, SM $R_f$=0.35 and Product $R_f$=0.45. Reaction mixture was concentrated under reduced pressure to afford 0.1.2 g of crude compound. The crude reaction mixture was purified by column chromatography using silica 60/120 using Methanol: dichloromethane as mobile phase. The column (5×10 cm) was packed in dichloromethane and started eluting in Methanol in gradient manner starting with fraction collection (25-mL fractions) from 1.5% to 2.0% Methanol in dichloromethane. Compound started eluting with 1.5% Methanol in dichloromethane. Fraction containing such TLC profile was collected together to obtain pure 3-(1H-1,2,4-triazol-3-yl)-5-(trifluoromethyl)benzonitrile (500 mg), Yield (60%); Mass: (ES+) 238.1 (M+1).

Synthesis of (Z)-isopropyl 3-(3-(3-cyano-5-(trifluoromethyl)phenyl)-1H-1,2,4-triazol-1-yl)acrylate

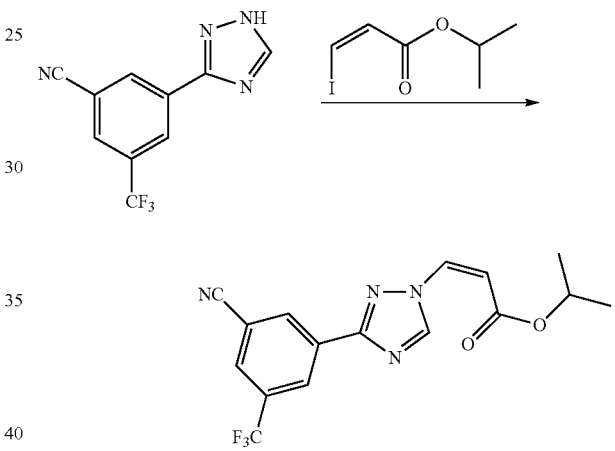

In 3-neck 50 mL round-bottomed flask, 3-(1H-1,2,4-triazol-3-yl)-5-(trifluoromethyl)benzonitrile (0.2 g, 1 eq.) and DABCO (0.188 g, 2.0 eq.) was dissolved in DMF (2.0 mL, 10 Vol) and added Iodoacrylate (0.22 g, 1.1 eq.) and reaction mixture was stirred at 25° C. for 1-2 hr. The progress of the reaction was followed by TLC analysis on silica gel with 10% Methanol:dichloromethane as mobile phase and visualization with UV, SM $R_f$=0.30 and Product $R_f$=0.55. Reaction mixture was concentrated under reduced pressure to afford 0.300 g of crude compound. The crude reaction mixture was purified by column chromatography using silica 60/120 using Methanol:dichloromethane as mobile phase. The column (5×10 cm) was packed in dichloromethane and started eluting in Methanol in gradient manner starting with fraction collection (25-mL fractions) from 0.5% to 0.7% Methanol in dichloromethane. Compound started eluting with 0.5% Methanol in dichloromethane. Fraction containing such TLC profile was collected together to obtain pure compound (60 mg), Yield (20.4%); (Z)-isopropyl 3-(3-(3-cyano-5-(trifluoromethyl)phenyl)-1H-1,2,4-triazol-1-yl)acrylate $^1$H NMR (400 MHz, CDCl$_3$) δ 9.76 (S, 1H), 7.97-8.65 (m, 3H), 7.28-7.30 (d, J=8.8, 1H), 5.77-5.80 (d, J=10.8 Hz, 1H), 5.13-5.19

(m, 1H), 1.34-1.36 (d, 6H); LCMS for $C_{16}H_{13}F_3N_4O_2$ [M–H]⁻ 350.3 found 348.97 at RT 4.101 min purity (98.75%).

Synthesis of (Z)-3-(3-(3-cyano-5-(trifluoromethyl)phenyl)-1H-1,2,4-triazol-1-yl)acrylic acid

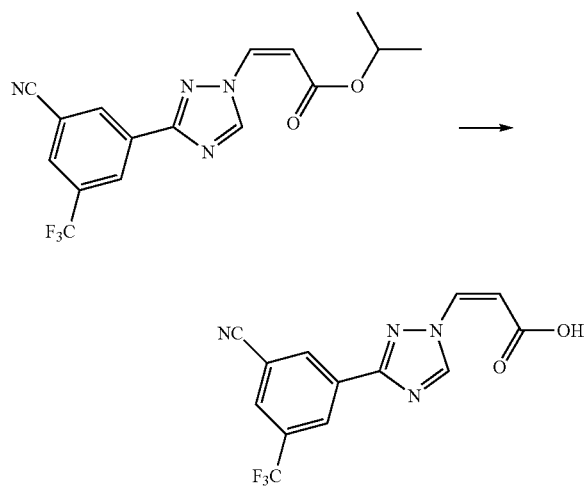

In 1-neck 25 mL round-bottomed flask, (Z)-isopropyl 3-(3-(3-cyano-5-(trifluoromethyl)phenyl)-1H-1,2,4-triazol-1-yl)acrylate (0.350 g, 1.0 eq.), was dissolved in THF (3.5 mL, 5 vol.), added water (3.5 mL, 3.5 Vol) and added LiOH (0.061 g, 1.5 eq.). Reaction mixture was stirred at RT for 2-3 hrs. The progress of the reaction was followed by TLC analysis on silica gel with 10% methanol:dichloromethane as mobile phase and visualization with UV, SM $R_f$=0.35 and Product $R_f$=0.15. Reaction mixture was quenched into the acidic ice-water slurry (30 mL) and extracted in the ethyl acetate (25 mL×3). Organic layer was washed with dil HCl solution (50 mL) followed by drying using anhydrous sodium sulphate. Organic layer was concentrated under reduced pressure to afford 270 mg of crude compound. The resulting crude (Z)-3-(3-(3-cyano-5-(trifluoromethyl)phenyl)-1H-1,2,4-triazol-1-yl)acrylic acid off white was used for further stage, yield (83%); Mass: (ES+) 309.1 (M+1).

Synthesis of (Z)-3-(3-(3-cyano-5-(trifluoromethyl)phenyl)-1H-1,2,4-triazol-1-yl)acrylic (isobutyl carbonic) anhydride

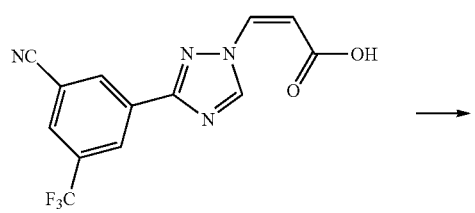

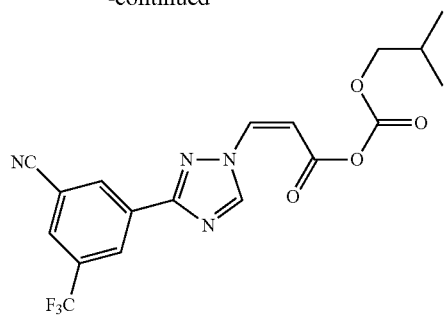

In a 3-neck 25 mL round-bottomed flask, (Z)-3-(3-(3-cyano-5-(trifluoromethyl)phenyl)-1H-1,2,4-triazol-1-yl) acrylic acid (0.20 g, 1.0 eq) was dissolved in 11 ml of THF at 0° C. under $N_2$ atmosphere, added 4-methyl morpholine (0.14 g, 1.4 eq) and isobutyl chloroformate (0.213 g, 1.5 eq). Reaction mixture was stirred at 0 C for 1 h. The progress of the reaction was followed by TLC analysis on silica gel with 10% methanol:dichloromethane as mobile phase and visualization with UV, SM $R_f$=0.15 and Product $R_f$=0.40. Reaction was stirred for 1 h and white solid was separated and (Z)-3-(3-(3-cyano-5-(trifluoromethyl)phenyl)-1H-1,2,4-triazol-1-yl) acrylic (isobutyl carbonic) anhydride was collected by filtration on a Büchner funnel and washed with THF (15 mL). The filtrate was followed as such for next stage; Mass: (ES+) 408.9 (M+1).

Synthesis of (Z)-3-(3-(3-cyano-5-(trifluoromethyl)phenyl)-1H-1,2,4-triazol-1-yl)acrylohydrazide

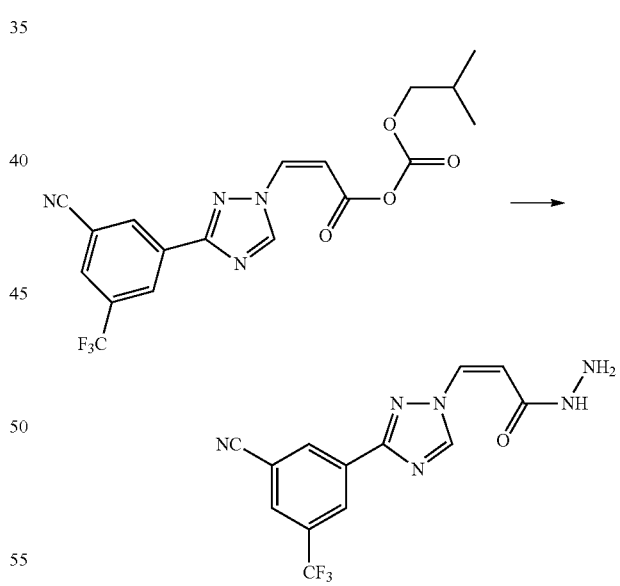

In a 3-neck 25 mL round-bottomed flask, (Z)-3-(3-(3-cyano-5-(trifluoromethyl)phenyl)-1H-1,2,4-triazol-1-yl) acrylic (isobutyl carbonic) anhydride (mother liquor of step 1) at 0° C. under $N_2$ atmosphere added hydrazine hydrate (0.230 g, 5.7 eq.). Reaction mixture was stirred at 0° C. for 1 h. The progress of the reaction was followed by TLC analysis on silica gel with 10% methanol:dichloromethane as mobile phase and visualization with UV, SM $R_f$=0.40 and Product $R_f$=0.25. The resulting yellow reaction mass was poured in 30 mL water and extracted with 3×20 mL ethylacetate. Organic layer was washed with brine solution followed by drying using anhydrous sodium sulphate. Organic layer was concentrated under reduced pressure to afford 0.200 g of crude (Z)-3-(3-(3-cyano-5-(trifluoromethyl)phenyl)-1H-1,2,4-triazol-1-yl)acrylohydrazide and it was used as such without further purification; Mass: (ES+) 366.9 (M+1).

Synthesis of (Z)-3-(1-(2-(1,3,4-oxadiazol-2-yl)vinyl)-1H-1,2,4-triazol-3-yl)-5-(trifluoromethyl)benzonitrile (I-35)

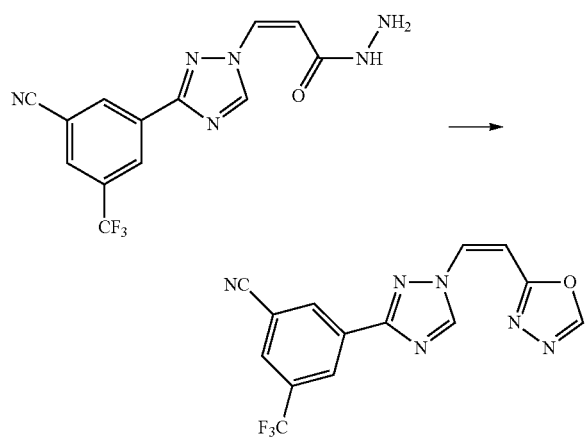

In a 3-neck 25 mL round-bottomed flask, (Z)-3-(3-(3-cyano-5-(trifluoromethyl)phenyl)-1H-1,2,4-triazol-1-yl)acrylohydrazide (0.200 g, 1.0 eq.) under $N_2$ atmosphere was added trimethyl orthoformate (0.173 g, 3.0 eq.) and Methane sulphonic acid (0.006 g, 0.1 eq.). Reaction mixture was refluxed at 80° C. for 1 h. The progress of the reaction was followed by TLC analysis on silica gel with 10% methanol: dichloromethane as mobile phase and visualization with UV, SM $R_f$=0.25 and Product $R_f$=0.41. The resulting yellow reaction mass was poured in 30 mL water and extracted with 3×20 mL ethylacetate. Organic layer was washed with brine solution followed by drying using anhydrous sodium sulphate. Organic layer was concentrated under reduced pressure to afford 0.130 g of crude compound. The crude reaction mixture was purified by column chromatography using silica 60/120 using methanol: dichloromethane as mobile phase. The column (2×10 cm) was packed in dichloromethane and started eluting in Methanol in gradient manner starting with fraction collection (25-mL fractions) from 1.5% to 2.5% methanol in dichloromethane. Compound started eluting with 1.5% methanol in dichloromethane. Fraction containing such TLC profile was collected together to obtain pure compound (0.010 g), Yield (10%); (Z)-3-(1-(2-(1,3,4-oxadiazol-2-yl)vinyl)-1H-1,2,4-triazol-3-yl)-5-(trifluoromethyl)benzonitrile $^1$H NMR (400 MHz, CDCl$_3$) δ 10.34 (S, 1H), 7.99-8.67 (m, 4H), 7.52-7.55 (d, J=11.2, 1H), 6.33-6.36 (d, J=11.2 Hz, 1H); LCMS for $C_{14}H_7F_3N_6O$ [M–H]$^-$ 332.2 found 330.94 at RT 3.319 min purity (98.10%).

Example 15

Synthesis of (Z)-3-(1-(2-(1,3,4-oxadiazol-2-yl)vinyl)-1H-1,2,4-triazol-3-yl)-5-(trifluoromethyl)phenol (I-36)

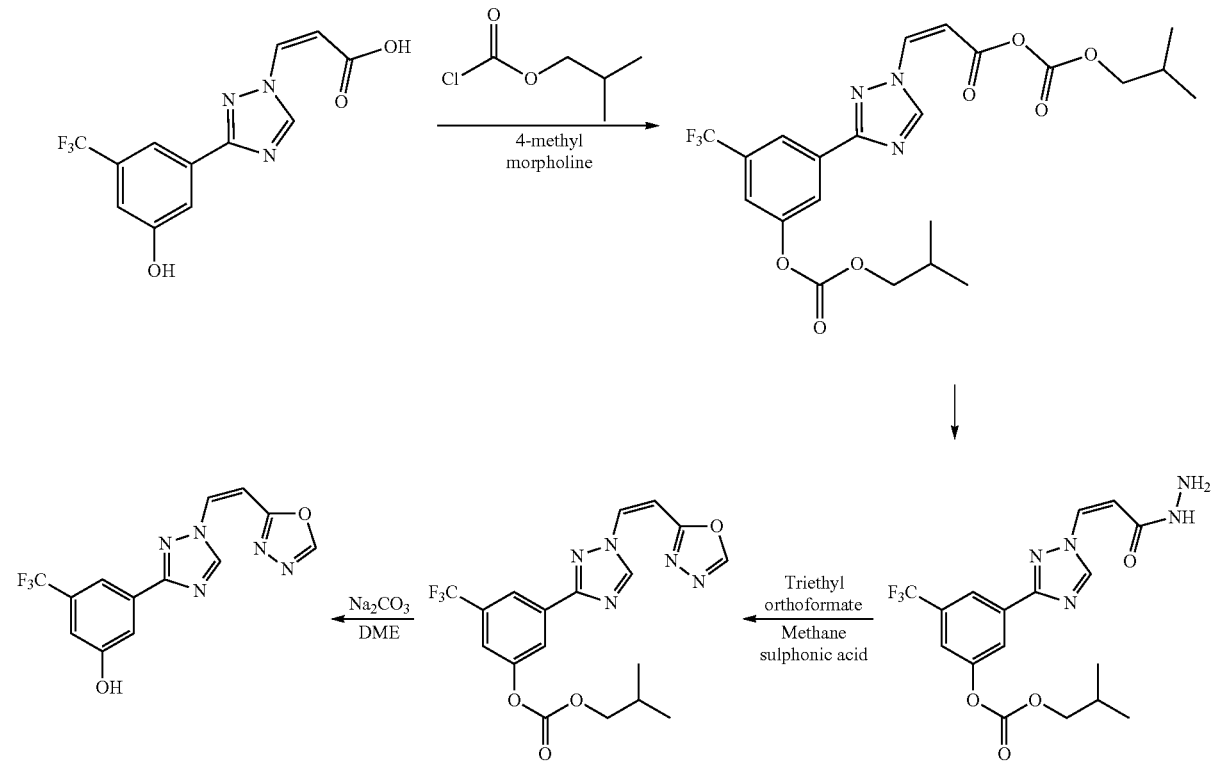

Synthesis of (Z)-3-(3-(3-(isobutoxycarbonyloxy)-5-(trifluoromethyl)phenyl)-1H-1,2,4-triazol-1-yl)acrylic (isobutyl carbonic) anhydride

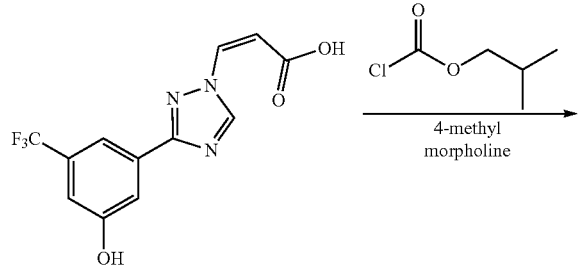

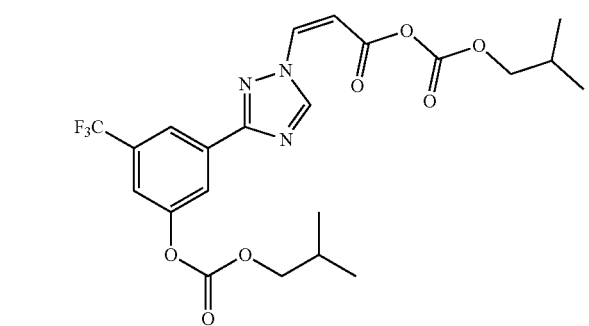

In a 100 mL, 3N round-bottomed flask equipped with nitrogen inlet, and a rubber septum, (Z)-3-(3-(3-hydroxy-5-(trifluoromethyl)phenyl)-1H-1,2,4-triazol-1-yl)acrylic acid (1.5 g, 1.0 eq.) was dissolved in THF (15 mL). The reaction mixture was cooled to 0° C. To this reaction mixture was added Isobutyl chloroformate (1.64 g, 2.4 eq.) and 4-methylmorpholine (1.06 g, 2.1 eq.). The reaction mixture was maintained at 0° C. for 1 h. The progress of the reaction was followed by TLC analysis on silica gel with 10% MeOH-dichloromethane as mobile phase. SM $R_f$=0.20 and Product $R_f$=0.6. Reaction mixture was filtered through celite bed. The filtrate was used for next step without any work up and purification.

Synthesis of (Z)-3-(1-(3-hydrazinyl-3-oxoprop-1-enyl)-1H-1,2,4-triazol-3-yl)-5-(trifluoromethyl)phenyl isobutyl carbonate

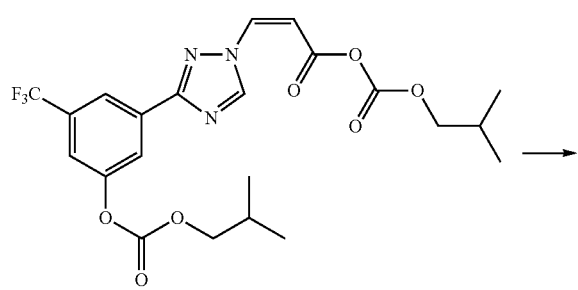

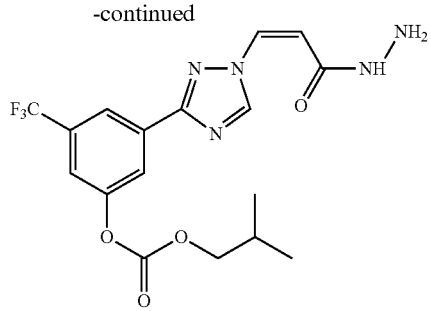

In a 100-mL, 3N round-bottomed flask equipped with nitrogen inlet, and a rubber septum, (Z)-3-(3-(3-(isobutoxycarbonyloxy)-5-(trifluoromethyl)phenyl)-1H-1,2,4-triazol-1-yl)acrylic (isobutyl carbonic) anhydride was cooled at 0° C. and added hydrazine hydrate (1.43 g, 5.7 eq.). Reaction mixture was stirred at 0° C. for 15 min. The progress of the reaction was followed by TLC analysis on silica gel with 10% MeOH-dichloromethane as mobile phase. SM $R_f$=0.6 and Product $R_f$=0.4. Reaction mixture was poured into ice water (100 mL) and extracted with EtOAc (3×50 mL). The combined organic layers were washed with brine solution (3×50 mL), dried over MgSO$_4$, filtered, and concentrated by rotary evaporation (25° C., 20 mmHg) to afford 2 g of Crude compound which was used for next step without further purification.

Synthesis of (Z)-3-(1-(2-(1,3,4-oxadiazol-2-yl)vinyl)-1H-1,2,4-triazol-3-yl)-5-(trifluoromethyl)phenyl isobutyl carbonate

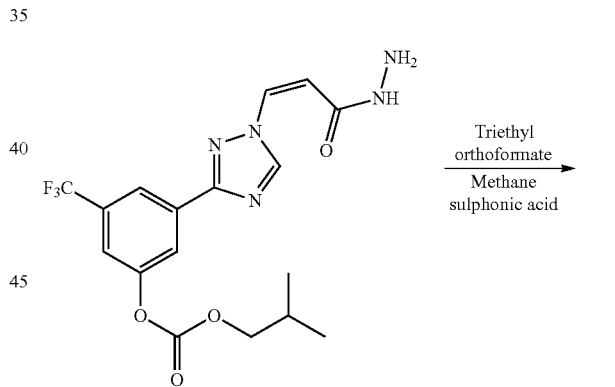

In a 100-mL, 3-neck round-bottomed flask equipped with nitrogen inlet, and a rubber septum, (Z)-3-(1-(3-hydrazinyl-3-oxoprop-1-enyl)-1H-1,2,4-triazol-3-yl)-5-(trifluoromethyl)phenyl isobutyl carbonate (2 g, 1.0 eq.) was dissolved in THF (20 mL, 10V). Trimethylorthoformate (0.56 g, 1.1 eq.)

and methanesulphonic acid (0.23 g, 0.5 eq.) were added and the reaction was refluxed at 70° C. for 2-3 h. The progress of the reaction was followed by TLC analysis on silica gel with 10% MeOH-dichloromethane as mobile phase. SM $R_f$=0.40 and Product $R_f$=0.5. Reaction mixture was poured into ice water (100 mL) and extracted with EtOAc (3×50 mL). The combined organic layers were washed with brine solution (3×50 mL), dried over $MgSO_4$, filtered, and concentrated by rotary evaporation (25° C., 20 mmHg) to afford 2.5 g of crude compound. The crude reaction mixture was purified by column chromatography using silica 60/120 using dichloromethane:Methanol as mobile phase. The column was packed in dichloromethane and started eluting in dichloromethane in gradient manner starting with fraction collection (25-mL fractions). Compound started eluting with 0.8% Methanol in dichloromethane. Fractions containing such TLC profile was collected together to obtain pure compound (0.1 g).

Synthesis of (Z)-3-(1-(2-(1,3,4-oxadiazol-2-yl)vinyl)-1H-1,2,4-triazol-3-yl)-5-(trifluoromethyl)phenol (I-36)

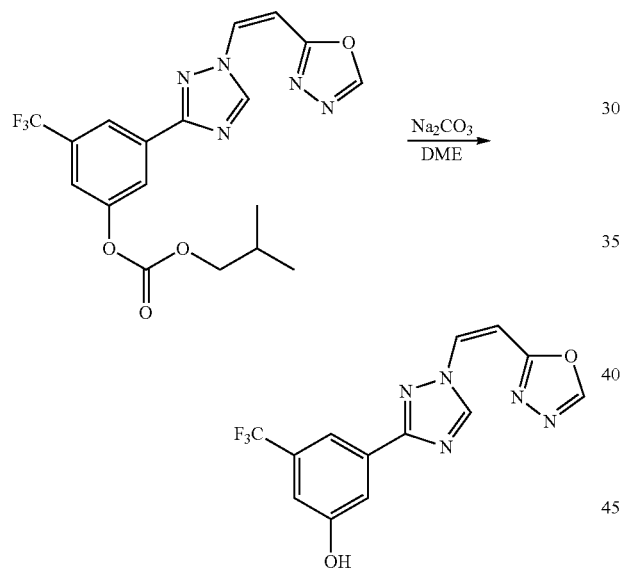

In a 50-mL, 3-neck round-bottomed flask equipped with nitrogen inlet, and a rubber septum, (Z)-3-(1-(2-(1,3,4-oxadiazol-2-yl)vinyl)-1H-1,2,4-triazol-3-yl)-5-(trifluoromethyl)phenyl isobutyl carbonate (0.1 g, 1.0 eq.) was dissolved in dimethoxyethane (10 mL, 100V). $Na_2CO_3$ (0.62 g, 2.5 eq.) and water (10 mL) were added and the reaction mixture was refluxed at 70° C. for 2-3 h. The progress of the reaction was followed by TLC analysis on silica gel with 10% MeOH-dichloromethane as mobile phase. Reaction mixture was poured into ice water (100 mL) and extracted with EtOAc (3×15 mL). The combined organic layers were washed with brine solution (3×15 mL), dried over $MgSO_4$, filtered, and concentrated by rotary evaporation (25° C., 20 mmHg) to afford 0.1 g of Crude compound. The crude reaction mixture was purified by column chromatography using silica 60/120 using dichloromethane: Methanol as mobile phase. The column was packed in dichloromethane and started eluting in dichloromethane in gradient manner starting with fraction collection (25-mL fractions). Compound started eluting with 1.2% Methanol in dichloromethane. Fraction containing such TLC profile was collected together to obtain pure compound (0.02 g); (Z)-3-(1-(2-(1,3,4-oxadiazol-2-yl)vinyl)-1H-1,2,4-triazol-3-yl)-5-(trifluoromethyl)phenol; NMR (400 MHz, $CDCl_3$) δ 10.51 (S, 1H), 9.42 (S, 1H), 9.32 (S, 1H), 7.72-7.75 (d, J=12.0 Hz, 1H), 7.14 (S, 1H), 6.63-6.66 (d, J=12.0 Hz, 1H): LCMS for $C_{13}H_8F_3N_5O_2$ [M+H]$^+$: 323.23 found 324.24 at RT 2.317 min, purity (97.59%).

Example 16

Synthesis of (Z)-2-(2-(3-(3-isopropoxy-5-(trifluoromethyl)phenyl)-1H-1,2,4-triazol-1-yl)vinyl)pyridine (I-37)

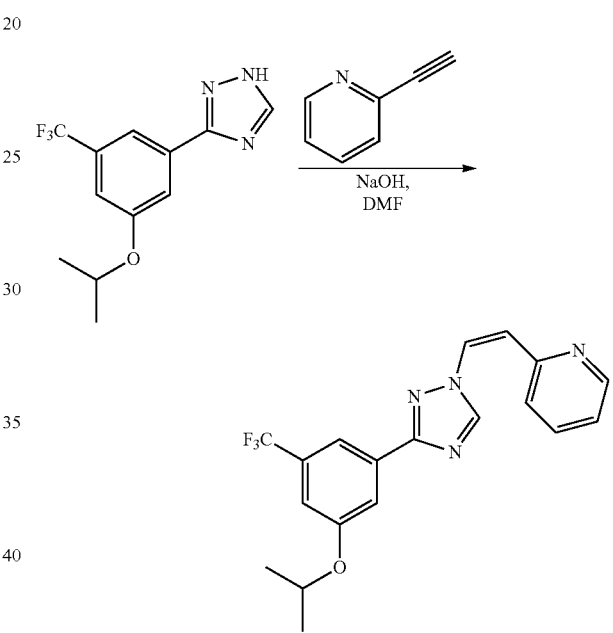

In a 25 mL, 3 Neck round-bottomed flask equipped with nitrogen inlet and a rubber septum, 3-(3-isopropxy-5-(trifluoromethyl)phenyl)-1H-1,2,4-triazole (0.1 g, 1.0 eq.), 2-ethynylpyridine (0.042 g, 1.1 eq.) and sodium hydroxide (0.026 g, 2.5 eq.) were dissolved in DMF (5.0 mL). The reaction mixture was stirred at 75-80° C. The progress of the reaction was followed by TLC analysis on silica gel with 30% ethyl acetate-hexane as mobile phase which shows that starting material was consumed after 15 h. Reaction mixture was diluted by water and extract with ethyl acetate, combined organic layer was dried over sodium sulfate and distilled under reduce pressure (25° C., 20 mmHg) to obtain crude material. The crude compound was purified by column chromatography using 60/120 silica gel and ethyl acetate in hexane as mobile phase. The column was packed in hexane and started eluting in ethyl acetate in gradient manner starting with fraction collection. The compound started eluting from 17% ethyl acetate in hexane. Fractions containing such TLC profile were collected together to obtain pure compound 0.009 g; LCMS (%): Retention time 2.869 min (83.97%); (Z)-2-(2-(3-(3-isopropoxy-5-(trifluoromethyl)phenyl)-1H-

1,2,4-triazole-1-yl)vinyl)pyridine; ¹H NMR (400 MHz, DMSO) δ 9.41 (s, 1H), 8.60-8.61 (d, 1H, J=4 Hz), 7.81-7.86 (doublet of triplet, 1H), 7.78 (s, 1H), 7.71 (s, 1H), 7.48-7.50 (d, 1H, J=8 Hz), 7.34-7.37 (t, 1H), 7.29-7.32 (m, 2H), 6.59-6.62 (d, 1H, J=10.4 Hz), 4.78-4.81 (m, 1H), 1.33-1.35 (d, 6H), LCMS for $C_{19}H_{17}F_3N_4O$ [M+H]⁺ 374 found at 375 at RT 2.869 min (LCMS: 83.97%).

Example 17

Synthesis of (Z)-3-(3-methoxy-5-(trifluoromethyl) phenyl)-1-styryl-1H-1,2,4-triazole (I-38)

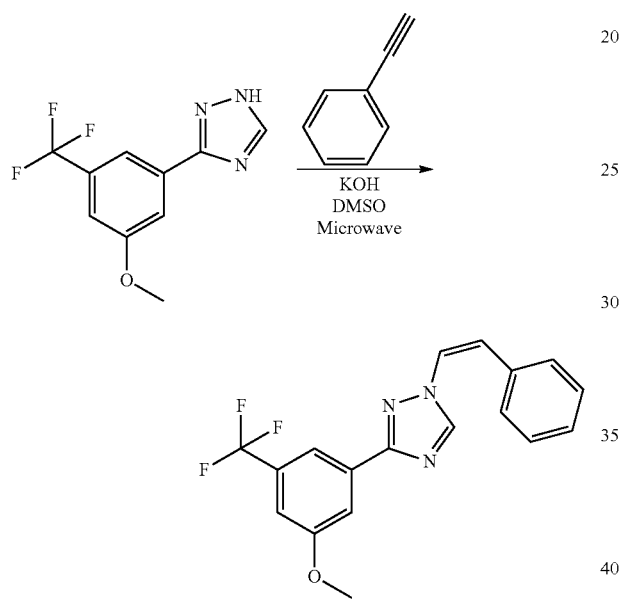

In a 10 mL microwave seal tube 3-(3-methoxy-5-(trifluoromethyl)phenyl)-1H-1,2,4-triazole (0.5 g, 1.0 eq.) and ethynylbenzene (0.22 ml, 1.0 eq.) were dissolved in DMSO (5 mL). KOH (0.29 g, 2.5 eq.) was added and the reaction mixture was irradiated at 120° C. for 45 min in microwave. The completion of the reaction was confirmed by TLC using 30% EtOAc in hexane as mobile phase. Reaction mixture was quenched into ice water slurry. Extract compound in ethyl acetate. Organic layer washed with water, dried over $Na_2SO_4$, filtered, and concentrated by rotary evaporation (40° C., 20 mmHg) to afford 0.373 g of brown oil. The crude reaction mixture was purified by column chromatography using silica 60/120 using ethyl acetate:hexane as mobile phase. The column was packed in hexane and started eluting in ethyl acetate in gradient manner starting with fraction collection from 5% to 10% ethyl acetate in hexane. Compound started eluting with 14% ethyl acetate in hexane. Fraction containing such TLC profile was collected together to obtain pure compound (30 mg); (Z)-3-(3-methoxy-5-(trifluoromethyl)phenyl)-1-styryl-1H-1,2,4-triazole: ¹H NMR (400 MHz, CDCl₃) δ 8.65 (S 1H), 7.79 (S 1H), 7.72 (S, 1H), 7.25-7.37 (m 6H), 7.19-7.22 (d, 1H, J=12 Hz), 6.68-6.71 (d, 1H, J=12 Hz), 3.93 (s, 3H); LCMS for Chemical Formula $C_{18}H_{14}F_3N_3O$ [M+H]⁺ 345.3 found at 345.8 at RT 4.400 min (LCMS: 98.47%).

Example 18

Synthesis of (Z)-3-(3-isopropoxy-5-(trifluoromethyl) phenyl)-1-styryl-1H-1,2,4-triazole (I-39)

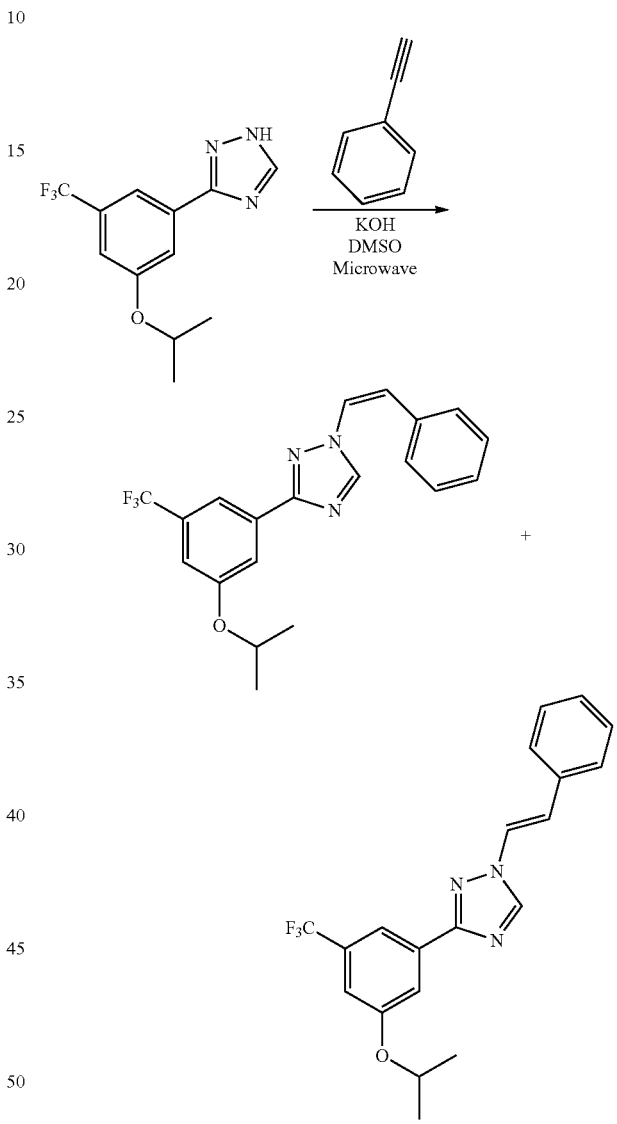

In a 10 mL microwave seal tube 3-(3-isopropoxy-5-(trifluoromethyl)phenyl)-1H-1,2,4-triazole (0.5 g, 1.0 eq.) and ethynylbenzene (0.25 mL, 1.2 eq.) were dissolved in DMSO (5 mL). KOH (0.29 g, 2.5 eq.) was added and the reaction mixture was irradiated at 120° C. for 45 min in CEM Microwave. The completion of the reaction was confirmed by TLC using 30% EtOAc-hexane as mobile phase. Reaction mixture was quenched into ice water slurry. Compound was extracted by ethyl acetate. Organic layer was washed with brine, dried over $Na_2SO_4$, filtered and concentrated by rotary evaporation (40° C., 20 mmHg) to afford 0.373 g of brown oil. The crude reaction mixture was purified by column chromatography using silica 60/120 using ethyl acetate:hexane as mobile phase. The column was packed in hexane and started eluting in ethyl acetate in gradient manner starting with fraction collection from 5% to 10% ethyl acetate in hexane. Compound started eluting with 14% ethyl acetate in hexane. Fraction containing such TLC profile was collected together to obtain pure compound (30 mg); LCMS (%): Retention time for cis 4.7970 min (100.0%); For trans 3.975 min (98.06%).

Cis isomer: (Z)-3-(3-isopropoxy oxy-5-(trifluoromethyl)phenyl)-1-styryl-1H-1,2,4-triazole $^1$H NMR (400 MHz, CDCl$_3$) δ 7.95-7.97 (d, 1H, J=4 Hz), 7.81 (s, 1H), 7.16-7.47 (m, 6H), 6.99-7.01 (d, 1H, J=12 Hz), 4.68-4.74 (m, 1H), 1.34-1.40 (d, 6H) LCMS for Chemical Formula $C_{20}H_{18}F_3N_3O$ [M+H]$^+$ 373.4 found 373.8 at RT 4.797 min (Purity: 100%).

Trans Isomer: (E)-3-(3-isopropoxy oxy-5-(trifluoromethyl)phenyl)-1-styryl-1H-1,2,4-triazole $^1$H NMR (400 MHz, DMSO-d$_6$) δ 8.96 (s, 1H), 8.10-8.13 (d, 1H, J=8 Hz), 7.89 (s, 1H), 7.83 (s, 1H), 7.62-7.64 (d, 2H, J=8 Hz), 7.33-7.44 (m, 4H), 4.84-4.87 (m, 1H), 1.33-1.34 (d, 6H). LCMS for Chemical Formula $C_{20}H_{18}F_3N_3O$ [M+H]$^+$ 373.4 found 373.8 at RT 3.795 min (LCMS: 98.06%).

Inhibition of Nuclear Export

The inhibition of Crm1 induced nuclear export of compounds of the invention were determined and are shown in Table 1. The evaluation of the affinity of compounds for the Crm1 protein was determined in the RevGFP assay. Compounds of the invention are active in Rev-GFP assay with IC50 less than <10 µM with the most preferred compounds having activities less than an IC50 of 1 µM.

Experimental protocol: Rev is a protein from human immunodeficiency virus type 1 (HIV-1) and contains a nuclear export signal (NES) in its C-terminal domain and a nuclear localization signal (NLS) in its N-terminal domain. Nuclear export of Rev protein is dependent on the classical NES/Crm1 pathway (Neville et al, 1997). Nuclear accumulation of Rev can be observed in cells treated with specific inhibitors of Crm1, such as LMB (Kau et al, 2003). In this assay, U2OS-RevGFP cells are seeded onto clear-bottom, black, 384-well plates the day before the experiment. Compounds are serially diluted 1:2 starting from 40 µM in a separate 384-well plate in DMEM, and then transferred onto cells. Cells are incubated with compound for ~1 hr before fixation with 3.7% formaldehyde and nuclei staining with Hoechst 33258. The amount of GFP in cell nuclei will be measured and compound IC50s determined (Kau et al, 2003).

MTT Cell Proliferation Assay

The MTT cell proliferation assay was used to study the cytotoxic properties of the compounds. The assay was performed according to the method described by Roche Molecular Biochemicals with minor modifications. The assay is based on the cleavage of the tetrazolium salt, MTT, in the presence of an electron-coupling reagent. The water-insoluble formazan salt produced must be solubilized in an additional step. Cells, grown in a 96-well tissue culture plate, are incubated with the MTT solution for approximately 4 hours. After this incubation period, a water-insoluble formazan dye is formed. After solubilization, the formazan dye is quantitated using a scanning multi-well spectrophotometer (ELISA reader). The absorbance revealed directly correlates to the cell number. The cells were seeded at 1.5×10$^4$ cells in each well of 96-well plate in 200 µL of fresh culture medium and were allowed to attach for overnight. The stock solutions of the compounds were diluted in cell culture medium to obtain eight concentrations of each drug, ranging from 1 nM to 20 µM. After 72 h of treatment the medium was aspirated and the cells were washed once with sterile 1×PBS. Each plate contained the samples, negative control and blank. The DMSO at less than 1% v/v was used as a negative control. In most cases the assay was performed in triplicates and the results were presented as a mean percent inhibition to the negative control±SE. The following formula was used to calculate the percent of inhibition: Inhibition (%)=(1−(ODo/OD))×100.

Tumor cells were assayed for viability in the absence or presence of drug/control treatments, and drug combination dose response studies were analyzed graphically by correlating the fraction of surviving cells with drug concentrations for each drug.

Cellular data is presented in Table 1, below, where A=<1 µM; B=1-10 µM; C=>10 µM; NT=Not Tested.

TABLE 1

| Compound # | Example | Structure | Name | Rev Export (%)/[IC$_{50}$] or Cytotoxicity [EC$_{50}$] |
|---|---|---|---|---|
| I-26 | 1 | 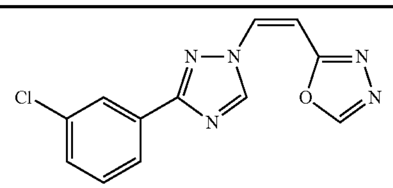 | (Z)-2-(2-(3-(3-chlorophenyl)-1H-1,2,4-triazol-1-yl)vinyl)-1,3,4-oxadiazole | A |
| I-27 | 2 | 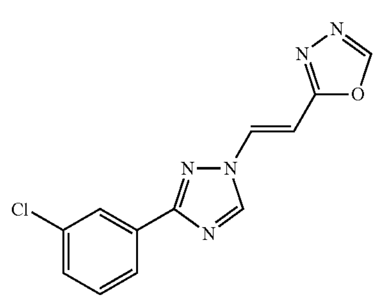 [SMILES: Clc1cccc(-c2ncn(/C=C/c3nnco3)n2)c1] | (E)-2-(2-(3-(3-methoxy-5-(trifluoromethyl)phenyl)-1H-1,2,4-triazol-1-yl)vinyl)-1,3,4-oxadiazole | B |

TABLE 1-continued

| Compound # | Example | Structure | Name | Rev Export (%)/[IC$_{50}$] or Cytotoxicity [EC$_{50}$] |
|---|---|---|---|---|
| I-28 | 3 | 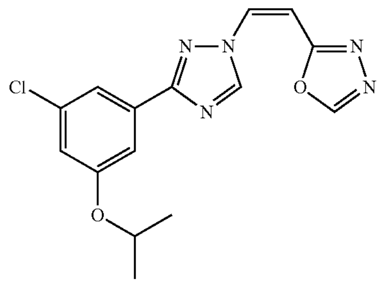 | (Z)-2-(2-(3-(3-chloro-5-isopropoxyphenyl)-1H-1,2,4-triazol-1-yl)vinyl)-1,3,4-oxadiazole | A |
| I-29 | 4 | 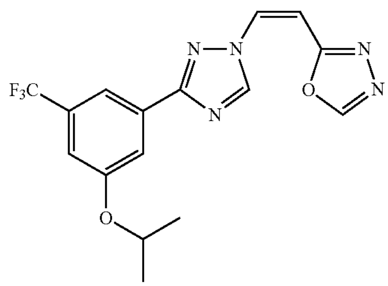 [SMILES: CC(C)Oc1cc(-c2ncn(/C=C\c3nnco3)n2)cc(C(F)(F)F)c1] | (Z)-2-(2-(3-(3-isopropoxy-5-(trifluoromethyl)phenyl)-1H-1,2,4-triazol-1-yl)vinyl)-1,3,4-oxadiazole | A |
| I-1 | 5 | 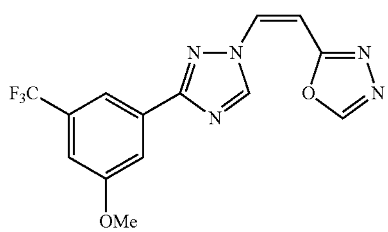 | (Z)-2-(2-(3-(3-methoxy-5-(trifluoromethyl)phenyl)-1H-1,2,4-triazol-1-yl)vinyl)-1,3,4-oxadiazole | A |
| I-2 | 6 | 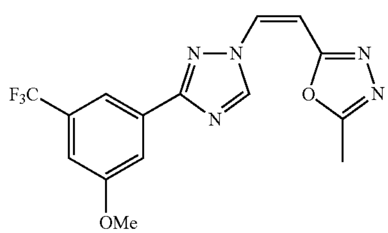 [SMILES: COc1cc(-c2ncn(/C=C\c3nnc(C)o3)n2)cc(C(F)(F)F)c1] | (Z)-2-(2-(3-(3-methoxy-5-(trifluoromethyl)phenyl)-1H-1,2,4-triazol-1-yl)vinyl)-5-methyl-1,3,4-oxadiazole | A |
| I-3 | — | 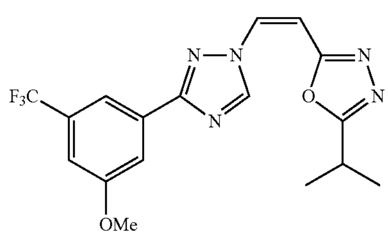 [SMILES: COc1cc(-c2ncn(/C=C\c3nnc(C(C)C)o3)n2)cc(C(F)(F)F)c1] | (Z)-2-isopropyl-5-(2-(3-(3-methoxy-5-(trifluoromethyl)phenyl)-1H-1,2,4-triazol-1-yl)vinyl)-1,3,4-oxadiazole | NT |
| I-4 | — | 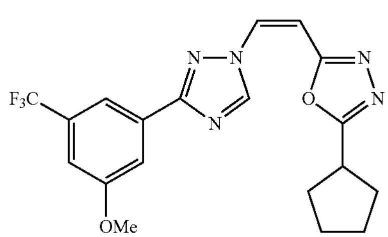 [SMILES: COc1cc(-c2ncn(/C=C\c3nnc(C4CCCC4)o3)n2)cc(C(F)(F)F)c1] | (Z)-2-cyclopentyl-5-(2-(3-(3-methoxy-5-(trifluoromethyl)phenyl)-1H-1,2,4-triazol-1-yl)vinyl)-1,3,4-oxadiazole | NT |

TABLE 1-continued

| Compound # | Example | Structure | Name | Rev Export (%)/[IC$_{50}$] or Cytotoxicity [EC$_{50}$] |
|---|---|---|---|---|
| I-5 | — | 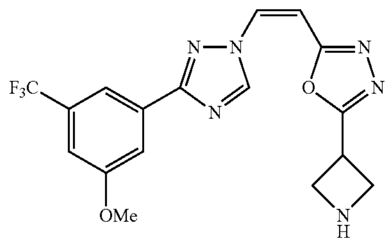 [SMILES: COc1cc(-c2ncn(/C=C\c3nnc(C4CNC4)o3)n2)cc(C(F)(F)F)c1] | (Z)-2-(azetidin-3-yl)-5-(2-(3-(3-methoxy-5-(trifluoromethyl)phenyl)-1H-1,2,4-triazol-1-yl)vinyl)-1,3,4-oxadiazole | NT |
| I-6 | — | 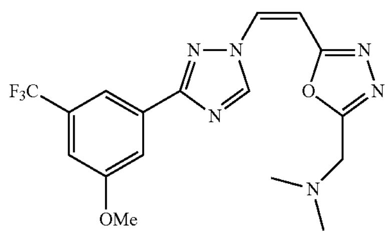 [SMILES: COc1cc(-c2ncn(/C=C\c3nnc(CN(C)C)o3)n2)cc(C(F)(F)F)c1] | (Z)-1-(5-(2-(3-(3-methoxy-5-(trifluoromethyl)phenyl)-1H-1,2,4-triazol-1-yl)vinyl)-1,3,4-oxadiazol-2-yl)-N,N-dimethylmethanamine | NT |
| I-9 | — | 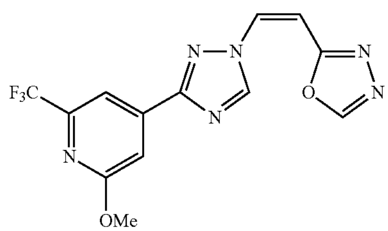 | (Z)-2-(2-(3-(2-methoxy-6-(trifluoromethyl)pyridin-4-yl)-1H-1,2,4-triazol-1-yl)vinyl)-1,3,4-oxadiazole | NT |
| I-10 | 7 | 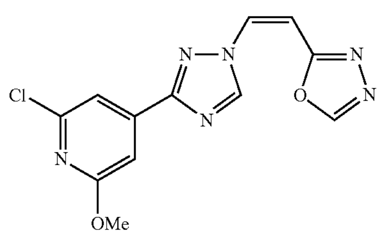 [SMILES: COc1cc(-c2ncn(/C=C\c3nnco3)n2)cc(Cl)n1] | (Z)-2-(2-(3-(2-chloro-6-methoxypyridin-4-yl)-1H-1,2,4-triazol-1-yl)vinyl)-1,3,4-oxadiazole | A |
| I-7 | — | 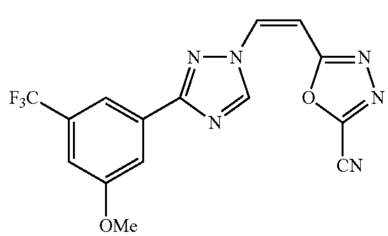 [SMILES: COc1cc(-c2ncn(/C=C\c3nnc(C#N)o3)n2)cc(C(F)(F)F)c1] | (Z)-5-(2-(3-(3-methoxy-5-(trifluoromethyl)phenyl)-1H-1,2,4-triazol-1-yl)vinyl)-1,3,4-oxadiazole-2-carbonitrile | NT |
| I-8 | — | 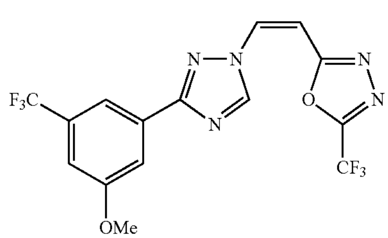 | (Z)-2-(2-(3-(3-methoxy-5-(trifluoromethyl)phenyl)-1H-1,2,4-triazol-1-yl)vinyl)-5-(trifluoromethyl)-1,3,4-oxadiazole | NT |

TABLE 1-continued

| Compound # | Example | Structure | Name | Rev Export (%)/[IC$_{50}$] or Cytotoxicity [EC$_{50}$] |
|---|---|---|---|---|
| I-11 | — | 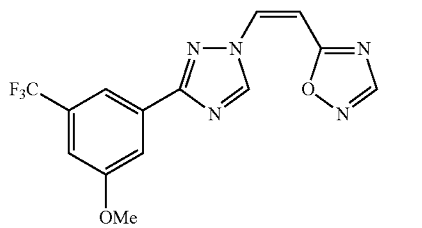 [SMILES: COc1cc(-c2ncn(/C=C\c3ncno3)n2)cc(C(F)(F)F)c1] | (Z)-5-(2-(3-(3-methoxy-5-(trifluoromethyl)phenyl)-1H-1,2,4-triazol-1-yl)vinyl)-1,2,4-oxadiazole | NT |
| I-12 | — | 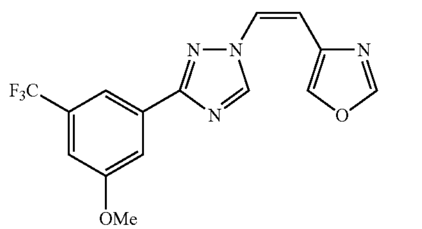 [SMILES: COc1cc(-c2ncn(/C=C\c3cocn3)n2)cc(C(F)(F)F)c1] | (Z)-4-(2-(3-(3-methoxy-5-(trifluoromethyl)phenyl)-1H-1,2,4-triazol-1-yl)vinyl)oxazole | NT |
| I-13 | — | 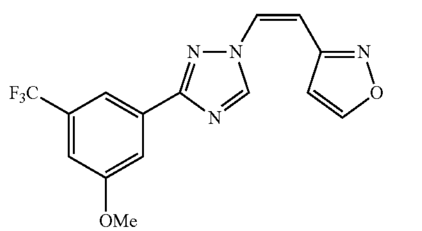 [SMILES: COc1cc(-c2ncn(/C=C\c3ccon3)n2)cc(C(F)(F)F)c1] | (Z)-3-(2-(3-(3-methoxy-5-(trifluoromethyl)phenyl)-1H-1,2,4-triazol-1-yl)vinyl)isoxazole | NT |
| I-14 | — | 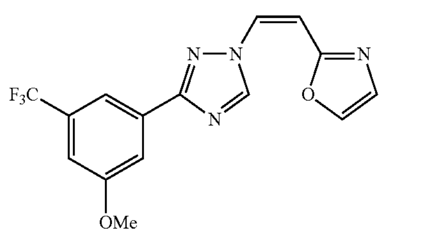 | (Z)-2-(2-(3-(3-methoxy-5-(trifluoromethyl)phenyl)-1H-1,2,4-triazol-1-yl)vinyl)oxazole | NT |
| I-15 | — | 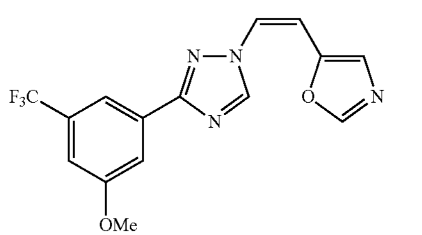 [SMILES: COc1cc(-c2ncn(/C=C\c3cnco3)n2)cc(C(F)(F)F)c1] | (Z)-5-(2-(3-(3-methoxy-5-(trifluoromethyl)phenyl)-1H-1,2,4-triazol-1-yl)vinyl)oxazole | NT |
| I-16 | — | 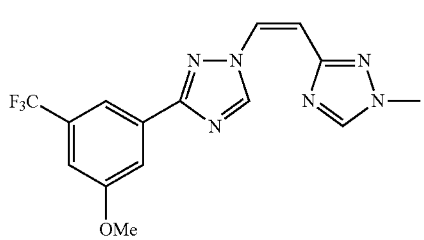 [SMILES: COc1cc(-c2ncn(/C=C\c3ncn(C)n3)n2)cc(C(F)(F)F)c1] | (Z)-3-(3-methoxy-5-(trifluoromethyl)phenyl)-1-(2-(1-methyl-1H-1,2,4-triazol-3-yl)vinyl)-1H-1,2,4-triazole | NT |

TABLE 1-continued

| Compound # | Example | Structure | Name | Rev Export (%)/[IC$_{50}$] or Cytotoxicity [EC$_{50}$] |
|---|---|---|---|---|
| I-17 | — | 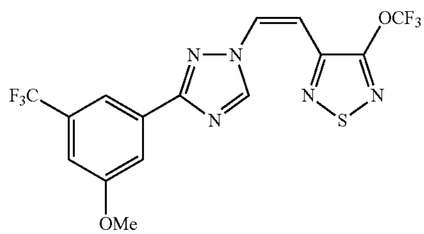 [SMILES: COc1cc(-c2ncn(/C=C\c3nsnc3OC(F)(F)F)n2)cc(C(F)(F)F)c1] | (Z)-3-(2-(3-(3-methoxy-5-(trifluoromethyl)phenyl)-1H-1,2,4-triazol-1-yl)vinyl)-4-(trifluoromethoxy)-1,2,5-thiadiazole | NT |
| I-18 | — | 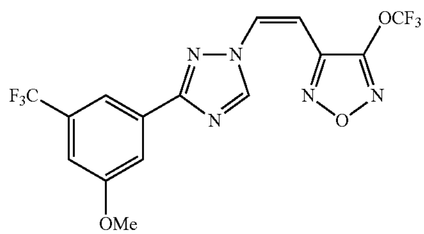 | (Z)-3-(2-(3-(3-methoxy-5-(trifluoromethyl)phenyl)-1H-1,2,4-triazol-1-yl)vinyl)-4-(trifluoromethoxy)-1,2,5-oxadiazole | NT |
| I-19 | — | 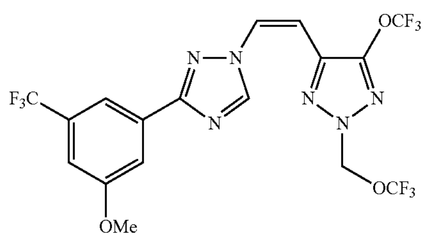 [SMILES: COc1cc(-c2ncn(/C=C\c3nn(COC(F)(F)F)nc3OC(F)(F)F)n2)cc(C(F)(F)F)c1] | (Z)-4-(2-(3-(3-methoxy-5-(trifluoromethyl)phenyl)-1H-1,2,4-triazol-1-yl)vinyl)-2-(2,2,2-trifluoroethyl)-5-(trifluoromethoxy)-2H-1,2,3-triazole | NT |
| I-20 | — | 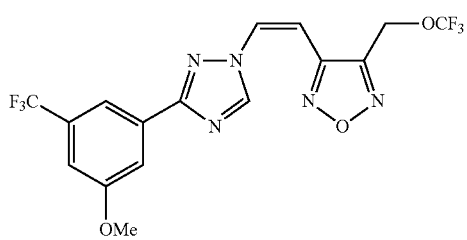 [SMILES: COc1cc(-c2ncn(/C=C\c3nonc3COC(F)(F)F)n2)cc(C(F)(F)F)c1] | (Z)-3-(2-(3-(3-methoxy-5-(trifluoromethyl)phenyl)-1H-1,2,4-triazol-1-yl)vinyl)-4-(2,2,2-trifluoroethyl)-1,2,5-oxadiazole | NT |
| I-21 | 8 | 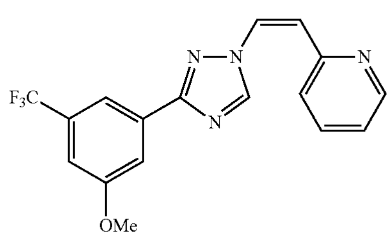 [SMILES: COc1cc(-c2ncn(/C=C\c3ccccn3)n2)cc(C(F)(F)F)c1] | (Z)-2-(2-(3-(3-methoxy-5-(trifluoromethyl)phenyl)-1H-1,2,4-triazol-1-yl)vinyl)pyridine | C |
| I-22 | — | 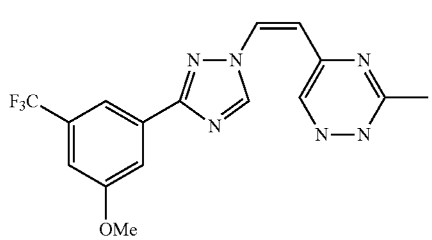 [SMILES: COc1cc(-c2ncn(/C=C\C3=CNNC(C)=N3)n2)cc(C(F)(F)F)c1] | (Z)-5-(2-(3-(3-methoxy-5-(trifluoromethyl)phenyl)-1H-1,2,4-triazol-1-yl)vinyl)-3-methyl-1,2,4-triazine | NT |

TABLE 1-continued

| Compound # | Example | Structure | Name | Rev Export (%)/[IC$_{50}$] or Cytotoxicity [EC$_{50}$] |
|---|---|---|---|---|
| I-23 | — | 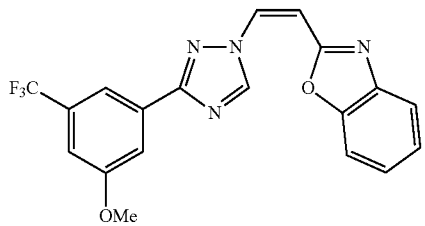 [SMILES: COc1cc(-c2ncn(/C=C\c3nc4ccccc4o3)n2)cc(C(F)(F)F)c1] | (Z)-2-(2-(3-(3-methoxy-5-(trifluoromethyl)phenyl)-1H-1,2,4-triazol-1-yl)vinyl)benzo[d]oxazole | NT |
| I-24 | — | 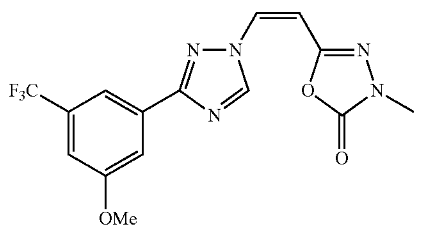 [SMILES: COc1cc(-c2ncn(/C=C\c3nn(C)c(=O)o3)n2)cc(C(F)(F)F)c1] | (Z)-5-(2-(3-(3-methoxy-5-(trifluoromethyl)phenyl)-1H-1,2,4-triazol-1-yl)vinyl)-3-methyl-1,3,4-oxadiazol-2(3H)-one | NT |
| I-25 | — | 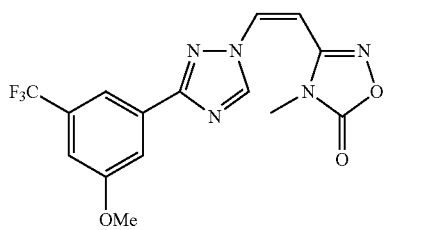 [SMILES: COc1cc(-c2ncn(/C=C\c3noc(=O)n3C)n2)cc(C(F)(F)F)c1] | (Z)-3-(2-(3-(3-methoxy-5-(trifluoromethyl)phenyl)-1H-1,2,4-triazol-1-yl)vinyl)-4-methyl-1,2,4-oxadiazol-5(4H)-one | NT |
| I-30 | 9 | 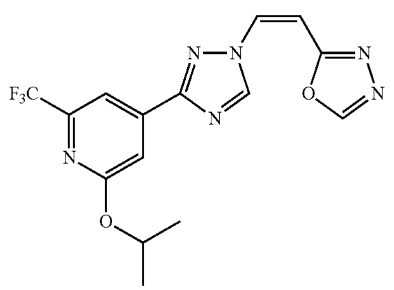 [SMILES: CC(C)Oc1cc(-c2ncn(/C=C\c3nnco3)n2)cc(C(F)(F)F)n1] | (Z)-2-(2-(3-(2-isopropoxy-6-(trifluoromethyl)pyridin-4-yl)-1H-1,2,4-triazol-1-yl)vinyl)-1,3,4-oxadiazole | A |
| I-31 | 10 | 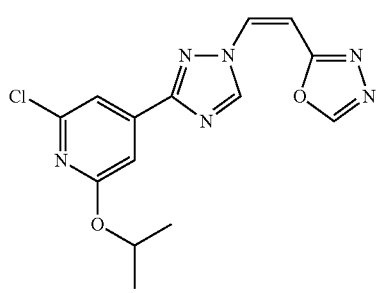 | (Z)-2-(2-(3-(2-chloro-6-isopropoxypyridin-4-yl)-1H-1,2,4-triazol-1-yl)vinyl)-1,3,4-oxadiazole | A |
| I-32 | 11 | 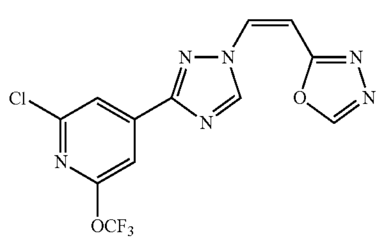 [SMILES: FC(F)(F)Oc1cc(-c2ncn(/C=C\c3nnco3)n2)cc(Cl)n1] | (Z)-2-(2-(3-(2-chloro-6-(trifluoromethoxy)pyridin-4-yl)-1H-1,2,4-triazol-1-yl)vinyl)-1,3,4-oxadiazole | A |

TABLE 1-continued

| Compound # | Example | Structure | Name | Rev Export (%)/[IC$_{50}$] or Cytotoxicity [EC$_{50}$] |
|---|---|---|---|---|
| I-33 | 12 | 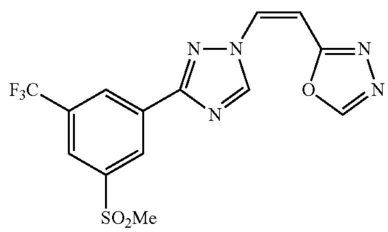 [SMILES: CS(=O)(=O)c1cc(-c2ncn(/C=C\c3nnco3)n2)cc(C(F)(F)F)c1] | (Z)-2-(2-(3-(3-(methylsulfonyl)-5-(trifluoromethyl)phenyl)-1H-1,2,4-triazol-1-yl)vinyl)-1,3,4-oxadiazole | A |
| I-34 | 13 | 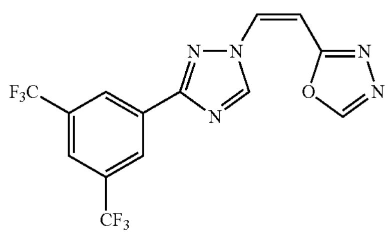 [SMILES: FC(F)(F)c1cc(-c2ncn(/C=C\c3nnco3)n2)cc(C(F)(F)F)c1] | (Z)-2-(2-(3-(3,5-bis(trifluoromethyl)phenyl)-1H-1,2,4-triazol-1-yl)vinyl)-1,3,4-oxadiazole | A |
| I-35 | 14 | 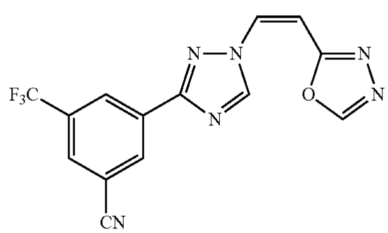 [SMILES: Oc1cc(-c2ncn(/C=C\c3nnco3)n2)cc(C(F)(F)F)c1] | (Z)-3-(1-(2-(1,3,4-oxadiazol-2-yl)vinyl)-1H-1,2,4-triazol-3-yl)-5-(trifluoromethyl)benzonitrile | A |
| I-36 | 15 | 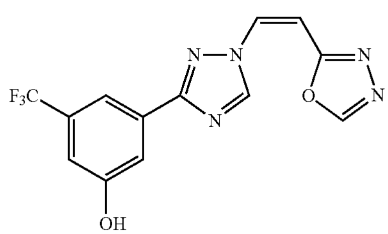 | (Z)-3-(1-(2-(1,3,4-oxadiazol-2-yl)vinyl)-1H-1,2,4-triazol-3-yl)-5-(trifluoromethyl)phenol | A |
| I-37 | 16 | 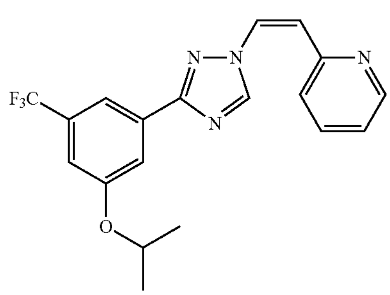 [SMILES: CC(C)Oc1cc(-c2ncn(/C=C\c3ccccn3)n2)cc(C(F)(F)F)c1] | (Z)-2-(2-(3-(3-isopropoxy-5-(trifluoromethyl)phenyl)-1H-1,2,4-triazol-1-yl)vinyl)pyridine | A |
| I-38 | 17 | 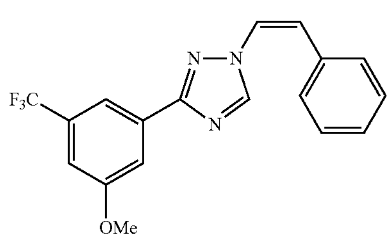 [SMILES: COc1cc(-c2ncn(/C=C\c3ccccc3)n2)cc(C(F)(F)F)c1] | (Z)-3-(3-methoxy-5-(trifluoromethyl)phenyl)-1-styryl-1H-1,2,4-triazole | C |

TABLE 1-continued

| Compound # | Example | Structure | Name | Rev Export (%)/[IC$_{50}$] or Cytotoxicity [EC$_{50}$] |
|---|---|---|---|---|
| I-39 | 18 | 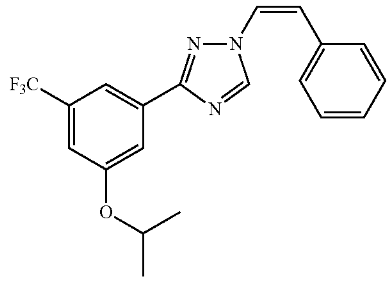 [SMILES: CC(C)Oc1cc(-c2ncn(/C=C\c3ccccc3)n2)cc(C(F)(F)F)c1] | (Z)-3-(3-isopropoxy-5-(trifluoromethyl)phenyl)-1-styryl-1H-1,2,4-triazole | C |

HCT-116 In Vivo Assay

Study Design.

Female balb c nude mice (nu/nu) aged 6 to 8 weeks were obtained from Charles River Laboratories and were randomly and prospectively divided into six groups of ten mice. Mice were inoculated s.c. in flanks with $1\times10^6$ HCT-116 tumor cells. When cells reached 100-200 mm$^3$, animals were randomized into treatment groups of 5-10 mice each, excluding mice with the largest and smallest tumors. Mice were treated with vehicle, standard of care drugs (5-FU) or compounds of the invention at the indicated doses and regimen. Animals' weights and condition were recorded daily, and tumors were measured daily. On Day 37 (2 hours after the final dose), all mice were sacrificed, plasma and tumor tissue were collected for PK/PD analysis. Tumors were divided in 4 sections (3, flash-frozen in separate vials and 1 fixed in formalin for paraffin block preparation).

HCT-116 Cell Culture.

HCT-116 Colorectal tumor cells (ATCC# CCL-247) were grown in the DMEM tissue culture media with 10% fetal bovine serum and 1% penicillin/streptomycin. Cells were routinely trypsinized and passaged 1:4. On the day of implantation, cells were washed in PBS, trypsinized and resuspended in complete media. Cells were washed 3× in serum free medium. Cells were resuspended to a density of $1\times10^7$ cells/ml prior to being implanted s.c. into mice in a volume of 0.1 mL using a 23G needle.

Tumor Measurement.

Tumors were monitored daily. Tumors appearing exceeding 1500 mm$^3$ were measured, and animals with tumors greater than 1500 mm$^3$ and/or tumors that became necrotic and/or hindered movement were euthanized. Tumors were measured twice weekly by measuring each tumor in 2 dimensions, along the largest dimension (length, L) and perpendicular to this dimension (width, W). Tumor weights were calculated using the standard formula: (L×W$^2$)/2. The mean tumor weight and standard error of the mean were calculated for each group at each time point.

Figure 2:
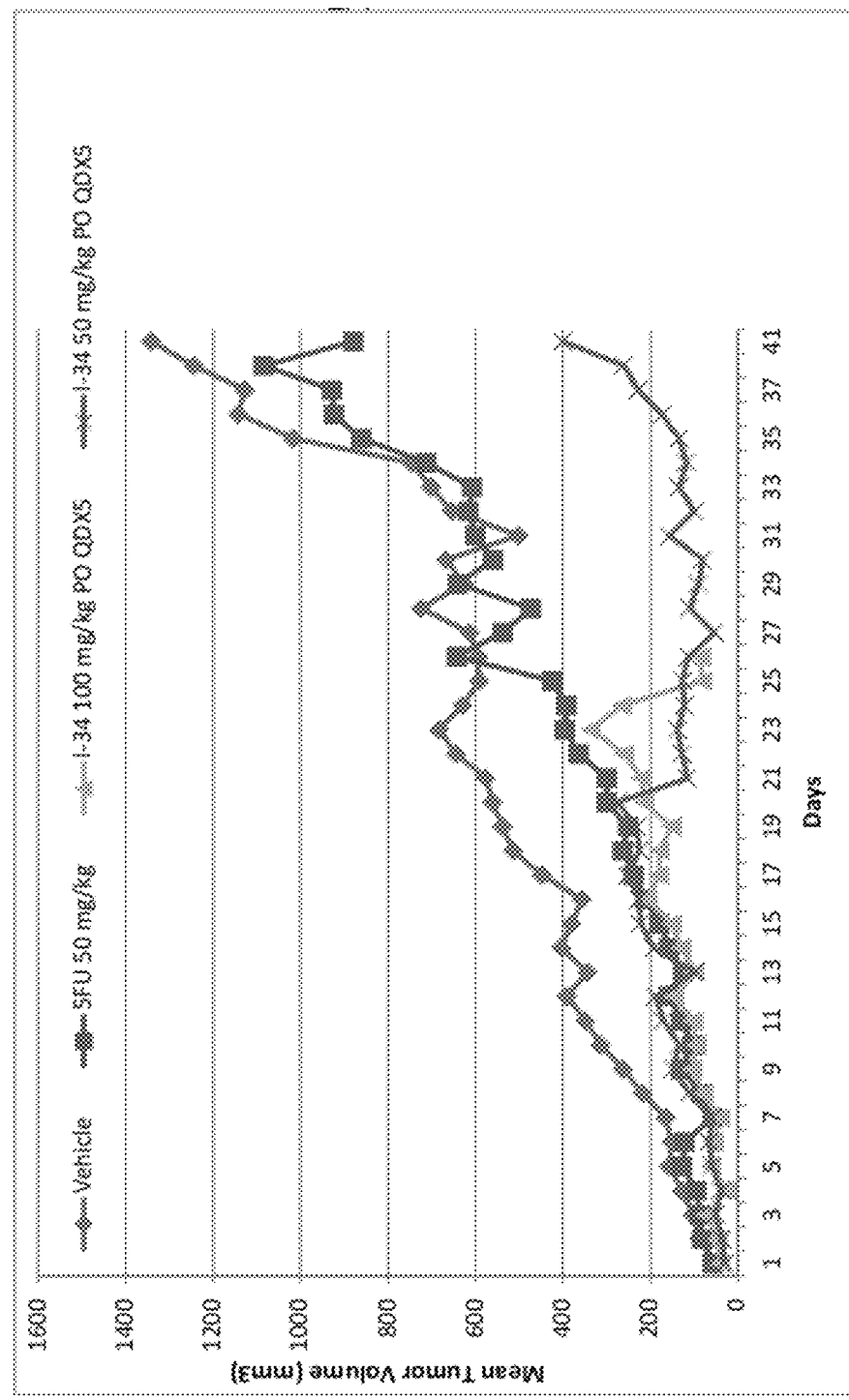
FIG. 2 is a graph depicting the results of an HCT-116 colorectal carcinoma xenograft model. HCT-116 cells were inoculated into female athymic Balb c. nu$^+$/nu$^+$ mice. Once tumors reached an average volume of 100 mm$^3$ the animals were dosed with vehicle, 50 mg/kg 5-fluorouracil intraperitoneally and 50 and 100 mg/kg I-34 orally. At Day 26, I-34 administered QDX5/week at 100 mg/kg displayed complete reduction of tumor growth in a statistically significant manner. Mice were euthanized on Day 26 due to 20% weight loss. At Day 37, I-34 administered QDX5/week at 50 mg/kg inhibited tumor growth by 85%. 5-FU inhibited tumor growth during the first 3 weeks in a statistically significant manner. By Day 37 5FU group animals were euthanized due to poor condition and no inhibition of tumor growth was observed when compared to vehicle group.

Statistical differences between treatment groups were determined using appropriate statistical techniques. A one-way ANOVA or ANOVA on ranks was used to evaluate the area-under the curve for weight gain and tumor volume. The results are presented in FIGS. 1 and 2.

MM1S In Vivo Assay 105 female athymic nude mice (8-9 weeks old, Harlan, USA) were grouped into seven (7) groups of 10 animals. Animals were randomized such that the group average tumor volume was between 100-200 mm$^3$. Group average body weights were matched as closely as possible once average tumor volumes were randomized. The live-phase portion of this study will be 28 days in duration from the start of until the average group tumor volume reaches 2,000 mm$^3$, whichever comes first. Mice are to be euthanized with samples collected as and when they individually reach a tumor volume of approximately 2,000 mm$^3$.

MM1s Cell Culture. MM1s cells were cultured in RPMI-1640 medium (cat#15-040 CV; mediatech) with 10% heat inactivated FBS cat #10082-147; Invitrogen, 1% Sodium bicarbonate 7.5% cat 20-035 CI; Mediatech, 1% Penicillin-Streptomycin 10,000 I.U/mL cat 30-002 CI; mediatech, 1% Sodium Pyruvate 100 mM cat 95037-578; VWR, 1% Hepes Buffer 1M cat 25-060 CI Mediatech, 1% L-glutamine, cat 25-005-CI; MediaTECH. Cells in exponential growth phase were inoculated as described below.

Inoculation with Tumor Cells.

Female athymic nude mice were acclimated for at least 3 days. Following acclimation, animals were ear-tagged and weighed prior to SC inoculation in the right flank with an inoculum of $2.5\times10^6$ MM1.s cells in 0.1 mL RPMI per mouse (with no Matrigel) using a 25G needle and 1 mL syringe. Cells were washed immediately before injection and resuspended in serum free medium (with no Matrigel).

Tumor Volume Measurement.

Tumor volumes were monitored three times per week throughout the study (typically Monday, Wednesday and Friday) and calculated using the formula: Tumor volume=½(a$^2$ b); where a=width (smallest dimension) and b=length. Once the average volume of the established tumors reached approximately 100 mm$^3$-200 mm$^3$ (all groups), mice were randomized and placed into the different treatment groups with similar starting tumor volumes of 100 mm$^3$-200 mm$^3$ in all groups. Although mice were assigned to treatment groups with average tumor volume taking priority over average body weight, both parameters were matched as closely as possible between treatment groups. On the same day as randomization, the first dose of drug was administered according to Table 1.

Endpoint Tumor Growth Inhibition (TGI).

Figure 4:
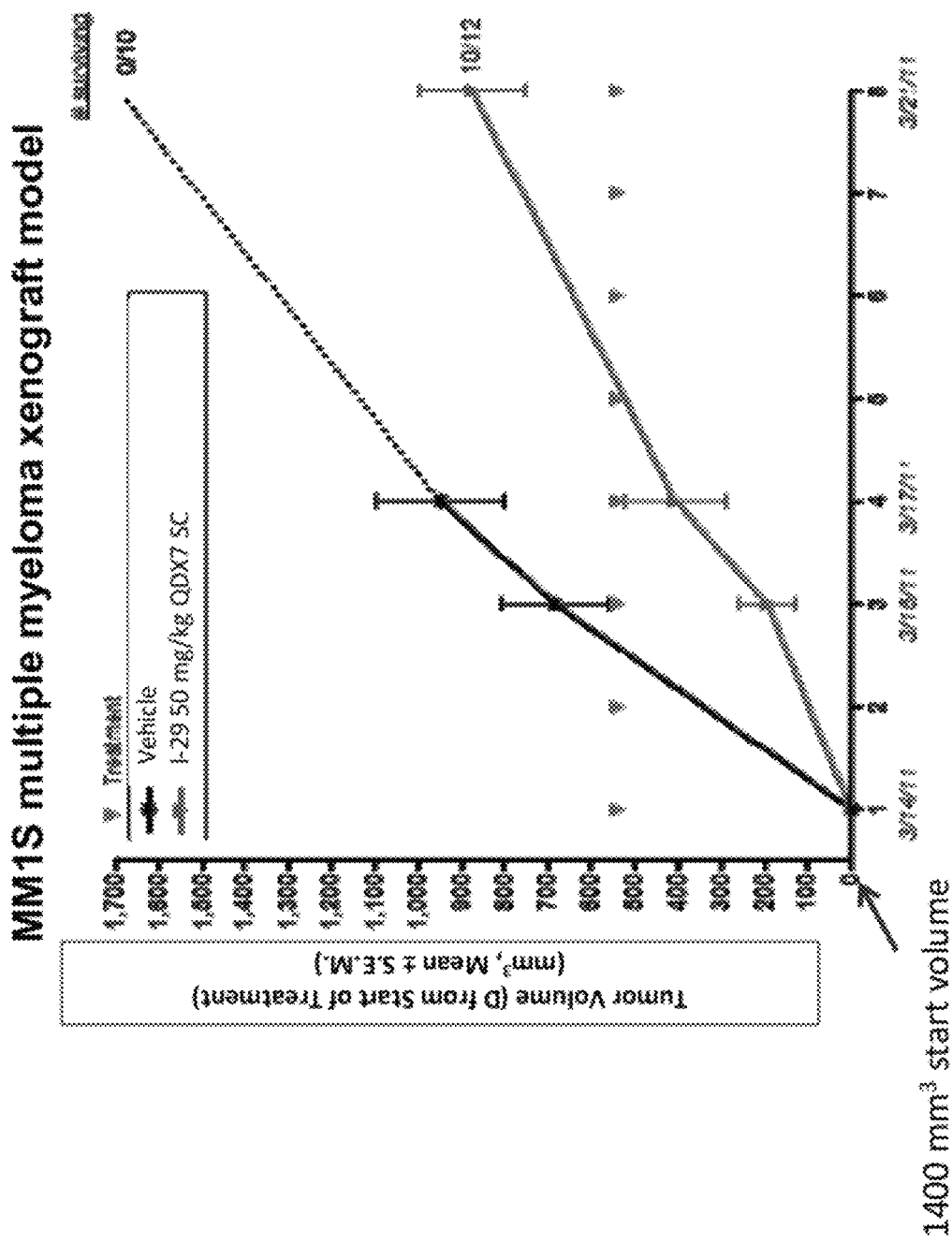
FIG. 4 is a graph depicting the results of a MM1.S multiple myeloma model. MM1.S cells were inoculated into female athymic nu$^+$/nu$^+$ mice. Once tumors reached an average volume of 1400 mm$^3$ the animals were dosed with vehicle or 50 mg/kg I-29 subcutaneously every day. On the fourth day of dosing, vehicle group animals (n=10) reached an average volume of 2300 mm$^3$ and had to be euthanized due to tumor burden and poor health. Following 8 doses I-29 displayed 50% reduction in tumor growth in a statistically significant manner and 10 out of 12 animals were still alive suggesting that not only I-29 inhibits tumor growth but also increases survival.

Animals were monitored as a group and their tumor volumes were measured three times per week at the same time of day. The experiment was terminated at the timepoints indicated in FIGS. 3 and 4. When the endpoint of the experiment was reached, all the animals are to be euthanized with tissue and sample collections performed. Results are presented in FIGS. 3 and 4.

BIBLIOGRAPHY

1. Cronshaw J M and Matunis M J. 2004. The nuclear pore complex: disease associations and functional correlations TRENDS Endocrin Metab. 15:34-39
2. Falini B et al. 2006. Both carboxy-terminus NES motif and mutated tryptophan(s) are crucial for aberrant nuclear export of nucleophosmin leukemic mutants in NPMc+ AML Blood. 107:4514-4523
3. Cai X and Liu X. 2008. Inhibition of Thr-55 phosphorylation restores p53 nuclear localization and sensitizes cancer cells to DNA damage. PNAS. 105:16958-16963.
4. Daelemans D, Afonina E, Nilsson J 2002 A synthetic HIV-1 Rev inhibitor interfering with the CRM1-mediated nuclear export. Proc Natl Acad Sci USA 99(22):14440-5.98052-2517
5. Davis J R et al. 2007. Controlling protein compartmentalization to overcome disease Pharmaceut Res. 24:17-27
6. Freundt E, Yu L, Park E, et al 2009 Molecular determinants for subcellular localization of the severe acute respiratory syndrome coronavirus open reading frame 3b protein. J Virol 83(13):6631-40
7. Ghildyal R, Ho A, Dias M, et al 2009 The respiratory syncytial virus matrix protein possesses a Crm1-mediated nuclear export mechanism. J Virol 83(11):5353-62
8. Ghosh C C et al 2008 Analysis of nucleocytoplasmic shuttling of NF kappa B proteins in human leukocytes. Methods Mol. Biol. 457:279-92.
9. Gupta N et al 2008 Retinal tau pathology in human glaucomas Can J Ophthalmol. 2008 February; 43(1):53-60
10. HoshinoL et al. 2008. Combined effects of p53 gene therapy and leptomycin B in human esophageal squamous cell carcinoma. Oncology. 75:113-119.
11. Lain S et al. 1999a An inhibitor of nuclear export activates the p53 response and induces the localization of HDM2 and p53 to U1A-positive nuclear bodies associated with the PODs Exp Cell Res. 248:457-472.
12. Lain S et al. 1999b. Accumulating active p53 in the nucleus by inhibition of nuclear export: a novel strategy to promote the p53 tumor suppressor function Exp Cell Res. 253:315.
13. Muller P A et al. 2009 Nuclear-cytosolic transport of COMMD1 regulates NF-kappaB and HIF-1 activity. Traffic on-line publication
14. Mutka S 2007 Nuclear Export Inhibitors (NEIs) as novel cancer therapies AACR Annual Meeting. Poster 5609.
15. Mutka S, Yang W, Dong S, et al. 2009. Identification of nuclear export inhibitors with potent anticancer activity in vivo. Cancer Res. 69: 510-7.
16. Nakahara J et al. 2009. Abnormal expression of TIP30 and arrested nucleocytoplasmic transport within oligodendrocyte precursor cells in multiple sclerosis J Clin Invest. 119:169-181
17. Noske A et al. 2008. Expression of the nuclear export protein chromosomal region maintenance/exportin 1/Xpo1 is a prognostic factor in human ovarian cancer
18. Cancer. 112:1733-1743
19. Pollard V & Malim M. 1998 The HIV-1 Rev protein 52:491-532.
20. Rawlinson S, Pryor M, Wright P, Jans D 2009 CRM1-mediated nuclear export of dengue virus RNA polymerase NS5 modulates interleukin-8 induction and virus production J Biol Chem 284(23):15589-97
21. Sanchez V, Mahr J, Orazio N, et al 2007 Nuclear export of the human cytomegalovirus tegument protein pp 65 requires cyclin-dependent kinase activity and the Crm1 exporter J Virol 81(21):11730-6.
22. Sorokin A V et al. 2007. Nucleocytoplasmic transport of proteins Biochemistry. 72:1439-1457.
23. Terry L J et al. 2007. Crossing the nuclear envelope: hierarchical regulation of nucleocytoplasmic transport Science. 318:1412-1416
24. Van der Watt P J et al. 2008. The Karyopherin proteins, Crm1 and Karyopherin beta1, are overexpressed in cervical cancer and are critical for cancer cell survival and proliferation Int J Canc. 124:1829-1840
25. Walsh M D et al. 2008 Exportin 1 inhibition attenuates nuclear factor-kappaB-dependent gene expression. Shock 29:160-166
26. Williams P, Verhagen J, Elliott G 2008 Characterization of a CRM1-dependent nuclear export signal in the C terminus of herpes simplex virus type 1 tegument protein UL47 J Virol 82(21):10946-52.
27. Yang W 2007 Anti-tumor activity of novel nuclear export inhibitors (NEIs) in multiple murine leukemia models AACR Annual Meeting. Poster 5597.
28. Yao Y et al. 2009. The expression of CRM1 is associated with prognosis in human osteosarcoma Oncol Rep. 21:229-35.
29. Zimmerman T L et al 2006 Nuclear export of retinoid X receptor alpha in response to interleukin-1beta-mediated cell signaling: roles for JNK and SER260 J Biol Chem 281:15434-15440

We claim:
1. A compound represented by formula II:

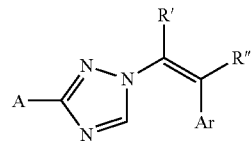

or a pharmaceutically acceptable salt thereof, wherein:
A is selected from an optionally substituted phenyl ring or an optionally substituted pyridyl ring; and
Ar is phenyl, pyridyl, or a 5 membered monocyclic heteroaryl ring having 1-3 heteroatoms independently selected from nitrogen, oxygen, or sulfur,
wherein A and Ar are optionally and independently substituted with one or more $R^1$ substituents;
each $R^1$ is independently selected from the group of F, Cl, Br, I, —$NO_2$, —CN, —$N_3$, or -$L^1$-R;
R is optionally substituted $C_{1-8}$ alkyl, $C_{2-8}$ alkenyl, $C_{2-8}$ alkynyl, haloalkyl, phenyl, a 3-7 membered saturated or partially unsaturated cycloalkyl ring, an 8-10 membered bicyclic saturated, partially unsaturated or aryl carbocyclic ring, a 4-7-membered saturated or partially unsaturated heterocycloalkyl ring having 1-4 heteroatoms independently selected from nitrogen, oxygen, or sulfur; a 5-6 membered monocyclic heteroaryl ring having 1-3 heteroatoms independently selected from nitrogen, oxygen, or sulfur; or an 8-10 membered bicyclic heteroaryl ring having 1-4 heteroatoms independently selected from nitrogen, oxygen, or sulfur;
$L^1$ is a covalent bond or an optionally substituted bivalent $C_{1-6}$ hydrocarbon chain, wherein one or more methylene units of $L^1$ is optionally and independently replaced by -Cy-, —O—, —S—, —N($R^a$)—, —C(O)—, —C(S)—, —C(O)N($R^a$)—, —N($R^a$)C (O)N(R$^a$)—, —N(R$^a$)C(O)—, —N(R$^a$)C(O)O—, —OC(O)N(R$^a$)—, —S(O)—, —S(O)$_2$—, —S(O)$_2$N(R$^a$)—, —N(R$^a$)S(O)$_2$—, —OC(O)—, or —C(O)O—;

-Cy- is an optionally substituted bivalent ring selected from a 3-7 membered saturated or partially unsaturated cycloalkylene ring, a 4-7-membered saturated or partially unsaturated heterocycloalkylene ring having 1-4 heteroatoms independently selected from nitrogen, oxygen, or sulfur, phenylene, a 5-6 membered monocyclic heteroarylene having 1-3 heteroatoms independently selected from nitrogen, oxygen, or sulfur, an 8-10 membered bicyclic arylene, or an 8-10 membered bicyclic heteroarylene having 1-4 heteroatoms independently selected from nitrogen, oxygen, or sulfur;

each R$^a$ is independently for each occurrence —H, —R or —C(O)R; and each R' and R" is —H.

2. The compound of claim 1, wherein the compound is represented by a structural formula selected from:

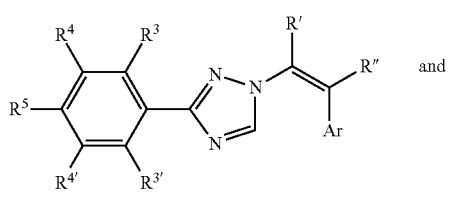

III

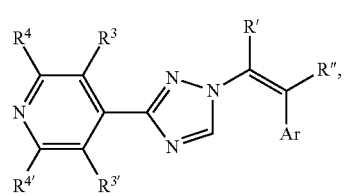

III-a or a pharmaceutically acceptable salt thereof, wherein:

each of R$^3$, R$^{3'}$, R$^4$, R$^{4'}$ and R$^5$ are independently —H, F, Cl, Br, I, —NO$_2$, —CN, —N$_3$, or -L$^1$-R.

3. The compound of claim 2, wherein R$^4$ is —CF$_3$ and R$^{4'}$ is —OMe.

4. The compound of claim 1, wherein the compound is represented by the following structural formula:

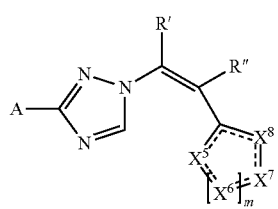

V or a pharmaceutically acceptable salt thereof, wherein:

m is 1;

each of X$^5$, X$^6$, X$^7$ and X$^8$ is independently selected from O, S, N, N(R$^a$), and C(R$^2$), as valency permits, wherein at least one of X$^5$, X$^6$, X$^7$ and X$^8$ is either N or NR$^a$, and wherein 1-3 heteroatoms are present; and R$^2$ is independently for each occurrence —H, F, Cl, Br, I, —NO$_2$, —CN, —N$_3$, or -L$^1$-R.

5. The compound of claim 4, wherein at least one of X$^5$, X$^6$, X$^7$ and X$^8$ is N.

6. The compound of claim 5, wherein the compound is represented by a structural formula selected from:

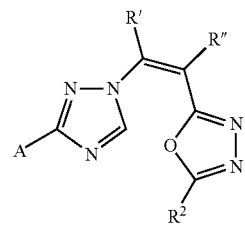

VI

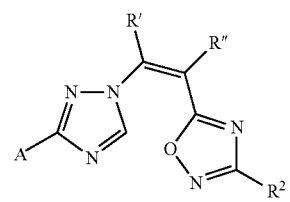

VII

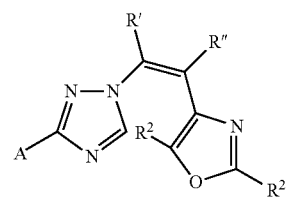

VIII

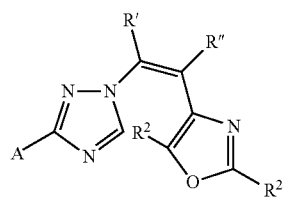

IX

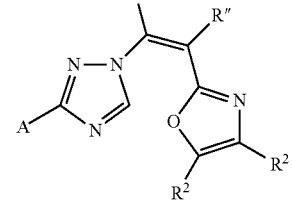

X

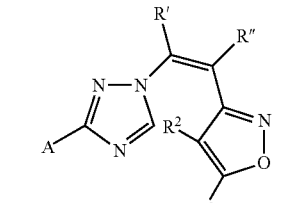

XI

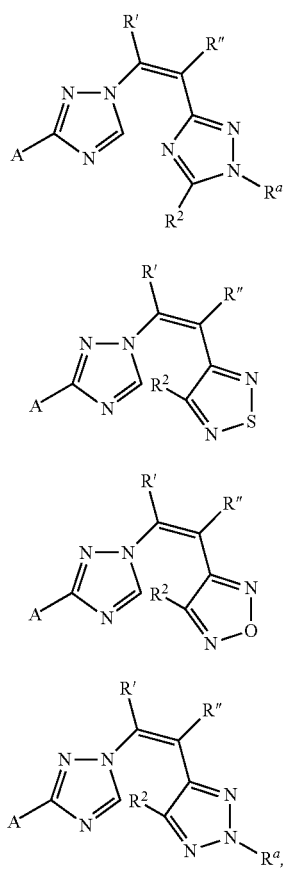
or a pharmaceutically acceptable salt of any of the foregoing.
7. A compound selected from:
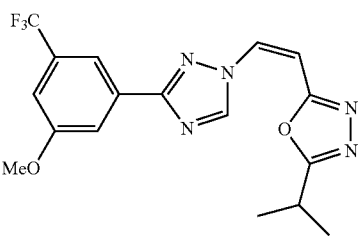
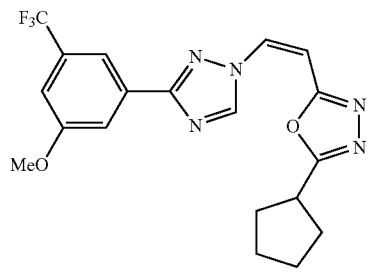
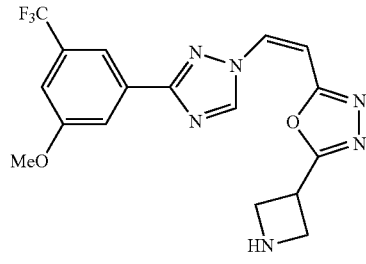
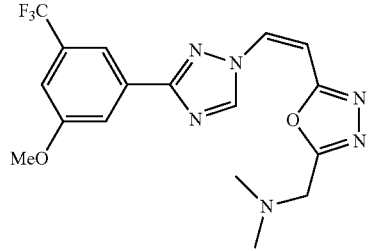
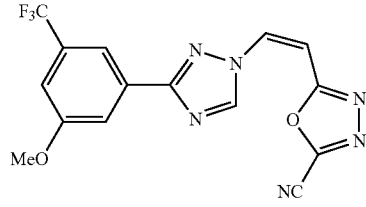
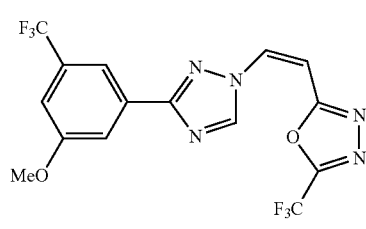
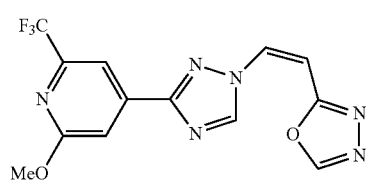
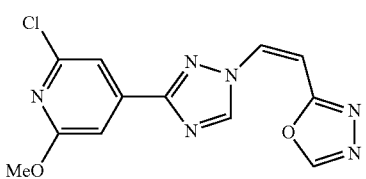

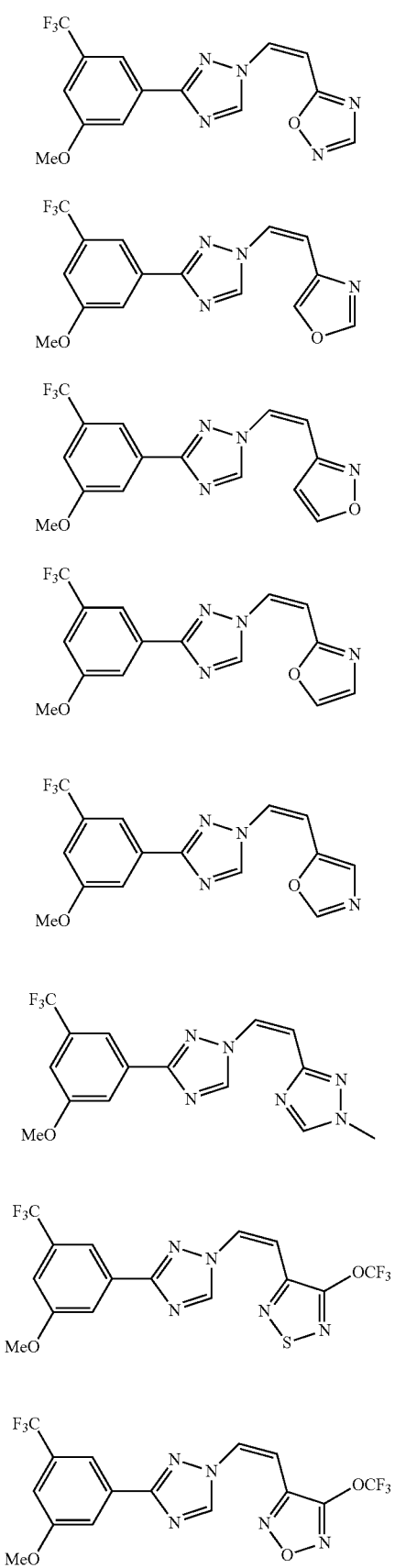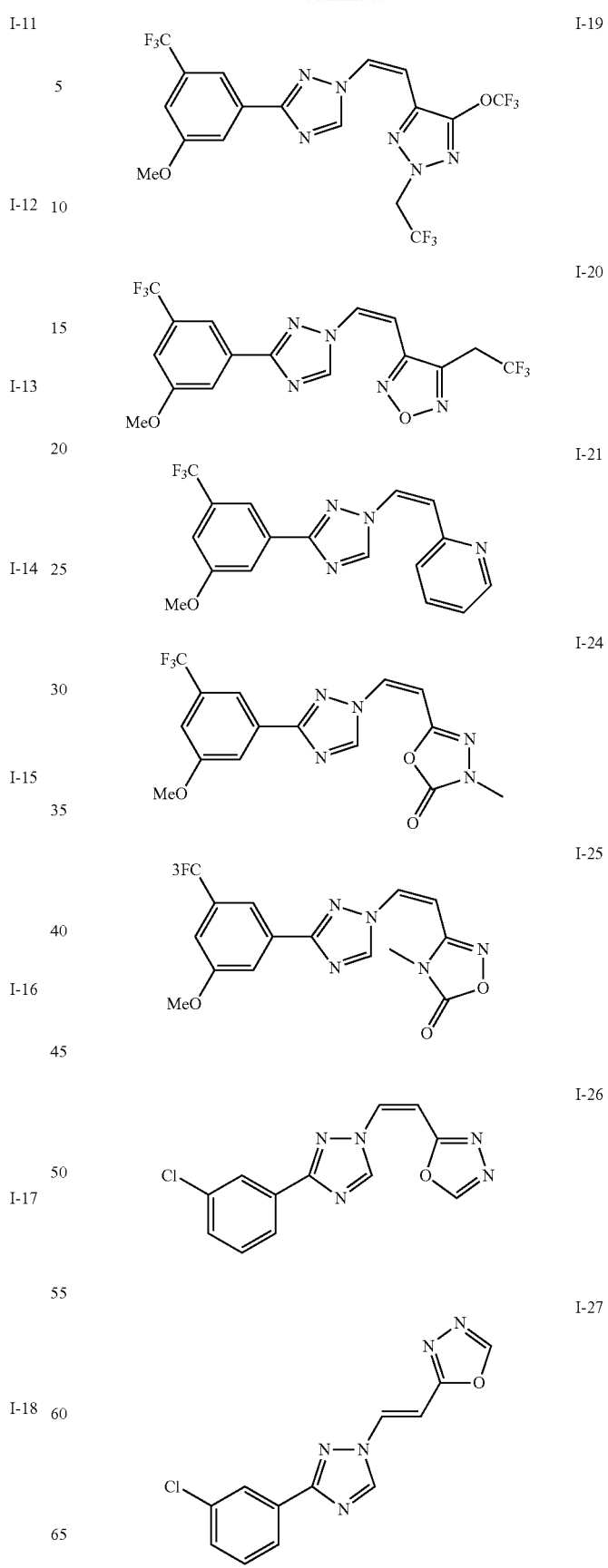

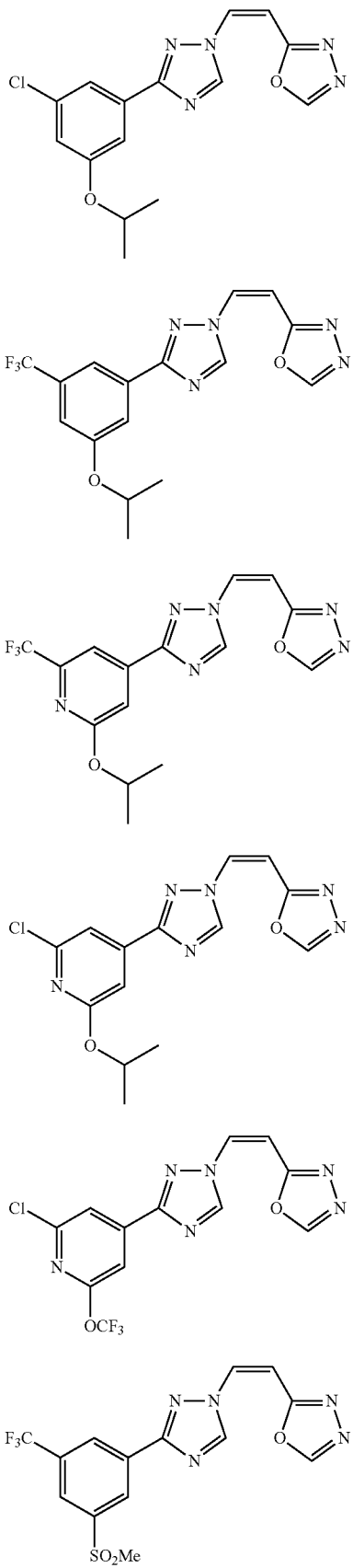
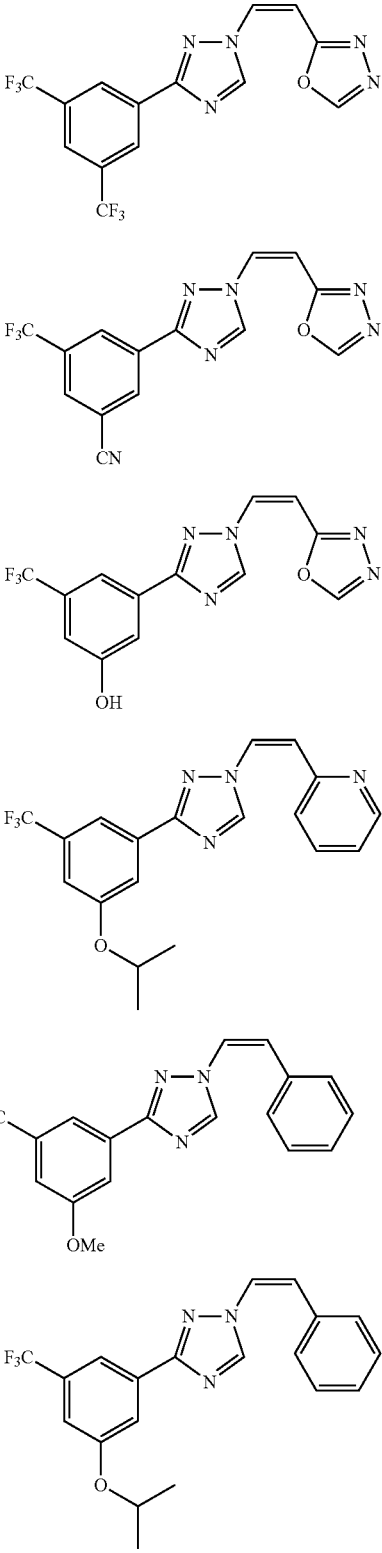
or a pharmaceutically acceptable salt of any of the foregoing.
8. A pharmaceutical composition comprising a compound of claim 1, or a pharmaceutically acceptable salt thereof, and a pharmaceutically acceptable excipient.

9. The compound of claim 1, wherein the compound is a Z double bond isomer.

10. The compound of claim 1, wherein the compound is an E double bond isomer.

* * * * *